(12) United States Patent
Wada et al.

(10) Patent No.: US 7,341,817 B2
(45) Date of Patent: Mar. 11, 2008

(54) PHOTOSENSITIVE COMPOSITION, COMPOUND FOR USE IN THE PHOTOSENSITIVE COMPOSITION, AND PATTERN FORMING METHOD USING THE PHOTOSENSITIVE COMPOSITION

(75) Inventors: Kenji Wada, Shizuoka (JP); Kunihiko Kodama, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 78 days.

(21) Appl. No.: 10/993,094

(22) Filed: Nov. 22, 2004

(65) Prior Publication Data
US 2005/0123859 A1 Jun. 9, 2005

(30) Foreign Application Priority Data
Nov. 21, 2003 (JP) ............ P.2003-392790
Jul. 30, 2004 (JP) ............ P.2004-222931

(51) Int. Cl.
*G03F 7/004* (2006.01)
*G03F 7/30* (2006.01)

(52) U.S. Cl. ............ 430/270.1; 430/905; 430/910; 430/921; 558/56; 562/83

(58) Field of Classification Search ............ 430/270.1, 430/326, 905, 907, 910, 921, 944; 558/56; 562/83
See application file for complete search history.

(56) References Cited

U.S. PATENT DOCUMENTS

| | | | |
|---|---|---|---|
| 5,344,742 A * | 9/1994 | Sinta et al. ............ | 430/270.1 |
| 5,670,691 A | 9/1997 | Spangler et al. | |
| 5,965,319 A * | 10/1999 | Kobayashi ............ | 430/176 |
| 6,440,634 B1 * | 8/2002 | Ohsawa et al. ......... | 430/270.1 |
| 6,492,091 B2 * | 12/2002 | Kodama et al. ......... | 430/270.1 |
| 6,933,094 B2 * | 8/2005 | Miyaji et al. ............ | 430/270.1 |
| 2003/0068573 A1 * | 4/2003 | Takata et al. ............ | 430/270.1 |
| 2003/0203308 A1 | 10/2003 | Mizutani et al. | |
| 2003/0215738 A1 * | 11/2003 | Ohsawa et al. ......... | 430/270.1 |

FOREIGN PATENT DOCUMENTS

| | | |
|---|---|---|
| EP | 0 708 368 A | 4/1996 |
| EP | 0 708 368 A1 | 4/1996 |
| EP | 1 243 968 A | 9/2002 |
| EP | 1 376 232 A | 1/2004 |
| EP | 1 376 232 A1 | 1/2004 |
| EP | 1 457 819 A | 9/2004 |
| EP | 1 457 819 A2 | 9/2004 |
| EP | 1 462 858 A | 9/2004 |
| EP | 1 462 858 A1 | 9/2004 |
| JP | 2002-23353 A | 1/2002 |
| JP | 2002-236359 A | 8/2002 |
| JP | 2003-114523 A | 4/2003 |
| JP | 2003-149812 A | 5/2003 |
| JP | 2003-162059 A | 6/2003 |
| JP | 2003-316004 A | 11/2003 |

OTHER PUBLICATIONS

Partial European Search Report dated Apr. 5, 2005.
Hiroshi Ito et al, "Influence of acid generator structure on T-top formation in high temperature bake process for environmental stabilization". Proceedings of SPIE—The International Society for Optical Engineering, vol. 2438, 1995, pp. 53-60, XP-002437097.

* cited by examiner

*Primary Examiner*—John S. Chu
(74) *Attorney, Agent, or Firm*—Sughrue Mion, PLLC.

(57) ABSTRACT

A photosensitive composition comprising a compound capable of generating a specific sulfonic acid upon irradiation with actinic rays or a radiation; a compound capable of generating a specific sulfonic acid upon irradiation with an actinic ray or a radiation; and a pattern forming method using a photosensitive composition comprising a compound capable of generating a specific sulfonic acid upon irradiation with an actinic ray or a radiation.

31 Claims, No Drawings

PHOTOSENSITIVE COMPOSITION, COMPOUND FOR USE IN THE PHOTOSENSITIVE COMPOSITION, AND PATTERN FORMING METHOD USING THE PHOTOSENSITIVE COMPOSITION

BACKGROUND OF THE INVENTION

1. Field of the Invention

The present invention relates to a photosensitive composition capable of changing its properties by undergoing a reaction upon irradiation with an actinic ray or a radiation, a compound for use in the photosensitive composition, and a pattern forming method using the photosensitive composition. More specifically, the present invention relates to a photosensitive composition for use in the production process of a semiconductor such as IC, in the production of a circuit substrate of liquid crystal, thermal head and the like, in other photofabrication processes or in the lithographic printing plate or acid-curable composition, and also relates to a compound for use in the photosensitive composition and a pattern forming method using the photosensitive composition.

2. Description of the Related Art

The chemical amplification resist composition is a pattern forming material capable of forming a pattern on a substrate by producing an acid in the exposed area upon irradiation with a radiation such as far ultraviolet light and through a reaction using this acid as the catalyst, causing change in the solubility in a developer between the active radiation-irradiated area and the non-irradiated area.

In the case of using a KrF excimer laser as the exposure light source, a resin having small absorption in the region of 248 nm and having a basic skeleton of poly(hydroxystyrene) is primarily used as the main component and this is an excellent system capable of forming a good pattern with high sensitivity and high resolution as compared with conventional naphthoquinone-diazide/novolak resin systems.

In the case of using a light source of emitting light at wavelengths shorter than that, for example, in using an ArF excimer laser (193 nm) as the light source, a satisfactory pattern cannot be formed even by the above-described chemical amplification system because the compound having an aromatic group substantially has large absorption in the region of 193 nm.

In order to solve this problem, a resist containing a resin having an alicyclic hydrocarbon structure has been developed for use with an ArF excimer laser.

As for the acid generator which is a main constituent component of the chemical amplification resist, various compounds have been also found and JP-A-2002-23353 (the term "JP-A" as used herein means an "unexamined published Japanese patent application"), JP-A-2003-149812 and JP-A-2003-114523 describe a compound capable of generating an aromatic sulfonic acid upon irradiation with an actinic ray or a radiation.

However, these are not satisfied in many points and various improvements are demanded. For example, in the case of using a wafer having a large aperture, fluctuation of the temperature in the wafer plane at the heating (PEB) by a hot plate or the like after exposure is found to affect the pattern obtained, and the improvement of such PEB temperature dependency is demanded as well as good profile.

SUMMARY OF THE INVENTION

Accordingly, an object of the present invention is to provide a photosensitive composition exhibiting small PEB temperature dependency and giving a good profile, a compound for use in the photosensitive composition, and a pattern forming method using the photosensitive composition.

The present invention has the following constitutions and by these constitutions, the object of the present invention can be attained.

(1) A photosensitive composition comprising (A) a compound capable of generating a sulfonic acid represented by formula (I) upon irradiation with an actinic ray or a radiation:

wherein

Rf represents an organic group having a fluorine atom,
R represents a hydroxyl group or an organic group,
Ar represents an aromatic group,
l represents an integer of 1 to 6,
m represents an integer of 0 to 4, and
n represents an integer of 0 to 4,
provided that m+n represents an integer of 1 or more.

(2) The photosensitive composition as described in (1), wherein the compound (A) capable of generating a sulfonic acid represented by formula (I) upon irradiation with an actinic ray or a radiation is a sulfonium salt compound of the sulfonic acid represented by formula (I), an iodonium salt compound of the sulfonic acid represented by formula (I), or an ester compound of the sulfonic acid represented by formula (I).

(3) The photosensitive composition as described in (1), wherein the compound (A) capable of generating a sulfonic acid represented by formula (I) upon irradiation with an actinic ray or a radiation is represented by any one of formulae (A1) to (A5):

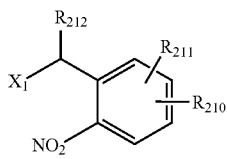
(A5)

wherein in formula (A1), $R_{201}$, $R_{202}$ and $R_{203}$ each independently represents an organic group, and $X^-$ represents a sulfonate anion resulting from removal of the hydrogen atom from the sulfonic acid (—SO$_3$H) of formula (I);

in formula (A2), $R_{204}$ and $R_{205}$ each independently represents an aryl group, an alkyl group or a cycloalkyl group, and $X^-$ represents a sulfonate anion resulting from removal of the hydrogen atom from the sulfonic acid (—SO$_3$H) of formula (I);

in formula (A3),

A represents an alkylene group, an alkenylene group or an arylene group, and $X_1$ represents a monovalent group resulting from removal of the hydrogen atom from the sulfonic acid (—SO$_3$H) of formula (I);

in formula (A4), $R_{208}$ represents an alkyl group or an aryl group, $R_{209}$ represents an alkyl group, a cyano group or an alkoxycarbonyl group, and $X_1$ represents a monovalent group resulting from removal of the hydrogen atom from the sulfonic acid (—SO$_3$H) of formula (I); and in formula (A5), $R_{210}$ and $R_{211}$ each independently represents a hydrogen atom, an alkyl group, a cyano group, a nitro group or an alkoxycarbonyl group, $R_{212}$ represents a hydrogen atom, an alkyl group, a cyano group or an alkoxycarbonyl group, and $X_1$ represents a monovalent group resulting from removal of the hydrogen atom from the sulfonic acid (—SO$_3$H) of formula (I).

(4) A compound (A) capable of generating a sulfonic acid represented by formula (I) upon irradiation with an actinic ray or a radiation:

$$(Rf)_m\!-\!\underset{(R)_n}{\overset{(F)_l}{Ar}}\!-\!SO_3H \quad (I)$$

wherein

Rf represents an organic group having a fluorine atom,

R represents a hydroxyl group or an organic group,

Ar represents an aromatic group, l represents an integer of 1 to 6, m represents an integer of 0 to 4, and n represents an integer of 0 to 4, provided that m+n represents an integer of 1 or more.

(5) The compound as described in (4), wherein the compound (A) capable of generating a sulfonic acid represented by formula (I) upon irradiation with an actinic ray or a radiation is a sulfonium salt compound of the sulfonic acid represented by formula (I), an iodonium salt compound of the sulfonic acid represented by formula (I), or an ester compound of the sulfonic acid represented by formula (I).

(6) A compound represented by formula (I) or a salt thereof:

$$(Rf)_m\!-\!\underset{(R)_n}{\overset{(F)_l}{Ar}}\!-\!SO_3H \quad (I)$$

wherein

Rf represents an organic group having a fluorine atom,

R represents a hydroxyl group or an organic group,

Ar represents an aromatic group, l represents an integer of 1 to 6, m represents an integer of 0 to 4, and n represents an integer of 0 to 4, provided that m+n represents an integer of 1 or more.

(7) A compound represented by any one of formulae (A1) to (A5):

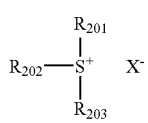
(A1)

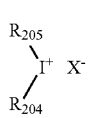
(A2)

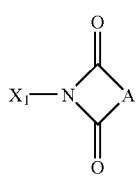
(A3)

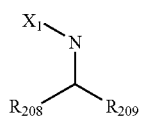
(A4)

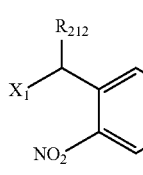
(A5)

wherein in formula (A1), $R_{201}$, $R_{202}$ and $R_{203}$ each independently represents an organic group, and X⁻ represents a sulfonate anion resulting from removal of the hydrogen atom from a sulfonic acid (—SO₃H) of formula (I);

in formula (A2), $R_{204}$ and $R_{205}$ each independently represents an aryl group, an alkyl group or a cycloalkyl group, and X⁻ represents a sulfonate anion resulting from removal of the hydrogen atom from a sulfonic acid (—SO₃H) of formula (I);

in formula (A3),

A represents an alkylene group, an alkenylene group or an arylene group, and $X_1$ represents a monovalent group resulting from removal of the hydrogen atom from a sulfonic acid (—SO₃H) of formula (I);

in formula (A4), $R_{208}$ represents an alkyl group or an aryl group, $R_{209}$ represents an alkyl group, a cyano group or an alkoxycarbonyl group, and $X_1$ represents a monovalent group resulting from removal of the hydrogen atom from a sulfonic acid (—SO₃H) of formula (I); and in formula (A5), $R_{210}$ and $R_{211}$ each independently represents a hydrogen atom, an alkyl group, a cyano group, a nitro group or an alkoxycarbonyl group, $R_{212}$ represents a hydrogen atom, an alkyl group, a cyano group or an alkoxycarbonyl group, and $X_1$ represents a monovalent group resulting from removal of the hydrogen atom from a sulfonic acid (—SO₃H) of formula (I):

(I)

wherein

Rf represents an organic group having a fluorine atom,

R represents a hydroxyl group or an organic group,

Ar represents an aromatic group, l represents an integer of 1 to 6, m represents an integer of 0 to 4, and n represents an integer of 0 to 4, provided that m+n represents an integer of 1 or more.

(8) A pattern forming method comprising steps of forming a resist film from the photosensitive composition described in any one of (1) to (3) above and exposing and developing the resist film.

Furthermore, the preferred embodiment of the present invention includes the following constitutions.

(9) The photosensitive composition as described in any one of (1) to (3) above, which further comprises (A') a compound capable of generating a sulfonic acid except for formula (I) upon irradiation with an actinic ray or a radiation.

(10) The photosensitive composition as described in (9) above, wherein the component (A') is a sulfonium salt of a fluorine-substituted alkanesulfonic acid.

(11) A positive photosensitive composition comprising:

(A) a compound capable of generating a sulfonic acid represented by formula (I) upon irradiation with an actinic ray or a radiation, and (B) a resin capable of decomposing under the action of an acid to increase a solubility of the resin in an alkali developer.

(12) The positive photosensitive composition as described in (11) above, wherein the resin (B) capable of decomposing under the action of an acid to increase the solubility in an alkali developer has a fluorine atom in the main or side chain.

(13) The positive photosensitive composition as described in (12) above, wherein the resin (B) capable of decomposing under the action of an acid to increase the solubility in an alkali developer has a hexafluoro-isopropanol structure.

(14) The positive photosensitive composition as described in (11) above, wherein the resin (B) capable of decomposing under the action of an acid to increase the solubility in an alkali developer has a hydroxystyrene structural unit.

(15) The positive photosensitive composition as described in (14), wherein the resin (B) capable of decomposing under the action of an acid to increase the solubility in an alkali developer further has at least one repeating unit selected from 2-alkyl-2-adamantyl(meth)-acrylate and dialkyl(l-adamantyl)methyl (meth)acrylate.

(16) The positive photosensitive composition as described in (11) above, wherein the resin (B) capable of decomposing under the action of an acid to increase the solubility in an alkali developer has a monocyclic or polycyclic alicyclic hydrocarbon structure.

(17) The positive photosensitive composition as described in (16), wherein the resin (B) capable of decomposing under the action of an acid to increase the solubility in an alkali developer has at least one repeating unit selected from 2-alkyl-2-adamantyl(meth)-acrylate and dialkyl(1-adamantyl)methyl(meth)acrylate, at least one repeating unit having a lactone structure, and at least one repeating unit having a hydroxyl group.

(18) The positive photosensitive composition as described in (16) or (17), wherein the resin (B) capable of decomposing under the action of an acid to increase the solubility in an alkali developer further has a repeating unit having a carboxyl group.

(19) The positive photosensitive composition as described in (11) above, wherein the resin (B) capable of decomposing under the action of an acid to increase the, solubility in an alkali developer has a silicon atom in the main or side chain.

(20) The positive photosensitive composition as described in (11) above, wherein the resin (B) capable of decomposing under the action of an acid to increase the solubility in an alkali developer further has a repeating unit having a lactone structure.

(21) The positive photosensitive composition as described in any one of (11) to (20) above, which further comprises (C) a dissolution inhibiting compound capable of decomposing under the action of an acid to increase the solubility in an alkali developer and having a molecular weight of 3,000 or less.

(22) A positive photosensitive composition comprising:

(A) a compound capable of generating a sulfonic acid represented by formula (I) upon irradiation with an actinic ray or a radiation, (D) a resin soluble in an alkali developer, and (C) a dissolution inhibiting compound capable of decomposing under the action of an acid to increase the solubility in an alkali developer and having a molecular weight of 3,000 or less.

(23) A negative photosensitive composition comprising:

(A) a compound capable of generating a sulfonic acid represented by formula (I) upon irradiation with an actinic ray or a radiation, (D) a resin soluble in an alkali developer, and (E) an acid crosslinking agent capable of crosslinking with the alkali developer-soluble resin under the action of an acid.

(24) The photosensitive composition as described in any one of (1) to (3) and (9) to (23), which further comprises (F) a basic compound and/or (G) a fluorine-containing and/or silicon-containing surfactant (a surfactant containing at least one of a fluorine atom and a silicon atom).

(25) The photosensitive composition as described in (24), wherein the basic compound (F) is: a compound having a structure selected from an imidazole structure, a diazabicyclo structure, an onium hydroxide structure, an onium carboxylate structure, a trialkylamine structure, an aniline structure and a pyridine structure; an alkylamine derivative having a hydroxyl group and/or an ether bond; or an aniline derivative having a hydroxyl group and/or an ether bond.

DETAILED DESCRIPTION OF THE INVENTION

The present invention is described in detail below.

In the present invention, when a group (atomic group) is denoted without specifying "substituted or unsubstituted", the group includes a group having no substituent and a group having a substituent. For example, "an alkyl group" includes not only an alkyl group having no substituent (unsubstituted alkyl group) but also an alkyl group having a substituent (substituted alkyl group).

The positive photosensitive composition, preferably positive resist composition, of the present invention comprises (A) a compound capable of generating a sulfonic acid represented by formula (I) upon irradiation with an actinic ray or a radiation and (B) a resin capable of decomposing under the action of an acid to increase a solubility of the resin in an alkali developer and if desired, further comprises (C) a dissolution inhibiting compound capable of decomposing under the action of an acid to increase a solubility of the dissolution inhibiting compound in an alkali developer and having a molecular weight of 3,000 or less. Alternatively, the positive photosensitive composition comprises (A) a compound capable of generating a sulfonic acid represented by formula (I) upon irradiation with an actinic ray or a radiation, (D) a resin soluble in an alkali developer and (C) a dissolution inhibiting compound capable of decomposing under the action of an acid to increase the solubility in an alkali developer and having a molecular weight of 3,000 or less.

The negative photosensitive composition, preferably negative resist composition, of the present invention comprises (A) a compound capable of generating a sulfonic acid represented by formula (I) upon irradiation with an actinic ray or a radiation, (D) a resin soluble in an alkali developer and (E) an acid crosslinking agent capable of crosslinking with the alkali developer-soluble resin under the action of an acid.

[1] (A) Compound capable of generating a sulfonic acid represented by formula (I) upon irradiation with an actinic ray or a radiation The photosensitive composition of the present invention comprises a compound capable of generating a sulfonic acid represented by the following formula (I) upon irradiation with an actinic ray or a radiation (hereinafter sometimes referred to as a "compound (A)").

wherein
Rf represents an organic group having a fluorine atom,
R represents a hydroxyl group or an organic group,
Ar represents an aromatic group,
l represents an integer of 1 to 6,
m represents an integer of 0 to 4, and
n represents an integer of 0 to 4,
provided that m+n represents an integer of 1 or more.

Examples of the organic group represented by R in formula (I) include an alkyl group, a cycloalkyl group, an alkoxy group, an aryloxy group, an aralkyloxy group, a cycloalkoxy group, an alkoxycarbonyl group, an aryloxycarbonyl group, an acyloxy group, an alkylthio group, an arylthio group, an acyl group, an acylamino group, an alkenyloxy group, an arylcarbonyloxy group, an alkylcarbonyloxy group, an alkylaminocarbonyl group, an alkylcarbonylamino group, an alkylsilyloxy group and a cyano group. A plurality of these organic groups may be bonded by a single bond, an ether bond, an ester bond, an amide bond, a sulfide bond, a urea bond or the like. The organic group represented by R is preferably an organic group having from 2 to 30 carbon atoms, more preferably from 4 to 30 carbon atoms, still more preferably from 6 to 30 carbon atoms, yet still more preferably from 8 to 24 carbon atoms.

The alkyl group in the organic group of R is preferably a linear or branched alkyl group having from 1 to 30 carbon atoms, such as methyl group, ethyl group, propyl group, isopropyl group, n-butyl group, sec-butyl group, tert-butyl group, hexyl group, heptyl group, octyl group, nonyl group, decyl group, undecyl group and dodecyl group. The alkyl group may have a substituent. Preferred examples of the substituent of the alkyl group include an alkoxy group, a cycloalkyl group, an acyl group, an acyloxy group, a chlorine atom, a bromine atom, an iodine atom, a hydroxyl group and a carboxyl group.

The cycloalkyl group in the organic group of R is preferably a monocyclic or polycyclic cycloalkyl group having from 3 to 30 carbon atoms, such as cyclopropyl group, cyclobutyl group, cyclopentyl group, cyclohexyl group, norbornyl group and adamantyl group. The cycloalkyl group may have a substituent. Preferred examples of the substituent of the cycloalkyl group include an alkyl group, an alkoxy group, an acyl group, an acyloxy group, a chlorine atom, a bromine atom, an iodine atom, a hydroxyl group and a carboxyl group.

The alkoxy group in the organic group of R is preferably a linear or branched alkoxy group having from 1 to 30 carbon atoms, such as methoxy group, ethoxy group, propoxy group, isopropoxy group, n-butoxy group, isobutoxy group, sec-butoxy group, tert-butoxy group, hexyloxy group, heptyloxy group, octyloxy group, nonyloxy group, decyloxy group, undecyloxy group and dodecyloxy group. The alkoxy group may have a substituent. Preferred examples of the substituent of the alkoxy group include an alkoxy group, an aryl group, an acyl group, an acyloxy group, a chlorine atom, a bromine atom, an iodine atom, a cycloalkyl group, a cycloalkoxy group, a siloxane group, a hydroxyl group and a carboxyl group.

The aryloxy group in the organic group of R is preferably an aryloxy group having from 6 to 20 carbon atoms, such as phenoxy group. The aryloxy group may have a substituent. Preferred examples of the substituent of the aryloxy group include an alkyl group, a cycloalkyl group, an alkoxy group, an acyl group, a formyl group, a nitro group, an acylamino group, a sulfonylamino group, a chlorine atom, a bromine atom, an iodine atom, an alkoxycarbonyl group, a cyano group, a hydroxyl group and a carboxyl group.

The aralkyloxy group is preferably an aralkyloxy group having from 6 to 20 carbon atoms, such as benzyloxy group and phenethyl group. The aralkyloxy group may have a substituent. Preferred examples of the substituent of the aralkyloxy group include an alkyl group, a cycloalkyl group, an alkoxy group, an acyl group, a formyl group, a nitro group, an acylamino group, a sulfonylamino group, a chlorine atom, a bromine atom, an iodine atom, an alkoxycarbonyl group, a cyano group, a hydroxyl group and a carboxyl group.

The cycloalkoxy group in the organic group of R is preferably a monocyclic or polycyclic cycloalkoxy group having from 3 to 30 carbon atoms, such as cyclopropoxy group, cyclobutoxy group, cyclopentyloxy group, cyclohexyloxy group, norbornyloxy group, menthyloxy group and adamantyloxy group. The cycloalkoxy group may have a substituent. Preferred examples of the substituent of the cycloalkoxy group include an alkyl group, an alkoxy group, an acyl group, an acyloxy group, a chlorine atom, a bromine atom, an iodine atom, a hydroxyl group and a carboxyl group.

The alkoxycarbonyl group in the organic group of R is preferably an alkoxycarbonyl group having from 1 to 30 carbon atoms, such as methoxycarbonyl group, ethoxycarbonyl group, butoxycarbonyl group, octyloxycarbonyl group and dodecyloxycarbonyl group. The alkoxycarbonyl group may have a substituent. Preferred examples of the substituent of the alkoxycarbonyl group include an alkoxy group, an acyl group, an acyloxy group, a cycloalkyl group, a chlorine atom, a bromine atom, an iodine atom, a hydroxyl group and a carboxyl group.

The aryloxycarbonyl group in the organic group of R is preferably an aryloxycarbonyl group having from 6 to 20 carbon atoms, such as phenoxycarbonyl group. The aryloxycarbonyl group may have a substituent. Preferred examples of the substituent of the aryloxycarbonyl group include an alkyl group, a cycloalkyl group, an alkoxy group, an acyl group, a formyl group, a nitro group, an acylamino group, a sulfonylamino group, a chlorine atom, a bromine atom, an iodine atom, a hydroxyl group, a carboxyl group, an alkoxycarbonyl group and a cyano group.

The acyloxy group in the organic group of P is preferably an acyloxy group having from 1 to 30 carbon atoms, such as acetoxy group, methyl-butynoyloxy group, methyl-decynoyloxy group, propionyloxy group, butyryloxy group, valeryloxy group, palmitoyloxy group and benzoyloxy group. The acyloxy group may have a substituent. Preferred examples of the substituent of the acyloxy group include an alkyl group, a cycloalkyl group, analkoxy group, an acyl group, a formyl group, a nitro group, an acylamino group, a sulfonylamino group, a chlorine atom, a bromine atom, an iodine atom, a hydroxyl group, a carboxyl group, an alkoxycarbonyl group and a cyano group.

The alkylthio group in the organic group of R is preferably an alkylthio group having from 1 to 30 carbon atoms, such as methylthio group, ethylthio group, propylthio group, isopropylthio group, n-butylthio group, sec-butylthio group, tert-butylthio group, hexylthio group, heptylthio group, octylthio group, nonylthio group, decylthio group, undecylthio group and dodecylthio group. The alkylthio group may have a substituent. Preferred examples of the substituent of the alkylthio group include an alkoxy group, an acyl group, an acyloxy group, a cycloalkyl group, a chlorine atom, a bromine atom, an iodine atom, a hydroxyl group and a carboxyl group.

The arylthio group in the organic group of R is preferably an arylthio group having from 6 to 20 carbon atoms, such as phenylthio group. The arylthio group may have a substituent. Preferred examples of the substituent of the arylthio group include an alkyl group, a cycloalkyl group, an alkoxy group, an acyl group, a formyl group, a nitro group, an acylamino group, a sulfonylamino group, a chlorine atom, a bromine atom, an iodine atom, a hydroxyl group, a carboxyl group, an alkoxycarbonyl group and a cyano group.

The acyl group in the organic group of R is preferably an acyl group having from 1 to 30 carbon atoms, such as acetyl group, propionyl group, pivaloyl group, butyryl group, valeryl group, palmitoyl group and benzoyl group. The acyl group may have a substituent. Preferred examples of the substituent of the acyl group include an alkyl group, a cycloalkyl group, an alkoxy group, an acyl group, a formyl group, a nitro group, an acylamino group, a sulfonylamino group, a chlorine atom, a bromine atom, an iodine atom, a hydroxyl group, a carboxyl group, an alkoxycarbonyl group and a cyano group.

The acylamino group in the organic group of R is preferably an acylamino group having from 1 to 30 carbon atoms, such as acetylamino group, propionylamino group, pivaloylamino group, butyrylamino group and benzoylamino group. The acylamino group may have a substituent. Preferred examples of the substituent of the acylamino group include an alkyl group, a cycloalkyl group, an alkoxy group, an acyl group, a formyl group, a nitro group, an acylamino group, a sulfonylamino group, a chlorine atom, a bromine atom, an iodine atom, a hydroxyl group, a carboxyl group, an alkoxycarbonyl group and a cyano group.

The alkenyloxy group in the organic group of R is preferably an alkenyloxy group having from 1 to 30 carbon atoms, such as vinyloxy group, propenyloxy group and butenyloxy group. The alkenyloxy group may have a substituent. Preferred examples of the substituent of the alkenyloxy group include an alkoxy group, an acyl group, an acyloxy group, a cycloalkyl group, a chlorine atom, a bromine atom, an iodine atom, a hydroxyl group and a carboxyl group.

The arylcarbonyloxy group in the organic group of R is preferably an arylcarbonyloxy group having from 6 to 20 carbon atoms, such as phenylcarbonyloxy group. The arylcarbonyloxy group may have a substituent. Preferred examples of the substituent of the arylcarbonyloxy group include an alkyl group, a cycloalkyl group, an alkoxy group, an acyl group, a formyl group, a nitro group, an acylamino group, a sulfonylamino group, an alkoxycarbonyl group, a cyano group, a chlorine atom, a bromine atom, an iodine atom, a hydroxyl group and a carboxyl group.

The alkylcarbonyloxy group in the organic group of R is preferably an alkylcarbonyloxy group having from 1 to 30 carbon atoms, such as methylcarbonyloxy group, ethylcarbonyloxy group, propylcarbonyloxy group and butylcarbonyloxy group. The alkylcarbonyloxy group may have a substituent. Preferred examples of the substituent of the alkylcarbonyloxy group include an alkoxy group, an acyl group, an acyloxy group, a cycloalkyl group, a chlorine atom, a bromine atom, an iodine atom, a hydroxyl group and a carboxyl group.

The alkylaminocarbonyl group in the organic group of R is preferably an alkylaminocarbonyl group having from 1 to 30 carbon atoms, such as methylaminocarbonyl group, ethylaminocarbonyl group, propylaminocarbonyl group and butylaminocarbonyl group. The alkylaminocarbonyl group may have a substituent. Preferred examples of the substituent of the alkylaminocarbonyl group include an alkoxy group, an acyl group, an acyloxy group, a cycloalkyl group, a chlorine atom, a bromine atom, an iodine atom, a hydroxyl group and a carboxyl group.

The alkylcarbonylamino group in the organic group of R is preferably an alkylcarbonylamino group having from 1 to 30 carbon atoms, such as methylcarbonylamino group, ethylcarbonylamino group, propylcarbonylamino group and butylcarbonylamino group. The alkylcarbonylamino group may have a substituent. Preferred examples of the substituent of the alkylcarbonylamino group include an alkoxy group, an acyl group, an acyloxy group, a cycloalkyl group, a chlorine atom, a bromine atom, an iodine atom, a hydroxyl group and a carboxyl group.

The alkylsilyloxy group in the organic group of R is preferably an alkylsilyloxy group having from 1 to 30 carbon atoms, such as trimethylsilyloxy group and tert-butyldimethylsilyloxy group. The alkylsilyloxy group may have a substituent. Preferred examples of the substituent of the alkylsilyloxy group include an alkoxy group, an acyl group, an acyloxy group, a cycloalkyl group, a chlorine atom, a bromine atom, an iodine atom, a hydroxyl group and a carboxyl group.

In the alkyl or cycloalkyl group of these alkyl, cycloalkyl, alkoxy, aralkyloxy, cycloalkoxy, alkoxycarbonyl, acyloxy, alkylthio, acyl and acylamino groups, the alkyl or cycloalkyl chain may have one or multiple linking group(s) such as oxygen atom, sulfur atom and ester group.

R is preferably an alkyl group, a cycloalkyl group, an alkoxy group, an aralkyloxy group, a cycloalkoxy group, an alkylthio group or an arylthio group, more preferably an alkoxy group, an aralkyloxy group, a cycloalkoxy group, an alkylthio group or an arylthio group, still more preferably an alkoxy group, an aralkyloxy group, a cycloalkoxy group, an alkylthio group or an arylthio group, yet still more preferably an alkylthio group or an aryl thio group. When R is an alkylthio group or an arylthio group, a photosensitive composition not only excellent in the PEB temperature dependency and profile but also having high sensitivity can be obtained.

In the case where n is an integer of 2 or more, multiple Rs may be the same or different.

Examples of the organic group having a fluorine atom represented by Rf include the organic groups described above for R where a part or all of the hydrogen atoms are displaced by a fluorine atom. In the case where m is an integer of 2 or more, multiple Rfs may be the same or different.

The sum of carbon atoms of Rf and R is preferably from 4 to 34 carbon atoms, more preferably from 6 to 30 carbon atoms, still more preferably from 8 to 24 carbon atoms. By adjusting the number of carbon atoms in Rf and R, the diffusibility of acid can be controlled and in turn the resolution can be enhanced.

The aromatic group represented by Ar is preferably an aromatic group having from 6 to 20 carbon atoms, such as phenyl group and naphthyl group. The aromatic group may further has a substituent. Preferred examples of the substituent of the aromatic group include a nitro group, a sulfonylamino group, a chlorine atom, a bromine atom, an iodine atom and a carboxyl group.

m is preferably an integer of 0 to 3, more preferably from 0 to 2, still more preferably 0 or 1.

n is preferably an integer of 0 to 3, more preferably from 0 to 2, still more preferably 0 or 1.

l is preferably an integer of 2 to 5, more preferably 3 or 4, still more preferably 4.

m+n is preferably an integer of 1 to 3, more preferably 1 or 2, still more preferably 1.

The sulfonic acid represented by formula (I) and a salt thereof are novel compounds.

Examples of the sulfonate include metal sulfonate and onium sulfonate.

Examples of the metal in the metal sulfonate include $Na^+$, $Li^+$, $K^+$, $Cs^+$, $Ca^{2+}$ and $Ba^{2+}$.

Examples of the onium cation in the onium sulfonate include ammonium cation.

The sulfonic acid represented by formula (I) is preferably represented by the following formula (Ia), more preferably formula (Ib), still more preferably formula (Ic). In these formulae, R, Rf, l, m and n have the same meanings as R, Rf, l, m and n in formula (I).

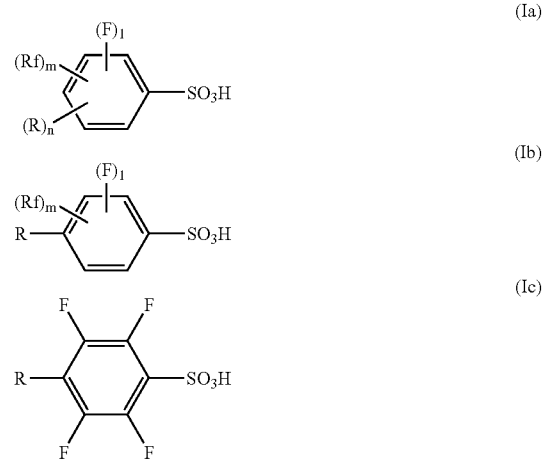

Specific preferred examples of the sulfonic acid represented by formula (I) are set forth below, but the present invention is not limited thereto.

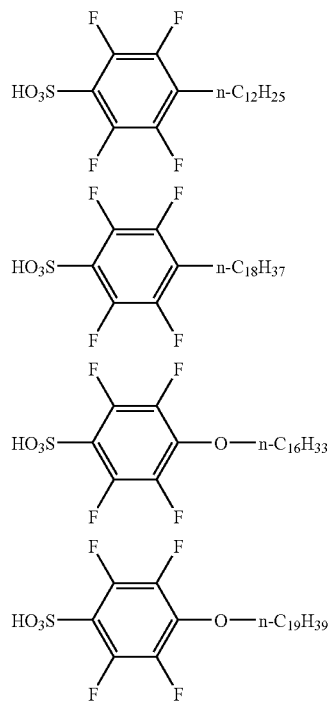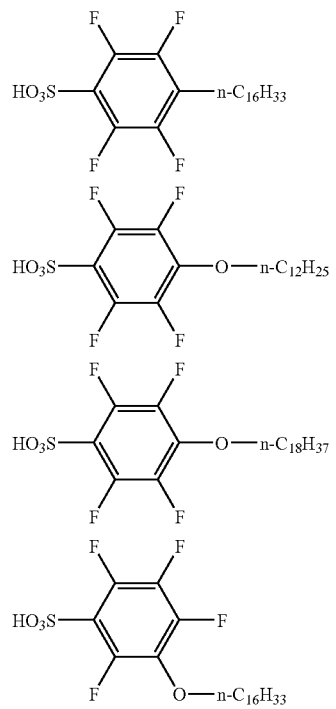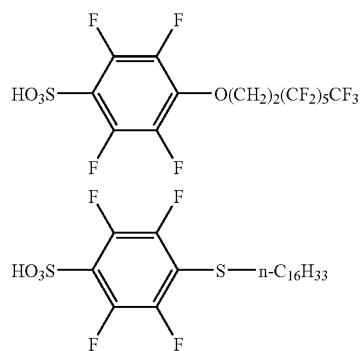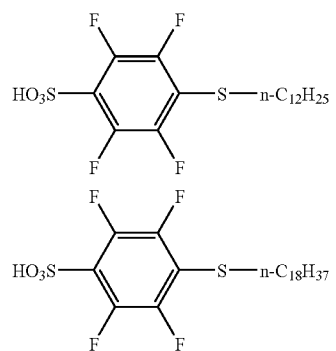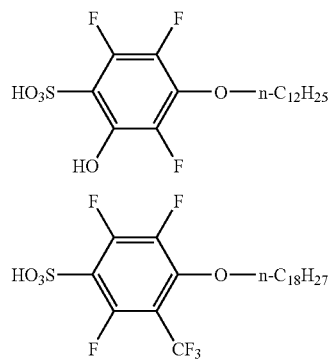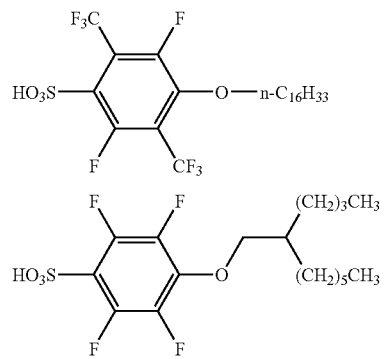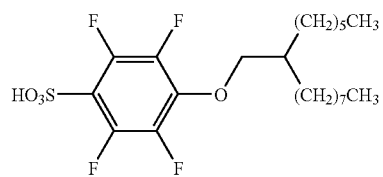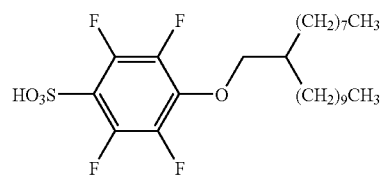

-continued
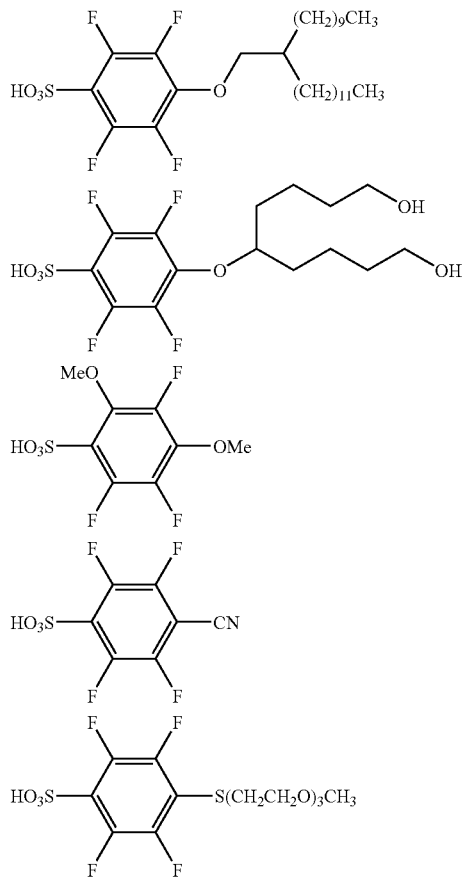
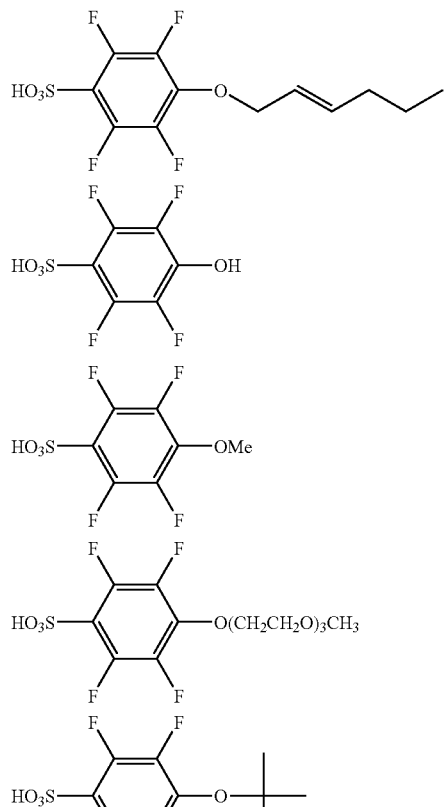
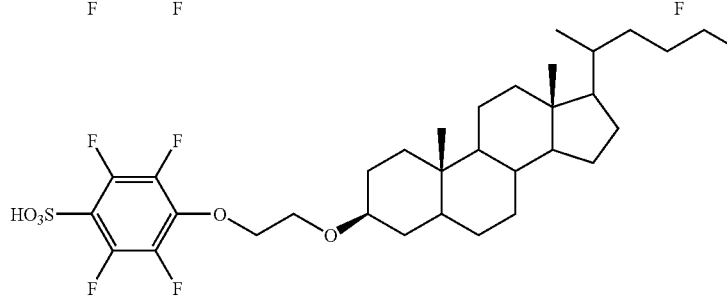
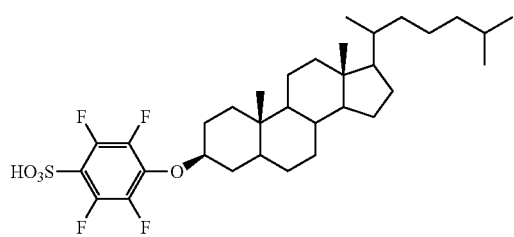
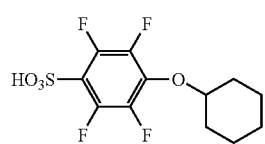
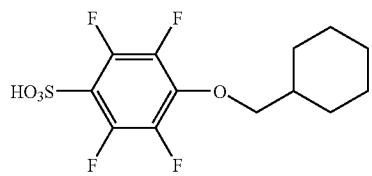
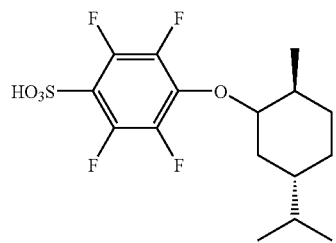

-continued
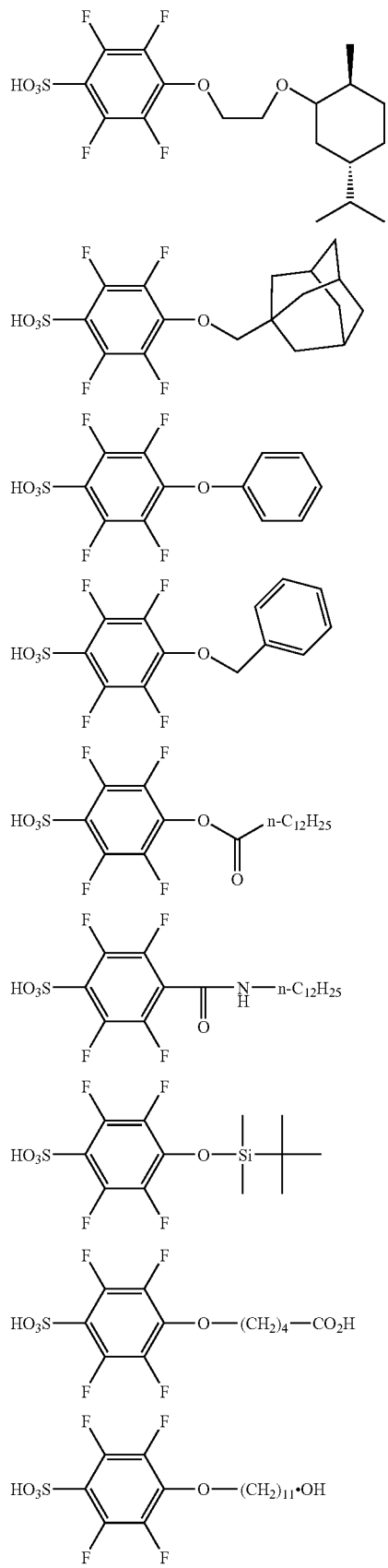
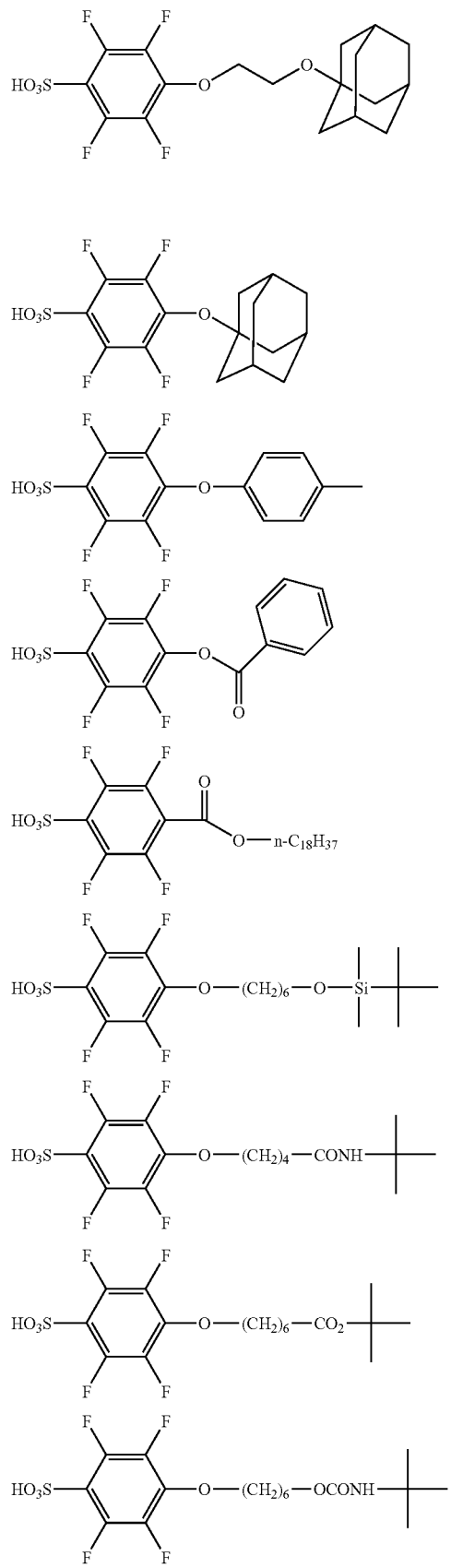

-continued
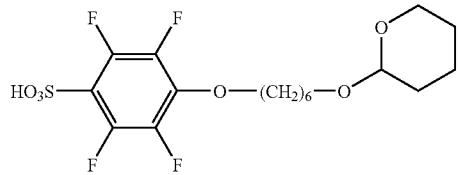
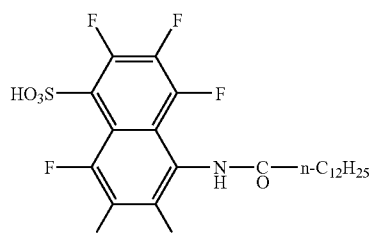
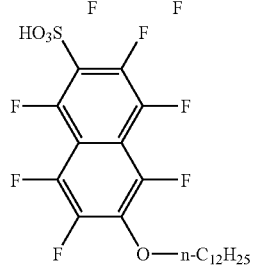
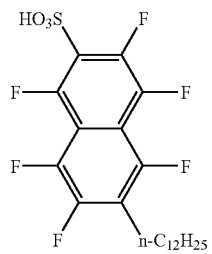
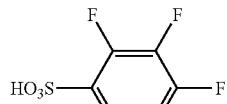
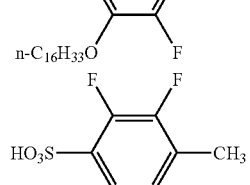
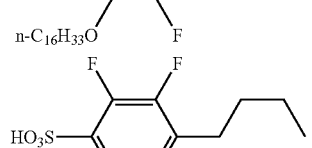
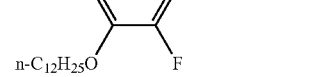
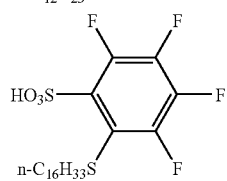
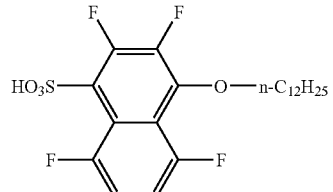
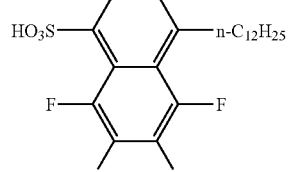
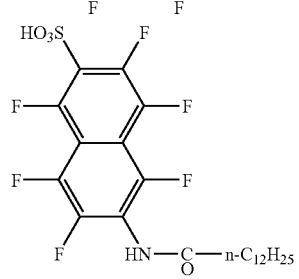
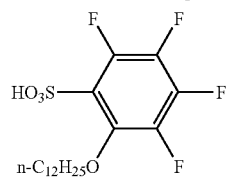
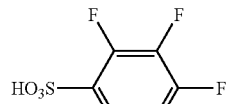
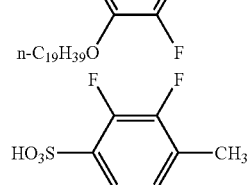
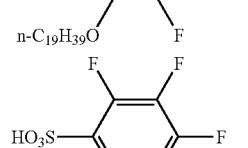
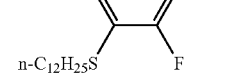
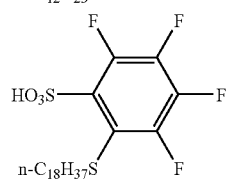

-continued
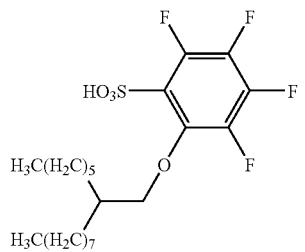
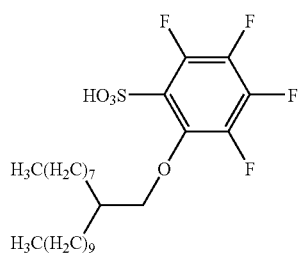
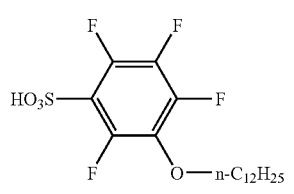
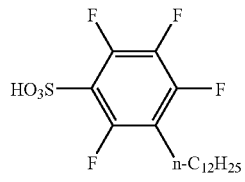
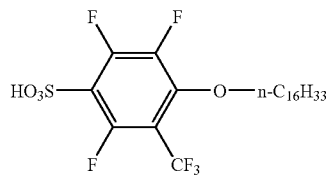
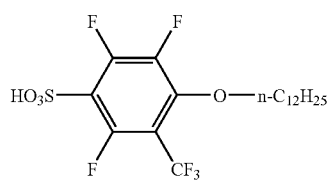
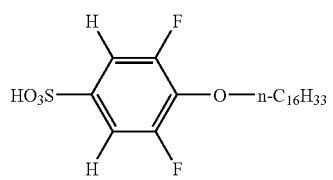
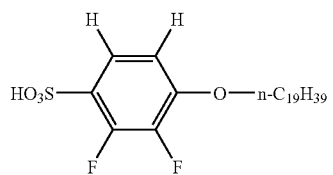
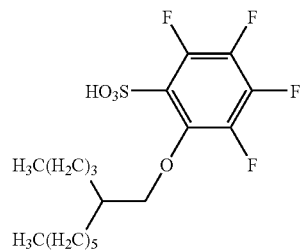
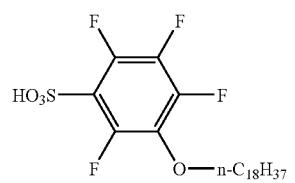
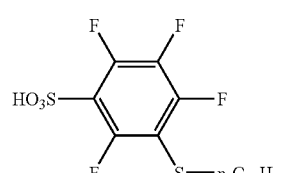
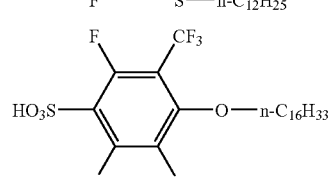
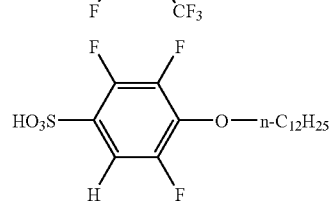
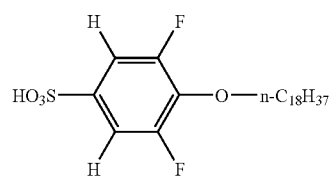
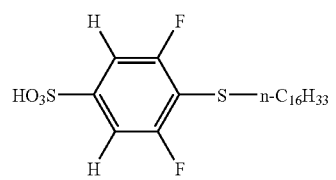
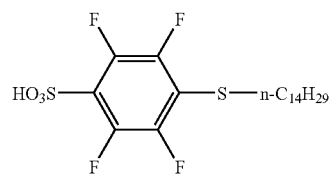

-continued
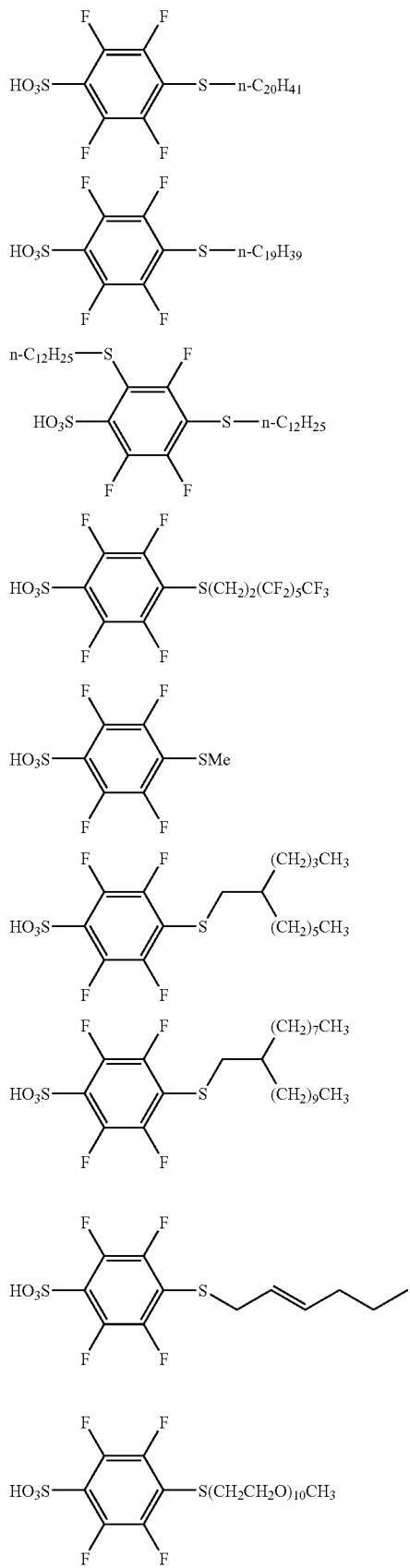
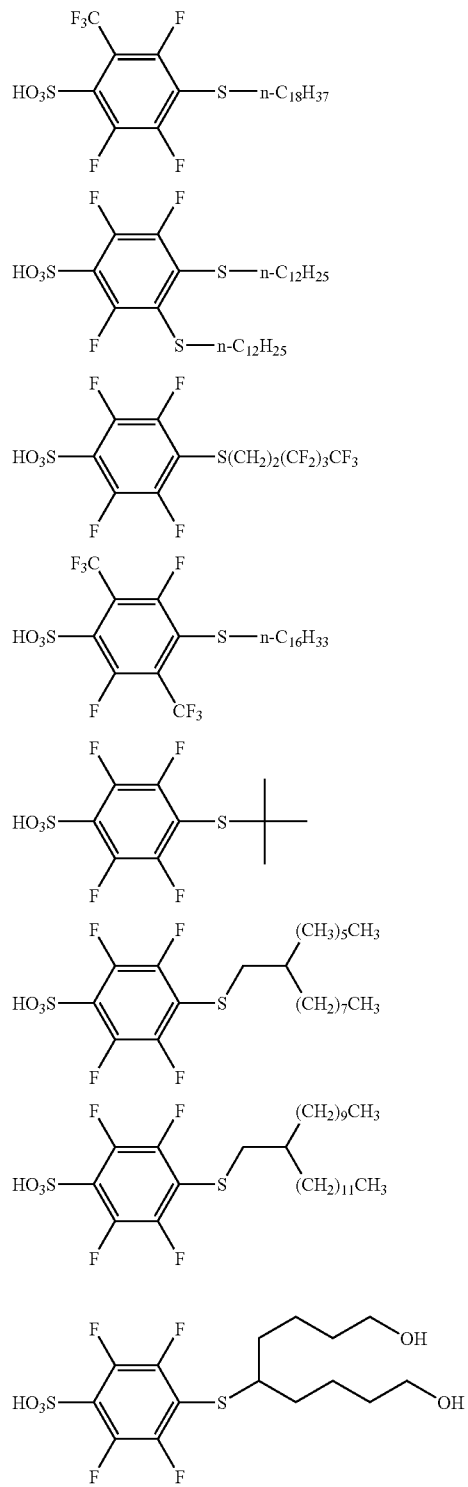

-continued
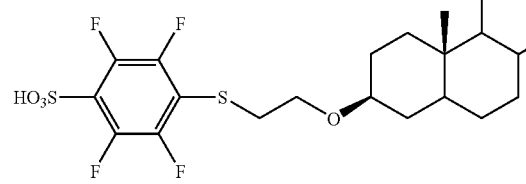
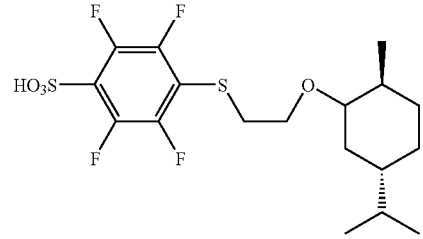
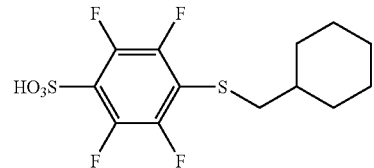
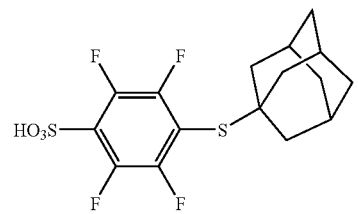
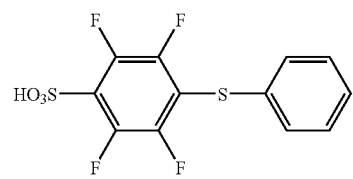
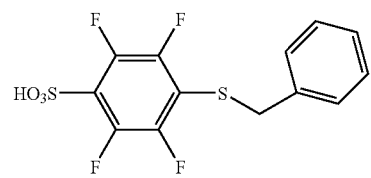
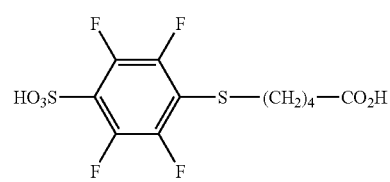
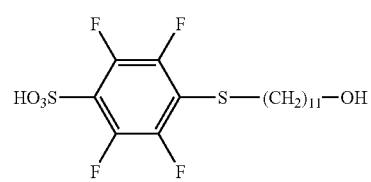
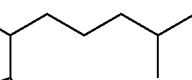
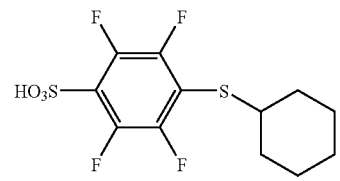
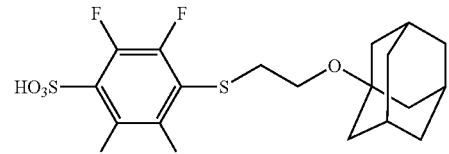
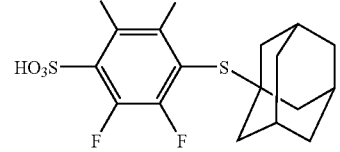
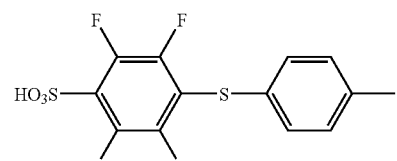
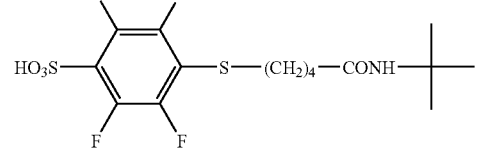
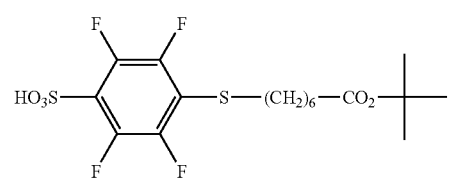
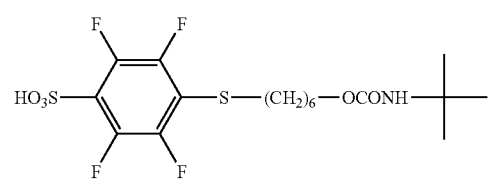

-continued

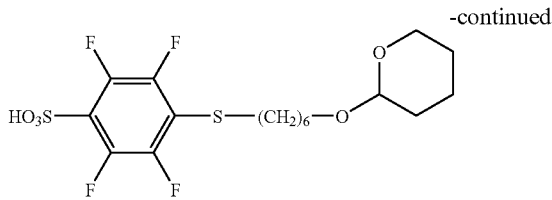 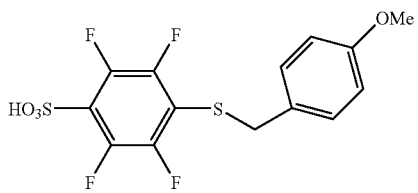

The compound capable of generating a sulfonic acid represented by formula (I) upon irradiation with an actinic ray or a radiation is preferably a sulfonium salt compound of the sulfonic acid represented by formula (I), an iodonium salt compound of the sulfonic acid represented by formula (I) or an ester compound of the sulfonic acid represented by formula (I), more preferably a compound represented by any one of the following formulae (A1) to (A5).

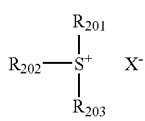 (A1)

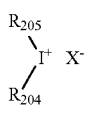 (A2)

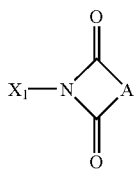 (A3)

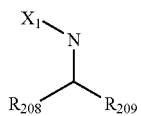 (A4)

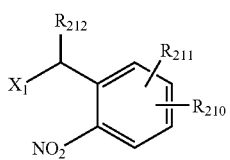 (A5)

In formula (A1), $R_{201}$, $R_{202}$ and $R_{203}$ each independently represents an organic group, and $X^-$ represents a sulfonate anion resulting from removal of the hydrogen atom from the sulfonic acid (—$SO_3H$) of formula (I).

The number of carbon atoms in the organic group represented by $R_{201}$, $R_{202}$ and $R_{203}$ is generally from 1 to 30, preferably from 1 to 20.

Two out of $R_{201}$ to $R_{203}$ may combine to form a ring structure and the ring may contain an oxygen atom, a sulfur atom, an ester bond, an amide bond or a carbonyl group.

Examples of the group formed when two out of $R_{201}$ to $R_{203}$ are combined include an alkylene group (e.g., butylene, pentylene).

Specific examples of the organic group represented by $R_{201}$, $R_{202}$ and $R_{203}$ include corresponding groups in Compounds (A1a), (A1b) and (A1c) which are described later.

The compound may be a compound having a plurality of structures represented by formula (A1), for example, a compound where at least one of $R_{201}$ to $R_{203}$ in the compound represented by formula (A1) is bonded to at least one of $R_{201}$ to $R_{203}$ in another compound represented by formula (A1).

The component (A1) is more preferably a compound (A1a), (A1b) or (A1c) described below.

The compound (A1a) is an arylsulfonium compound where at least one of $R_{201}$ to $R_{203}$ in formula (A1) is an aryl group, that is, a compound having an arylsulfonium as the cation.

In the arylsulfonium compound, $R_{201}$ to $R_{203}$ all may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, a diarylcycloalkylsulfonium compound, an aryldialkyl-sulfonium compound, an aryldicycloalkylsulfonium compound and an arylalkylcycloalkylsulfonium compound.

The aryl group in the arylsulfonium compound is preferably a phenyl group or a naphthyl group, more preferably a phenyl group. In the case where the arylsulfonium compound has two or more aryl groups, these two or more aryl groups may be the same or different.

The alkyl group which is present, if desired, in the arylsulfonium compound is preferably a linear or branched alkyl group having from 1 to 15 carbon atoms, such as methyl group, ethyl group, propyl group, n-butyl group, sec-butyl group and tert-butyl group.

The cycloalkyl group which is present, if desired, in the arylsulfonium compound is preferably a cycloalkyl group having from 3 to 15 carbon atoms, such as cyclopropyl group, cyclobutyl group and cyclohexyl group.

The aryl group, alkyl group and cycloalkyl group represented by $R_{201}$ to $R_{203}$ each may have, as a substituent, an alkyl group (for example, having from 1 to 15 carbon atoms), a cycloalkyl group (for example, having from 3 to 15 carbon atoms), an aryl group (for example, having from 6 to 14 carbon atoms), an alkoxy group (for example, having from 1 to 15 carbon atoms), a halogen atom, a hydroxyl group or a phenylthio group. The substituent is preferably a linear or branched alkyl group having from 1 to 12 carbon atoms, a cycloalkyl group having from 3 to 12 carbon atoms or an alkoxy group having from 1 to 12 carbon atoms, and most preferably an alkyl group having from 1 to 4 carbon atoms or an alkoxy group having from 1 to 4 carbon atoms. The substituent may be substituted to any one of three groups $R_{201}$ to $R_{203}$ or may be substituted to all of these three groups. In the case where $R_{201}$ to $R_{203}$ each is an aryl group, the substituent is preferably substituted at the p-position of the aryl group.

The compound (A1b) is described below.

The compound (A1b) is a compound where $R_{201}$ to $R_{203}$ in formula (A1) each independently represents an organic group not containing an aromatic ring. The aromatic ring as used herein includes an aromatic ring containing a heteroatom.

The organic group not containing an aromatic ring represented by $R_{201}$ to $R_{203}$ generally has from 1 to 30 carbon atoms, preferably from 1 to 20 carbon atoms.

$R_{201}$ to $R_{203}$ each independently represents preferably an alkyl group, a cycloalkyl group, an allyl group or a vinyl group, more preferably a linear or branched oxoalkyl group which may have a double bond in the chain, an oxocycloalkyl group or an alkoxycarbonylmethyl group, still more preferably a linear or branched 2-oxoalkyl group or a 2-oxocycloalkyl group, yet still more preferably a linear or branched 2-oxoalkyl group.

The alkyl group represented by $R_{201}$ to $R_{203}$ may be either linear or branched and is preferably a linear or branched alkyl group having from 1 to 20 carbon atoms (e.g., methyl, ethyl, propyl, butyl, pentyl).

The cycloalkyl group represented by $R_{201}$ to $R_{203}$ is preferably a cycloalkyl group having from 3 to 10 carbon atoms (e.g., cyclopentyl, cyclohexyl, norbornyl).

The 2-oxoalkyl group and 2-oxocycloalkyl group represented by $R_{201}$ to $R_{203}$ are preferably the above-described alkyl group and cycloalkyl group each having >C=O at the 2-position.

The alkoxy group in the alkoxycarbonylmethyl group represented by $R_{201}$ to $R_{203}$ is preferably an alkoxy group having from 1 to 5 carbon atoms (e.g., methoxy, ethoxy, propoxy, butoxy, pentyloxy).

$R_{201}$ to $R_{203}$ each may be further substituted by a halogen atom, an alkoxy group (for example, having from 1 to 5 carbon atoms), a hydroxyl group, a cyano group or a nitro group.

The compound (A1c) is a compound represented by the following formula (A1c) and this is a compound having an arylacylsulfonium salt structure.

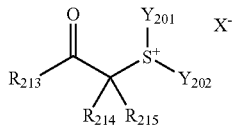

(A1c)

In formula (A1c), $R_{213}$ represents an aryl group, preferably a phenyl group or a naphthyl group.

The substituent on $R_{213}$ is preferably an alkyl group, an alkoxy group, an acyl group, a nitro group, a hydroxyl group, an alkoxycarbonyl group or a carboxy group.

$R_{214}$ and $R_{215}$ each independently represents a hydrogen atom or an alkyl group.

$Y_{201}$ and $Y_{202}$ each independently represents an alkyl group, a cycloalkyl group, an aryl group or a vinyl group.

$X^-$ represents a sulfonate anion resulting from removal of the hydrogen atom from the sulfonic acid (—$SO_3H$) of formula (I).

$R_{213}$ and $R_{214}$ may combine to form a ring structure, $R_{214}$ and $R_{215}$ may combine to form a ring structure, and $Y_{201}$ and $Y_{202}$ may combine to form a ring structure. These ring structures each may contain an oxygen atom, a sulfur atom, an ester bond or an amide bond.

The alkyl group represented by Y201 and $Y_{202}$ is preferably a linear or branched alkyl group having from 1 to 20 carbon atoms and preferably a 2-oxoalkyl group having >C=O at the 2-position of the alkyl group, an alkoxycarbonylalkyl group (preferably with an alkoxy group having from 2 to 20 carbon atoms) or a carboxyalkyl group.

The cycloalkyl group represented by $Y_{201}$ and $Y_{202}$ is preferably a cycloalkyl group having from 3 to 20 carbon atoms.

Examples of the group formed when $R_{213}$ and $R_{214}$, $R_{214}$ and $R_{215}$, or $Y_{201}$ and $Y_{202}$ are combined include a butylene group and a pentylene group.

$Y_{201}$ and $Y_{202}$ each is preferably an alkyl group having 4 or more carbon atoms, more preferably from 4 to 16 carbon atoms, still more preferably from 4 to 12 carbon atoms.

A compound where at least one of $R_{214}$ and $R_{215}$ is an alkyl group is preferred, and a compound where $R_{214}$ and $R_{215}$ both are an alkyl group is more preferred.

In formula (A2), $R_{204}$ and $R_{205}$ each independently represents an aryl group, an alkyl group or a cycloalkyl group, and $X^-$ represents a sulfonate anion resulting from removal of the hydrogen atom from the sulfonic acid (—$SO_3H$) of formula (I).

The aryl group represented by $R_{204}$ and $R_{205}$ is preferably a phenyl group or a naphthyl group, more preferably a phenyl group.

The alkyl group represented by $R_{204}$ and $R_{205}$ is preferably a linear or branched alkyl group having from 1 to 10 carbon atoms, such as methyl group, ethyl group, propyl group, butyl group and pentyl group.

The cycloalkyl group represented by $R_{204}$ and $R_{205}$ is preferably a cycloalkyl group having from 3 to 10 carbon atoms, such as cyclopentyl group, cyclohexyl group and norbornyl group.

Examples of the substituent which may be substituted to $R_{204}$ and $R_{205}$ include an alkyl group (for example, having from 1 to 15 carbon atoms), a cycloalkyl group (for example, having from 3 to 15 carbon atoms), an aryl group (for example, having from 6 to 15 carbon atoms), an alkoxy group (for example, having from 1 to 15 carbon atoms), a halogen atom, a hydroxyl group and a phenylthio group.

In formula (A3),

A represents an alkylene group, an alkenylene group or an arylene group, and $X_1$ represents a monovalent group resulting from removal of the hydrogen atom from the sulfonic acid (—$SO_3H$) of formula (I).

In formula (A4), $R_{208}$ represents an alkyl group or an aryl group, $R_{209}$ represents an alkyl group, a cyano group or an alkoxycarbonyl group, preferably an oxoalkyl group, a halogen-substituted alkyl group or a cyano group, and $X_1$ represents a monovalent group resulting from removal of the hydrogen atom from the sulfonic acid (—$SO_3H$) of formula (I).

In formula (A5), $R_{210}$ and $R_{211}$ each independently represents a hydrogen atom, an alkyl group, a cyano group, a nitro group or an alkoxycarbonyl group, preferably a halogen-substituted alkyl group, a nitro group or a cyano group, $R_{212}$ represents a hydrogen atom, an alkyl group, a cyano group or an alkoxycarbonyl group, and $X_1$ represents a monovalent group resulting from removal of the hydrogen atom from the sulfonic acid (—$SO_3H$) of formula (I).

The compound capable of generating a sulfonic acid represented by formula (I) upon irradiation with an actinic ray or a radiation is preferably a compound represented by formula (A1), more preferably a compound represented by any one of formulae (A1a) to (A1c).

Specific examples of the compound capable of generating a sulfonic acid represented by formula (I) upon irradiation with an actinic ray or a radiation are set forth below, but the present invention is not limited thereto.

(A-1)

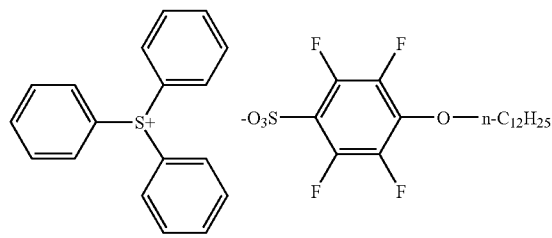

(A-2)

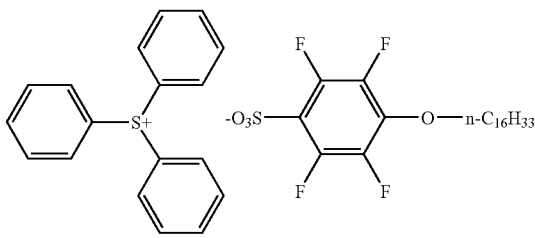

(A-3)

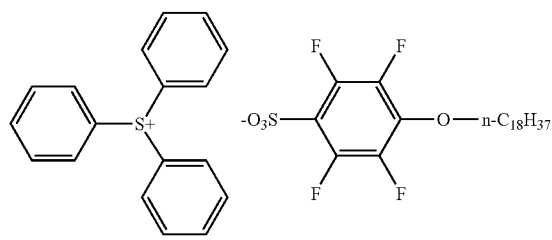

(A-4)

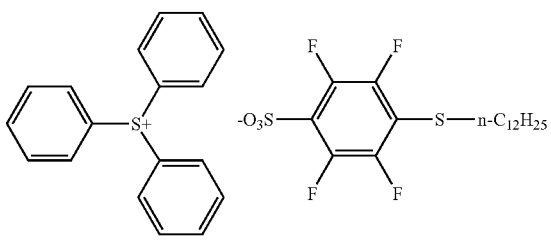

(A-5)

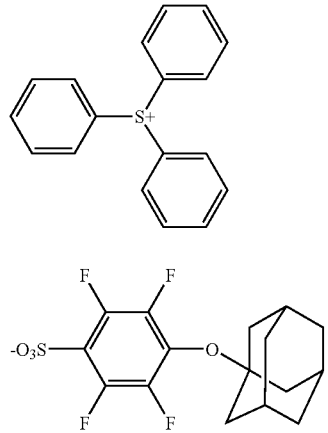

(A-6)

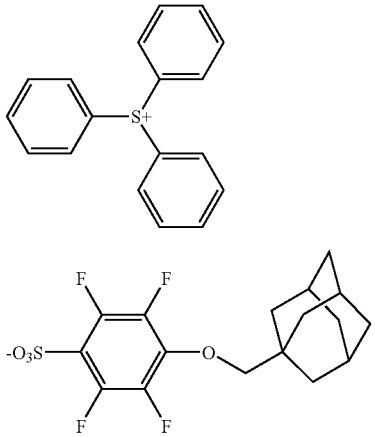

(A-7)

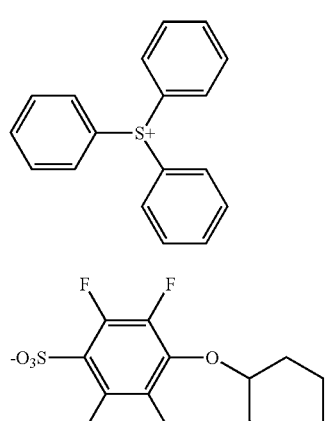

(A-8)

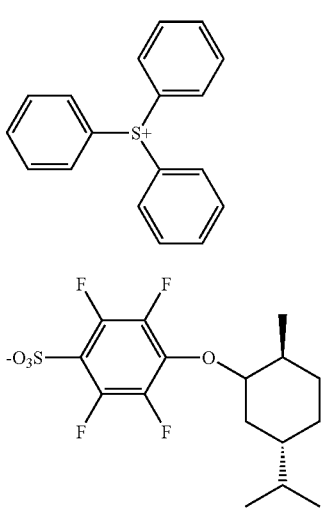

-continued
(A-9)
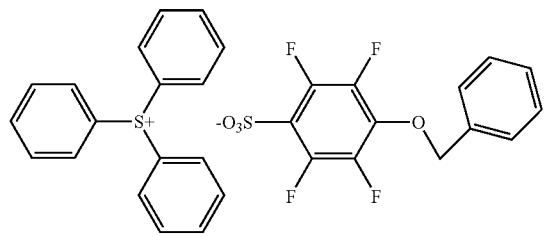
(A-10)
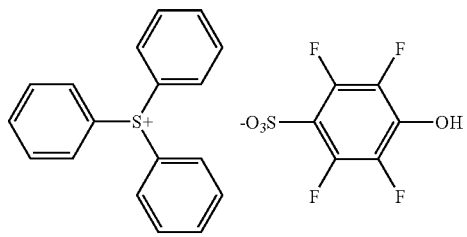
(A-11)
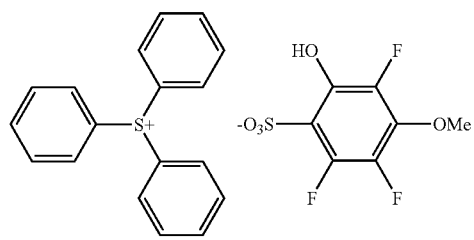
(A-12)
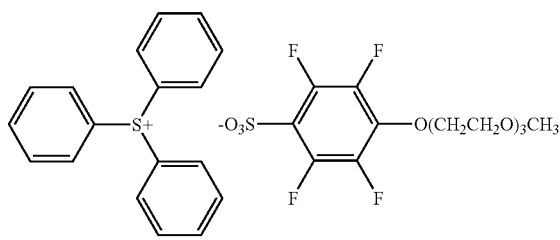
(A-13)
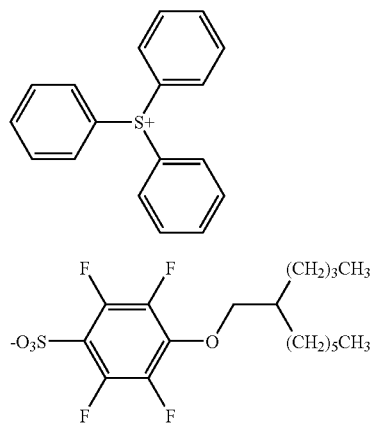
(A-14)
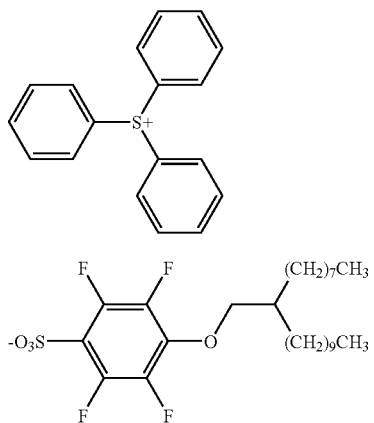
(A-15)
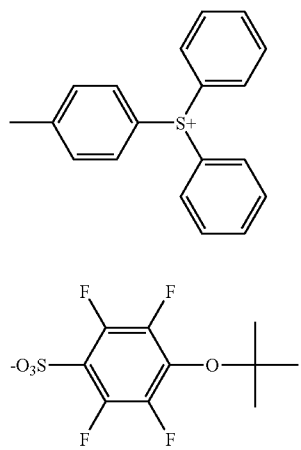
(A-16)
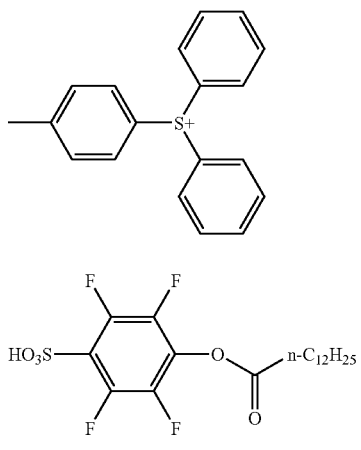

-continued
(A-17)
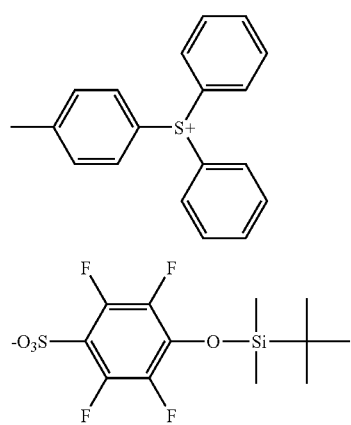
(A-18)
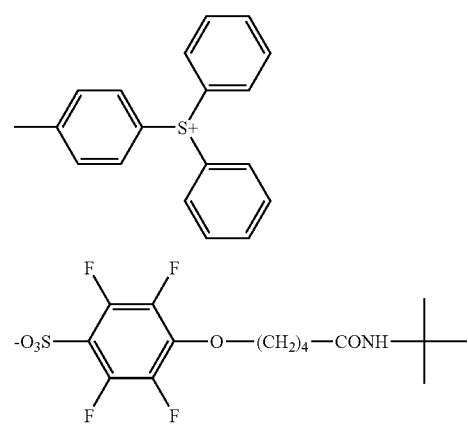
(A-19)
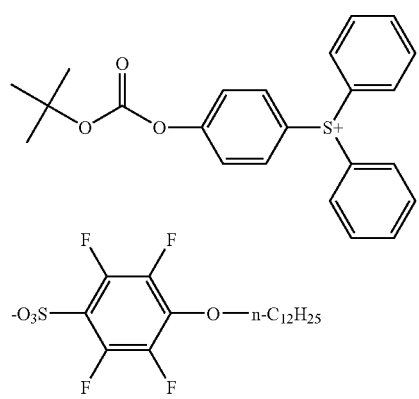
(A-20)
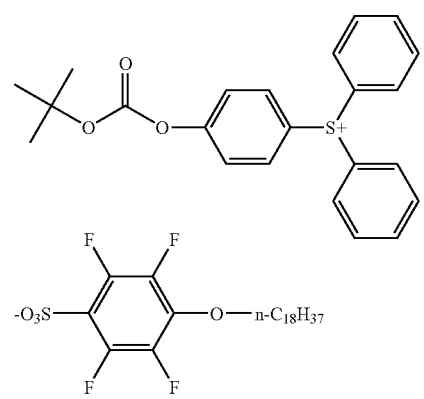
(A-21)
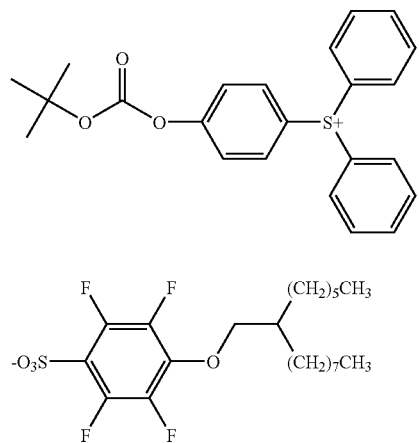
(A-22)
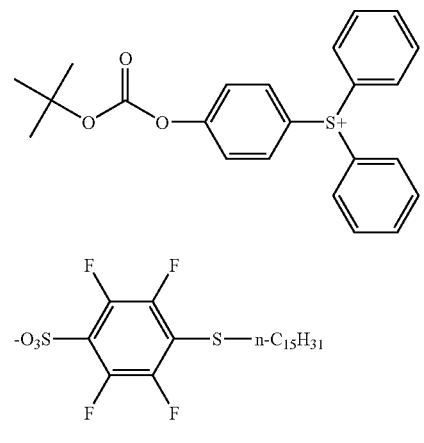

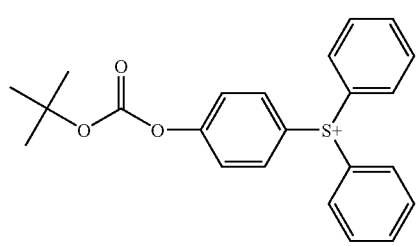
(A-23)
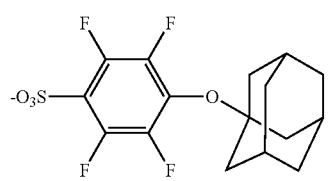
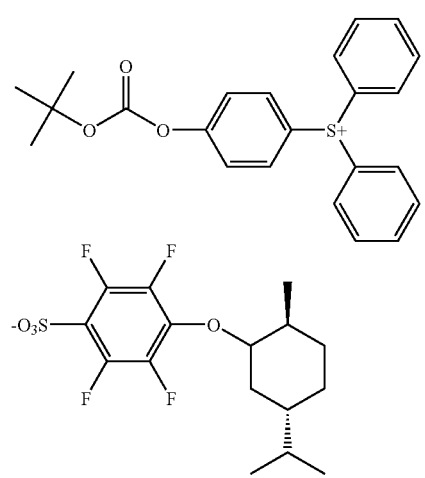
(A-24)
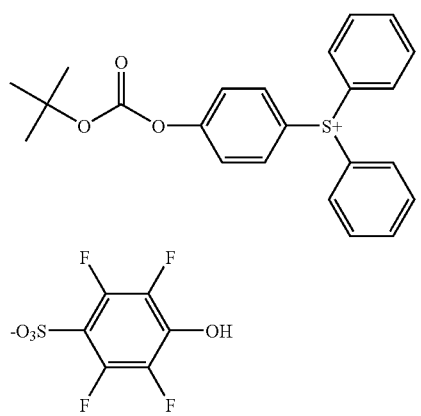
(A-25)
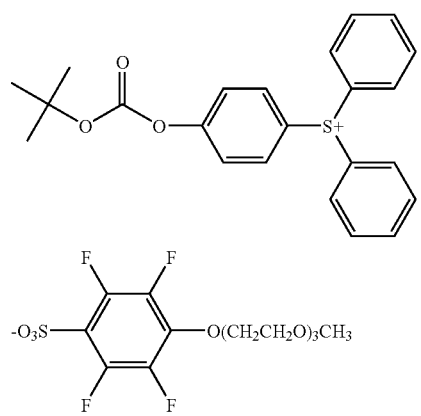
(A-26)
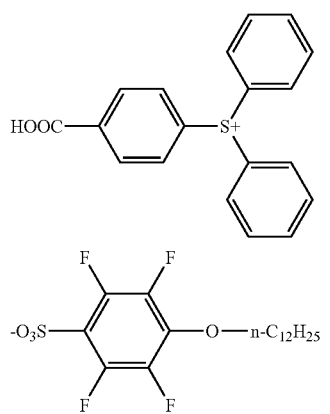
(A-27)
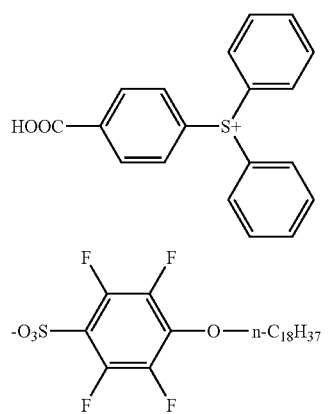
(A-28)

-continued
(A-29) 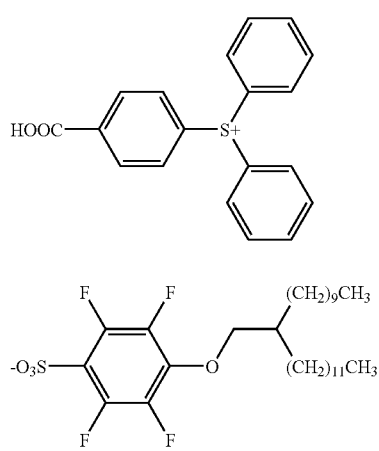
(A-30) 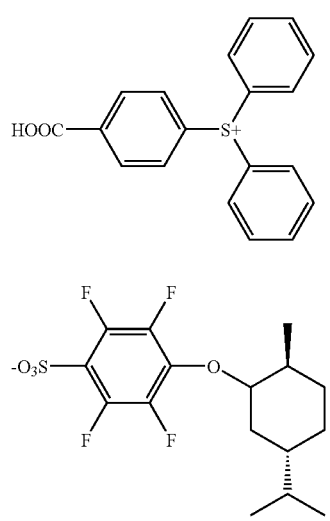
(A-31) 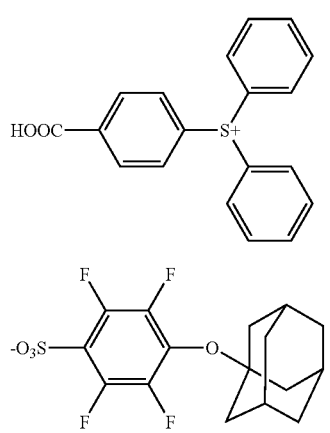
(A-32) 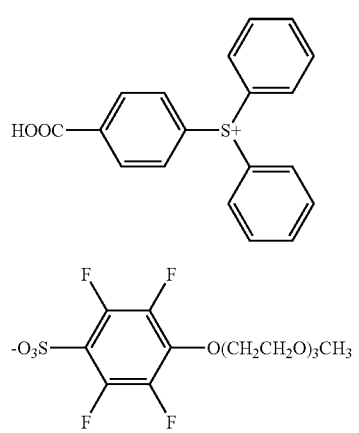
(A-33) 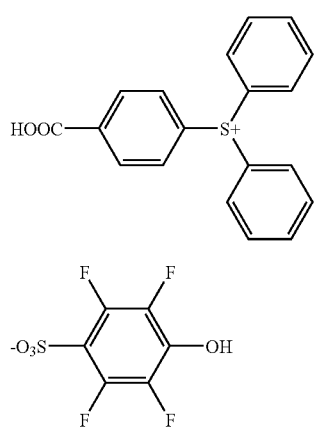
(A-34) 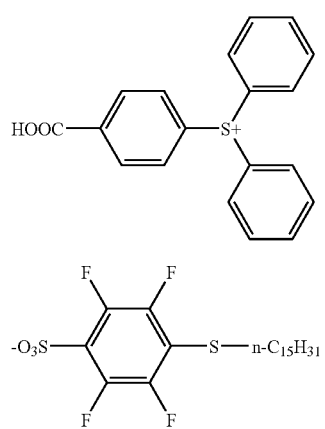

-continued
(A-35)
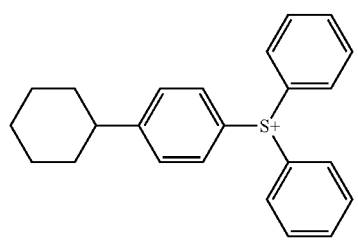
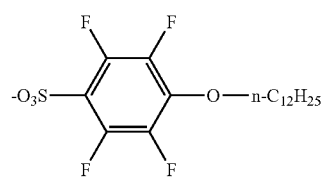
(A-36)
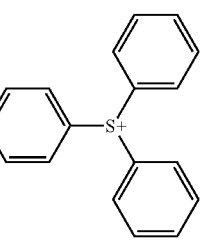
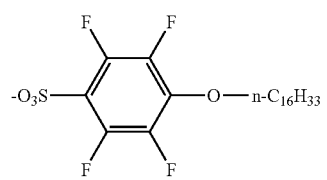
(A-37)
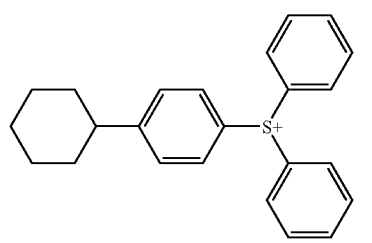
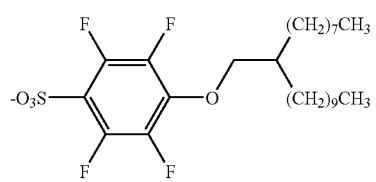
(A-38)
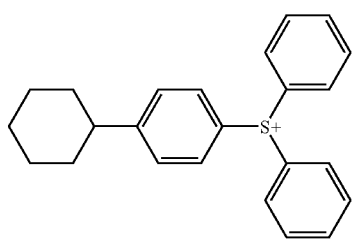
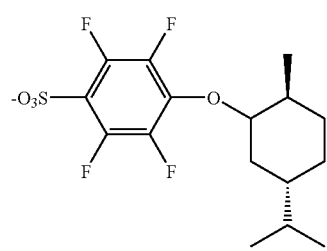
(A-39)
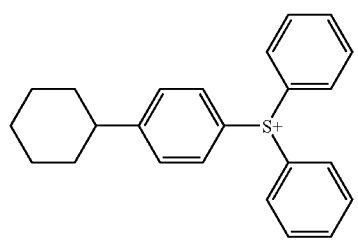
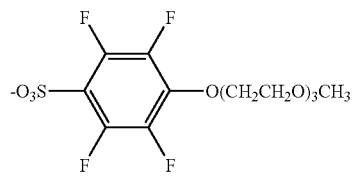
(A-40)
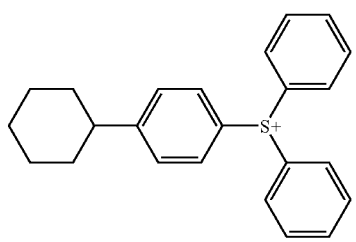
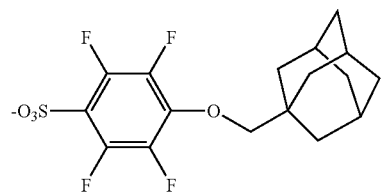

-continued
(A-41)
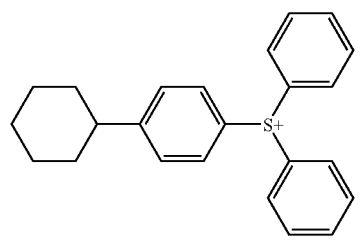
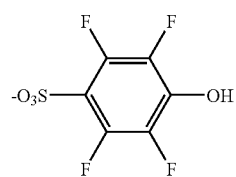
(A-42)
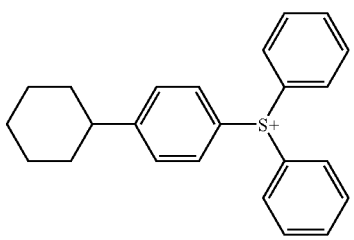
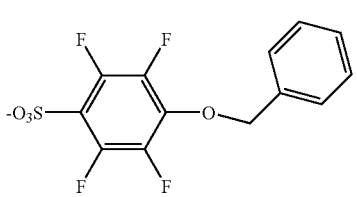
(A-43)
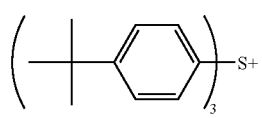
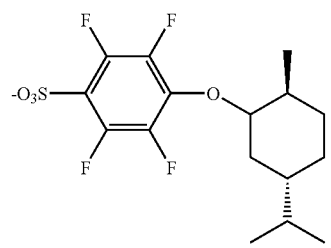
(A-44)
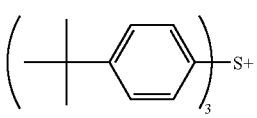
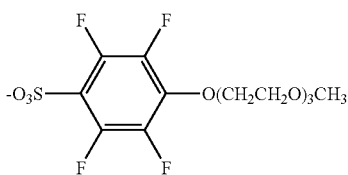
(A-45)
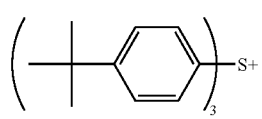
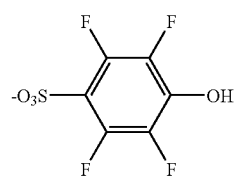
(A-46)
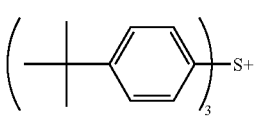
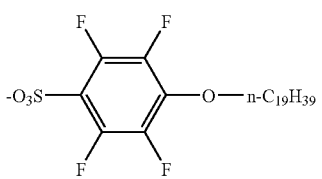
(A-47)
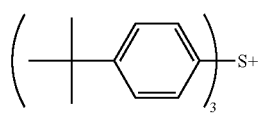
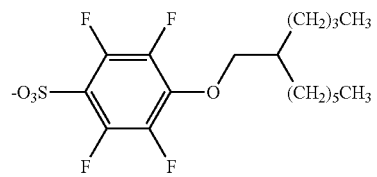
(A-48)
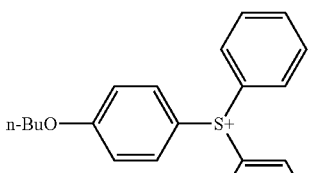
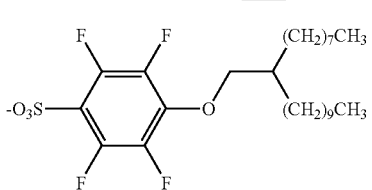

-continued
(A-49)
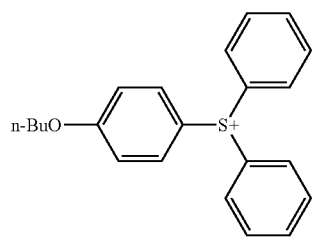
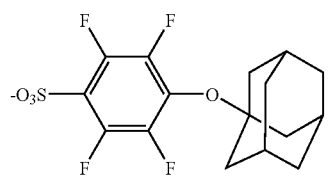
(A-51)
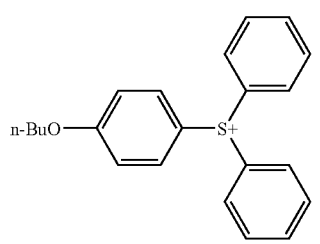
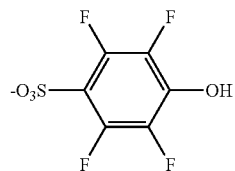
(A-53)
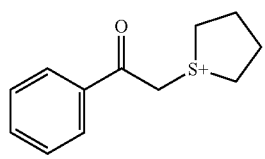
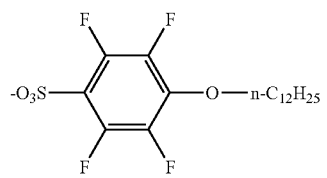
(A-55)
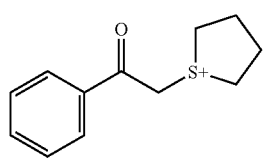
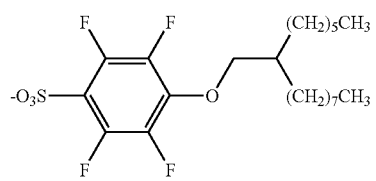
(A-50)
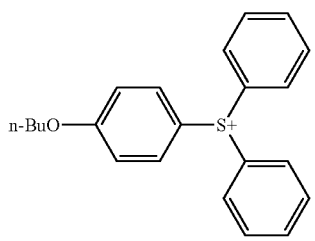
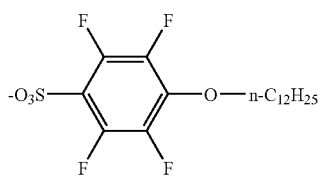
(A-52)
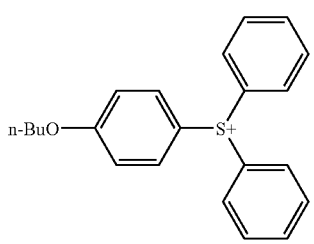
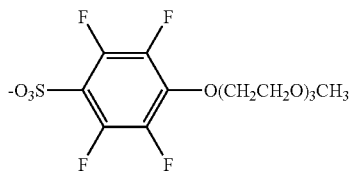
(A-54)
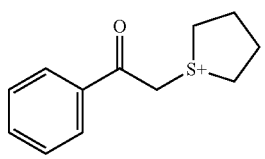
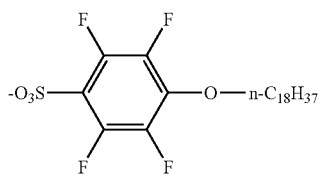
(A-56)
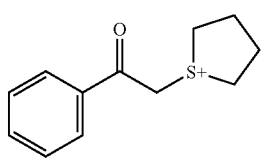
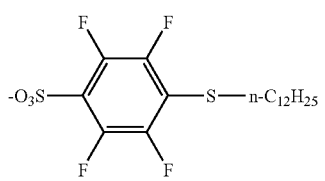

-continued
(A-57)
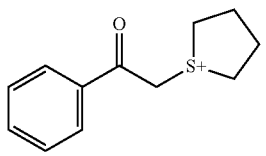
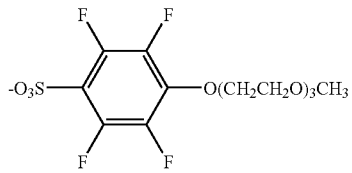
(A-58)
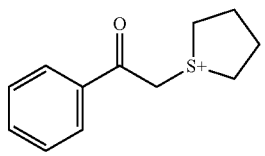
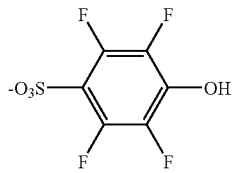
(A-59)
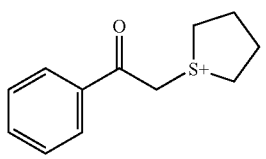
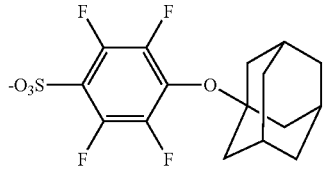
(A-60)
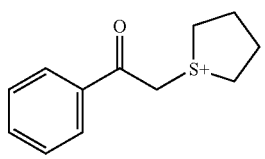
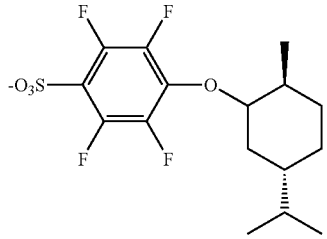
(A-61)
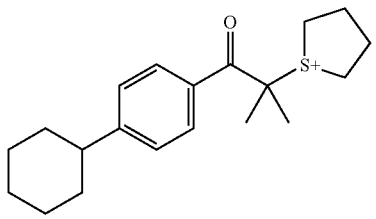
(A-62)
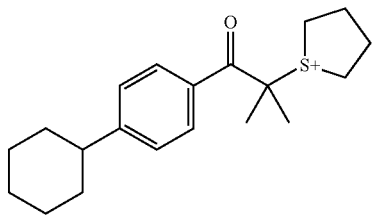
(A-63)
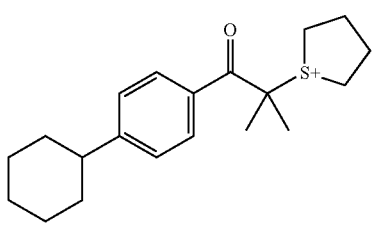
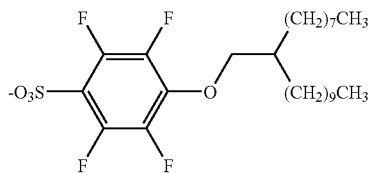
(A-64)
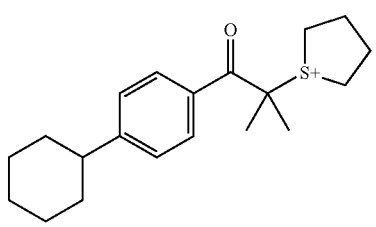
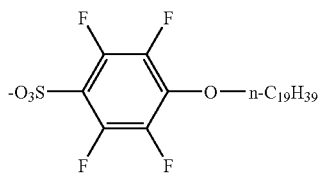
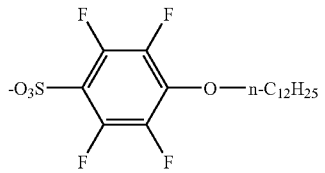
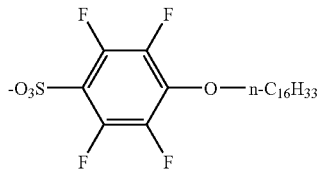

-continued
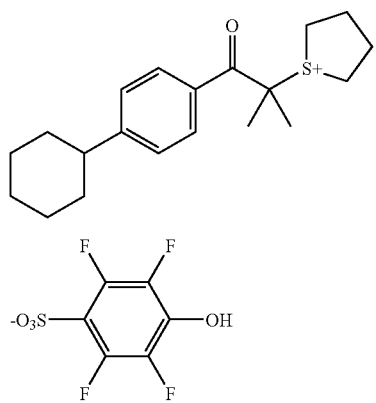
(A-65)
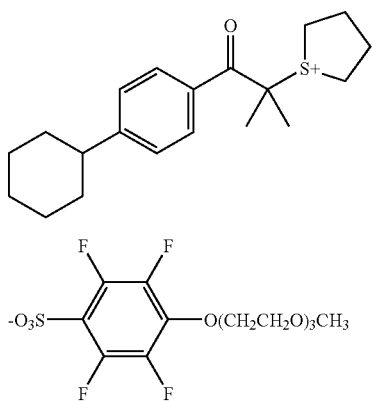
(A-66)
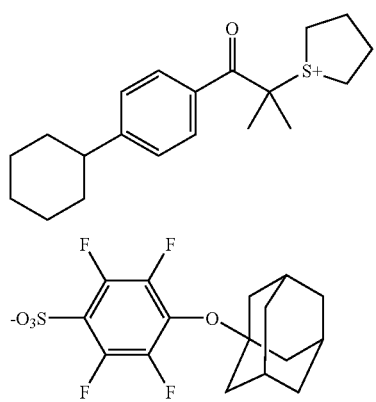
(A-67)
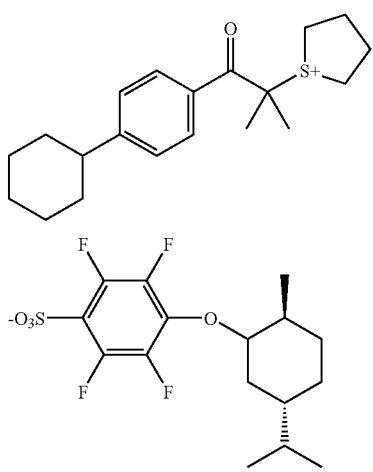
(A-68)
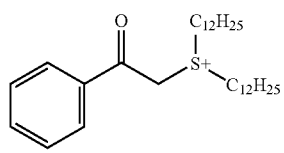
(A-69)
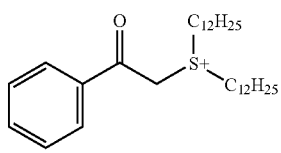
(A-70)
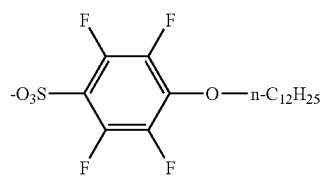
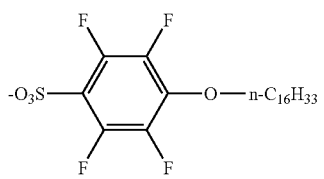
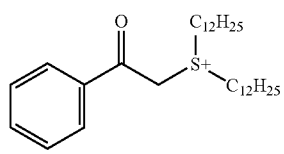
(A-71)
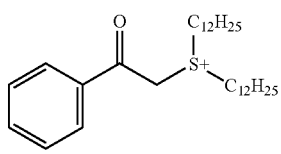
(A-72)
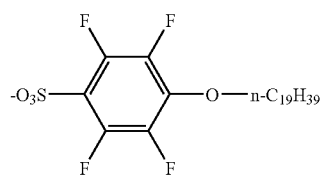
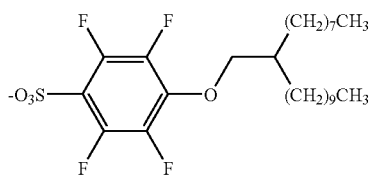

-continued
(A-73)
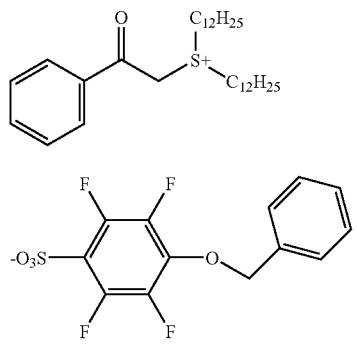
(A-74)
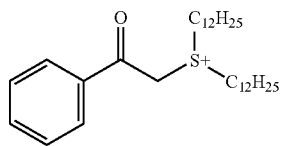
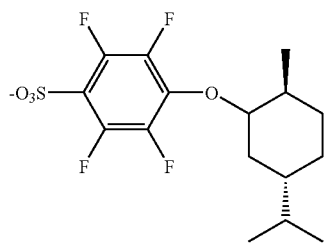
(A-75)
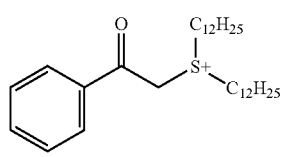
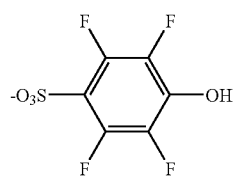
(A-76)
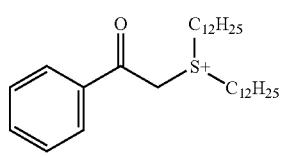
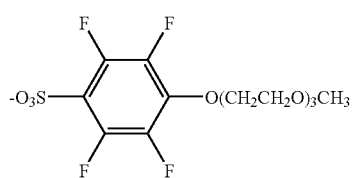
(A-77)
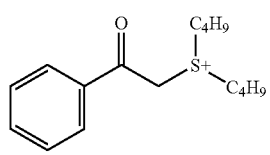
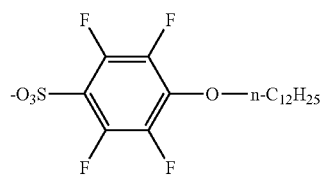
(A-78)
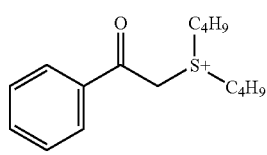
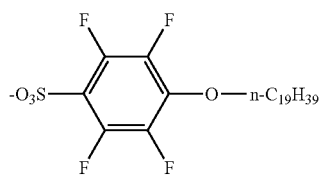
(A-79)
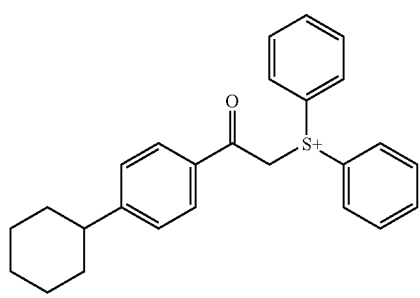
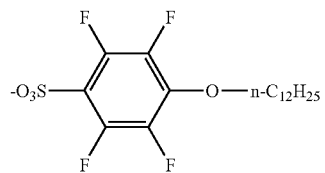
(A-80)
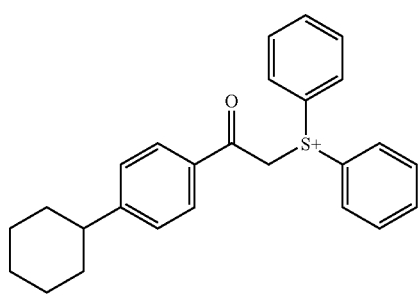
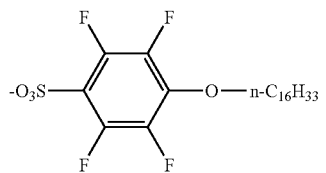

-continued
(A-81)
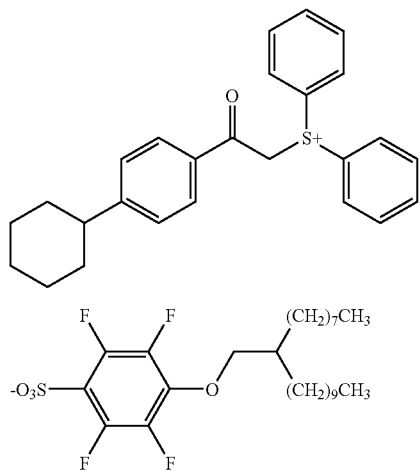
(A-82)
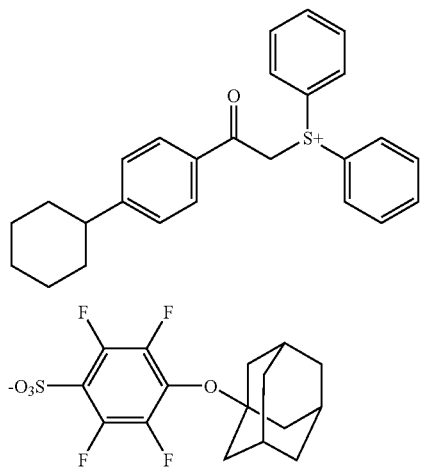
(A-83)
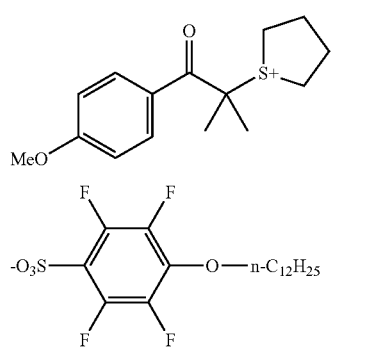
(A-84)
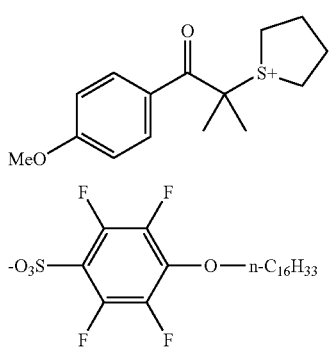
(A-85)
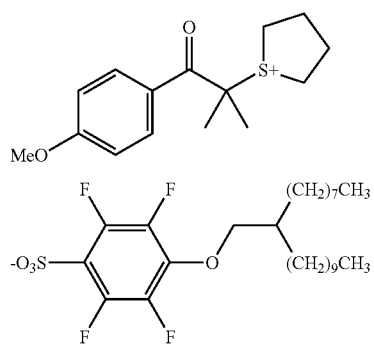
(A-86)
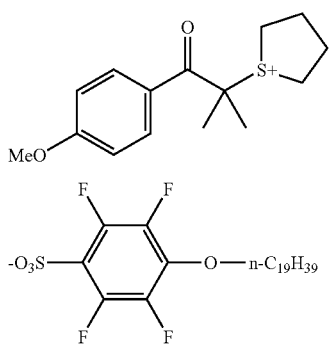
(A-87)
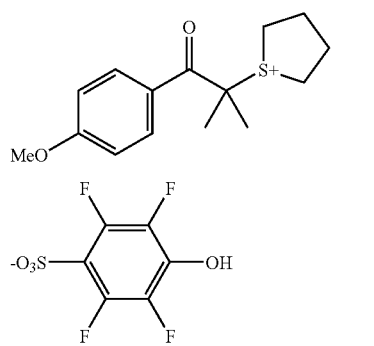
(A-88)
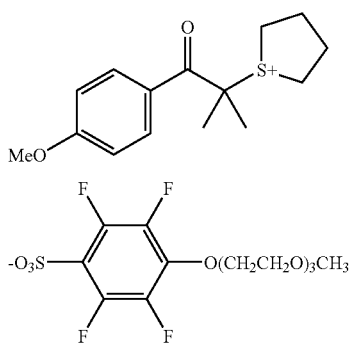

-continued
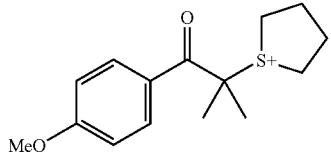
(A-89)
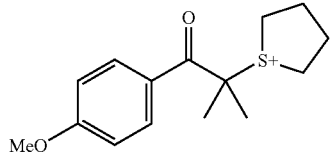
(A-90)
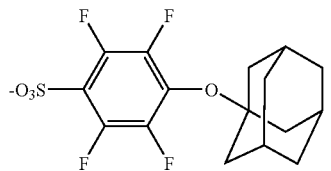
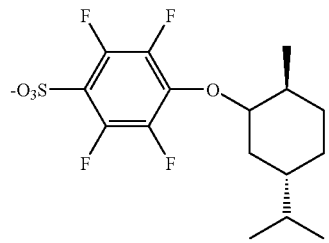
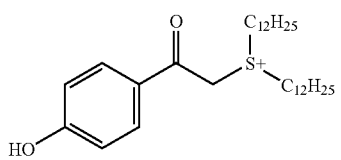
(A-91)
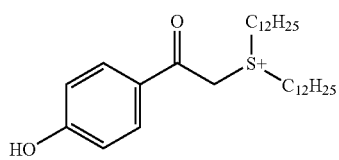
(A-92)
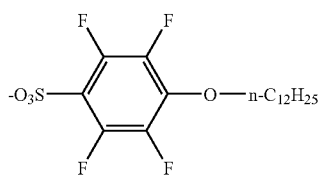
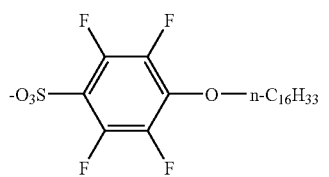
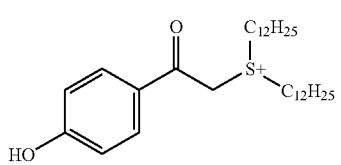
(A-93)
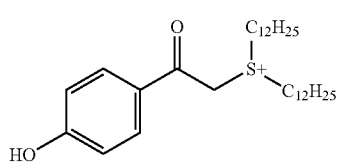
(A-94)
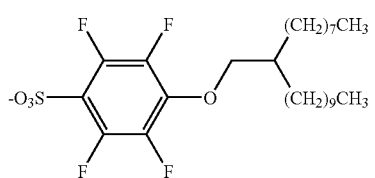
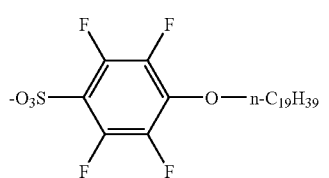
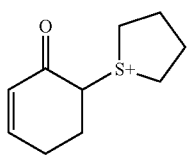
(A-95)
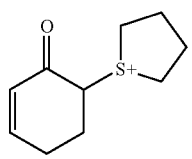
(A-96)
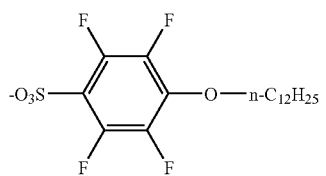
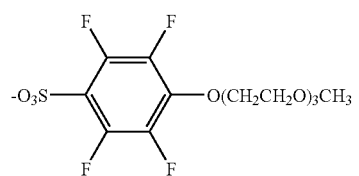

-continued
(A-97)
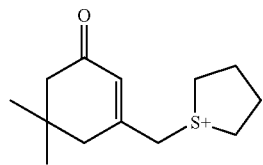
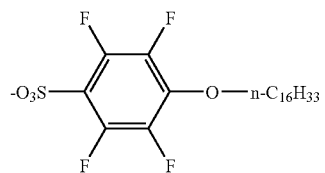
(A-98)
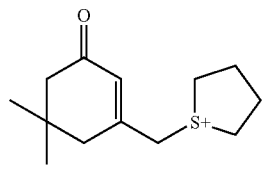
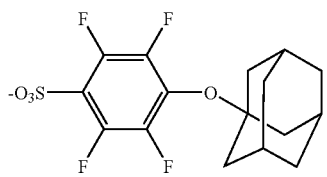
(A-99)
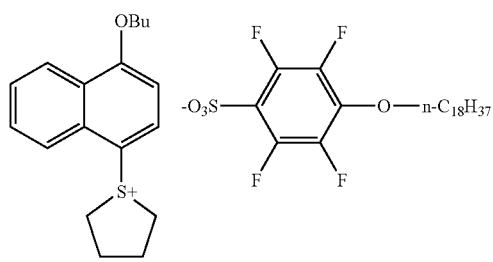
(A-100)
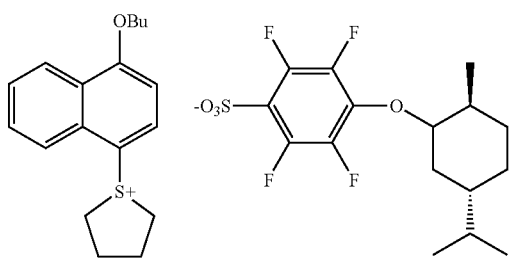
(A-101)
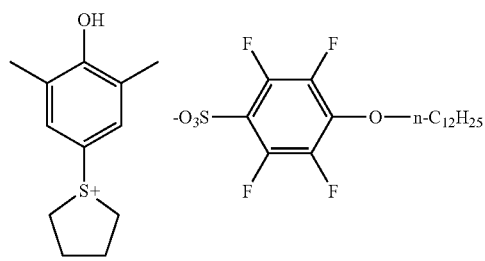
(A-102)
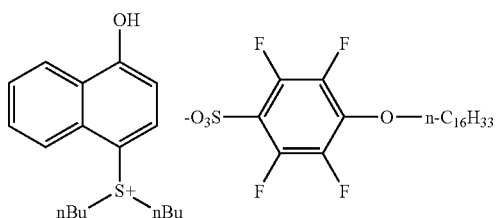
(A-103)
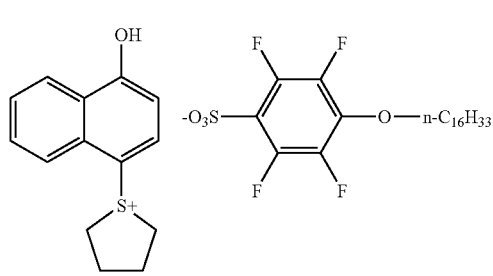
(A-104)
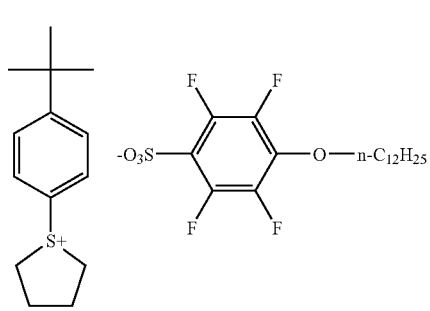
(A-105)
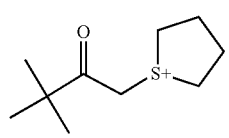
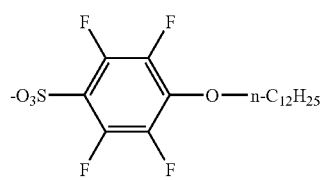
(A-106)
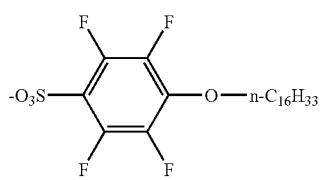

-continued
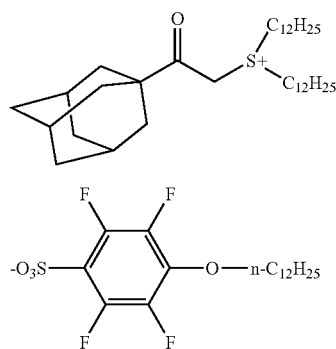
(A-107)
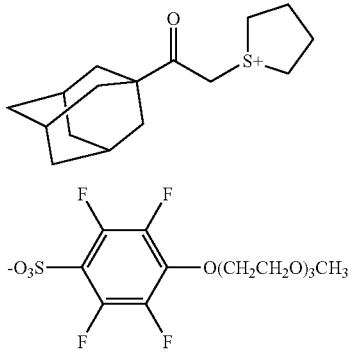
(A-108)
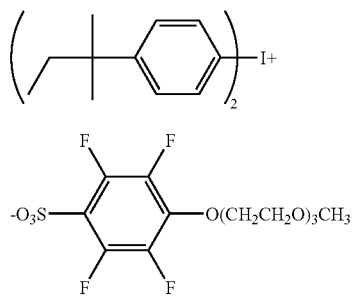
(A-109)
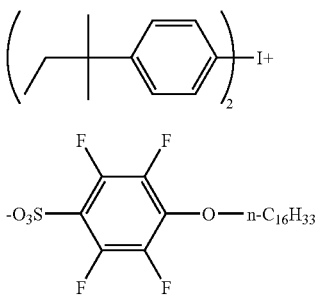
(A-110)
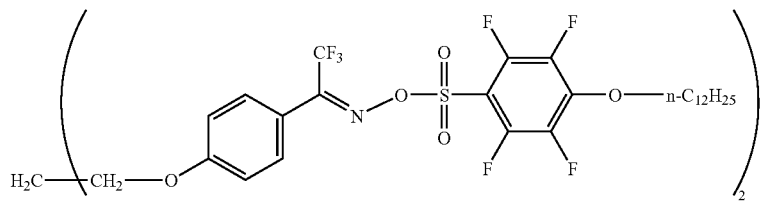
(A-111)
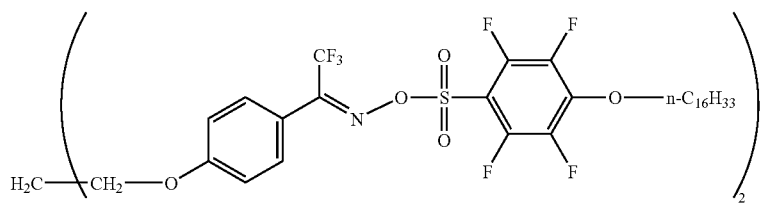
(A-112)
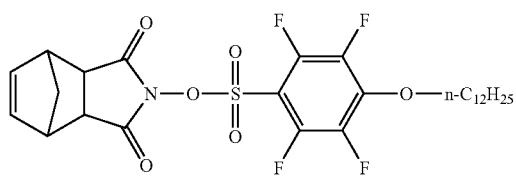
(A-113)
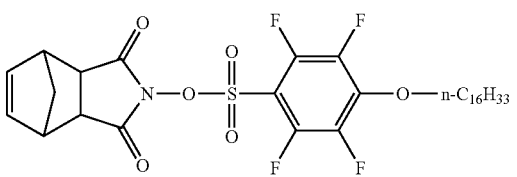
(A-114)
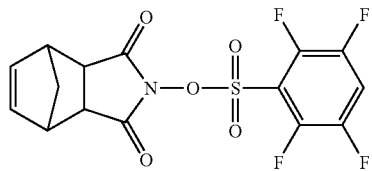
(A-115)
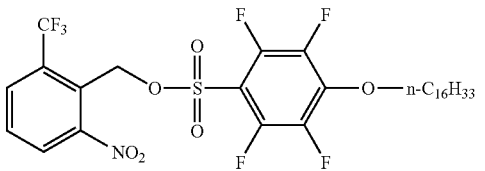
(A-116)
OCH₂CH₂OCH₂CH₂OCH₂CH₂OCH₃

-continued
(A-117)
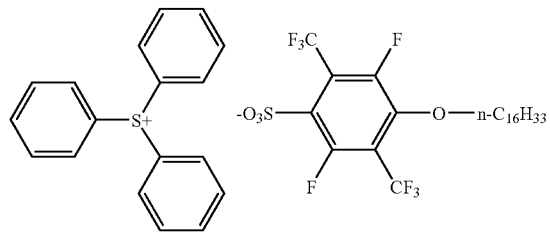
(A-118)
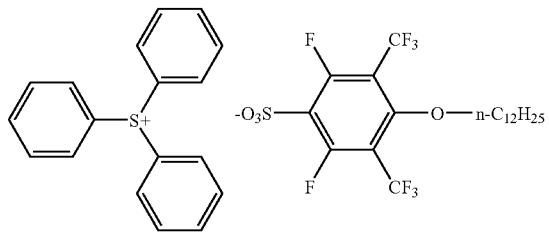
(A-119)
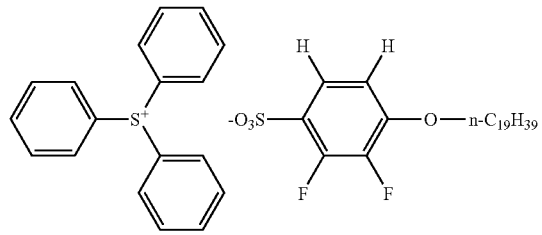
(A-120)
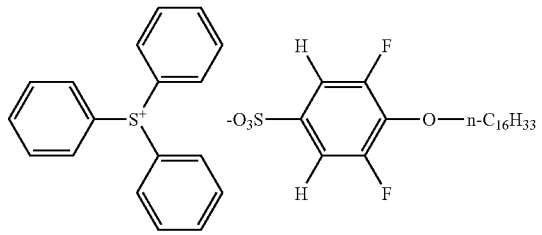
(A-121)
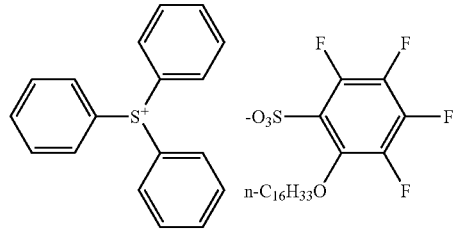
(A-122)
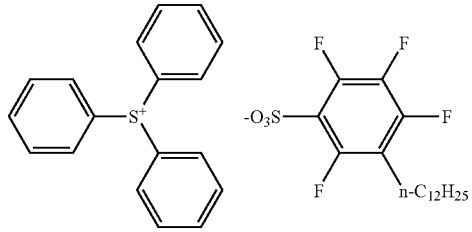
(A-123)
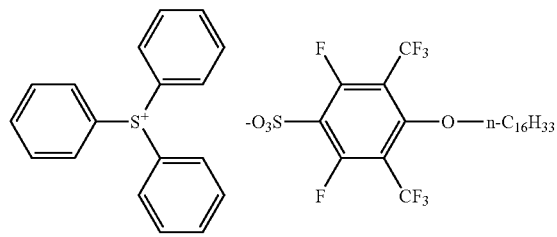
(A-124)
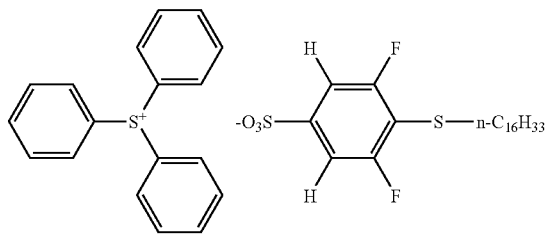
(A-125)
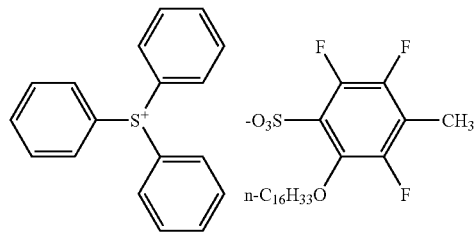
(A-126)
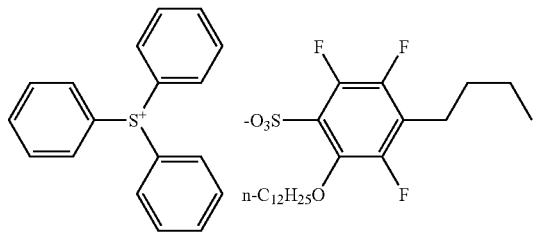
(A-127)
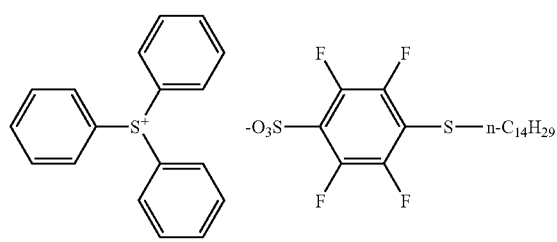
(A-128)
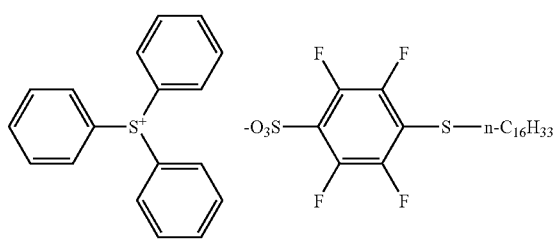

-continued
(A-129)
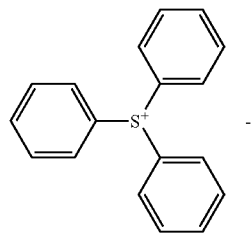 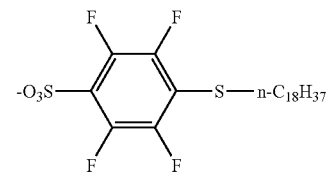
(A-130)
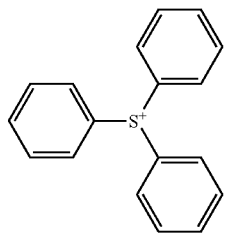 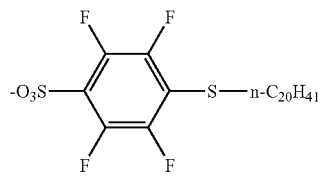
(A-131)
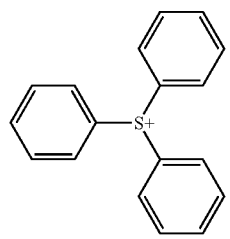
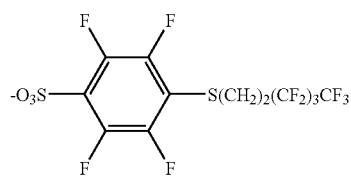
(A-132)
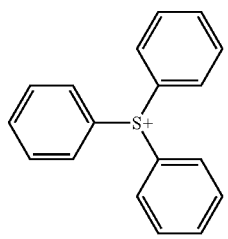
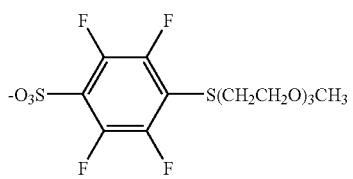
(A-133)
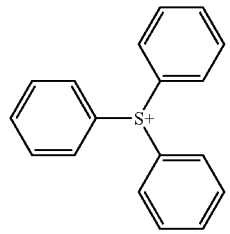
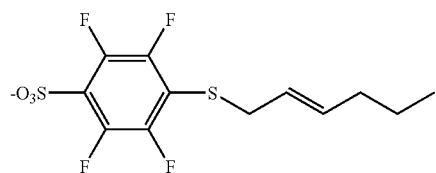
(A-134)
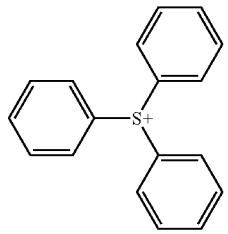
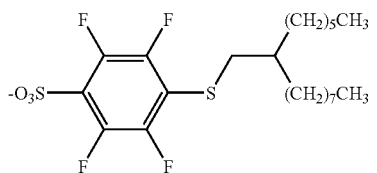
(A-135)
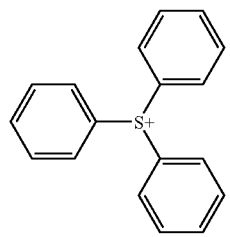
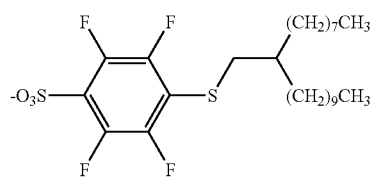
(A-136)
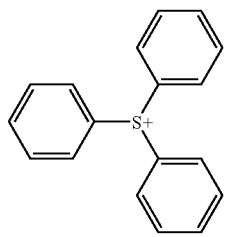
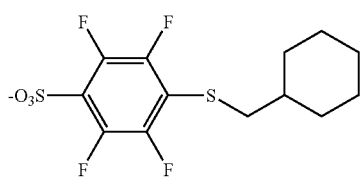

-continued
(A-137)
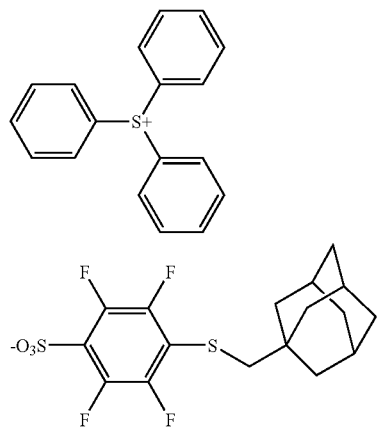
(A-138)
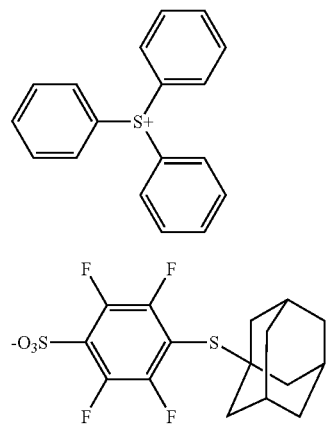
(A-139)
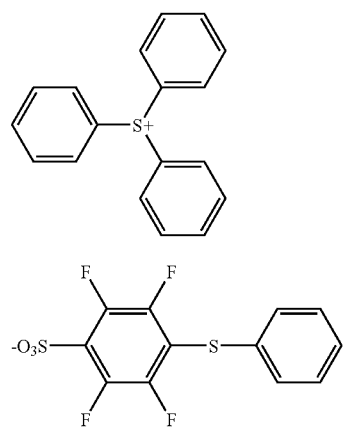
(A-140)
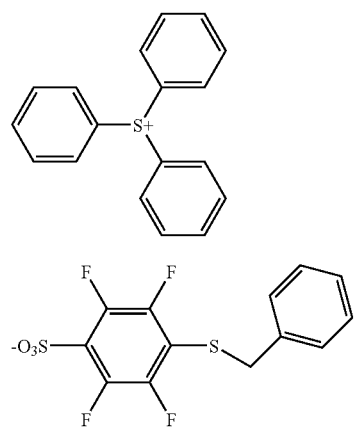
(A-141)
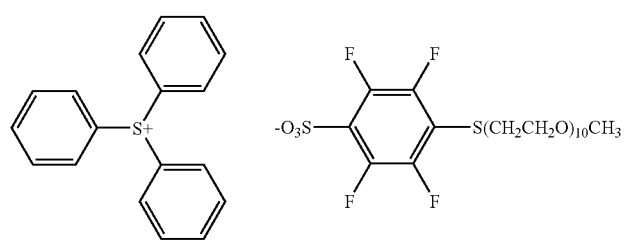
(A-142)
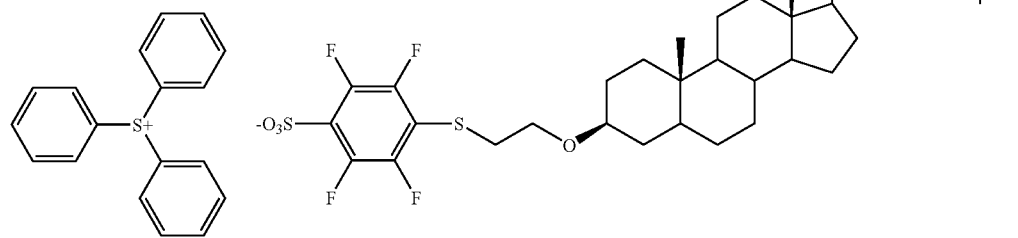

-continued

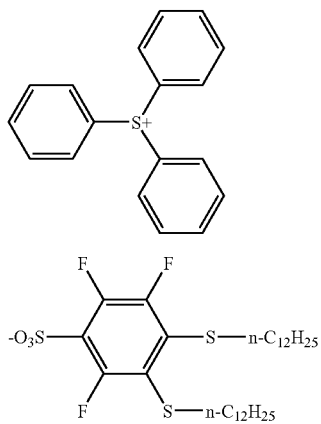
(A-143)

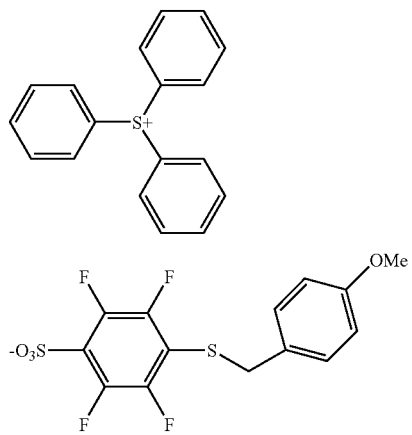
(A-144)

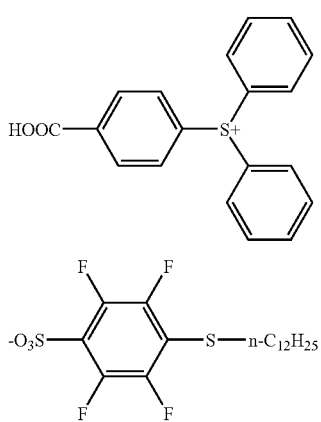
(A-145)

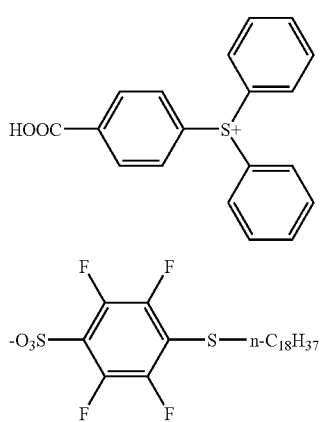
(A-146)

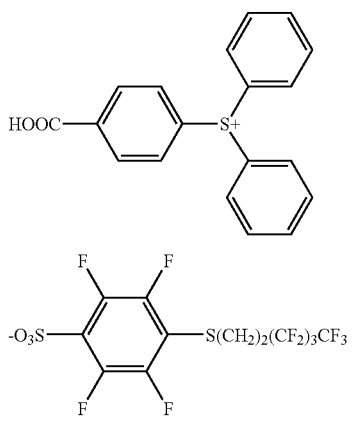
(A-147)

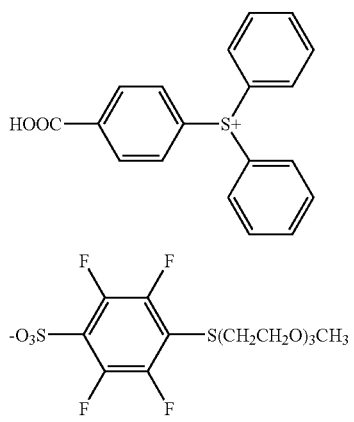
(A-148)

The compound (A) can be synthesized by preparing a derivative of the sulfonic acid represented by formula (I) and subjecting the derivative to salt exchange with an onium halide or esterification with a hydroxyl group-containing compound. The derivative of the sulfonic acid represented by formula (I) can be synthesized by using a method described, for example, in *J. Chem. Soc.*, Perkin Trans. 1, pp. 4265-4278 (2000).

The content of the compound (A) in the photosensitive composition of the present invention is, based on the solid content of the composition, preferably from 0.1 to 20 mass %, more preferably from 0.5 to 10 mass %, still more preferably from 1 to 7 mass % ("mass %" means wt % in this specifiation).

(Acid Generator Used in Combination)

In the present invention, a compound capable of decomposing upon irradiation with an actinic ray or a radiation to generate an acid may also be used in addition to the compound (A).

The amount of the photo-acid generator which can be used in combination is, in terms of the molar ratio (compound (A)/another acid generator), usually from 100/0 to 20/80, preferably from 100/0 to 40/60, more preferably from 100/0 to 50/50.

This photo-acid generator which can be used in combination may be appropriately selected from a photoinitiator for photocationic polymerization, a photoinitiator for photoradical polymerization, a photo-decoloring agent for dyes, a photo-discoloring agent, a known compound capable of generating an acid upon irradiation with an actinic ray or a radiation, which is used for microresist and the like, and a mixture thereof.

Examples thereof include diazonium salt, phosphonium salt, sulfonium salt, iodonium salt, imidosulfonate, oxime sulfonate, diazodisulfone, disulfone and o-nitrobenzyl sulfonate.

Also, a compound where the above-described group or compound capable of generating an acid upon irradiation with an actinic ray or a radiation is introduced into the polymer main or side chain, such as compounds described in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029, may be used.

Furthermore, a compound capable of generating an acid under the action of light described, for example, in U.S. Pat. No. 3,779,778 and European Patent 126,712 may also be used.

Among the compounds capable of decomposing upon irradiation with an actinic ray or a radiation to generate an acid, which can be used in combination, preferred are the compounds represented by the following formulae (ZI), (ZII) and (ZIII):

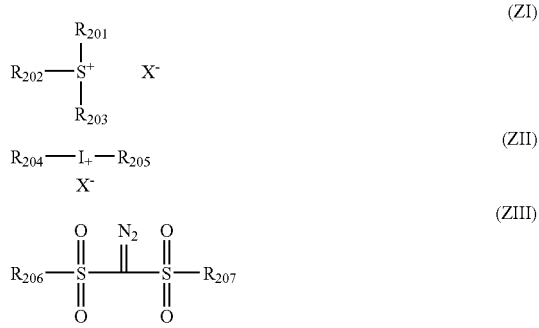

In formula (ZI), $R_{201}$, $R_{202}$ and $R_{203}$ each independently represents an organic group.

The number of carbons in the organic group represented by $R_{201}$, $R_{202}$ and $R_{203}$ is generally from 1 to 30, preferably from 1 to 20.

Two out of $R_{201}$ to $R_{203}$ may combine to form a ring structure and the ring may contain an oxygen atom, a sulfur atom, an ester bond, an amide bond or a carbonyl group.

Examples of the group formed when two out of $R_{201}$ to $R_{203}$ are combined include an alkylene group (e.g., butylene, pentylene).

$X^-$ represents a non-nucleophilic anion.

Examples of the non-nucleophilic anion represented by $X^-$ include sulfonate anion, carboxylate anion, sulfonylimide anion, bis(alkylsulfonyl)imide anion and tris(alkylsulfonyl)methyl anion.

The non-nucleophilic anion is an anion having an extremely low ability of causing a nucleophilic reaction and this anion can prevent the decomposition in aging due to intramolecular nucleophilic reaction. By this anion, the aging stability of resist is enhanced.

Examples of the sulfonate anion include aliphatic sulfonate anion, aromatic sulfonate anion and camphor-sulfonate anion.

Examples of the carboxylate anion include aliphatic carboxylate anion, aromatic carboxylate anion and aralkylcarboxylate anion.

The aliphatic moiety in the aliphatic sulfonate anion may be an alkyl group or a cycloalkyl group but is preferably an alkyl group having from 1 to 30 carbon atoms or a cycloalkyl group having from 3 to 30 carbon atoms, such as methyl group, ethyl group, propyl group, isopropyl group, n-butyl group, isobutyl group, sec-butyl group, pentyl group, neopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, cyclopropyl group, cyclopentyl group, cyclohexyl group, adamantyl group, norbornyl group and boronyl group.

The aryl group in the aromatic sulfohate anion is preferably an aryl group having from 6 to 14 carbon atoms, such as phenyl group, tolyl group and naphthyl group.

The alkyl group, cycloalkyl group and aryl group in the aliphatic sulfonate anion and aromatic sulfonate anion each may have a substituent.

Examples of the substituent include a nitro group, a halogen atom (e.g., fluorine, chlorine, bromine, iodine), a carboxyl group, a hydroxyl group, an amino group, a cyano group, an alkoxy group (preferably having from 1 to 5 carbon atoms), a cycloalkyl group (preferably having from 3 to 15 carbon atoms), an aryl group (preferably having from 6 to 14 carbon atoms), an alkoxycarbonyl group (preferably having from 2 to 7 carbon atoms), an acyl group (preferably having from 2 to 12 carbon atoms) and an alkoxycarbonyloxy group (preferably having from 2 to 7 carbon atoms). Furthermore, examples of the substituent for the aryl group and ring structure in each group include an alkyl group (preferably having from 1 to 15 carbon atoms).

Examples of the aliphatic moiety in the aliphatic carboxylate anion are the same as those of the alkyl group and cycloalkyl group in the aliphatic sulfonate anion.

Examples of the aryl group in the aromatic carboxylate anion are the same as those of the aryl group in the aromatic sulfonate anion.

The aralkyl group in the aralkylcarboxylate anion is preferably an aralkyl group having from 6 to 12 carbon atoms, such as benzyl group, phenethyl group, naphthylmethyl group, naphthylethyl group and naphthylmethyl group.

The alkyl group, cycloalkyl group, aryl group and aralkyl group in the aliphatic carboxylate anion, aromatic carboxylate anion and aralkylcarboxylate anion each may have a substituent and examples of the substituent include the same halogen atom, alkyl group, cycloalkyl group, alkoxy group and alkylthio group described above regarding the aromatic sulfonate anion.

Examples of the sulfonylimide anion include saccharin anion.

The alkyl group in the bis(alkylsulfonyl)imide anion and tris(alkylsulfonyl)methyl anion is preferably an alkyl group having from 1 to 5 carbon atoms, such as methyl group, ethyl group, propyl group, isopropyl group, n-butyl group, isobutyl group, sec-butyl group, pentyl group and neopentyl group. The alkyl group may have a substituent and examples of the substituent include a halogen atom, a halogen atom-substituted alkyl group, an alkoxy group and an alkylthio group, with a halogen atom-substituted alkyl group being preferred.

Other examples of the non-nucleophilic anion include fluorinated phosphorus, fluorinated boron and fluorinated antimony.

The non-nucleophilic anion represented by $X^-$ is preferably an aliphatic sulfonate anion with the α-position of sulfonic acid being substituted by a fluorine atom, an aromatic sulfonate anion substituted by a fluorine atom or a group having a fluorine atom, a bis(alkylsulfonyl)imide anion with the alkyl group being substituted by a fluorine atom, or a tris(alkylsulfonyl)methide anion with the alkyl group being substituted by a fluorine atom, more preferably a perfluoroalkanesulfonate anion having from 4 to 8 carbon atoms or a benzenesulfonate anion having a fluorine atom, and most preferably a nonafluorobutanesulfonate anion, a perfluorooctanesulfonate anion, a pentafluorobenzene-sulfonate anion or a 3,5-bis(trifluoromethyl)benzene-sulfonate anion.

Specific examples of the organic group represented by $R_{201}$, $R_{202}$ and $R_{203}$ include corresponding groups in the compounds (ZI-1), (ZI-2) and (ZI-3) which are described later.

The compound may be a compound having a plurality of structures represented by formula (ZI), for example, a compound having a structure that at least one of $R_{201}$ to $R_{203}$ in the compound represented by formula (ZI) is bonded to at least one of $R_{201}$ to $R_{203}$ in another compound represented by formula (ZI).

The component (ZI) is more preferably a compound (ZI-1), (ZI-2) or (ZI-3) described below.

The compound (ZI-1) is an arylsulfonium compound where at least one of $R_{201}$ to $R_{203}$ in formula (ZI) is an aryl group, that is, a compound having an arylsulfonium as the cation.

In the arylsulfonium compound, $R_{201}$ to $R_{203}$ all may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkyl-sulfonium compound and an aryldicycloalkylsulfonium compound.

The aryl group in the arylsulfonium compound is preferably a phenyl group or a naphthyl group, more preferably a phenyl group. In the case where the arylsulfonium compound has two or more aryl groups, these two or more aryl groups may be the same of different.

The alkyl group which is present, if desired, in the arylsulfonium compound is preferably a linear or branched alkyl group having from 1 to 15 carbon atoms or a cycloalkyl group having from 3 to 15 carbon atoms, such as methyl group, ethyl group, propyl group, n-butyl group, sec-butyl group, tert-butyl group, cyclopropyl group, cyclobutyl group and cyclohexyl group.

The aryl group, alkyl group and cycloalkyl group represented by $R_{201}$ to $R_{203}$ each may have, as a substituent, an alkyl group (for example, having from 1 to 15 carbon atoms), a cycloalkyl group (for example, having from 3 to 15 carbon atoms), an aryl group (for example, having from 6 to 14 carbon atoms), an alkoxy group (for example, having from 1 to 15 carbon atoms), a halogen atom, a hydroxyl group or a phenylthio group. The substituent is preferably a linear or branched alkyl group having from 1 to 12 carbon atoms, a cycloalkyl group having from 3 to 12 carbon atoms or a linear, branched or cyclic alkoxy group having from 1 to 12 carbon atoms, and most preferably an alkyl group having from 1 to 4 carbon atoms or an alkoxy group having from 1 to 4 carbon atoms. The substituent may be substituted to any one of three groups $R_{201}$ to $R_{203}$ or may be substituted to all of these three groups. In the case where $R_{201}$ to $R_{203}$ each is an aryl group, the substituent is preferably substituted at the p-position of the aryl group.

The compound (ZI-2) is described below.

The compound (ZI-2) is a compound where $R_{201}$ to $R_{203}$ in formula (1) each independently represents an organic group not containing an aromatic ring. The aromatic ring as used herein includes an aromatic ring containing a heteroatom.

The organic group not containing an aromatic ring represented by $R_{201}$ to $R_{203}$ generally has from 1 to 30 carbon atoms, preferably from 1 to 20 carbon atoms.

$R_{201}$ to $R_{203}$ each independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, and most preferably a linear or branched 2-oxoalkyl group.

The alkyl group and cycloalkyl group represented by $R_{201}$ to $R_{203}$ are preferably a linear or branched alkyl group having from 1 to 10 carbon atoms (e.g., methyl, ethyl, propyl, butyl, pentyl) and a cycloalkyl group having from 3 to 10 carbon atoms (e.g., cyclopentyl, cyclohexyl, norbornyl). The alkyl group is more preferably a 2-oxoalkyl group or an alkoxycarbonylmethyl group. The cycloalkyl group is more preferably a 2-oxocycloalkyl group.

The 2-oxoalkyl group may be either linear or branched and is preferably a group having >C=O at the 2-position of the above-described alkyl group.

The 2-oxocycloalkyl group is preferably a group having >C=O at the 2-position of the above-described cycloalkyl group.

The alkoxy group in the alkoxycarbonylmethyl group is preferably an alkyl group having from 1 to 5 carbon atoms (e.g., methoxy, ethoxy, propoxy, butoxy, pentyloxy).

$R_{201}$ to $R_{203}$ each may be further substituted by a halogen atom, an alkoxy group (for example, having from 1 to 5 carbon atoms), a hydroxyl group, a cyano group or a nitro group.

The compound (ZI-3) is a compound represented by the following formula (ZI-3) and this is a compound having a phenacylsulfonium salt structure.

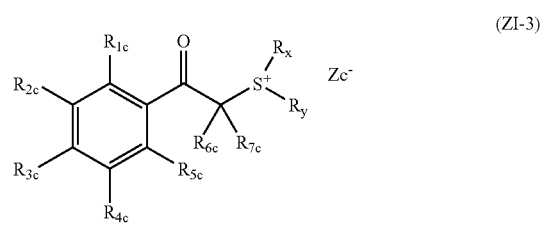

(ZI-3)

In formula (ZI-3), $R_{1c}$ to $R_{5c}$ each independently represents a hydrogen atom, an alkyl group, a cycloalkyl group, an alkoxy group or a halogen atom.

$R_{6c}$ and $R_{7c}$ each represents a hydrogen atom, an alkyl group or a cycloalkyl group.

$R_x$ and $R_y$ each independently represents an alkyl group, a cycloalkyl group, an allyl group or a vinyl group.

Any two or more out of $R_{1c}$ to $R_{5c}$ or each of the pairs $R_{6c}$ and $R_{7c}$, and $R_x$ and $R_y$ may combine to form a ring structure and the ring structure may contain an oxygen atom, a sulfur atom, an ester bond or an amide bond. Examples of the group formed when any two or more of $R_{1c}$ to $R_{5c}$ or each of the pairs $R_{6c}$ and $R_{7c}$, and $R_x$ and $R_y$ are combined include a butylene group and a pentylene group.

$Zc^-$ represents a non-nucleophilic anion and examples thereof are the same as those of the non-nucleophilic anion of $X^-$ in formula (ZI)

The alkyl group represented by $R_{1c}$ to $R_{7c}$ may be either linear or branched and this is, for example, an alkyl group having from 1 to 20 carbon atoms, preferably a linear or branched alkyl group having from 1 to 12 carbon atoms (e.g., methyl, ethyl, linear or branched propyl, linear or branched butyl, linear or branched pentyl), and the cycloalkyl group is, for example, a cyclic alkyl group having from 3 to 8 carbon atoms (e.g., cyclopentyl, cyclohexyl).

The alkoxy group represented by $R_{1c}$ to $R_{5c}$ may be linear, branched or cyclic and this is, for example, an alkoxy group having from 1 to 10 carbon atoms, preferably a linear or branched alkoxy group having from 1 to 5 carbon atoms (e.g., methoxy, ethoxy, linear or branched propoxy, linear or branched butoxy, linear or branched pentoxy) or a cyclic alkoxy group having from 3 to 8 carbon atoms (e.g., cyclopentyloxy, cyclohexyloxy).

A compound where any one of $R_{1c}$ to $R_{5c}$ is a linear or branched alkyl group, a cycloalkyl group or a linear, branched or cyclic alkoxy group is preferred, and a compound where the sum of carbon atoms of $R_{1c}$ to $R_{5c}$ is from 2 to 15 is more preferred. In this case, the solubility in solvent is more enhanced and the generation of particles during storage is prevented.

Examples of the alkyl group and cycloalkyl group represented by $R_x$ and $R_y$ are the same as those of the alkyl group and cycloalkyl group represented by $R_{1c}$ to $R_{7c}$. Among these, preferred are a 2-oxoalkyl group, a 2-oxocycloalkyl group and an alkoxycarbonylmethyl group.

Examples of the 2-oxoalkyl group and 2-oxocycloalkyl group include a group having >C=O at the 2-position of the alkyl group or cycloalkyl group represented by $R_{1c}$ to $R_{7c}$.

Examples of the alkoxy group in the alkoxy-carbonylmethyl group are the same as those of the alkoxy group represented by $R_{1c}$ to $R_{5c}$.

$R_x$ and $R_y$ each is preferably an alkyl or cycloalkyl group having 4 or more carbon atoms, more preferably 6 or more carbon atoms, still more preferably 8 or more carbon atoms.

In formulae (ZII) and (ZIII), $R_{204}$ to $R_{207}$ each independently represents an aryl group, an alkyl group or a cycloalkyl group.

The aryl group represented by $R_{204}$ to $R_{207}$ is preferably a phenyl group or a naphthyl group, more preferably a phenyl group.

The alkyl group and cycloalkyl group represented by $R_{204}$ to $R_{207}$ are preferably a linear or branched alkyl group having from 1 to 10 carbon atoms (e.g., methyl, ethyl, propyl, butyl, pentyl) and a cycloalkyl group having from 3 to 10 carbon atoms (e.g., cyclopentyl, cyclohexyl, norbornyl).

Examples of the substituent which may be substituted to $R_{204}$ to $R_{207}$ include an alkyl group (for example, having from 1 to 15 carbon atoms), a cycloalkyl group (for example, having from 3 to 15 carbon atoms), an aryl group (for example, having from 6 to 15 carbon atoms), an alkoxy group (for example, having from 1 to 15 carbon atoms), a halogen atom, a hydroxyl group and a phenylthio group.

$X^-$ represents a non-nucleophilic anion and examples thereof are the same as those of the non-nucleophilic anion represented by $X^-$ in formula (ZI).

Other examples of the compound capable of decomposing upon irradiation with an actinic ray or a radiation to generate an acid, which can be used in combination, include the compounds represented by the following formulae (ZIV), (ZV) and (ZVI):

(ZIV)

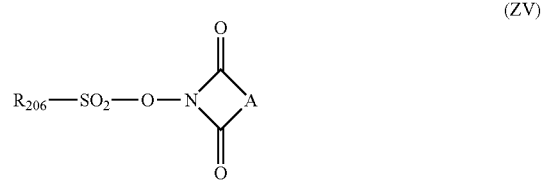

(ZV)

(ZVI)

In formulae (ZIV) to (ZVI), $Ar_3$ and $Ar_4$ each independently represents an aryl group, $R_{206}$, $R_{207}$ and $R_{208}$ each independently represents an alkyl group or an aryl group, and A represents an alkylene group, an alkenylene group or an arylene group.

Among the compounds capable of decomposing upon irradiation with an actinic ray or a radiation to generate an acid, which can be used in combination, more preferred are the compounds represented by formulae (ZI) to (ZIII).

The compound of decomposing upon irradiation with an actinic ray or a radiation to generate an acid, which can be used in combination, is preferably a compound capable of generating a sulfonic acid having one sulfonic acid group, more preferably a compound capable of generating a monovalent perfluoroalkanesulfonic acid or a compound capable of generating an aromatic sulfonic acid substituted by a fluorine atom or a group containing a fluorine atom, still more preferably a sulfonium salt of a monovalent perfluoroalkanesulfonic acid.

Particularly preferred examples of the compound capable of decomposing upon irradiation with an actinic ray or a radiation to generate an acid, which can be used in combination, are set forth below.

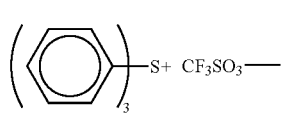

(z1)

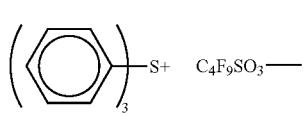

(z2)

-continued
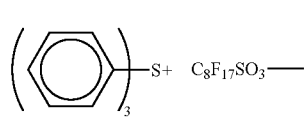 (z3)
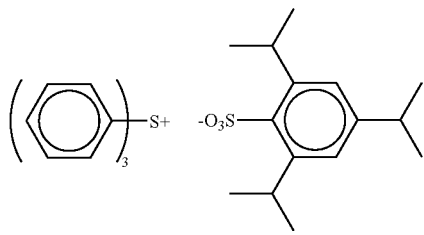 (z4)
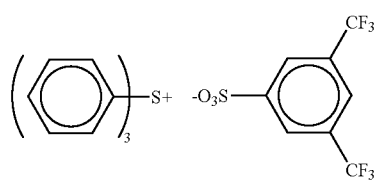 (z5)
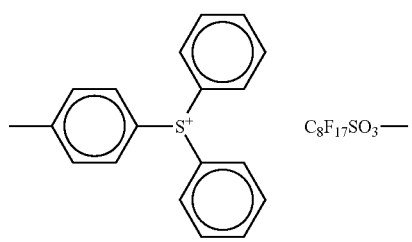 (z6)
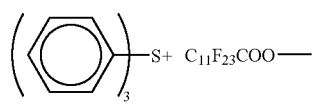 (z7)
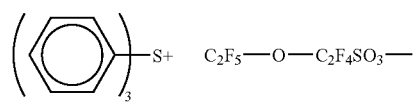 (z8)
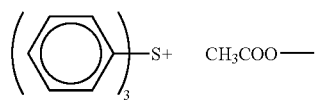 (z9)
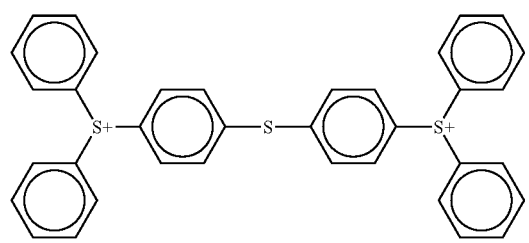
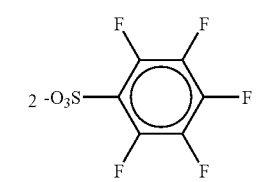 (z10)
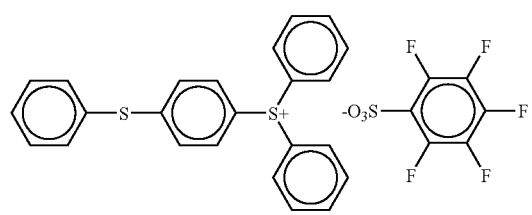 (z11)
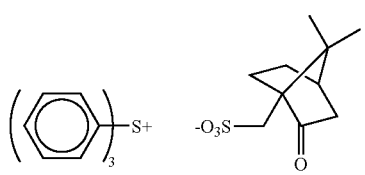 (z12)
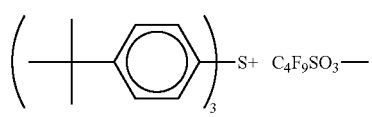 (z13)
(z14)

-continued
(z15) 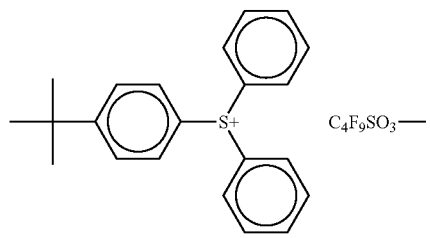
(z16) 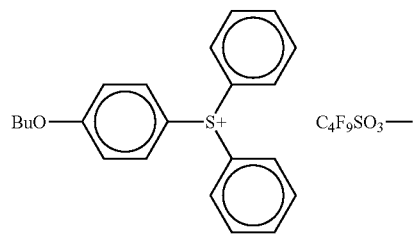
(z17) 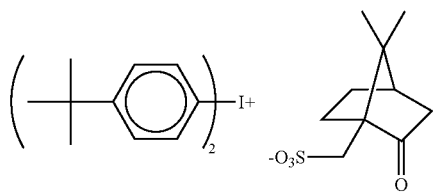
(z18) 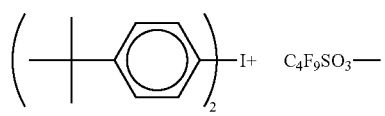
(z19) 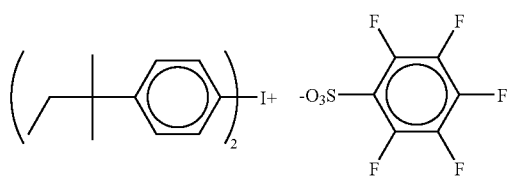
(z20) 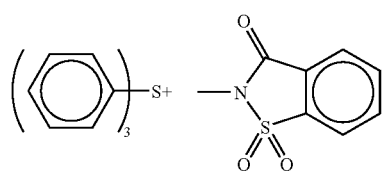
(z21) 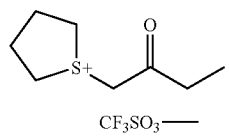
(z22) 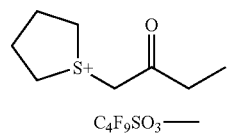
(z23) 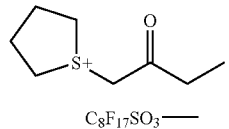
(z24) 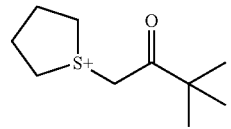
(z25) 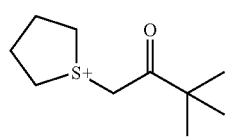
(z26) 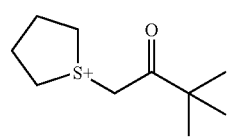
(z27) 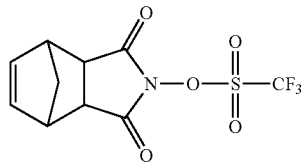
(z28) 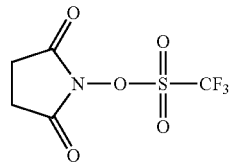
(z29) 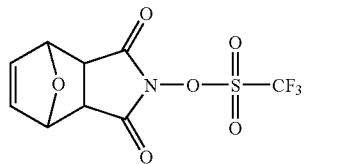
(z30) 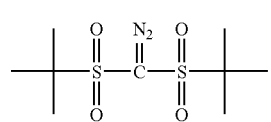
(z31) 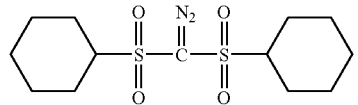
(z32)

-continued
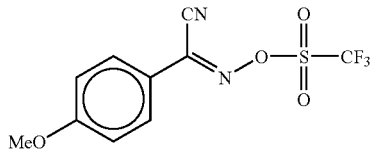
(z33)
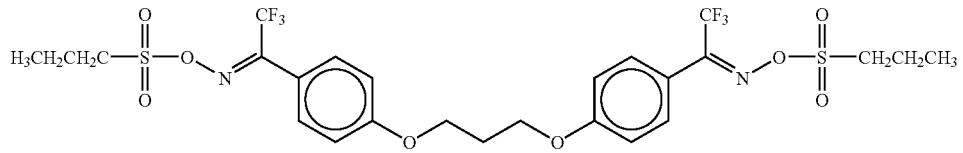
(z34)
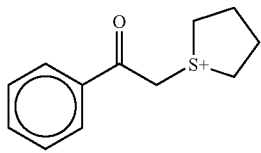
(z35)
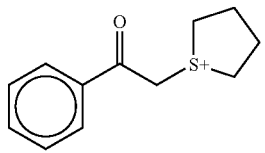
(z36)
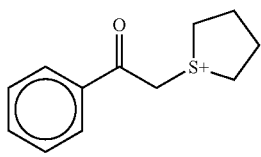
(z37)
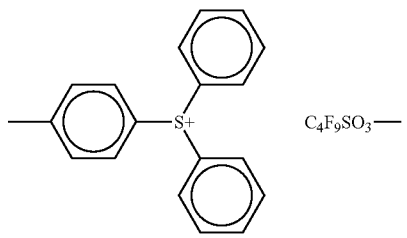
(z38)
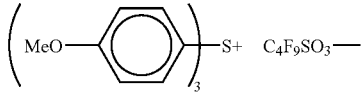
(z39)
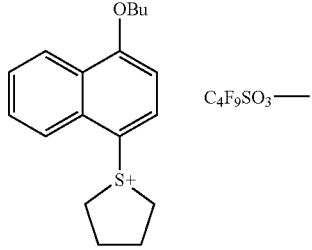
(z40)
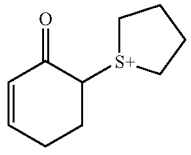
(z41)
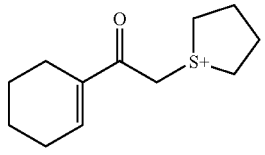
(z42)
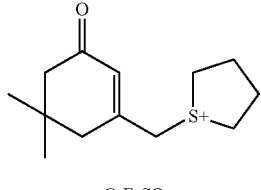
(z43)
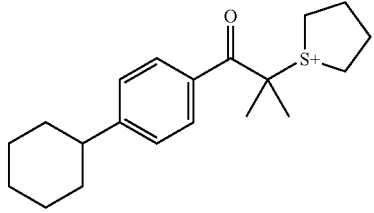
(z44)

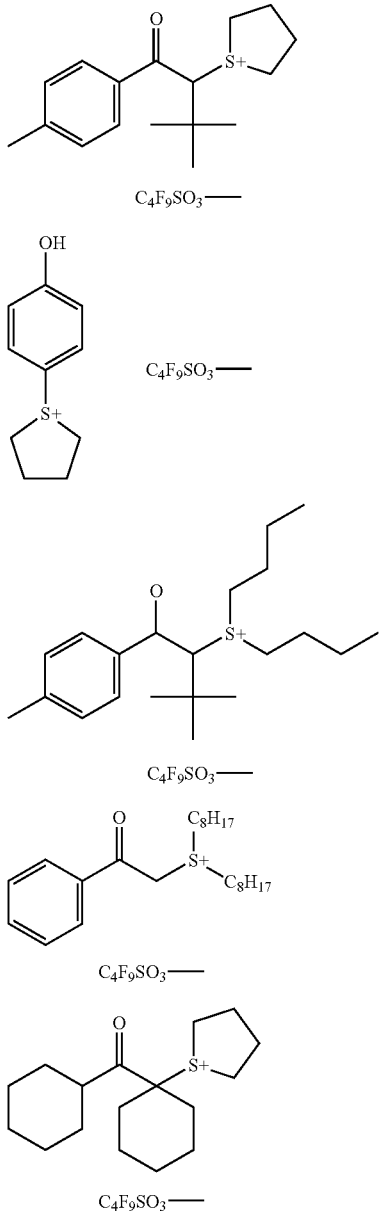

[2] (B) Resin capable of decomposing under the action of an acid to increase a solubility or the resin in an alkali developer (hereinafter sometimes referred to as a "component (B)")

The resin capable of decomposing under the action of an acid to increase the solubility in an alkali developer, which is used in the positive photosensitive composition of the present invention, is a resin where a group capable of decomposing under the action of an acid (hereinafter sometimes referred to as an "acid decomposable group") is present in ether one or both of the main chain and the side chain of resin. Among these, a resin having an acid decomposable group in the side chain is preferred.

The group capable of decomposing under the action of an acid is preferably a group resulting from displacement of the hydrogen atom of a —COOH or —OH group with a group which splits off under the action of an acid.

In the present invention, the acid decomposable group is an acetal group or a tertiary ester group.

In the case where the group capable of decomposing under the action of an acid is bonded as a side chain, the mother resin is an alkali-soluble resin having an —OH or —COOH group in the side chain. Examples thereof include alkali-soluble resins described later.

The alkali dissolution rate of the alkali-soluble resin is preferably 170 A/sec or more, more preferably 330 A/sec or more (A is angstrom), as measured (at 23° C.) in 0.261N tetramethylammonium hydroxide (TMAH).

From this standpoint, the alkali-soluble resin is preferably an alkali-soluble resin having a hydroxystyrene structure unit, such as an o-, m- or p-poly(hydroxystyrene) or a copolymer thereof, a hydrogenated poly(hydroxystyrene), a halogen- or alkyl-substituted poly(hydroxystyrene), a partially O-alkylated or O-acylated poly(hydroxystyrene), a styrene-hydroxystyrene copolymer, an α-methylstyrene-hydroxystyrene copolymer and a hydrogenated novolak resin.

Examples of the repeating unit having an acid decomposable group preferred in the present invention include tert-butoxycarbonyloxystyrene, 1-alkoxyethoxy-styrene and tertiary alkyl(meth)acrylate. Among these, preferred are 2-alkyl-2-adamantyl(meth)acrylate and dialkyl(1-adamantyl)methyl(meth)acrylate.

The component (B) for use in the present invention can be obtained by reacting an acid decomposable group precursor with an alkali-soluble resin or copolymerizing an acid decomposable group-bonded alkali-soluble resin monomer with various monomers, and this is disclosed in European Patent 254853, JP-A-2-25850, JP-A-3-223860 and JP-A-4-251259.

Specific examples of the component (B) for use in the present invention are set forth below, but the present invention is not limited thereto.

p-tert-Butoxystyrene/p-hydroxystyrene copolymer p-(tert-Butoxycarbonyloxy)styrene/p-hydroxystyrene copolymer p-(tert-Butoxycarbonylmethyloxy)styrene/p-hydroxystyrene copolymer 4-(tert-Butoxycarbonylmethyloxy)-3-methylstyrene/4-hydroxy-3-methylstyrene copolymer p-(tert-Butoxycarbonylmethyloxy)styrene/p-hydroxystyrene (10% hydrogenated product) copolymer m-(tert-Butoxycarbonylmethyloxy)styrene/m-hydroxystyrene copolymer o-(tert-Butoxycarbonylmethyloxy)styrene/o-hydroxystyrene copolymer p-(Cumyloxycarbonylmethyloxy)styrene/p-hydroxystyrene copolymer Cumyl methacrylate/methyl methacrylate copolymer 4-tert-Butoxycarbonylstyrene/dimethyl maleate copolymer Benzyl methacrylate/tetrahydropyranyl methacrylate copolymer p-(tert-Butoxycarbonylmethyloxy)styrene/p-hydroxystyrene/styrene copolymer p-tert-Butoxystyrene/p-hydroxystyrene/fumaronitrile copolymer tert-Butoxystyrene/hydroxyethyl methacrylate copolymer Styrene/N-(4-hydroxyphenyl)maleimide/N-(4-tert-butoxycarbonyloxyphenyl)maleimide copolymer p-Hydroxystyrene/tert-butyl methacrylate copolymer Styrene/p-hydroxystyrene/tert-butyl methacrylate copolymer p-Hydroxystyrene/tert-butyl acrylate copolymer Styrene/p-hydroxystyrene/tert-butyl acrylate copolymer p-(tert-Butoxycarbonylmethyloxy)styrene/p-hydroxystyrene/N-methylmaleimide copolymer tert-Butyl methacrylate/1-adamantylmethyl methacrylate copolymer p-Hydroxystyrene/tert-butyl acrylate/p-acetoxystyrene copolymer p-Hydroxystyrene/tert-butyl acrylate/p-(tert-butoxycarbonyloxy)styrene copolymer p-Hydroxystyrene/tert-butyl acrylate/p-(tert-butoxycarbonylmethyloxy)styrene copolymer

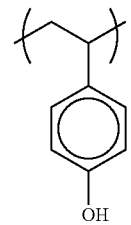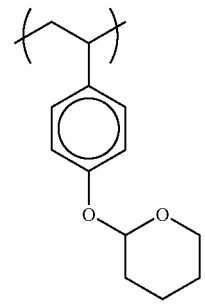

(R-1)

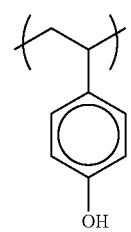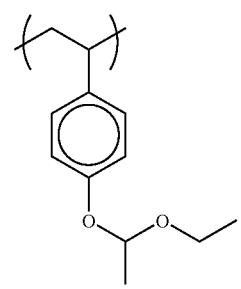

(R-2)

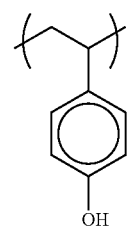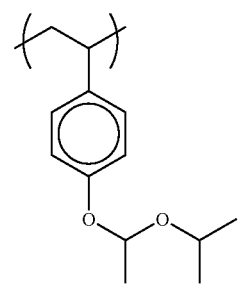

(R-3)

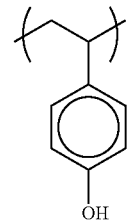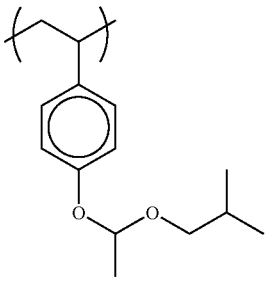

(R-4)

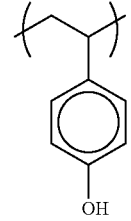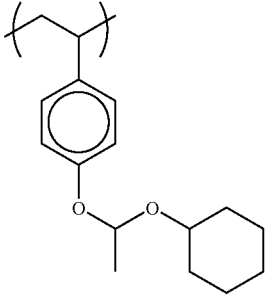

(R-5)

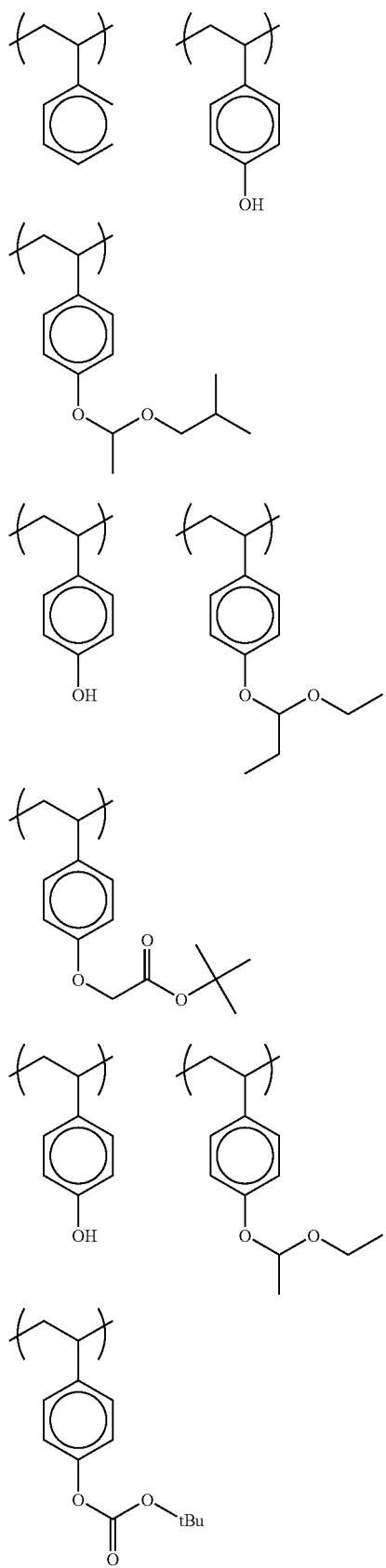
(R-6)
(R-7)
(R-8)
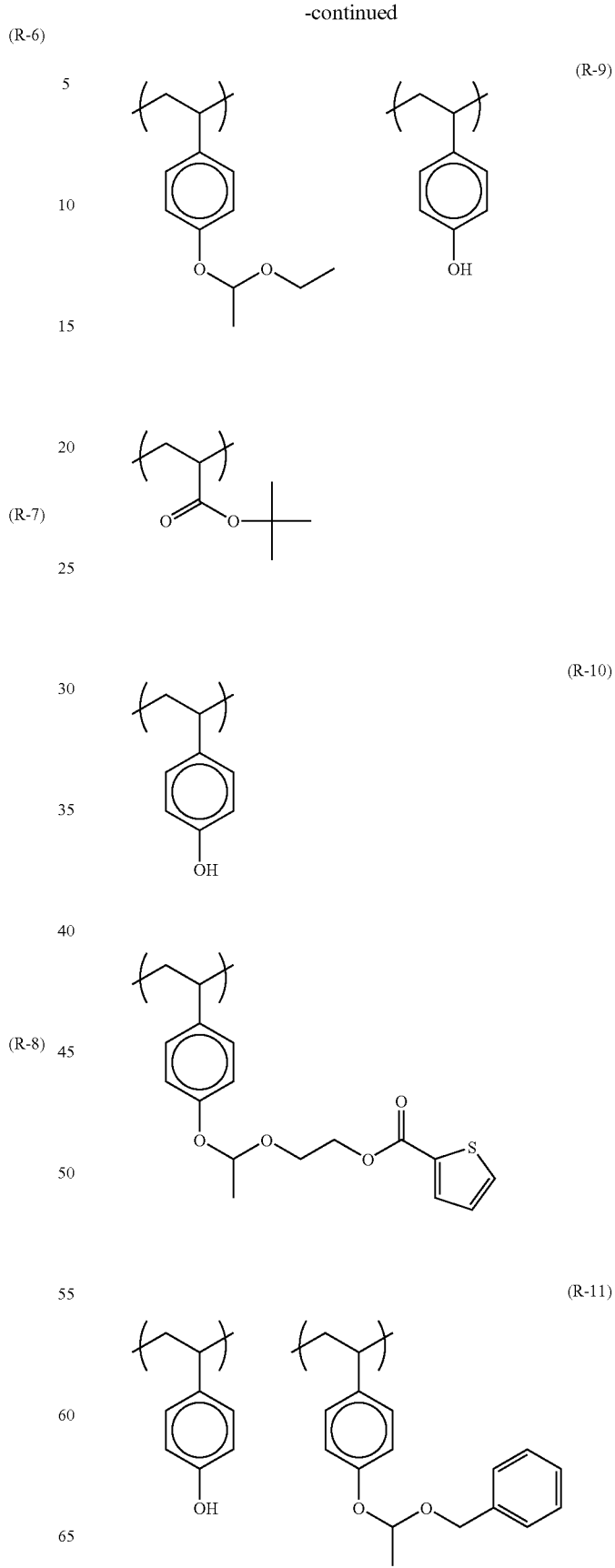
(R-9)
(R-10)
(R-11)

(R-12)
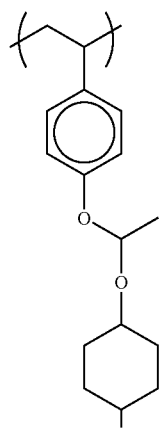
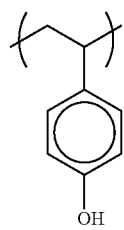
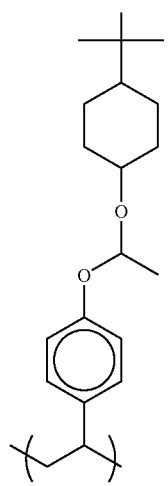
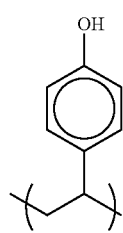
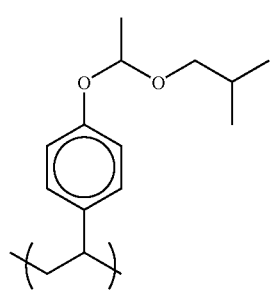
(R-13)
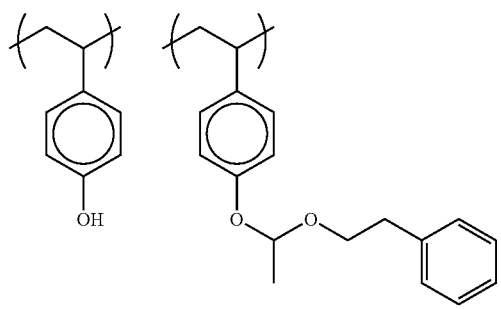
(R-14)
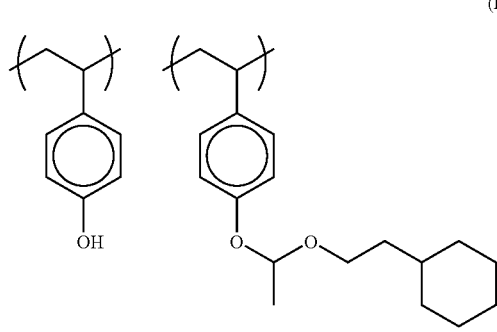
(R-15)
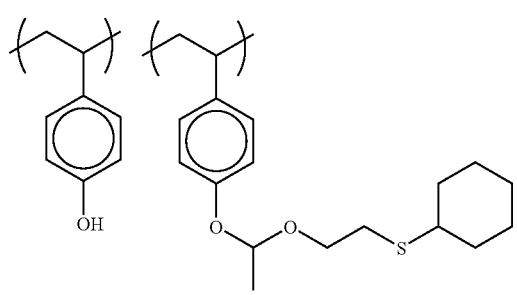
(R-16)
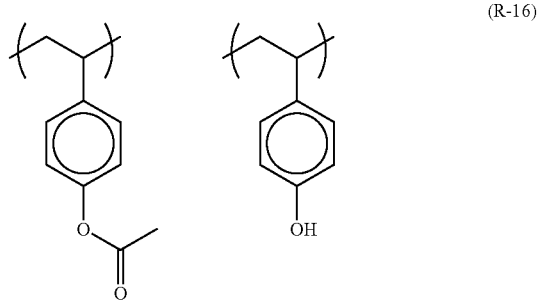
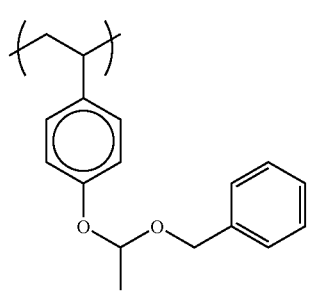

(R-17)
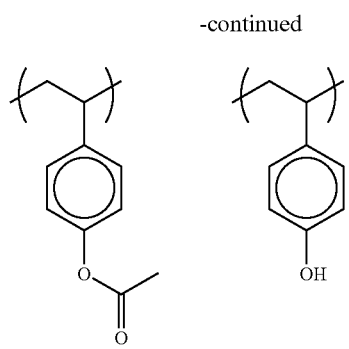
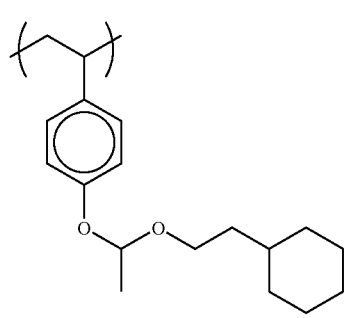
(R-18)
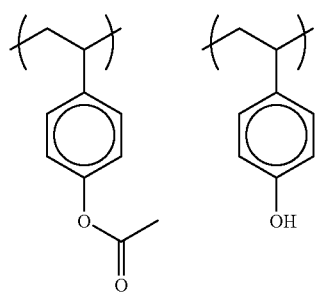
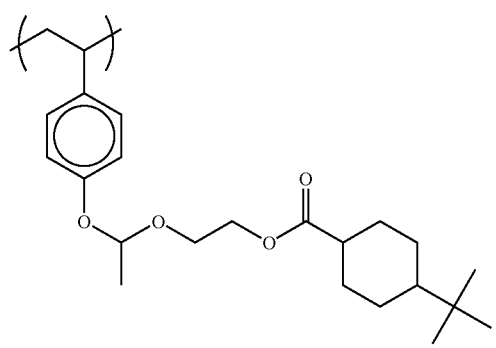
(R-19)
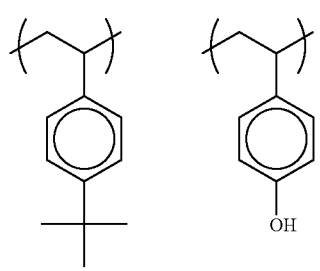
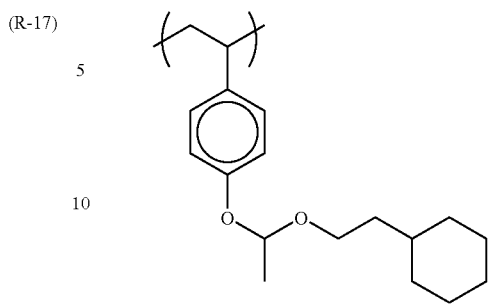
(R-20)
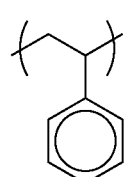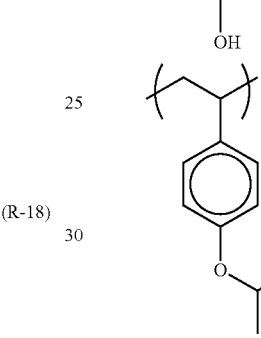
(R-21)
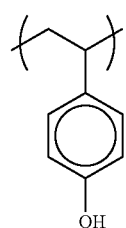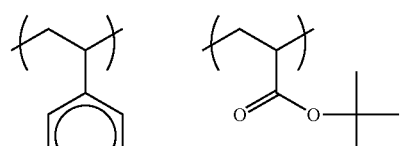
(R-22)
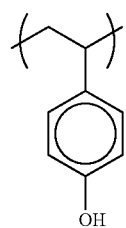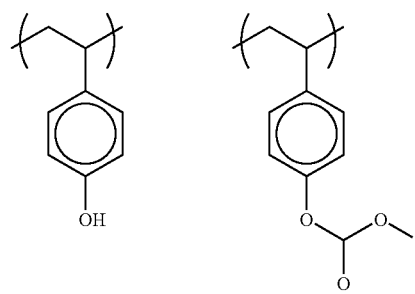
(R-23)
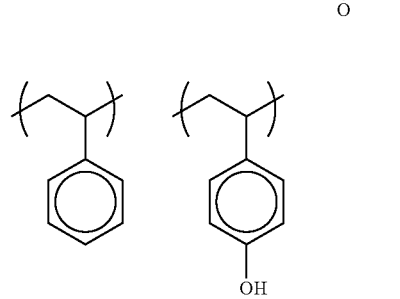

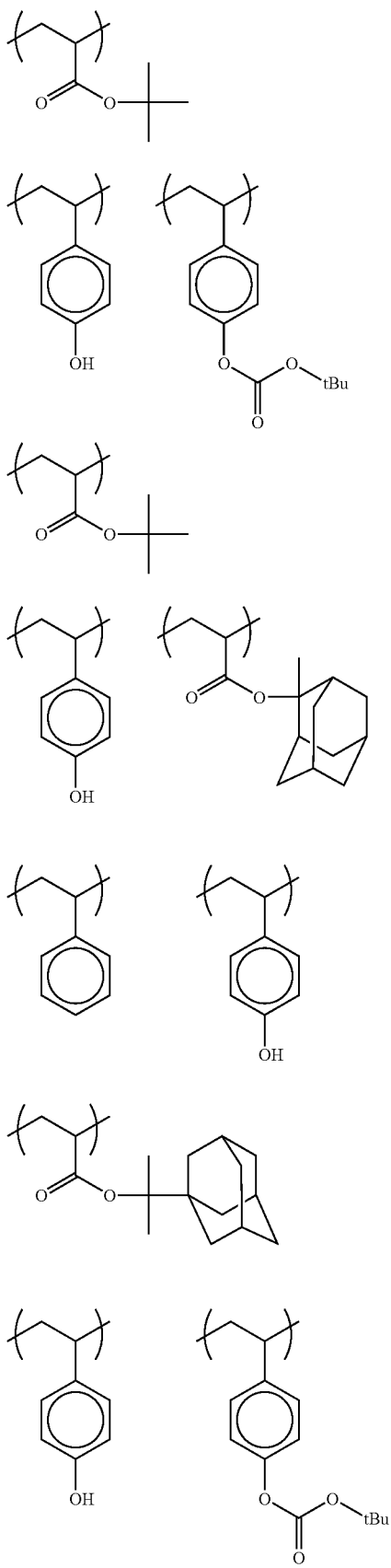
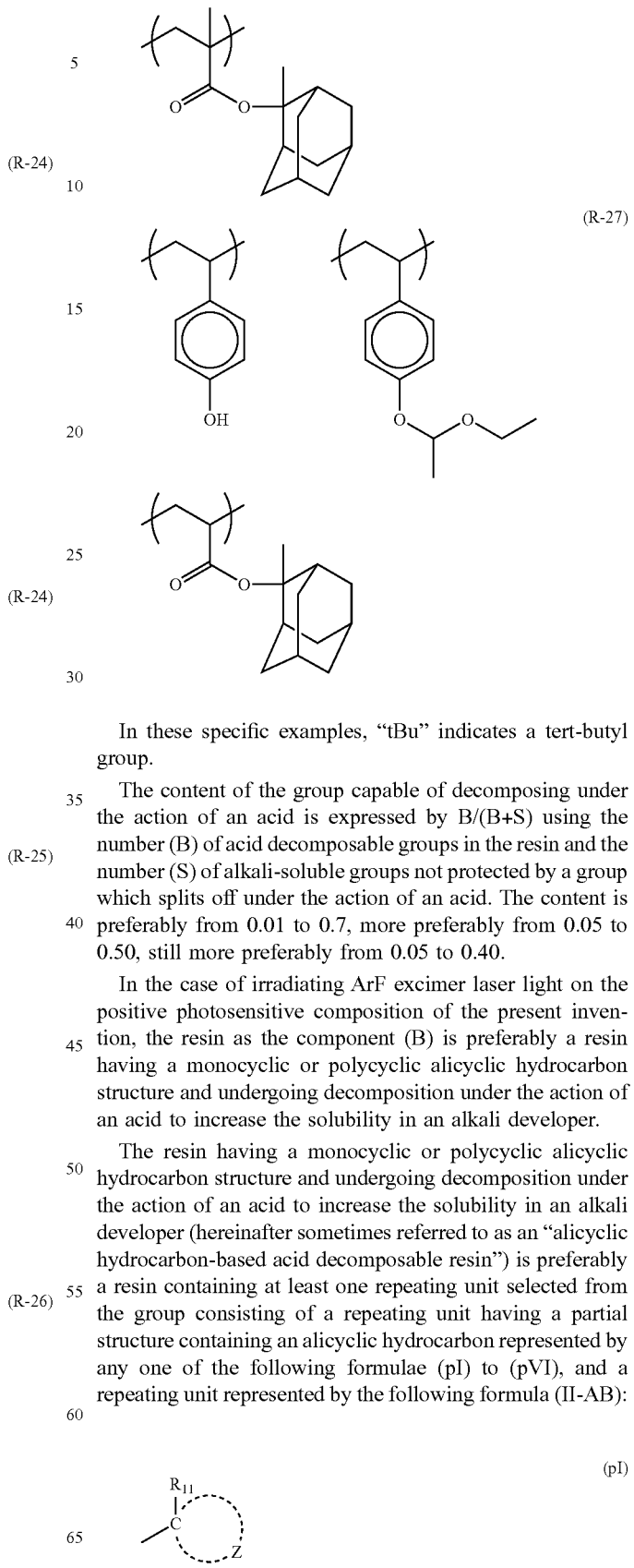

In these specific examples, "tBu" indicates a tert-butyl group.

The content of the group capable of decomposing under the action of an acid is expressed by B/(B+S) using the number (B) of acid decomposable groups in the resin and the number (S) of alkali-soluble groups not protected by a group which splits off under the action of an acid. The content is preferably from 0.01 to 0.7, more preferably from 0.05 to 0.50, still more preferably from 0.05 to 0.40.

In the case of irradiating ArF excimer laser light on the positive photosensitive composition of the present invention, the resin as the component (B) is preferably a resin having a monocyclic or polycyclic alicyclic hydrocarbon structure and undergoing decomposition under the action of an acid to increase the solubility in an alkali developer.

The resin having a monocyclic or polycyclic alicyclic hydrocarbon structure and undergoing decomposition under the action of an acid to increase the solubility in an alkali developer (hereinafter sometimes referred to as an "alicyclic hydrocarbon-based acid decomposable resin") is preferably a resin containing at least one repeating unit selected from the group consisting of a repeating unit having a partial structure containing an alicyclic hydrocarbon represented by any one of the following formulae (pI) to (pVI), and a repeating unit represented by the following formula (II-AB):

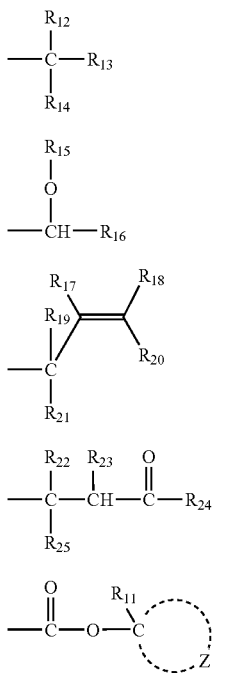

(pII)

(pIII)

(pIV)

(pV)

(pVI)

wherein $R_{11}$ represents a methyl group, an ethyl group, an n-propyl group, an isopropyl group, an n-butyl group, an isobutyl group or a sec-butyl group, Z represents an atomic group necessary for forming an alicyclic hydrocarbon group together with the carbon atom, $R_{12}$ to $R_{16}$ each independently represents a linear or branched alkyl group having from 1 to 4 carbon atoms or an alicyclic hydrocarbon group, provided that at least one of $R_{12}$ to $R_{14}$ or either one of $R_{15}$ and $R_{16}$ represents an alicyclic hydrocarbon group, $R_{17}$ to $R_{21}$ each independently represents a hydrogen atom, a linear or branched alkyl group having from 1 to 4 carbon atoms or an alicyclic hydrocarbon group, provided that at least one of $R_{17}$ to $R_{21}$ represents an alicyclic hydrocarbon group and that either one of $R_{19}$ and $R_{21}$ represents a linear or branched alkyl group having from 1 to 4 carbon atoms or an alicyclic hydrocarbon group, $R_{22}$ to $R_{25}$ each independently represents a hydrogen atom, a linear or branched alkyl group having from 1 to 4 carbon atoms or an alicyclic hydrocarbon group, provided that at least one of $R_{22}$ to $R_{25}$ represents an alicyclic hydrocarbon group, and $R_{23}$ and $R_{24}$ may combine with each other to form a ring).

(II-AB)

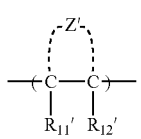

wherein $R_{11}'$ and $R_{12}'$ each independently represents a hydrogen atom, a cyano group, a halogen atom or an alkyl group, and Z' represents an atomic group for forming an alicyclic structure containing two bonded carbon atoms (C—C).

Formula (II-AB) is preferably the following formula (II-A) or (II-B)

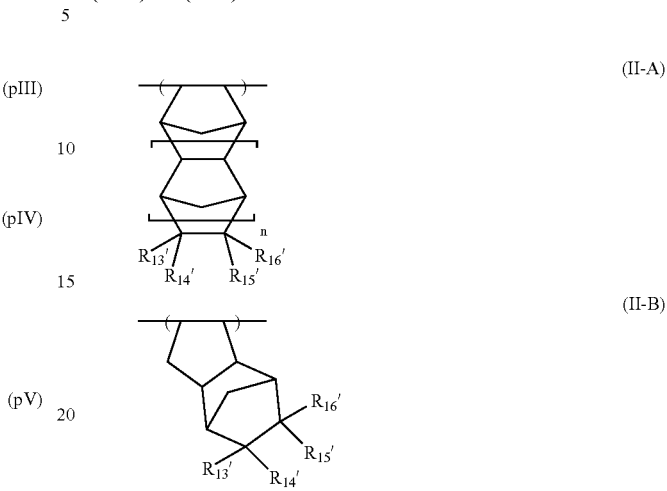

wherein $R_{13}'$ to $R_{16}'$ each independently represents a hydrogen atom, a halogen atom, a cyano group, —COOH, —COOR$_5$, a group capable of decomposing under the action of an acid, —C(=O)—X-A'-R$_{17}'$, an alkyl or cyclic hydrocarbon group, $R_5$ represents an alkyl group, a cyclic hydrocarbon group or a —Y group shown below, X represents an oxygen atom, a sulfur atom, —NH—, —NHSO$_2$— or —NHSO$_2$NH—, A' represents a sing bond or a divalent linking group, $R_{17}'$ represents —COOH, —COOR$_5$, —CN, a hydroxyl group, an alkoxy group, —CO—NH—R$_6$, —CO—NH—SO$_2$—R$_6$ or a —Y group shown below, $R_6$ represents an alkyl group or a cyclic hydrocarbon group, at least two out of $R_{13}'$ to $R_6'$ may combine to form a ring, and n represents 0 or 1: —Y group:

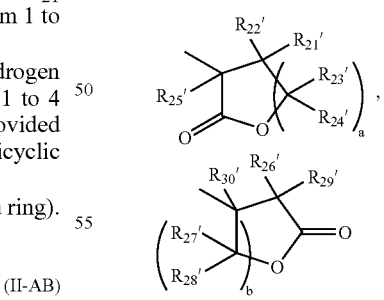

wherein $R_{21}'$ to $R_{30}'$ each independently represents a hydrogen atom or an alkyl group, and a and b each represents 1 or 2.

In formulae (pI) to (pVI), the alkyl group represented by $R_{12}$ to $R_{25}$ is a linear or branched alkyl group having from 1 to 4 carbon atoms. Examples of the alkyl group include a methyl group, an ethyl group, an n-propyl group, an isopropyl group, an n-butyl group, an isobutyl group, a sec-butyl group and a tert-butyl group.

Examples of the substituent which may be substituted to the alkyl group include an alkoxy group having from 1 to 4 carbon atoms, a halogen atom (e.g., fluorine, chlorine, bromine, iodine), an acyl group, an acyloxy group, a cyano group, a hydroxyl group, a carboxy group, an alkoxycarbonyl group and a nitro group.

The alicyclic hydrocarbon group represented by $R_{12}$ to $R_{25}$ and the alicyclic hydrocarbon group formed by Z and the carbon atoms each may be monocyclic or polycyclic. Specific examples thereof include a group having a monocyclo-, bicyclo-, tricyclo- or tetracyclo-structure having 5 or more carbon atoms. The carbon number thereof is preferably from 6 to 30, more preferably from 7 to 25. These alicyclic hydrocarbon groups may have a substituent.

Preferred examples of the alicyclic hydrocarbon groups include an adamantyl group, a noradamantyl group, a decalin residue, a tricyclodecanyl group, a tetracyclo-dodecanyl group, a norbornyl group, a cedrol group, a cyclohexyl group, a cycloheptyl group, a cyclooctyl group, a cyclodecanyl group and a cyclododecanyl group. Among these, more preferred are an adamantyl group, a decalin residue, a norbornyl group, a cedrol group, a cyclohexyl group, a cycloheptyl group, a cyclooctyl group, a cyclodecanyl group and a cyclododecanyl group.

Examples of the substituent of the alicyclic hydrocarbon group include an alkyl group, a halogen atom, a hydroxyl group, an alkoxy group, a carboxyl group and an alkoxycarbonyl group. The alkyl group is preferably a lower alkyl group such as methyl group, ethyl group, propyl group, isopropyl group and butyl group, more preferably a methyl group, an ethyl group, a propyl group or an isopropyl group. Examples of the alkoxy group include an alkoxy group having from 1 to 4 carbon atoms, such as methoxy group, ethoxy group, propoxy group and butoxy group. The alkyl group, alkoxy group and alkoxycarbonyl group each may further have a substituent and examples of the substituent include a hydroxyl group, a halogen atom and an alkoxy group.

The structures represented by formulae (pI) to (pVI) each can be used for the protection of an alkali-soluble group in the resin. Examples of the alkali-soluble group include various groups known in this technical field.

Specific examples thereof include a carboxylic acid group, a sulfonic acid group, a phenol group and a thiol group. Among these, preferred are a carboxylic acid group and a sulfonic acid group.

Preferred examples of the alkali-soluble group protected by a structure represented by any one of formulae (pI) to (pVI) in the resin include structures where the hydrogen atom of a carboxyl group is substituted by a structure represented by any one of formulae (pI) to (pVI).

The repeating unit having an alkali-soluble group protected by a structure represented by any one of formulae (pI) to (pVI) is preferably a repeating unit represented by the following formula (pA):

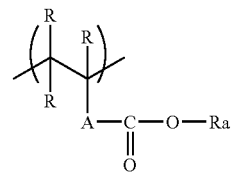

(pA)

wherein R represents a hydrogen atom, a halogen atom or a linear or branched alkyl group having from 1 to 4 carbon atoms, and multiple Rs may be the same or different;

A represents a single bond, or a sole group or a combination of two or more groups selected from the group consisting of an alkylene group, an ether group, a thioether group, a carbonyl group, an ester group, an amido group, a sulfonamido group, a urethane group and a urea group; and Ra represents any one group of formulae (pI) to (pVI).

The repeating unit represented by formula (pA) is most preferably a repeating unit comprising 2-alkyl-2-adamantyl (meth)acrylate or dialkyl(l-adamantyl)methyl(meth)acrylate.

Specific examples of the repeating unit represented by formula (pA) are set forth below.

(In formulae, Rx is H, $CH_3$ or $CF_3$.)

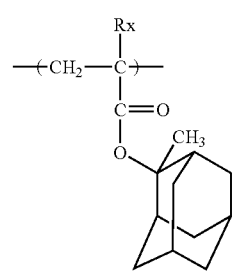

1

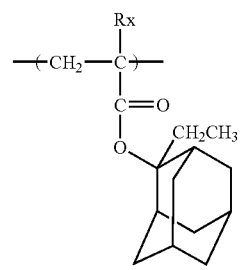

2

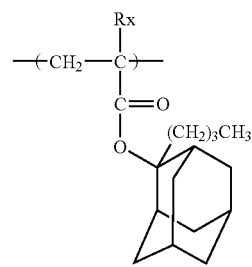

3

4
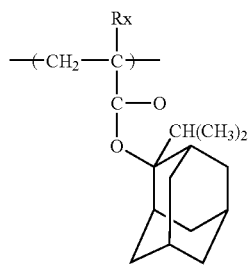
5
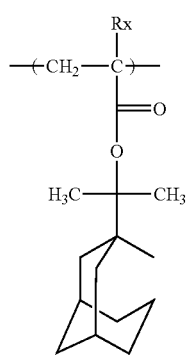
6
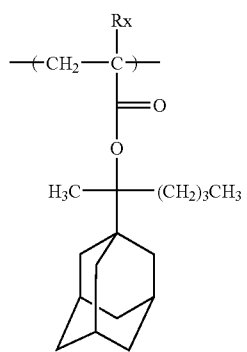
7
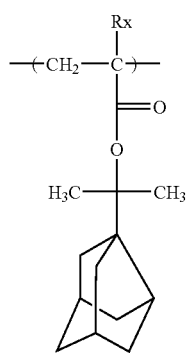
8
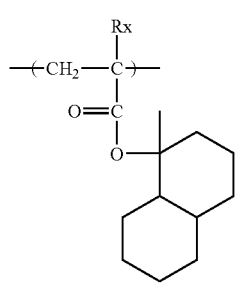
9
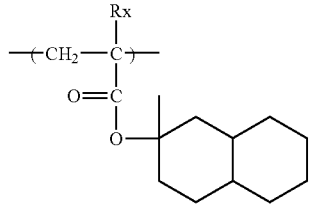
10
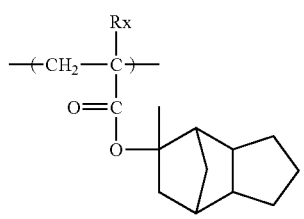
11
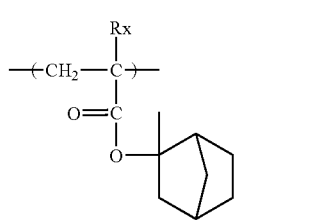
12
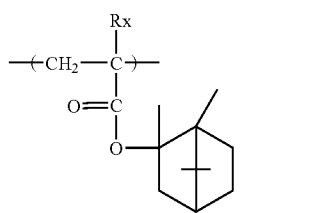
13
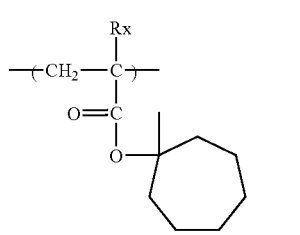
14
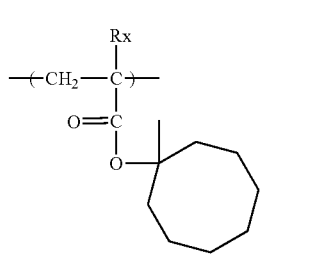
15
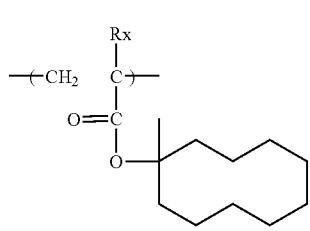

-continued

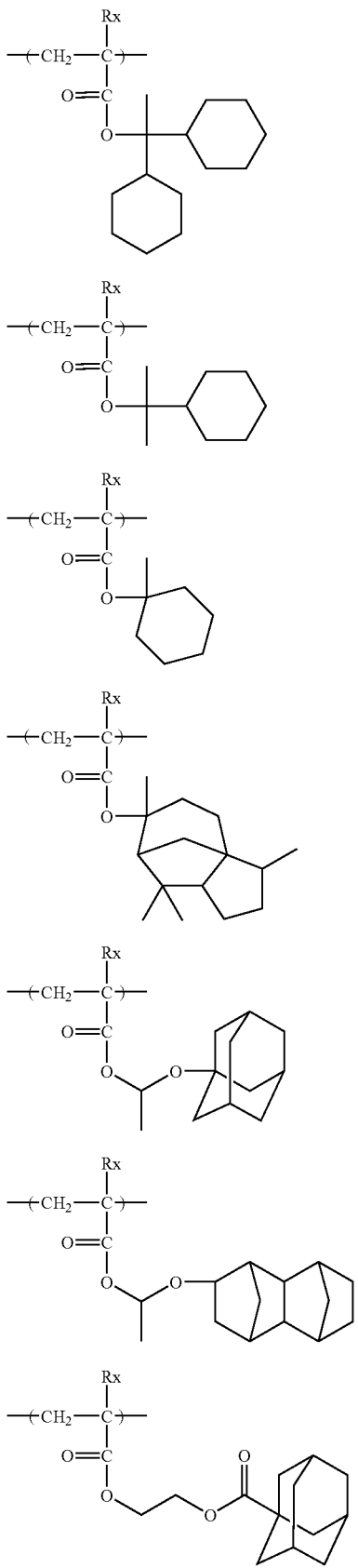

-continued

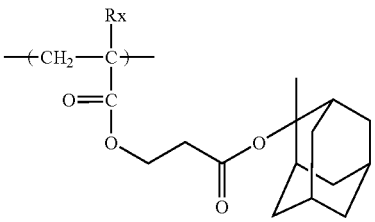

Examples of the halogen atom represented by $R_{11}'$ and $R_{12}'$ in formula (II-AB) include a chlorine atom, a bromine atom, a fluorine atom and an iodine atom.

The alkyl group represented by $R_{11}'$ and $R_{12}'$ is preferably a linear or branched alkyl group having from 1 to 10 carbon atoms, more preferably a linear or branched alkyl group having from 1 to 6 carbon atoms, still more preferably a methyl group, an ethyl group, a propyl group, an isopropyl group, an n-butyl group, an isobutyl group, a sec-butyl group or a tert-butyl group.

Examples of the substituent which is further substituted to the alkyl group include a hydroxyl group, a halogen atom, a carboxyl group, an alkoxy group, an acyl group, a cyano group and an acyloxy group. Examples of the halogen atom include a chlorine atom, a bromine atom, a fluorine atom and an iodine atom, examples of the alkoxy group include an alkoxy group having from 1 to 4 carbon atoms, such as methoxy group, ethoxy group, propoxy group and butoxy group, examples of the acyl group include a formyl group and an acetyl group, and examples of the acyloxy group include an acetoxy group.

The atomic group for forming an alicyclic structure, represented by Z', is an atomic group for forming a repeating unit of alicyclic hydrocarbon which may have a substituent, in the resin and among these atomic groups, preferred are an atomic group for forming a crosslinked alicyclic structure to form a crosslinked alicyclic hydrocarbon repeating unit.

Examples of the skeleton of alicyclic hydrocarbon formed are the same as those of the alicyclic hydrocarbon group of $R_{11}$ to $R_{25}$ in formulae (pI) to (pVI)

The alicyclic hydrocarbon skeleton may have a substituent and examples of the substituent include $R_{13}'$ to $R_{16}'$ in formulae (II-A) and (II-B).

Among the crosslinked alicyclic hydrocarbon repeating units, the repeating units represented by formulae (II-A) and (II-B) are more preferred.

In the alicyclic hydrocarbon-based acid decomposable resin for use in the present invention, the acid decomposable group may be contained in the —C(=O)—X—A'—$R_{17}'$ or may be contained as a substituent of Z' in formula (II-AB).

The structure of the acid decomposable group is represented by —C(=O)—$X_1$—$R_0$.

In this formula, $R_0$ represents, for example, a tertiary alkyl group such as tert-butyl group and tert-amyl group, a 1-alkoxyethyl group such as isoboronyl group, 1-ethoxyethyl group, 1-butoxyethyl group, 1-isobutoxyethyl group and 1-cyclohexyloxyethyl group, an alkoxymethyl group such as 1-methoxymethyl group and 1-ethoxymethyl group, a 3-oxoalkyl group, a tetrahydropyranyl group, a tetrahydrofuranyl group, a trialkylsilylester group, a 3-oxocyclohexyl ester group, a 2-methyl-2-adamantyl group or a mevalonic lactone residue, and $X_1$ has the same meaning as X above.

Examples of the halogen atom represented by $R_{13}'$ to $R_{16}'$ include a chlorine atom, a bromine atom, a fluorine atom and an iodine atom.

The alkyl group represented by $R_{13}'$ to $R_{16}'$, $R_5$, $R_6$ and $R_{21}'$ to $R_{30}'$ is preferably a linear or branched alkyl group having from 1 to 10 carbon atoms, more preferably a linear or branched alkyl group having from 1 to 6 carbon atoms, still more preferably a methyl group, an ethyl group, a propyl group, an isopropyl group, an n-butyl group, an isobutyl group, a sec-butyl group or a tert-butyl group.

The cyclic hydrocarbon group represented by $R_{13}'$ to $R_{16}'$, $R_5$ and $R_6$ is, for example, a cyclic alkyl group or a crosslinked hydrocarbon and examples thereof include a cyclopropyl group, a cyclopentyl group, a cyclohexyl group, an adamantyl group, a 2-methyl-2-adamantyl group, a norbornyl group, a boronyl group, an isoboronyl group, a tricyclodecanyl group, a dicyclopentenyl group, a norbornane epoxy group, a menthyl group, an isomenthyl group, a neomenthyl group and a tetracyclododecanyl group.

The ring formed when at least two out of $R_{13}'$ to $R_{16}'$ are combined includes a ring having from 5 to 12 carbon atoms, such as cyclopentene, cyclohexene, cycloheptane and cyclooctane.

The alkoxy group represented by $R_{17}'$ includes an alkoxy group having from 1 to 4 carbon atoms, such as methoxy group, ethoxy group, propoxy group and butoxy group.

Examples of the substituent which is further substituted to the alkyl group, cyclic hydrocarbon group and alkoxy group include a hydroxyl group, a halogen atom, a carboxyl group, an alkoxy group, an acyl group, a cyano group, an acyloxy group, an alkyl group and a cyclic hydrocarbon group. Examples of the halogen atom include a chlorine atom, a bromine atom, a fluorine atom and an iodine atom, examples of the alkoxy group include an alkoxy group having from 1 to 4 carbon atoms, such as methoxy group, ethoxy group, propoxy group and butoxy group, examples of the acyl group include a formyl group and an acetyl group, and examples of the acyloxy group include an acetoxy group.

Examples of the alkyl group and cyclic hydrocarbon group include those described above.

The divalent linking group represented by A' includes a sole group or a combination of two or more groups, selected from the group consisting of an alkylene group, an ether group, a thioether group, a carbonyl group, an ester group, an amido group, a sulfonamido group, a urethane group and a urea group.

In the alicyclic hydrocarbon-based acid decomposable resin for use in the present invention, the group capable of decomposing under the action of an acid may be contained in at least one repeating unit out of the repeating unit having a partial structure containing an alicyclic hydrocarbon represented by any one of formulae (pI) to (pVI), the repeating unit represented by formula (II-AB), and the repeating unit of a copolymerization component which is described later.

Various substituents $R_{13}'$ to $R_{16}'$ in formulae (II-A) and (II-B) work out to the substituents of an atomic group for forming an alicyclic structure in formula (II-AB) or an atomic group Z for forming a crosslinked alicyclic structure.

Specific examples of the repeating units represented by formulae (II-A) and (II-B) are set forth below, but the present invention is not limited to these specific examples.

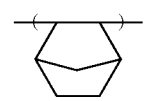

[II-1]

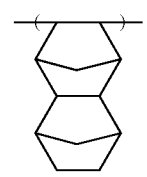

[II-2]

[II-3]

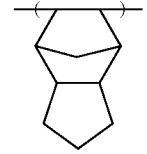

[II-4]

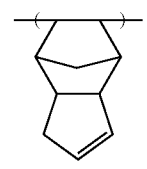

[II-5]

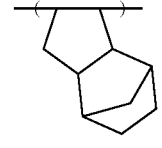

[II-6]

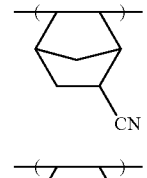

[II-7]

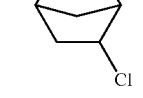

[II-8]

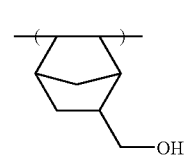

[II-9]

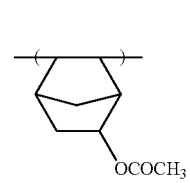

[II-10]

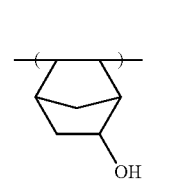

[II-11] 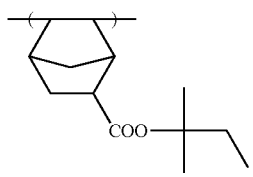
[II-12] 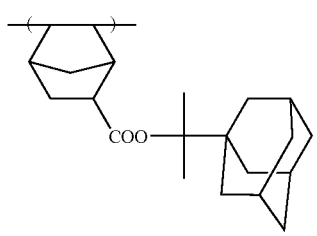
[II-13] 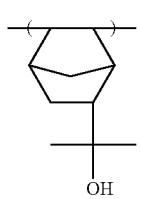
[II-14] 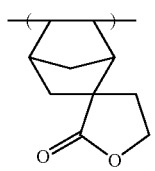
[II-15] 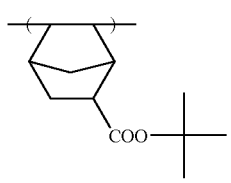
[II-16] 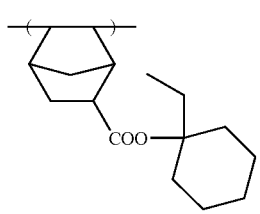
[II-17] 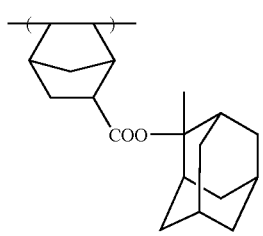
[II-18] 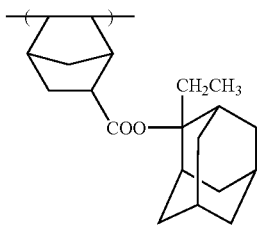
[II-19] 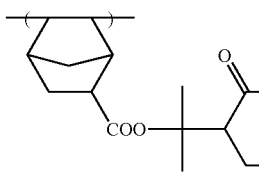
[II-20] 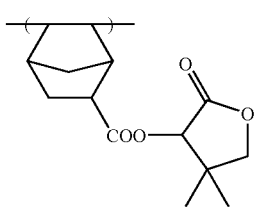
[II-21] 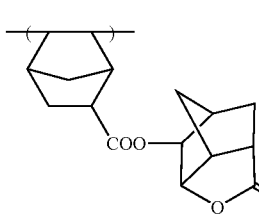
[II-22] 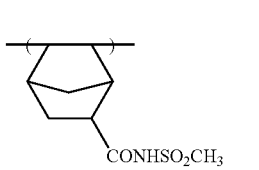
[II-23] 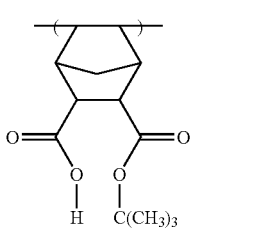
[II-24] 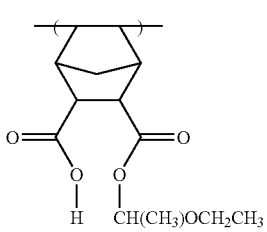

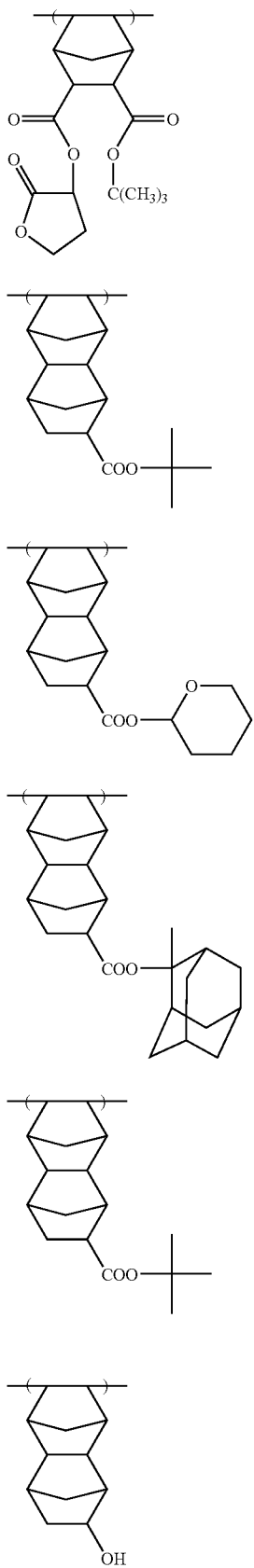
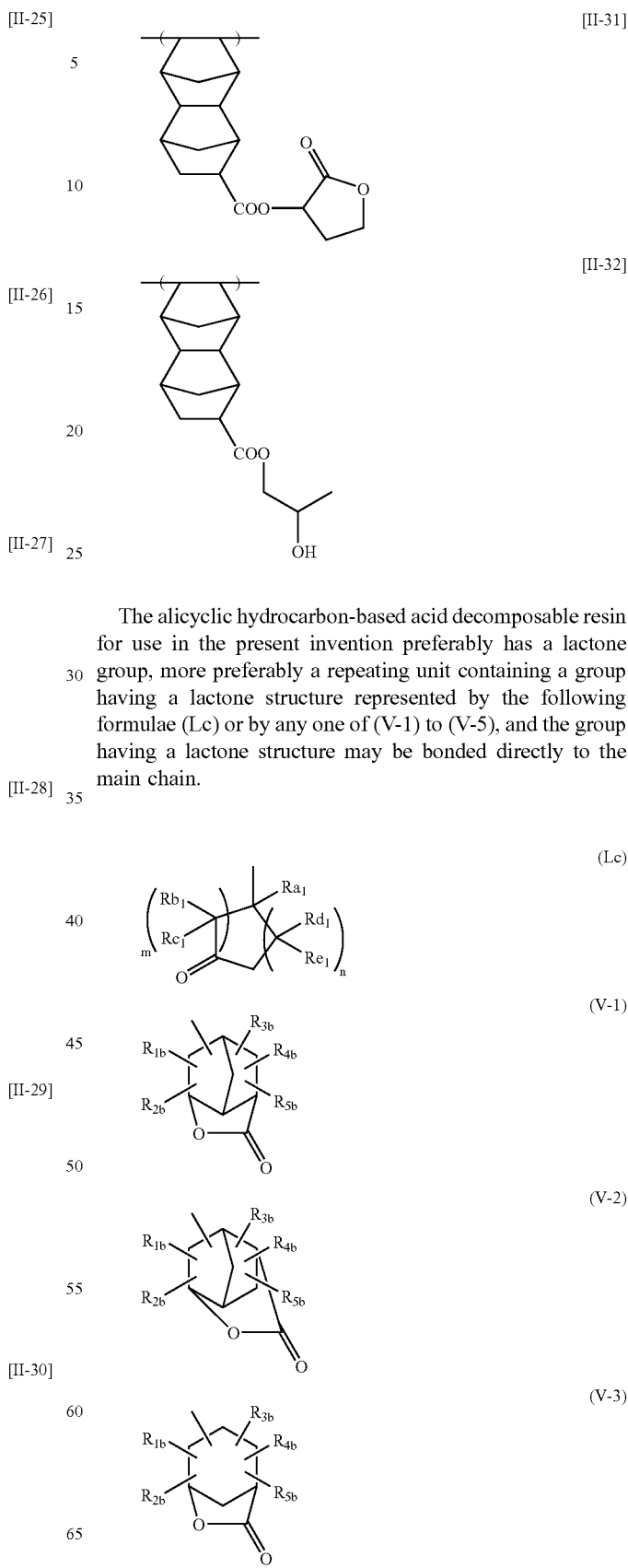
The alicyclic hydrocarbon-based acid decomposable resin for use in the present invention preferably has a lactone group, more preferably a repeating unit containing a group having a lactone structure represented by the following formulae (Lc) or by any one of (V-1) to (V-5), and the group having a lactone structure may be bonded directly to the main chain.

-continued

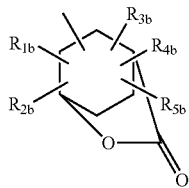
(V-4)

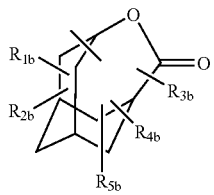
(V-5)

In formula (Lc), $Ra_1$, $Rb_1$, $Rc_1$, $Rd_1$ and $Re_1$ each independently represents a hydrogen atom or an alkyl group, m and n each independently represents an integer of 0 to 3, and m+n is from 2 to 6.

In formulae (V-1) to (V-5), $R_{1b}$ to $R_{5b}$ each independently represents a hydrogen atom, an alkyl group, a cycloalkyl group, an alkoxy group, an alkoxycarbonyl group, an alkylsulfonylimino group or an alkenyl group, and two out of $R_{1b}$ to $R_{5b}$ may combine to form a ring.

The alkyl group represented by $Ra_1$ to $Re_1$ in formula (Lc) and the alkyl group in the alkyl group, alkoxy group, alkoxycarbonyl group and alkylsulfonylimino group represented by $R_{1b}$ to $R_{5b}$ in formulae (V-1) to (V-5) include a linear or branched alkyl group and may have a substituent Examples of the repeating unit containing a group having a lactone structure represented by formula (Lc) or by any one of formulae (V-1) to (V-5) include a repeating unit where at least one of $R_{13}'$ to $R_{16}'$ in formula (II-A) or (II-B) has a group represented by formula (Lc) or by any one of formulae (V-1) to (V-5) (for example, where $R_5$ of —$COOR_5$ is a group represented by formula (Lc) or by any one of formulae (V-1) to (V-5)), and a repeating unit represented by the following formula (AI):

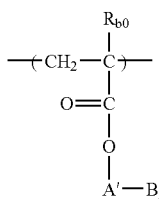
(AI)

In formula (AI), $R_{b0}$ represents a hydrogen atom, a halogen atom or an alkyl group having from 1 to 4 carbon atoms.

Examples of the halogen atom represented by $R_{b0}$ include a fluorine atom, a chlorine atom, a bromine atom and an iodine atom.

$R_{b0}$ is preferably a hydrogen atom.

A' represents a single bond, an ether group, an ester group, a carbonyl group, an alkylene group or a divalent group comprising a combination thereof.

$B_2$ represents a group represented by formula (Lc) or by any one of formulae (V-1) to (V-5).

Specific examples of the repeating unit containing a group having a lactone structure are set forth below, but the present invention is not limited thereto.

(In formulae, Rx is H, $CH_3$ or $CF_3$)

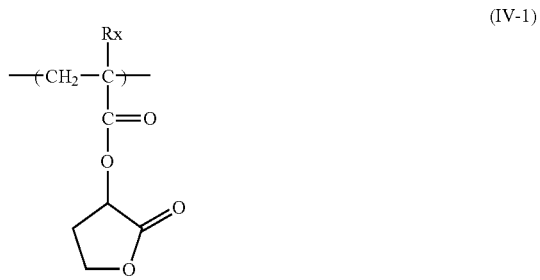
(IV-1)

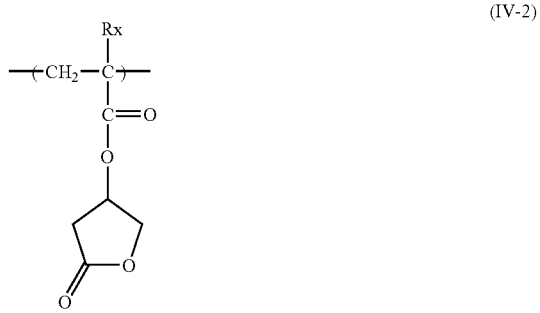
(IV-2)

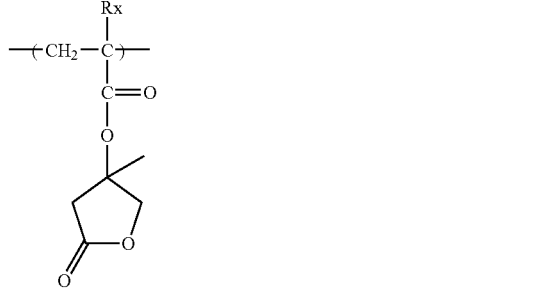
(IV-3)

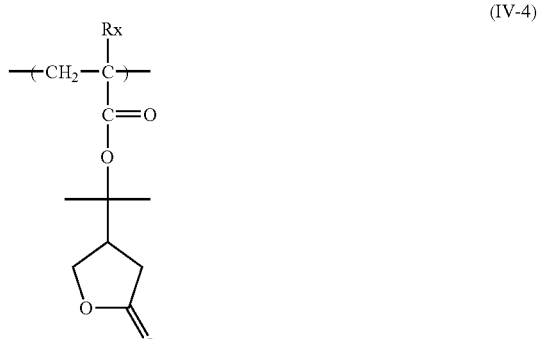
(IV-4)

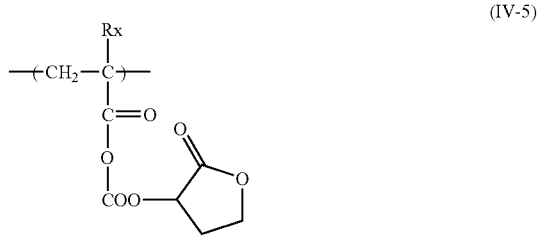
(IV-5)

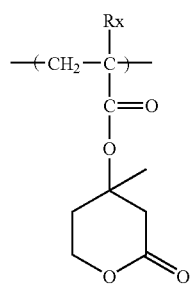 (IV-6)
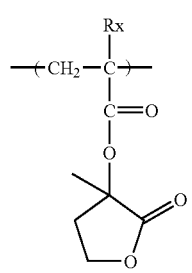 (IV-7)
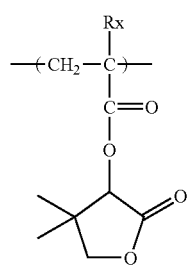 (IV-8)
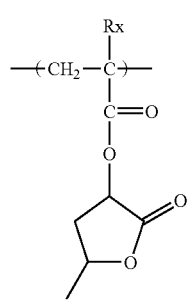 (IV-9)
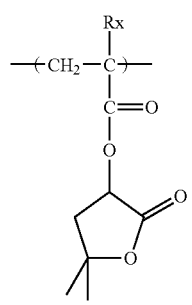 (IV-10)
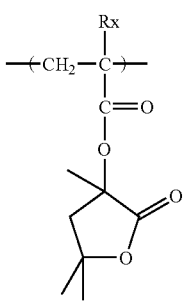 (IV-11)
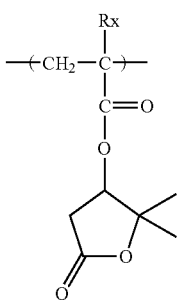 (IV-12)
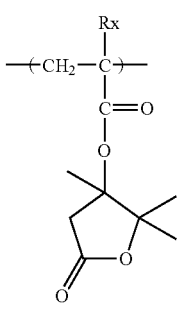 (IV-13)
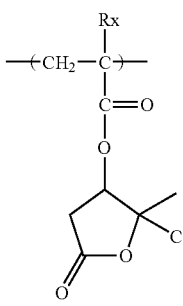 (IV-14)
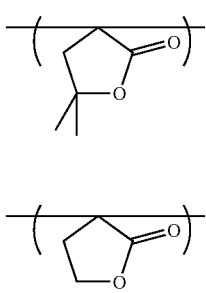 (IV-15) (IV-16)
(In formulae, Rx is H, CH₃ or CF₃)

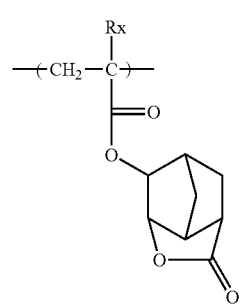 (Ib-1)
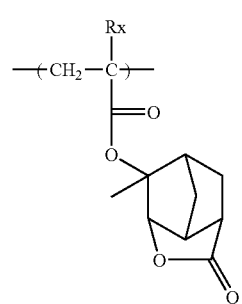 (Ib-2)
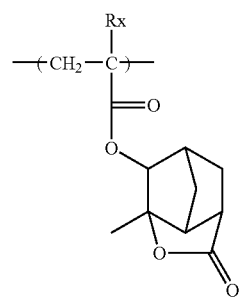 (Ib-3)
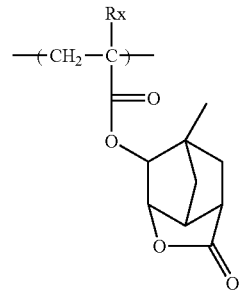 (Ib-4)
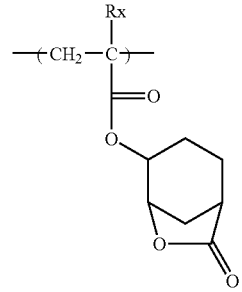 (Ib-5)
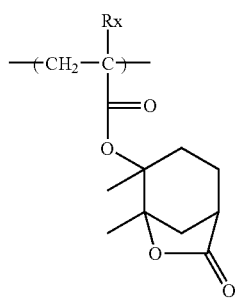 (Ib-6)
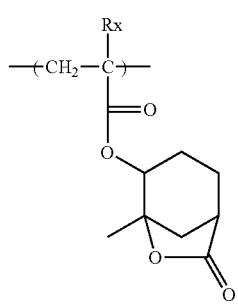 (Ib-7)
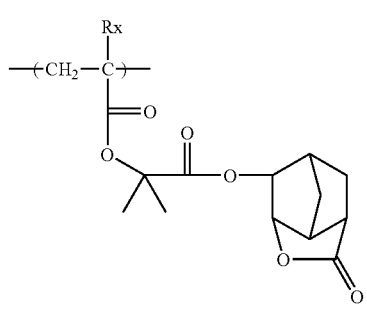 (Ib-8)
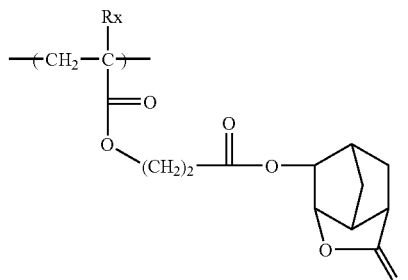 (Ib-9)
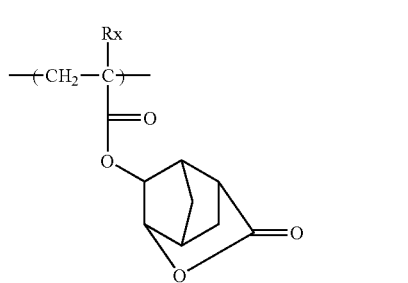 (Ib-10)

-continued

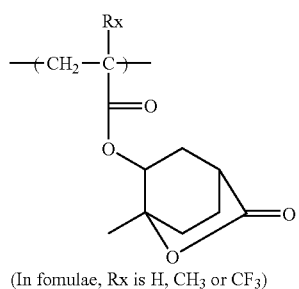

(Ib-11)

(In formulae, Rx is H, CH₃ or CF₃)

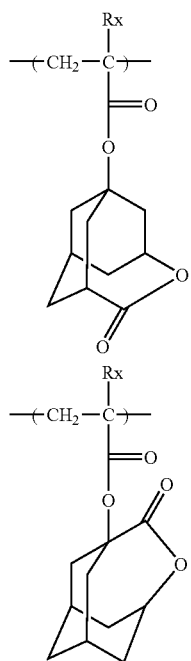

-continued

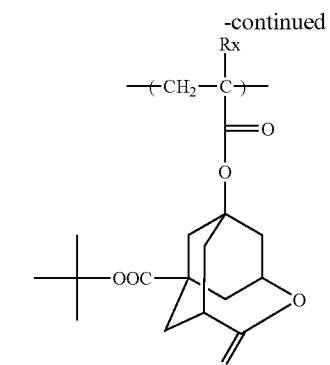

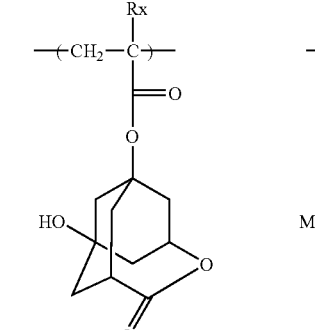

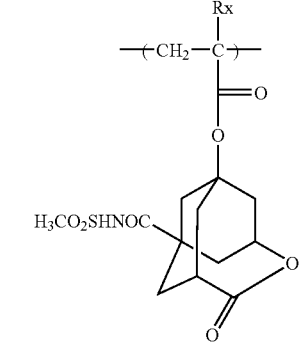

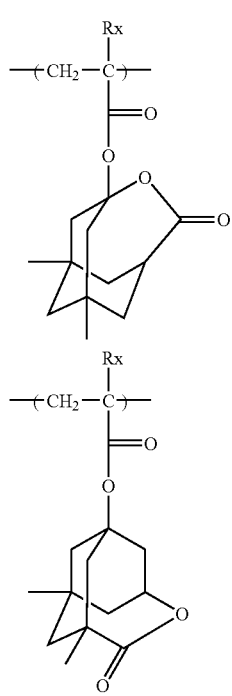

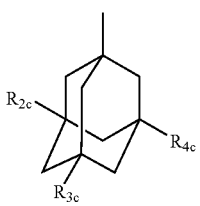

The alicyclic hydrocarbon-based acid decomposable resin for use in the present invention may contain a repeating unit having a group represented by the following formula (VII):

$$\text{(VII)}$$

[structure with $R_{2c}$, $R_{3c}$, $R_{4c}$ substituents on adamantane]

wherein $R_{2c}$ to $R_{4c}$ each independently represents a hydrogen atom or a hydroxyl group, provided that at least one of $R_{2c}$ to $R_{4c}$ represents a hydroxyl group.

The group represented by formula (VII) is preferably a dihydroxy form or a monohydroxy form, more preferably a dihydroxy form.

Examples of the repeating unit having a group represented by formula (VII) include a repeating unit where at least one of $R_{13}'$ to $R_{16}'$ in formula (II-A) or (II-B) has a group represented by formula (VII) (for example, where $R_5$ in —COO$R_5$ is a group represented by formula (VII)), and a repeating unit represented by the following formula (AII):

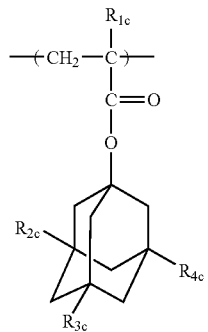
(AII)

wherein $R_{1c}$ represents a hydrogen atom or a methyl group, and $R_{2c}$ to $R_{4c}$ each independently represents a hydrogen atom or a hydroxyl group, provided that at least one of $R_{2c}$ to $R_{4c}$ represents a hydroxyl group. A repeating unit where two out of $R_{2c}$ to $R_{4c}$ are a hydroxyl group is preferred.

Specific examples of the repeating unit having the structure represented by formula (AII) are set forth below, but the present invention is not limited thereto.

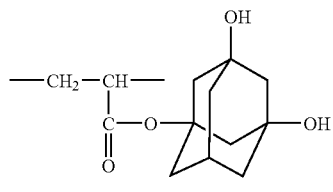
(1)

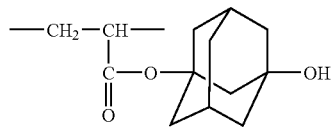
(2)

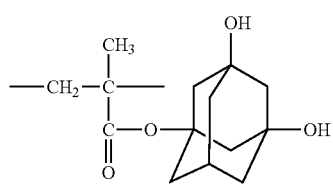
(3)

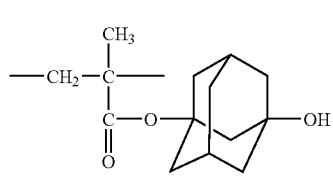
(4)

The alicyclic hydrocarbon-based acid decomposable resin for use in the present invention may contain a repeating unit represented by the following formula (VIII):

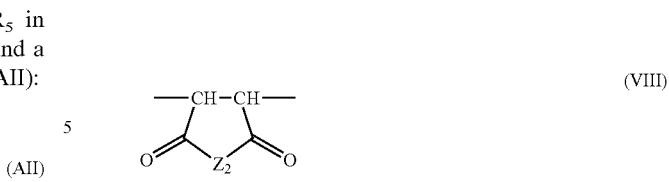
(VIII)

wherein $Z_2$ represents —O— or —N($R_{41}$)—, $R_{41}$, represents a hydrogen atom, a hydroxyl group, an alkyl group or —OSO$_2$—$R_{42}$, and $R_{42}$ represents an alkyl group, a cycloalkyl group or a camphor residue. The alkyl group represented by $R_{41}$ and $R_{42}$ may be substituted by a halogen atom (preferably a fluorine atom) or the like.

Specific examples of the repeating unit represented by formula (VIII) are set forth below, but the present invention is not limited thereto.

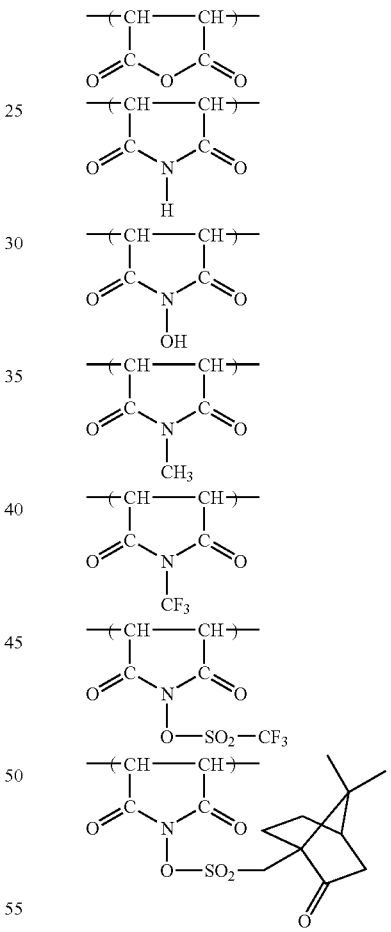

The alicyclic hydrocarbon-based acid decomposable resin for use in the present invention preferably has a repeating unit containing an alkali-soluble group, more preferably a repeating unit containing a carboxyl group. By having such a repeating unit, the resolution increases in uses of forming contact holes. The repeating unit containing a carboxyl group is preferably a repeating unit where a carboxyl group is directly bonded to the resin main chain, such as repeating unit by an acrylic acid or a methacrylic acid, or a repeating unit where a carboxyl group is bonded to the resin main chain through a linking group. The linking group may have a monocyclic or polycyclic hydrocarbon structure. Most preferred are an acrylic acid and a methacrylic acid.

The alicyclic hydrocarbon-based acid decomposable resin for use in the present invention may contain, in addition to the above-described repeating units, various repeating units for the purpose of controlling the dry etching resistance, suitability for standard developer, adhesion to substrate, resist profile and properties generally required of the resist, such as resolution, heat resistance and sensitivity.

Examples of such repeating structural units include repeating structural units corresponding to the monomers described below, but the present invention is not limited thereto.

By containing these repeating structural units, the performance required of the alicyclic hydrocarbon-based acid decomposable resin, particularly, (1) solubility in the coating solvent,
(2) film-forming property (glass transition point),
(3) alkali developability,
(4) film loss (selection of hydrophilic, hydro-phobic or alkali-soluble group),
(5) adhesion to substrate in unexposed area,
(6) dry etching resistance and the like can be subtly controlled.

Examples of the monomer include compounds having one addition polymerizable unsaturated bond, selected from acrylic acid esters, methacrylic acid esters, acrylamides, methacrylamides, allyl compounds, vinyl ethers and vinyl esters.

Other than these, an addition polymerizable unsaturated compound copolymerizable with the monomer corresponding to the above-described various repeating structural units may be copolymerized.

In the alicyclic hydrocarbon-based acid decomposable resin, the molar ratio of each repeating structural unit contained is appropriately determined to control the dry etching resistance of resist, suitability for standard developer, adhesion to substrate, resist profile and performances generally required of the resist, such as resolution, heat resistance and sensitivity.

Preferred embodiments of the alicyclic hydrocarbon-based acid decomposable resin for use in the present invention include:

(1) a resin having a partial structure containing an alicyclic hydrocarbon represented by any one of formulae (pI) to (pVI) (side chain type), and (2) a resin containing a repeating unit represented by formula (II-AB) (main chain type), and the resin of (2) further includes:

(3) a resin having a repeating unit represented by formula (II-AB), a maleic anhydride derivative and a (meth)acrylate structure (hybrid type).

In the alicyclic hydrocarbon-based acid decomposable resin, the content of the repeating unit having an acid decomposable group is preferably from 10 to 60 mol %, more preferably from 20 to 50 mol %, still more preferably from 25 to 40 mol %, based on all repeating structural units.

In the alicyclic hydrocarbon-based acid decomposable resin, the content of the repeating unit having a partial structure containing an alicyclic hydrocarbon represented by any one of formulae (pI) to (pVI) is preferably from 30 to 70 mol %, more preferably from 35 to 65 mol %, still more preferably from 40 to 60 mol %, based on all repeating structural units.

In the alicyclic hydrocarbon-based acid decomposable resin, the content of the repeating unit represented by formula (II-AB) is preferably from 10 to 60 mol %, more preferably from 15 to 55 mol %, still more preferably from 20 to 50 mol %, based on all repeating structural units.

In the resin, the content of the repeating unit based on the monomer as the further copolymerization component can also be appropriately selected according to the desired resist performance, but the content thereof is preferably 99 mol % or less, more preferably 90 mol % or less, still more preferably 80 mol % or less, based on the total molar number of the repeating structural unit having a partial structure containing an alicyclic hydrocarbon represented by any one of formulae (pI) to (pVI) and the repeating unit represented by formula (II-AB).

When the composition of the present invention is used for exposure with ArF, the resin preferably has no aromatic group in view of the transparency to ArF light.

The alicyclic hydrocarbon-based acid decomposable resin for use in the present invention can be synthesized by an ordinary method (for example, radical polymerization). In the general synthesis method, for example, monomer species are charged into a reaction vessel all at once or on the way of reaction and dissolved, if desired, in a reaction solvent such as tetrahydrofuran, 1,4-dioxane, ethers (e.g., diisopropyl ether), ketones (e.g., methyl ethyl ketone, methyl isobutyl ketone) and esters (e.g., ethyl acetate), or in a solvent which dissolves the composition of the present invention, such as propylene glycol monomethyl ether acetate described later. The obtained uniform solution is, if desired, heated in an inert gas atmosphere such as nitrogen or argon to start the polymerization by using a commercially available radical polymerization initiator (e.g., azo-based initiator, peroxide). If desired, the initiator may be added additionally or in parts. After the completion of reaction, the reactant is poured into a solvent and the desired polymer is recovered, for example, by a powder or solid recovery method. The reaction concentration is usually 20 mass % or more, preferably 30 mass % or more, more preferably 40 mass % or more, and the reaction temperature is from 10 to 150° C., preferably from 30 to 120° C., more preferably from 50 to 100° C.

In the case of using the composition of the present invention for the upper resist of a multilayer resist, the resin of the component (B) preferably has a silicon atom.

As for the resin having a silicon atom and undergoing decomposition under the action of an acid to increase the solubility in an alkali developer, a resin having a silicon atom in at least either main chain or side chain can be used. Examples of the resin having a siloxane structure in the side chain of resin include copolymers of an olefin-based monomer having a silicon atom in the side chain and a (meth) acrylic acid-based monomer having a maleic anhydride and an acid decomposable group in the side chain.

The resin having a silicon atom is preferably a resin having a trialkylsilyl structure or a monocyclic or polycyclic siloxane structure, more preferably a resin containing a repeating unit having a structure represented by any one of the following formulae (SS-1) to (SS-4), still more preferably a resin containing a (meth)acrylic acid ester-based, vinyl-based or acryl-based repeating unit having a structure represented by any one of formulae (SS-1) to (SS-4).

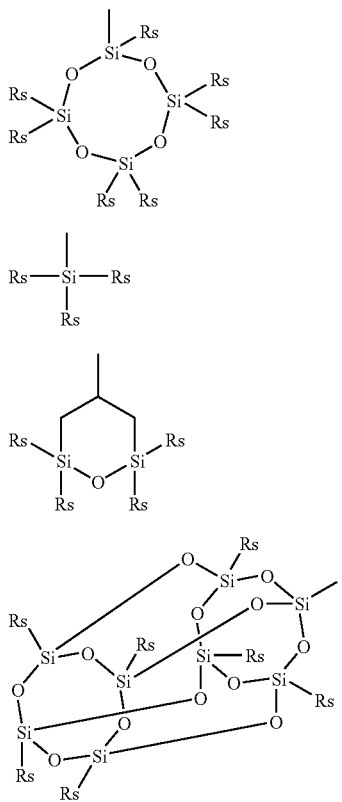

SS-1

SS-2

SS-3

SS-4

In formulae (SS-1) to (SS-4), Rs each independently represents an alkyl group having from 1 to 5 carbon atoms, preferably a methyl group or an ethyl group.

The resin having a silicon atom is preferably a resin containing two or more different repeating units having a silicon atom, more preferably a resin containing both (Sa) a repeating unit having from 1 to 4 silicon atoms and (Sb) a repeating unit having from 5 to 10 silicon atoms, still more preferably a resin containing at least one repeating unit having a structure represented by any one of formulae (SS-1) to (SS-3) and a repeating unit having a structure represented by formula (SS-4).

In the case of irradiating $F_2$ excimer laser light on the positive photosensitive composition of the present invention, the resin of the component (B) is preferably a resin having a structure that a fluorine atom is substituted to the main chain and/or the side chain of the polymer skeleton, and undergoing decomposition under the action of an acid to increase the solubility in an alkali developer (hereinafter sometimes referred to as a "fluorine group-containing resin"), more preferably a resin containing a hydroxyl group with the 1-position being substituted by a fluorine atom or a fluoroalkyl group, or a group where the hydroxyl group with the 1-position being substituted by a fluorine atom or a fluoroalkyl group is protected by an acid decomposable group, and most preferably a resin containing a hexafluoro-2-propanol structure or a structure that the hydroxyl group of hexafluoro-2-propanol is protected by an acid decomposable group. By introducing a fluorine atom, the transparency to far ultraviolet light, particularly $F_2$ (157 nm) light, can be enhanced.

Preferred examples of the fluorine group-containing resin as the acid decomposable resin (B) include a resin having at least one repeating unit represented by the following formulae (FA) to (FG):

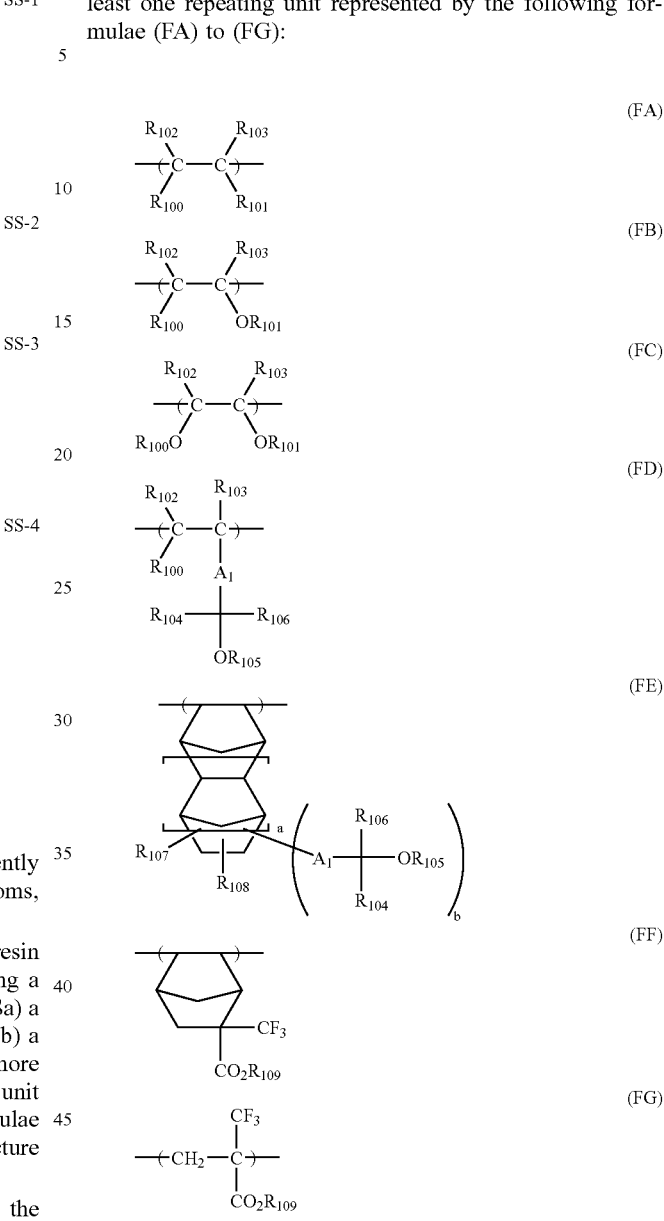

In these formulae, $R_{100}$ to $R_{103}$ each independently represents a hydrogen atom, a fluorine atom, an alkyl group, a cycloalkyl group, an aryl group, an aralkyl group, an alkenyl group, an alkynyl group, an acyl group or an acyloxy group.

$R_{104}$ and $R_{106}$ each is independently a hydrogen atom, a fluorine atom or an alkyl group and at least one of $R_{104}$ and $R_{106}$ is a fluorine atom or a fluoroalkyl group. $R_{104}$ and $R_{106}$ are preferably both a trifluoromethyl group.

$R_{105}$ is a hydrogen atom, an alkyl group, an acyl group, an alkoxycarbonyl group or a group capable of decomposing under the action of an acid.

$A_1$ is a single bond, a divalent linking group such as alkylene group, cycloalkylene group, alkenylene group, arylene group, —OCO—, —COO— and —CON($R_{24}$)—, or a linking group containing a plurality of these groups. $R_{24}$ is a hydrogen atom or an alkyl group.

$R_{107}$ and $R_{108}$ each is independently a hydrogen atom, a halogen atom, an alkyl group, an alkoxy group, an alkoxycarbonyl group or a group capable of decomposing under the action of an acid.

$R_{109}$ is a hydrogen atom, an alkyl group or a group capable of decomposing under the action of an acid.

b is 0, 1 or 2.

The repeating units represented by formulae (FA) to (FG) each contains at least one fluorine atom, preferably three or more fluorine atoms, per one repeating unit.

In formulae (FA) to (FG), the alkyl group is preferably an alkyl group having from 1 to 8 carbon atoms and specific examples thereof include a methyl group, an ethyl group, a propyl group, an n-butyl group, a sec-butyl group, a hexyl group, a 2-ethylhexyl group and an octyl group.

The cycloalkyl group may be monocyclic or polycyclic. The monocyclic type is preferably a cycloalkyl group having from 3 to 8 carbon atoms, such as cyclopropyl group, cyclopentyl group, cyclohexyl group, cycloheptyl group and cyclooctyl group. The polycyclic type is preferably a cycloalkyl group having from 6 to 20 carbon atoms, such as adamantyl group, norbornyl group, isoboronyl group, camphanyl group, dicyclopentyl group, α-pinel group, tricyclodecanyl group, tetracyclododecyl group and androstanyl group. In these monocyclic or polycyclic cycloalkyl groups, the carbon atom may be substituted by a heteroatom such as oxygen atom.

The fluoroalkyl group is preferably a fluoroalkyl group having from 1 to 12 carbon atoms and specific examples thereof include a trifluoromethyl group, a perfluoroethyl group, a perfluoropropyl group, a perfluoro-butyl group, a perfluorohexyl group, a perfluorooctyl group, a perfluorooctylethyl group and a perfluorododecyl group.

The aryl group is preferably an aryl group having from 6 to 15 carbon atoms and specific examples thereof include a phenyl group, a tolyl group, a dimethylphenyl group, a 2,4,6-trimethylphenyl group, a naphthyl group, an anthryl group and a 9,10-dimethoxyanthryl group.

The aralkyl group is preferably an aralkyl group having from 7 to 12 carbon atoms and specific examples thereof include a benzyl group, a phenethyl group and a naphthylmethyl group.

The alkenyl group is preferably an alkenyl group having from 2 to 8 carbon atoms and specific examples thereof include a vinyl group, an allyl group, a butenyl group and a cyclohexenyl group.

The alkoxy group is preferably an alkoxy group having from 1 to 8 carbon atoms and specific examples thereof include a methoxy group, an ethoxy group, an n-propoxy group, an iso-propoxy group, a butoxy group, a pentoxy group, an allyloxy group and an octoxy group.

The acyl group is preferably an acyl group having from 1 to 10 carbon atoms and specific examples thereof include a formyl group, an acetyl group, a propanoyl group, a butanoyl group, a pivaloyl group, an octanoyl group and a benzoyl group.

The acyloxy group is preferably an acyloxy group having from 2 to 12 carbon atoms, such as acetoxy group, propionyloxy group and benzoyloxy group.

The alkynyl group is preferably an alkynyl group having from 2 to 5 carbon atoms, such as ethynyl group, propynyl group and butynyl group.

The alkoxycarbonyl group is preferably a secondary alkoxycarbonyl group, more preferably a tertiary alkoxycarbonyl group, such as i-propoxycarbonyl group, tert-butoxycarbonyl group, tert-amyloxycarbonyl group and 1-methyl-1-cyclohexyloxycarbonyl group.

The halogen atom includes, for example, a fluorine atom, a chlorine atom, a bromine atom and an iodine atom.

The alkylene group is preferably an alkylene group having from 1 to 8 carbon atoms, which may have a substituent, such as methylene group, ethylene group, propylene group, butylene group, hexylene group and octylene group.

The alkenylene group is preferably an alkenylene group having from 2 to 6 carbon atoms, which may have a substituent, such as ethenylene group, propenylene group and butenylene group.

The cycloalkylene group is preferably a cycloalkylene group having from 5 to 8 carbon atoms, which may have a substituent, such as cyclopentylene group and cyclohexylene group.

The arylene group is preferably an arylene group having from 6 to 15 carbon atoms, which may have a substituent, such as phenylene group, tolylene group and naphthylene group.

These groups each may have a substituent and examples of the substituent include those having an active hydrogen, such as alkyl group, cycloalkyl group, aryl group, amino group, amido group, ureido group, urethane group, hydroxyl group and carboxyl group, a halogen atom (e.g., fluorine, chlorine, bromine, iodine), an alkoxy group (e.g., methoxy, ethoxy, propoxy, butoxy), a thioether group, an acyl group (e.g., acetyl, propanoyl, benzoyl), an acyloxy group (e.g., acetoxy, propanoyloxy, benzoyloxy), an alkoxycarbonyl group (e.g., methoxycarbonyl, ethoxycarbonyl, propoxycarbonyl), a cyano group and a nitro group.

The alkyl group, cycloalkyl group and aryl group include those described above, and the alkyl group may be further substituted by a fluorine atom or a cycloalkyl group.

Examples of the group capable of decomposing under the action of an acid, contained in the fluorine group-containing resin of the present invention, include —O—C($R_{36}$)($R_{37}$)($R_{38}$), —O—C($R_{36}$)($R_{37}$)(O$R_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($R_{38}$), —COO—C($R_{36}$)($R_{37}$)(O$R_{39}$).

$R_{36}$ to $R_{39}$ each represents an alkyl group, a cycloalkyl group, an aryl group, an aralkyl group or an alkenyl group, and $R_{01}$ and $R_{02}$ each represents a hydrogen atom, an alkyl group, a cycloalkyl group, an alkenyl group, an aralkyl group or an aryl group.

Specific preferred examples include an ether or ester group of a tertiary alkyl group such as tert-butyl group, tert-amyl group, 1-alkyl-1-cyclohexyl group, 2-alkyl-2-adamantyl group, 2-adamantyl-2-propyl group and 2-(4-methylcyclohexyl)-2-propyl group, an acetal or acetal ester group such as 1-alkoxy-1-ethoxy group and tetrahydropyranyl group, a tert-alkylcarbonate group and a tert-alkylcarbonylmethoxy group.

Specific examples of the repeating structural units represented by formulae (FA) to (FG) are set forth below, but the present invention is not limited thereto.

(F-1)

(F-2)

-continued
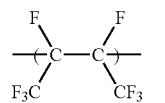 (F-3)
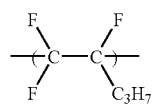 (F-4)
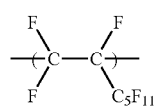 (F-5)
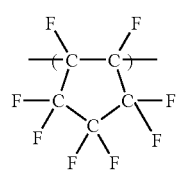 (F-6)
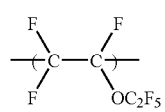 (F-7)
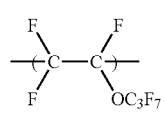 (F-8)
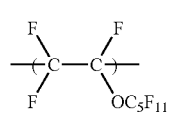 (F-9)
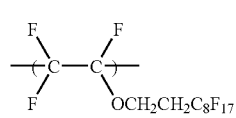 (F-10)
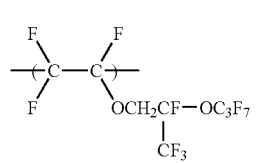 (F-11)
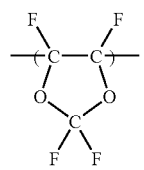 (F-12)
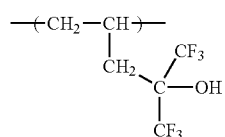 (F-13)
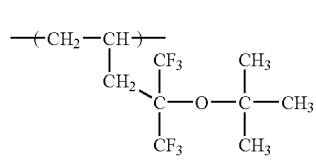 (F-14)
-continued
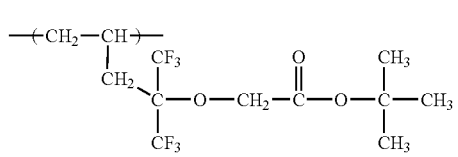 (F-15)
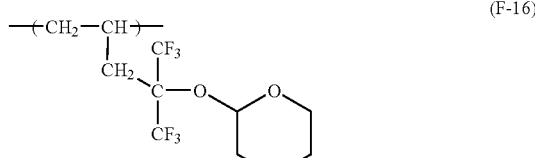 (F-16)
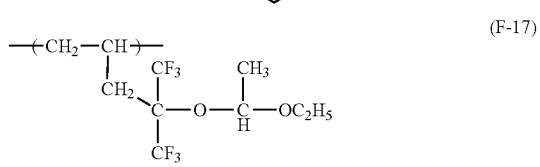 (F-17)
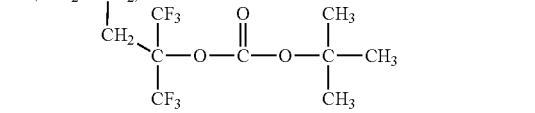 (F-18)
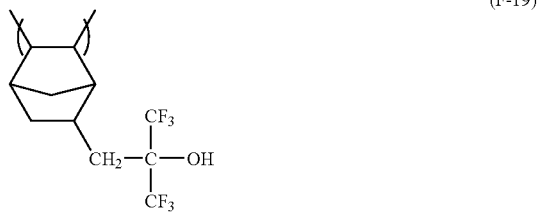 (F-19)
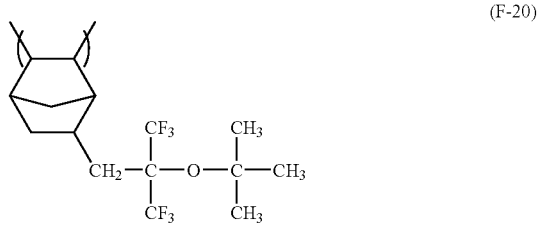 (F-20)
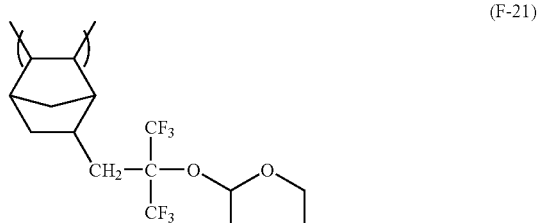 (F-21)
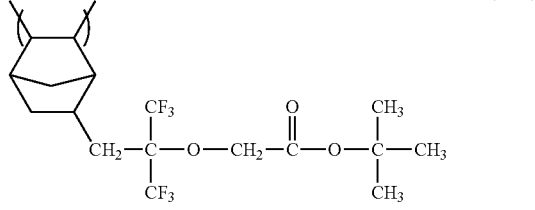 (F-22)

-continued
(F-23) 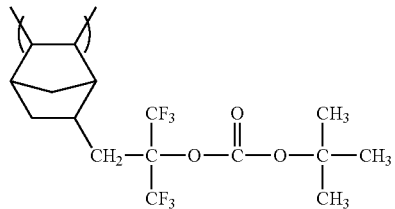
(F-24) 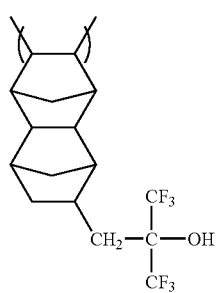
(F-25) 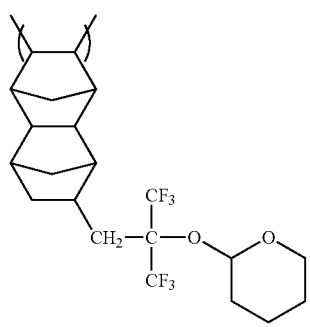
(F-26) 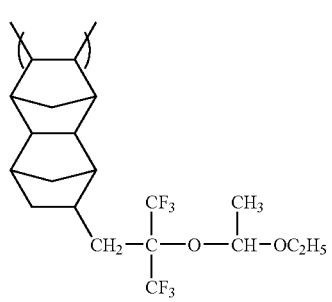
(F-27) 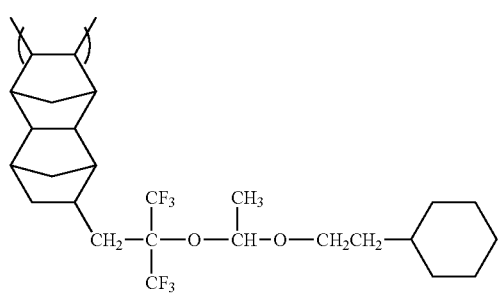
-continued
(F-28) 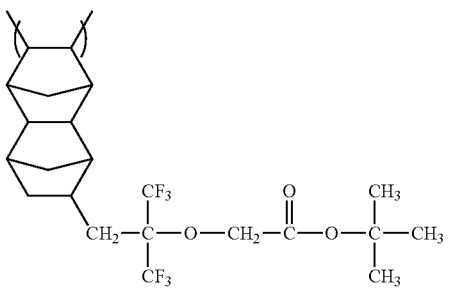
(F-29) 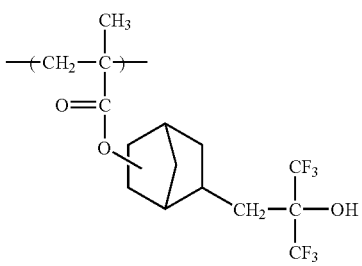
(F-30) 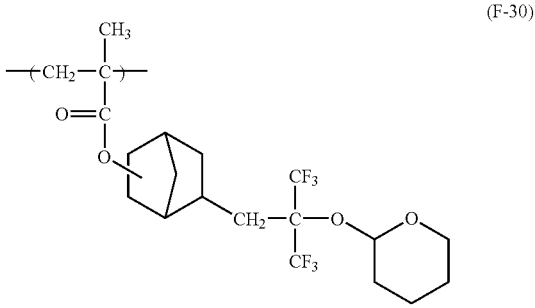
(F-31) 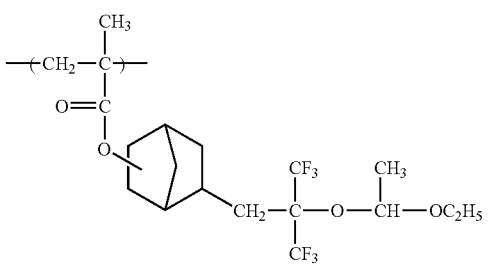
(F-32) 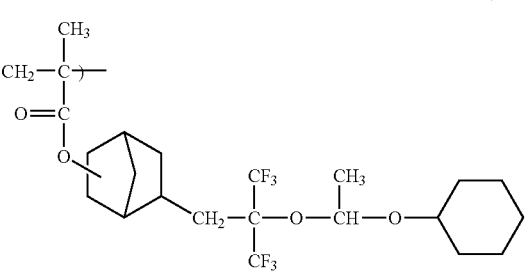

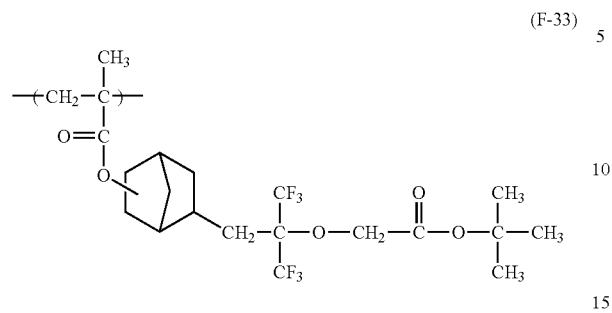
(F-33)
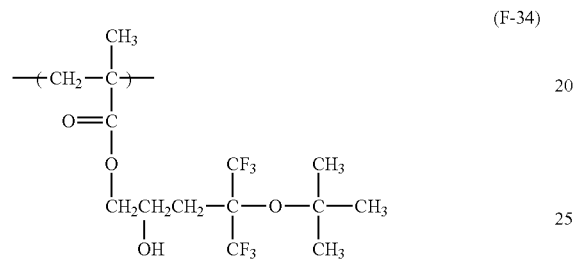
(F-34)
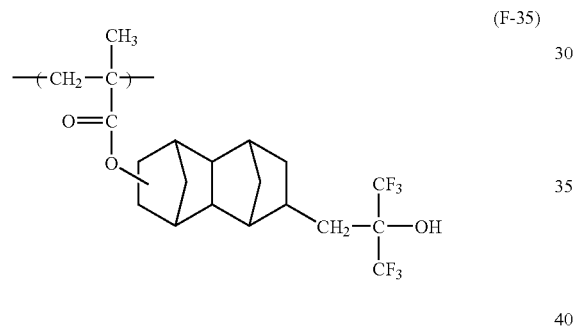
(F-35)
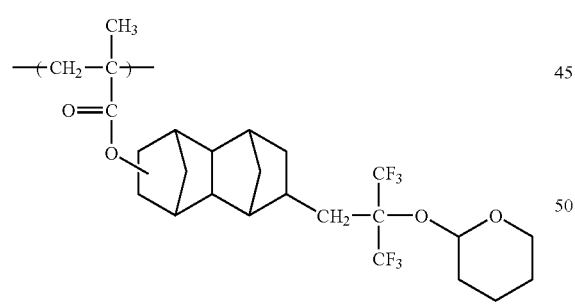
(F-36)
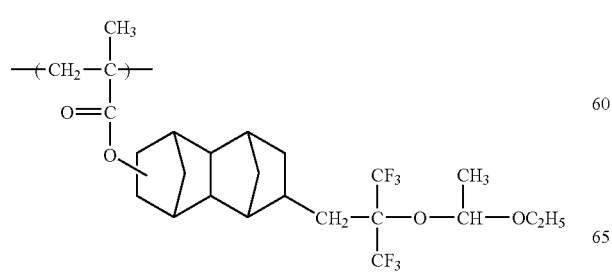
(F-37)
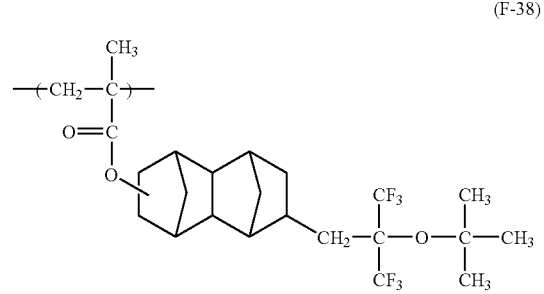
(F-38)
(F-39)
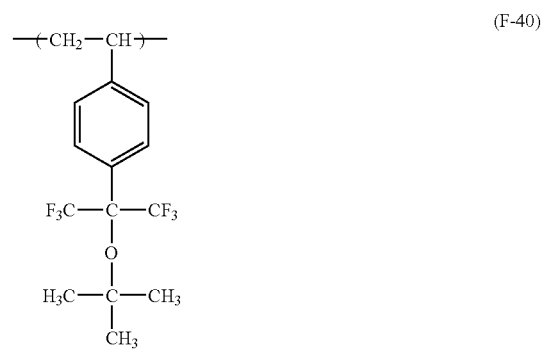
(F-40)
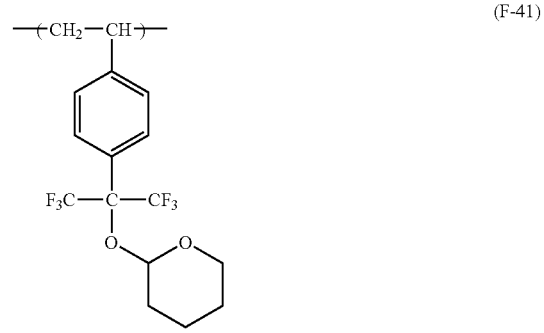
(F-41)
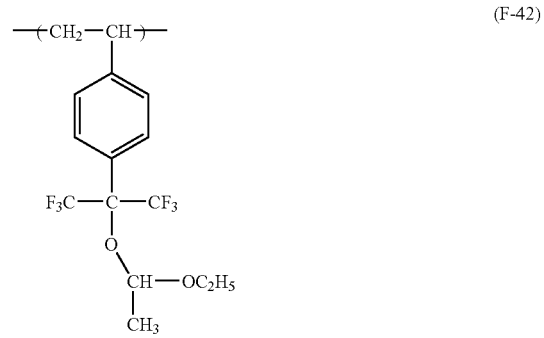
(F-42)

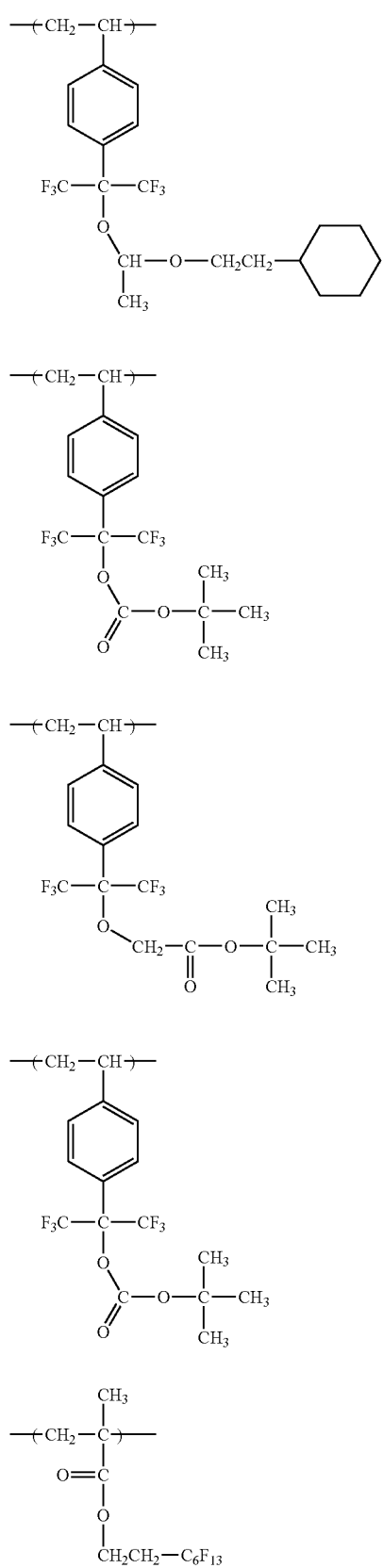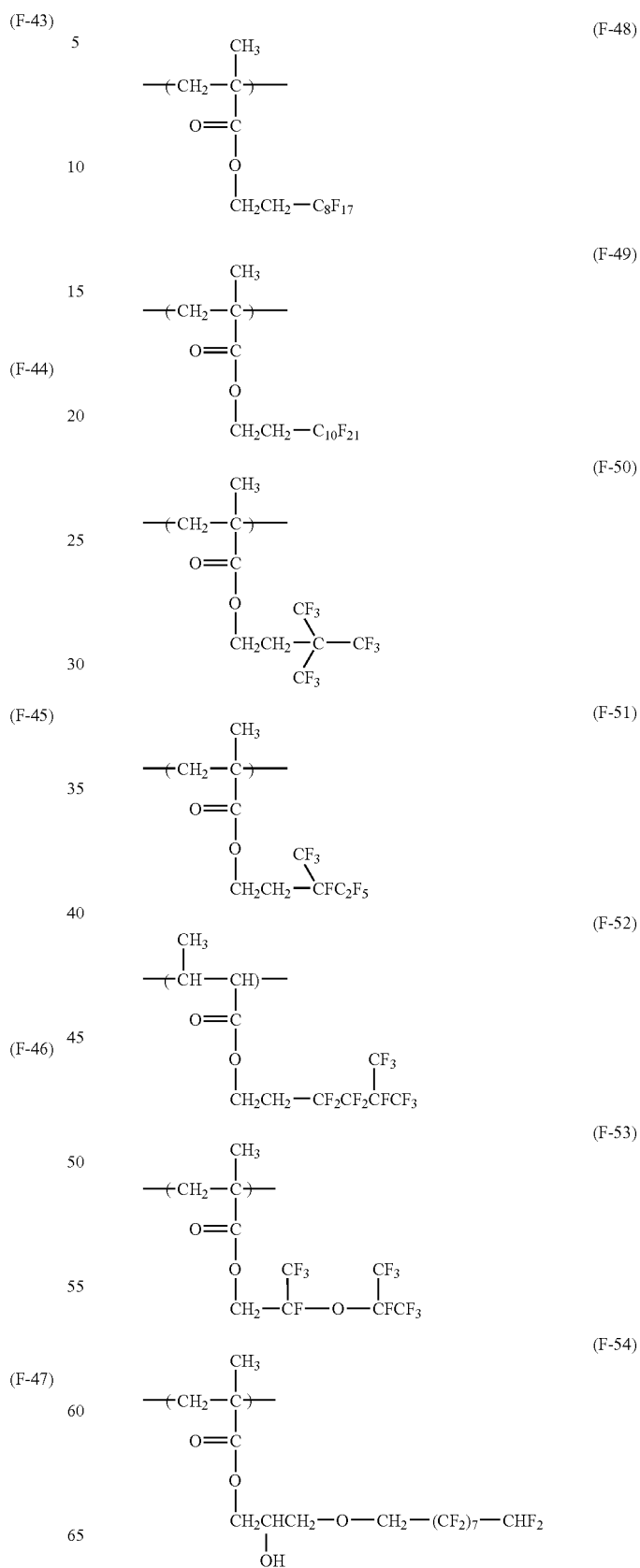

(F-55) — (F-65): chemical structures.

The total content of the repeating units represented by formulae (FA) to (FG) is generally from 10 to 80 mol %, preferably from 30 to 70 mol %, more preferably from 35 to 65 mol %, based on all repeating units constituting the resin.

In the fluorine-containing resin, in addition to these repeating structural units, other polymerizable monomers may be copolymerized for the purpose of enhancing the performance of resist of the present invention.

Examples of the copolymerization monomer which can be used include a compound having one addition polymerizable unsaturated bond, selected from acrylic acid esters other than those described above, acrylamides, methacrylic acid esters, methacrylamides, allyl compounds, vinyl ethers, vinyl esters, styrenes and crotonic acid esters.

From the standpoint of enhancing the dry etching resistance, controlling the alkali solubility and increasing the adhesive property to substrate, the fluorine-containing resin preferably contains another repeating unit as a copolymerization component in addition to the above-described fluorine atom-containing repeating unit. Preferred examples of the another repeating unit include:

1) a repeating unit having an alicyclic hydrocarbon structure represented by any one of formulae (p) to (pVI) or (II-AB), specifically, repeating units 1 to 23 and repeating units [II-1] to [II-32], preferably repeating units 1 to 23 where Rx is $CF_3$;

2) a repeating unit having a lactone structure represented by formula (Lc) or by any one of formulae (V-1) to (V-5), specifically, repeating units (IV-1) to (IV-16) and repeating units (Ib-1) to (Ib-11); and 3) a repeating unit derived from a maleic anhydride, a vinyl ether or a vinyl compound having a cyano group, represented by the following formula (XV), (XVI) or (XVII), specifically repeating units (C-1) to (C-15).

In these repeating units, a fluorine atom may or may not be contained.

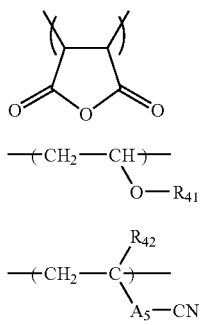

(XV)

—(CH$_2$—CH)—
         \
          O—R$_{41}$ (XVI)

—(CH$_2$—C)—
         / \
        R$_{42}$
         \
          A$_5$—CN (XVII)

wherein $R_{41}$ represents an alkyl group, a cycloalkyl group, an aralkyl group or an aryl group, and $R_{41}$ may be substituted by an aryl group, $R_{42}$ represents a hydrogen atom, a halogen atom, a cyano group or an alkyl group, $A_5$ represents a single bond, a divalent alkylene, alkenylene, cycloalkylene or arylene group, —O—CO—$R_{22}$, —CO—O—$R_{23}$— or —CO—N($R_{24}$)—$R_{25}$—, $R_{22}$, $R_{23}$ and $R_{25}$, which may be the same or different, each represents a single bond or a divalent alkylene, alkenylene, cycloalkylene or arylene group which may have an ether group, an ester group, an amide group, a urethane group or a ureido group, $R_{24}$ represents a hydrogen atom, an alkyl group, a cycloalkyl group, an aralkyl group or an aryl group, n represents 0 or 1, and x, y and z each represents an integer of 0 to 4.

Examples of each substituent are the same as those described above for the substituents of formula (FA) to (FG).

Specific examples of the repeating structural units represented by formulae (XVI) to (XVII) are set forth below, but the present invention is not limited thereto.

(C-1)

(C-2)

(C-3)

(C-4)

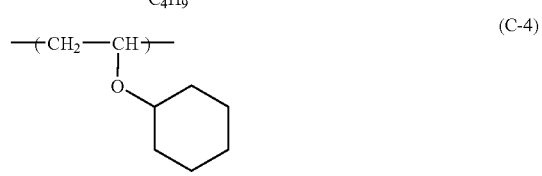

(C-5)

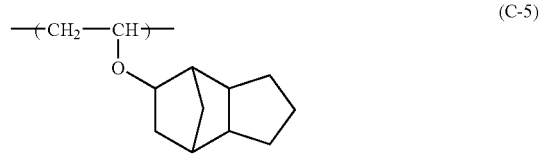

(C-6)

(C-7)

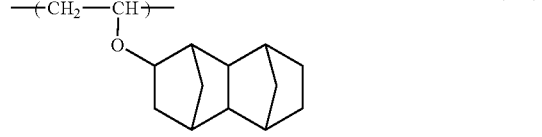

(C-8)

(C-9)

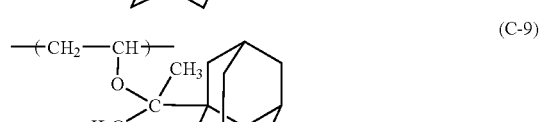

(C-10)

-continued

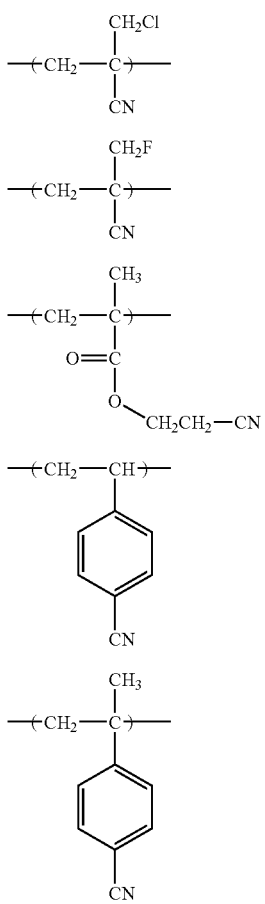

(C-11)
(C-12)
(C-13)
(C-14)
(C-15)

The content of the another repeating unit such as repeating units represented by formulae (XV) to (XVII) is generally from 0 to 70 mol %, preferably from 10 to 60 mol %, more preferably from 20 to 50 mol %, based on all repeating units constituting the resin.

The fluorine group-containing resin as the acid decomposable resin (B) may be contained in any repeating unit.

The content of the repeating unit having an acid decomposable group is preferably from 10 to 70 mol %, more preferably from 20 to 60 mol %, still more preferably from 30 to 60 mol %, based on all repeating units.

The fluorine group-containing resin can be synthesized by radical polymerization almost in the same manner as the alicyclic hydrocarbon-based acid decomposable resin.

The weight average molecular weight of the component (B) for use in the present invention is preferably from 1,000 to 200,000 in terms of polystyrene by GPC method. With a weight average molecular weight of 1,000 or more, the heat resistance and dry etching resistance can be increased and with a weight average molecular weight of 200,000 or less, the developability can be enhanced and at the same time, by virtue of very low viscosity, the film-forming property can be improved.

In the positive photosensitive composition of the present invention, the amount of the resin as the component (B) blended in the entire composition is preferably from 40 to 99.99 mass %, more preferably from 50 to 99.97 mass %, based on the entire solid content.

[3] (C) Dissolution inhibiting compound capable of decomposing under the action of an acid to increase a solubility of the dissolution inhibiting compound in an alkali developer and having a molecular weight of 3,000 or less (hereinafter sometimes referred to as a "component (C)" or "dissolution inhibiting compound")

In order to prevent reduction in the transmittance at 220 nm or less, the dissolution inhibiting compound (C) capable of decomposing under the action of an acid to increase the solubility in an alkali developer and having a molecular weight of 3,000 or less is preferably an alicyclic or aliphatic compound containing an acid decomposable group, such as acid decomposable group-containing cholic acid derivative described in *Proceeding of SPIE*, 2724, 355 (1996). Examples of the acid decomposable group and the alicyclic structure are the same as those described above for the alicyclic hydrocarbon-based acid decomposable resin.

In the case where the photosensitive composition of the present invention is exposed with a KrF excimer laser or irradiated with electron beams, the dissolution inhibiting compound preferably contains a structure that a phenolic hydroxyl group of a phenol compound is displaced by an acid decomposable group. The phenol compound preferably contains from 1 to 9 phenol skeletons, more preferably from 2 to 6 phenol skeletons.

The molecular weight of the dissolution inhibiting compound for use in the present invention is 3,000 or less, preferably from 300 to 3,000, more preferably from 500 to 2,500.

The amount of the dissolution inhibiting compound added is preferably from 3 to 50 mass %, more preferably from 5 to 40 mass %, based on the solid content of the photosensitive composition.

Specific examples of the dissolution inhibiting compound are set forth below, but the present invention is not limited thereto.

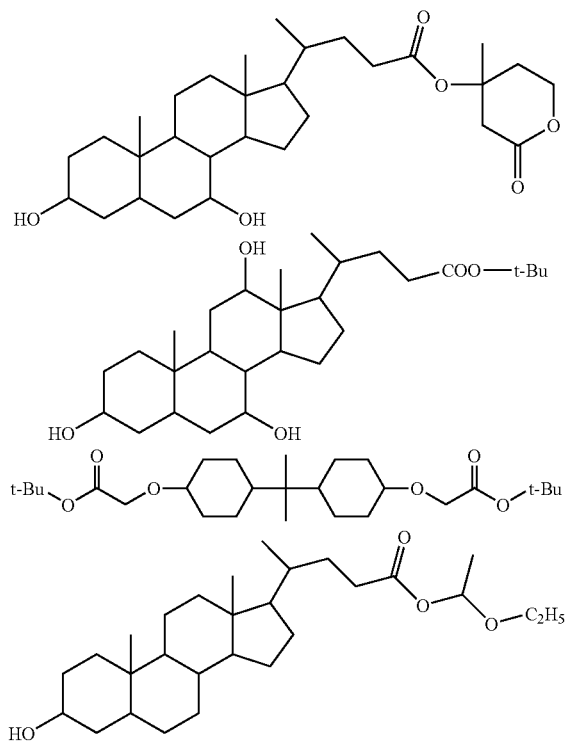

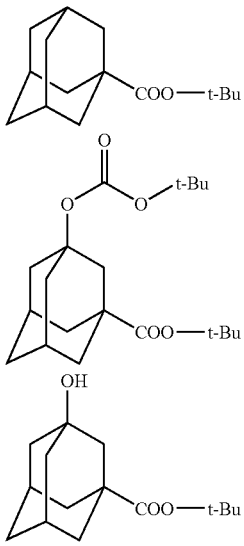

[4] (D) Resin soluble in alkali developer (hereinafter sometimes referred to as a "component (D)" or "alkali-soluble resin")

The alkali dissolution rate of the alkali-soluble resin is preferably 20 Å/sec or more, more preferably 200 Å/sec or more (Å is angstrom), as measured (at 23° C.) in 0.261N tetramethylammonium hydroxide (TMAH).

Examples of the alkali-soluble resin for use in the present invention include, but are not limited to, a novolak resin, a hydrogenated novolak resin, an acetone-pyrogallol resin, an o-polyhydroxystyrene, m-polyhydroxy-styrene, a p-polyhydroxystyrene, hydrogenated polyhydroxy-styrene, a halogen- or alkyl-substituted polyhydroxystyrene, a hydroxystyrene-N-substituted maleimide copolymer, an o/p- or m/p-hydroxystyrene copolymer, polyhydroxystyrene with the hydroxyl group being partially O-alkylated-(for example, 5 to 30 mol % being O-methylated, O-(1-methoxy)ethylated, O-(1-ethoxy)ethylated, O-2-tetrahydropyranylated or O-(tert-butoxycarbonyl)methylated) or O-acylated (for example, 5 to 30 mol % being o-acylated or O-(tert-butoxy) carbonylated), a styrene-maleic anhydride copolymer, a styrene-hydroxystyrene copolymer, an α-methylstyrene-hydroxystyrene copolymer, a carboxyl group-containing methacrylic resin and a derivative thereof, and a polyvinyl alcohol derivative.

Among these alkali-soluble resins, preferred are a novolak resin, an o-polyhydroxystyrene, an m-polyhydroxystyrene, a p-polyhydroxystyrene, a copolymer thereof, an alkyl-substituted polyhydroxystyrene, a partially O-alkylated or O-acylated polyhydroxystyrene, a styrene-hydroxystyrene copolymer and an α-methylstyrene-hydroxystyrene copolymer.

The novolak resin can be obtained by subjecting a predetermined monomer as the main component and an aldehyde to addition condensation in the presence of an acidic catalyst.

The weight average molecular weight of the alkali-soluble resin is 2,000 or more, preferably from 5,000 to 200,000, more preferably from 5,000 to 100,000.

The weight average molecular weight used herein is defined as the value measured by gel permeation chromatography and calculated in terms of polystyrene.

In the present invention, these alkali-soluble resins (D) may be used in combination of two or more thereof.

The amount of the alkali-soluble resin used is from 40 to 97 mass %, preferably from 60 to 90 mass %, based on the entire solid content of the photosensitive composition.

[5] (E) Acid crosslinking agent capable of crosslinking with the alkali-soluble resin under the action of an acid (hereinafter sometimes referred to as a "component (E)" or "crosslinking agent")

In the negative photosensitive composition of the present invention, a crosslinking agent is used.

The crosslinking agent may be any compound as long as it causes crosslinking of the resin soluble in an alkali developer under the action of an acid, but the following compounds (1) to (3) are preferred:

(1) a hydroxymethyl, alkoxymethyl or acyloxymethyl forms of phenol derivatives, (2) a compound having an N-hydroxymethyl group, an N-alkoxymethyl group or an N-acyloxymethyl group, and (3) a compound having an epoxy group.

The alkoxymethyl group is preferably an alkoxymethyl group having 6 or less carbon atoms and the acyloxymethyl group is preferably an acyloxymethyl group having 6 or less carbon atoms.

Among these crosslinking agents, particularly preferred are set forth below.

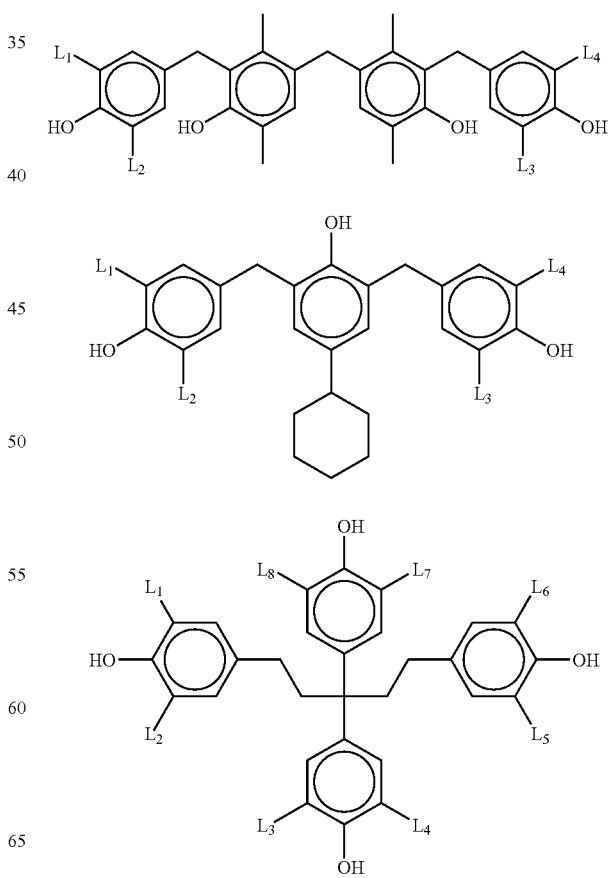

-continued

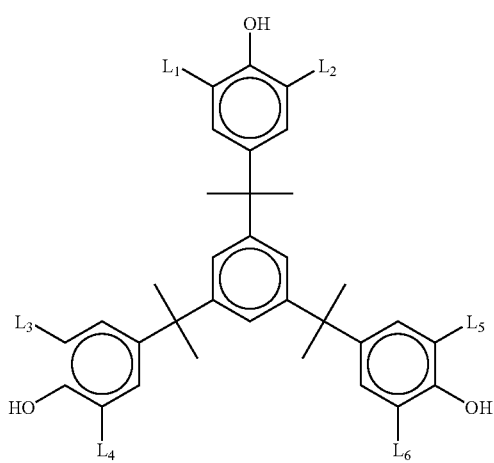

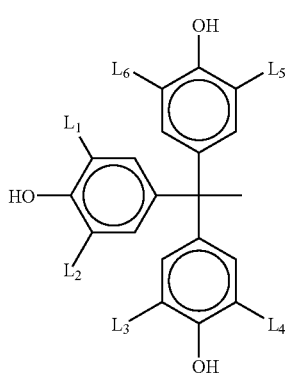

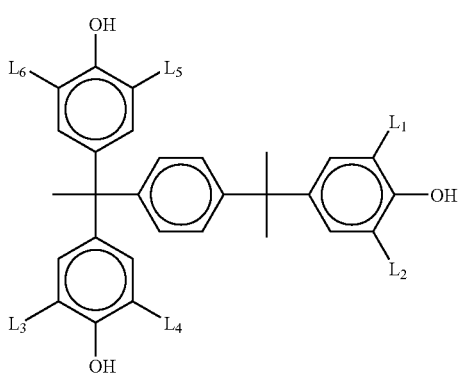

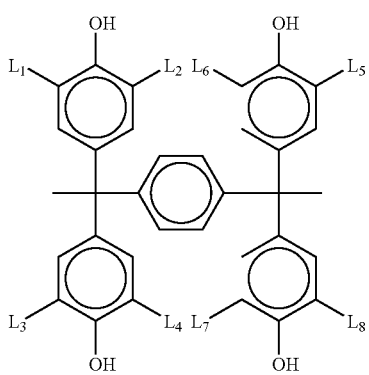

-continued

In these formulae, $L^1$ to $L^8$ may be the same or different and each represents a hydrogen atom, a hydroxymethyl group, a methoxymethyl group, an ethoxymethyl group or an alkyl group having from 1 to 6 carbon atoms.

The crosslinking agent is usually added in an amount of 3 to 70 mass %, preferably from 5 to 50 mass %, based on the solid content of the photosensitive composition.

<Other Components>

[6] (F) Basic compound

The photosensitive composition of the present invention preferably contains (F) a basic compound so as to reduce the change of performance in aging from exposure to heating.

Preferred structures of the basic compound include the structures represented by the following formulae (A) to (E).

(A)

wherein $R^{250}$, $R^{251}$ and $R^{252}$ each independently represents a hydrogen atom, an alkyl group having from 1 to 20 carbon atoms, a cycloalkyl group having from 3 to 20 carbon atoms or an aryl group having from 6 to 20 carbon atoms, and $R^{250}$ and $R^{251}$ may combine with each other to form a ring. These groups each may have a substituent. The alkyl group and cycloalkyl group having a substituent each is preferably an aminoalkyl group having from 1 to 20 carbon atoms, an aminocycloalkyl group having from 3 to 20 carbon atoms, a hydroxyalkyl group having from 1 to 20 carbon atoms or a hydroxycycloalkyl group having from 3 to 20 carbon atoms.

These groups each may contain an oxygen atom, a sulfur atom or a nitrogen atom in the alkyl chain.

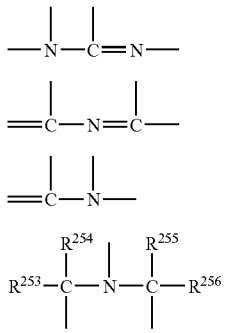

wherein $R^{253}$, $R^{254}$, $R^{255}$ and $R^{256}$ each independently represents an alkyl group having from 1 to 20 carbon atoms or a cycloalkyl group having from 3 to 6 carbon atoms.

Preferred examples of the compounds include guanidine, aminopyridine, pyrazole, pyrazoline, piperazine, aminomorpholine, aminoalkylmorpholine and piperidine, which each may have a substituent. More preferred examples include compounds having an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, and aniline derivatives having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]-octane, 1,5-diazabicyclo[4,3,0]non-5-ene and 1,8-diazabicyclo[5,4,0]undec-7-ene. Examples of the compound having an onium hydroxide structure include a triaryl-sulfonium hydroxide, a phenacylsulfonium hydroxide and a sulfonium hydroxide having a 2-oxoalkyl group, specifically, triphenylsulfonium hydroxide, tris(tert-butylphenyl)-sulfonium hydroxide, bis(tert-butylphenyl)iodonium hydroxide, phenacylthiophenium hydroxide and 2-oxopropyl-thiphenium hydroxide. Examples of the compound having an onium carboxylate structure include the compounds having an onium hydroxide structure where the anion moiety is converted into a carboxylate, such as acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline and N,N-dimethylaniline. Examples of the alkylamine derivative having a hydroxyl group and/or an ether bond include ethanolamine, diethanolamine, triethanolamine and tris(methoxyethoxyethyl) amine. Examples of the aniline derivative having a hydroxyl group and/or an ether bond include N,N-bis(hydroxyethyl) aniline.

These basic compounds are used individually or in combination of two or more thereof. The amount of the basic compound used is usually from 0.001 to 10 mass %, preferably from 0.01 to 5 mass %, based on the solid content of the photosensitive composition. The amount used is preferably 0.001 mass % or more for obtaining sufficiently high addition effect and preferably 10 mass % or less in view of sensitivity and developability of-unexposed area.

[7] (G) Fluorine-Containing and/or Silicon-Containing Surfactant

The photosensitive composition of the present invention preferably further contains any one or two or more of fluorine-containing and/or silicon-containing surfactants (a fluorine-containing surfactant, a silicon-containing surfactant and a surfactant containing both a fluorine atom and a silicon atom).

When the photosensitive composition of the present invention contains a fluorine-containing and/or silicon-containing surfactant, a resist pattern with good sensitivity, resolution and adhesion and less development defects can be obtained when an exposure light source of 250 nm or less, particularly 220 nm or less, is used.

Examples of the fluorine-containing and/or silicon-containing surfactant include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include fluorine-containing surfactants and silicon-containing surfactants, such as EFtop EF301 and EF303 (produced by Shin-Akita Kasei K.K.), Florad FC430 and 431 (produced by Sumitomo 3M Inc.), Megafac F171, F173, F176, F189 and R08 (produced by Dainippon Ink & Chemicals, Inc.), Surflon S-382, SC101, 102, 103, 104, 105 and 106 (produced by Asahi Glass Co., Ltd.), and Troysol S-366 (produced by Troy Chemical). In addition, polysiloxane polymer KP-341 (produced by Shin-Etsu Chemical Co., Ltd.) may also be used as the silicon-containing surfactant.

Other than those known surfactants, surfactants using a polymer having a fluoro-aliphatic group, which is derived from a fluoro-aliphatic compound produced by telomerization (also called telomer process) or oligomerization (also called oligomer process), may be used. The fluoro-aliphatic compound can be synthesized by the method described in JP-A-2002-90991.

The polymer having a fluoro-aliphatic group is preferably a copolymer of a fluoro-aliphatic group-containing monomer with (poly(oxyalkylene)) acrylate and/or (poly(oxyalkylene)) methacrylate and the polymer may have an irregular distribution or may be a block copolymer. Examples of the poly(oxyalkylene) group include a poly (oxy-ethylene) group, a poly(oxypropylene) group and a poly(oxy-butylene) group). This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer and a (poly(oxy-alkylene)) acrylate (or methacrylate) may be not only a binary copolymer but also a ternary or greater copolymer obtained by simultaneously copolymerizing two or more different fluoro-aliphatic group-containing monomers or two or more different (poly(oxyalkylene)) acrylates (or methacrylates).

Examples thereof include commercially available surfactants such as Megafac F178, F-470, F-473, F-475, F-476 and F-472 (produced by Dainippon Ink & Chemicals, Inc.). Other examples include copolymers of an acrylate (or methacrylate) having a $C_6F_{13}$ group with a (poly(oxy-alkylene)) acrylate (or methacrylate), copolymers of an acrylate (or methacrylate) having a $C_6F_{13}$ group with a (poly(oxyethylene)) acrylate (or methacrylate) and a (poly(oxypropylene)) acrylate (or methacrylate), copolymers of an acrylate (or methacrylate) having a $C_8F_{17}$ group with a (poly(oxyalkylene)) acrylate (or methacrylate), and copolymers of an acrylate (or methacrylate) having a $C_8F_{17}$ group with a (poly(oxyethylene)) acrylate (or methacrylate) and a (poly(oxypropylene)) acrylate (or methacrylate).

The amount of the fluorine-containing and/or silicon-containing surfactant used is preferably from 0.0001 to 2 mass %, more preferably from 0.001 to 1 mass %, based on the entire amount of the photosensitive composition (excluding the solvent).

[8] (H) Organic Solvent

In the photosensitive composition of the present invention, the above-described components are used by dissolving them in a predetermined organic solvent.

Examples of the organic solvent which can be used include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethylsulfoxide, N-methylpyrrolidone and tetrahydrofuran.

In the present invention, the organic solvents may be used individually or as a mixture thereof, but a mixed solvent obtained by mixing a solvent containing a hydroxyl group in the structure and a solvent not containing a hydroxyl group is preferably used. By using such a mixed solvent, the generation of particles during storage of the resist solution can be reduced.

Examples of the solvent containing a hydroxyl group include ethylene glycol, ethylene glycol monomethyl ether, ethylene glycol monoethyl ether, propylene glycol, propylene glycol monomethyl ether, propylene glycol monoethyl ether and ethyl lactate. Among these, propylene glycol monomethyl ether and ethyl lactate are preferred.

Examples of the solvent not containing a hydroxyl group include propylene glycol monomethyl ether acetate, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone, and butyl acetate are preferred, and propylene glycol monomethyl ether acetate, ethyl ethoxypropionate and 2-heptanone are most preferred.

The mixing ratio (by mass) of the solvent containing a hydroxyl group to the solvent not containing a hydroxyl group is from 1/99 to 99/1, preferably from 10/90 to 90/10, more preferably from 20/80 to 60/40. In view of the coating uniformity, a mixed solvent containing 50 mass % or more of a solvent not containing a hydroxyl group is particularly preferred.

<Other Additives>

The photosensitive composition of the present invention may further contain, if desired, a dye, a plasticizer, a surfactant other than the component (G), a photosensitizer and a compound capable of accelerating the solubility in a developer.

The compound capable of accelerating the dissolution in a developer, which can be used in the present invention, is a low molecular weight, compound containing two or more phenolic OH groups or one or more carboxy group and having a molecular weight of 1,000 or less. In the case of containing a carboxyl group, an alicyclic or aliphatic compound is preferred.

The amount of the dissolution accelerating compound added is preferably from 2 to 50 mass %, more preferably from 5 to 30 mass %, based on the resin of component (B) or the resin of component (D). The amount added is preferably 50 mass % or less from the standpoint of preventing the development residue or deformation of pattern at the development.

The phenol compound having a molecular weight of 1,000 or less can be easily synthesized by one skilled in the art based on the method described, for example, in JP-A-4-122938, JP-A-2-28531, U.S. Pat. No. 4,916,210 and European Patent 219294.

Specific examples of the alicyclic or aliphatic compound having a carboxy group include, but are not limited to, carboxylic acid derivatives having a steroid structure, such as cholic acid, deoxycholic acid and lithocholic acid, adamantane carboxylic acid derivatives, an adamantane dicarboxylic acid, a cyclohexanecarboxylic acid and a cyclohexanedicarboxylic acid.

In the present invention, surfactants other than (G) the fluorine-containing and/or silicon-containing surfactant can also be added. Specific examples thereof include nonionic surfactants such as polyoxyethylene alkyl ethers, polyoxyethylene alkylallyl ethers, polyoxy-ethylene.polyoxypropylene block copolymers, sorbitan fatty acid esters and polyoxyethylene sorbitan fatty acid esters.

One of these surfactants may be used alone or some of these surfactants may be used in combination.

<Use Method>

The photosensitive composition of the present invention is used by dissolving the above-described components in a predetermined organic solvent, preferably a mixed solvent described above, and coating the obtained solution on a predetermined support as follows.

For example, the photosensitive composition is coated on a substrate (e.g., silicon/silicon dioxide-coated substrate) such as substrate used in the production of precision integrated circuit elements, by an appropriate coating method such as spinner or coater, and dried to form a resist film. This resist film is subjected to irradiation with an actinic ray or a radiation through a predetermined mask and developed by baking, whereby a good pattern can be obtained.

Examples of the actinic ray or the radiation include infrared light, visible light, ultraviolet light, far ultraviolet light, X ray and electron beam. Among these, preferred are far ultraviolet light at a wavelength of 250 nm or less, more preferably 220 nm or less. Specific examples thereof include a KrF excimer laser (248 nm), an ArF excimer laser (193 nm), an $F_2$ excimer laser (157 nm), an X ray and an electron beam with an ArF excimer laser, an F$_2$ excimer laser and an EUV (13 nm) being preferred.

In the development step, an alkali developer is used as follows. The alkali developer which can be used for the resist composition is an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amine such as dimethylethanolamine and triethanolamine, quaternary ammonium salts such as tetramethylammonium hydroxide and tetraethylammonium hydroxide, or cyclic amines such as pyrrole and piperidine.

In the alkali developer, alcohols and a surfactant may also be added in an appropriate amount.

The alkali concentration of the alkali developer is usually from 0.1 to 20 mass %.

The pH of the alkali developer is usually from 10.0 to 15.0.

EXAMPLES

The present invention is described in greater detail below by referring to Examples, but the present invention should not be construed as being limited thereto.

Synthesis Example of Compound (A)

Synthesis Example 1

Synthesis of Compound (A-1)

Methylpropanyl pentafluorobenzenesulfonic acid ester (13.2 g (43.4 mmol)), 12.1 g (65.1 mmol) of 1-dodecanol, 1.47 g (4.34 mmol) of tetrabutylammonium hydrogensulfate, 130 mL of an aqueous 1M-sodium hydroxide solution and 130 mL of toluene were stirred at 70° C. for 12 hours. The reaction solution was rendered neutral by adding dilute sulfuric acid and the organic layer was dried over magnesium sulfate. After removing the solvent, the residue was purified by column chromatography (SiO$_2$, ethyl acetate/hexane=10/1) to obtain a colorless transparent oil (17.4 g). This oil was dissolved in 160 mL of acetonitrile and after adding 5.93 g (39.6 mmol) of sodium iodide, stirred at room temperature for 6 hours. The reaction solution was icecooled and the precipitated solid was filtered and vacuumdried to obtain 17.4 g (37 mmol, 85%) of 4-dodecyloxy-2,3,5,6-tetrafluorobenzenesulfonic acid as a whitish yellow solid.

$^1$H-NMR (300 MHz, (CD$_3$)$_2$SO) δ: 0.854 (t, 3H), 1.243 (bs, 16H, 1.392 (quintet, 2H), 1.655 (quintet, 2H, 4.212 (t, 2H).

$^{19}$F-NMR (300 MHz, (CD$_3$)$_2$SO) δ:

−137.11 (m, 2F), −152.66 (m, 2F).

Triphenylsulfonium iodide (2.82 g (7.21 mmol)), 1.26 g (7.57 mmol) of silver acetate, 80 mL of acetonitrile and 40 mL of water were added and stirred at room temperature for 1 hour. The resulting reaction solution was filtered to obtain a triphenylsulfonium acetate solution. Thereto, 3.00 g (6.87 mmol) of sodium sulfonate prepared above was added and stirred at room temperature for 3 hours. After adding 300 mL of chloroform, the organic layer was washed sequentially with water, with an aqueous saturated ammonium chloride solution and with water. The organic layer was filtered through a 0.1-μm filter and then the solvent was removed to obtain the objective compound (4.40 g, 84%) as a colorless transparent oil.

$^1$H-NMR (300 MHz, CDCl$_3$) δ:

0.877 (t, 3H), 1.262 (bs, 16H), 1.427 (quintet, 2H), 1.729 (m, 2H), 4.177 (t, 2H), 7.662-7.813 (m, 15H).

$^{19}$F-NMR (300 MHz, CDCl$_3$) δ: −140.01 (m, 2F), −156.21 (m, 2F).

Synthesis Example 2

Synthesis of Compound (A-10)

Triphenylsulfonium iodide (3.47 g (8.89 mmol)), 1.56 g (9.34 mmol) of silver acetate, 80 mL of acetonitrile and 40 mL of water were added and stirred at room temperature for 1 hour. The resulting reaction solution was filtered to obtain a triphenylsulfonium acetate solution. Thereto, 4.07 g (9.32 mmol) of sodium 4-hydroxy-2,3,5,6-tetrafluorobenzenesulfonate was added and stirred at room temperature for 3 hours. After removing the solvent, the residue was exsiccated and thereto, 70 mL of chloroform and 5 mL of methanol were added and stirred at 60° C. for 1 hour. The precipitated salt was filtered and the filtrate was exsiccated to obtain the objective compound (4.02 g, 89%) as a colorless transparent oil.

$^1$H-NMR (300 MHz, CD$_3$OD) δ: 7.768-7.782 (m, 15H).

$^{19}$F-NMR (300 MHz, CD$_3$OD) δ: −144.69 (m, 2F), −160.03 (m, 2F).

Synthesis Example 3

Synthesis of Compound (A-79)

A BF$_4$ salt of Compound (A-79) (5.2 g (10.9 mmol)) and 5.0 g (11.5 mmol) of 4-dodecyloxy-2,3,5,6-tetrafluoro-benzenesulfonic acid were dissolved in a mixed solvent of methanol (100 mL), acetonitrile (100 mL) and water (100 mL) and stirred at room temperature for 2 hours. The resulting solution was concentrated and after adding chloroform (300 mL), washed three times with water (200 mL). The organic layer was filtered through a 0.1-μm filter and then the solvent was removed to obtain the objective solid (5.37 g, 60%).

$^1$H-NMR (300 MHz, CDCl$_3$) δ:

0.878 (t, 3H), 1.236-1.438 (m, 23H), 1.780 (m, 7H), 2.511 (m, 1H), 4.198 (t, 2H), 6.454 (s, 2H), 7.309 (d, 2H), 7.676 (m, 6H), 8.156 (d, 2H), 8.270 (m, 4H).

$^{19}$F-NMR (300 MHz, CDCl$_3$) δ: −140.10 (m, 2F), −155.96 (m, 2F).

Synthesis Example 4

Synthesis of Compound (A-69)

A BF$_4$ salt of Compound (A-69) (5.02 g (8.72 mmol)) and 4.0 g (9.16 mmol) of 4-dodecyloxy-2,3,5,6-tetrafluoro-benzenesulfonic acid were dissolved in a mixed solvent of acetonitrile (100 mL) and water (100 mL) and stirred at room temperature for 2 hours. The resulting solution was concentrated and after adding chloroform (200 mL), washed three times with water (200 mL). After removing the solvent, the residue was purified by column chromatography (SiO$_2$, ethyl acetate/methanol=9/1) to obtain the objective solid (6.22 g, 78%).

¹H-NMR (300 MHz, CDCl₃) δ:
0.880 (t, 9H), 1.254 (bs, 48H), 1.436 (m, 6H), 1.773 (m, 2H), 1.878 (m, 4H), 3.621 (m, 2H), 3.798 (m, 2H), 4.190 (t, 2H), 5.702 (s, 2H), 7.505 (m, 2H), 7.782 (m, 1H), 8.125 (m, 2H).
¹⁹F-NMR (300 MHz, CDCl₃) δ: −139.13 (m, 2F), −156.03 (m, 2F).

Synthesis Example 5

Synthesis of Compound (A-83)

A BF₄ salt of Compound (A-83) (1.5 g (4.36 mmol)) and 2.0 g (4.58 mmol) of 4-dodecyloxy-2,3,5,6-tetrafluoro-benzenesulfonic acid were dissolved in a mixed solvent of acetonitrile (100 mL) and water (50 mL) and stirred at room temperature for 2 hours. The resulting solution was concentrated and after adding chloroform (200 mL), washed three times with water (200 mL). Then, the solvent was removed to obtain the objective solid (2.21 g, 75%).
¹H-NMR (300 MHz, (CD₃)₂SO) δ:
0.851 (t, 3H), 1.242 (bs, 16H), 1.434 (m, 2H), 1.777 (m, 2H), 2.000 (s, 6H), 2.182 (m, 4H), 3.616 (m, 4H), 3.886 (s, 3H), 4.208 (t, 2H), 7.110 (d, 2H), 8.110 (d, 2H)

¹⁹F-NMR (300 MHz, (CD₃)₂SO) δ:
−140.05 (m, 2F), −156.08 (m, 2F).

Synthesis Example 6

Synthesis of Compound (A-53)

A Br salt of Compound (A-53) (1.25 g (4.36 mmol)) and 2.0 g (4.58 mmol) of 4-dodecyloxy-2,3,5,6-tetrafluoro-benzenesulfonic acid were dissolved in a mixed solvent of acetonitrile (100 mL) and water (50 mL) and stirred at room temperature for 2 hours. The resulting solution was concentrated and after adding chloroform (200 mL), washed three times with water (200 mL). Then, the solvent was removed and the resulting solid was washed with diisopropyl ether and vacuum-dried to obtain the objective solid (2.43 g, 90%).
¹H-NMR (300 MHz, (CD₃)₂SO) δ:
0.857 (t, 3H), 1.266 (bs, 16H), 1.433 (m, 2H), 1.777 (m, 2H), 2.211 (m, 4H), 3.511 (m, 4H), 4.213 (t, 2H), 5.225 (s, 2H), 7.624 (m, 2H), 7.755 (m, 2H), 7.996 (m, 1H), 3.521 (m, 4H), 4.210 (t, 2H), 5.430 (s, 2H), 6.833 (d, 2H), 7.774 (d, 2H), 9.483 (s, 1H).

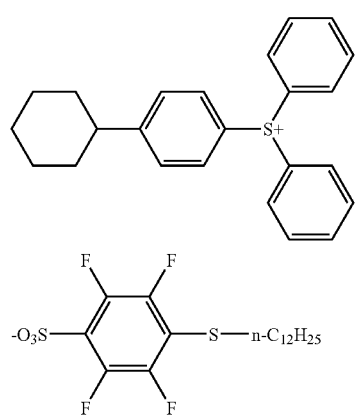

(A-149)

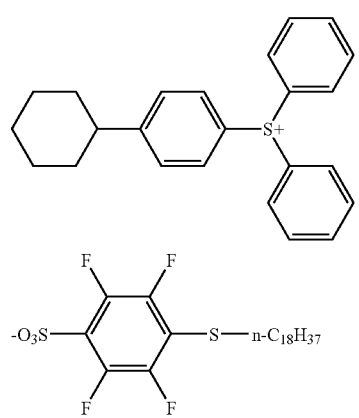

(A-150)

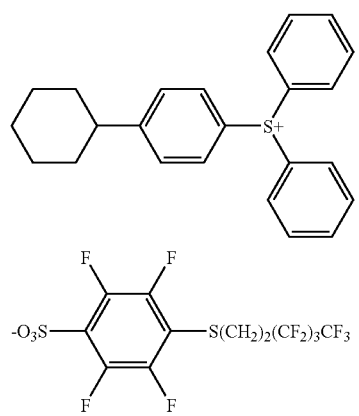

(A-151)

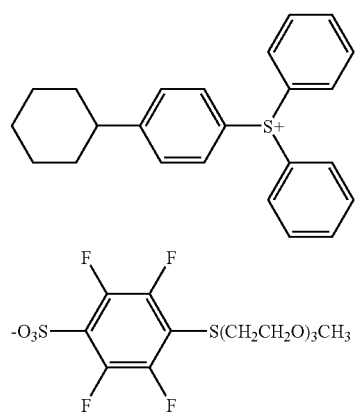

(A-152)

-continued
(A-153)
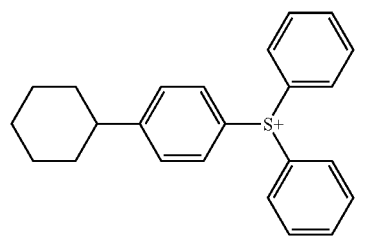
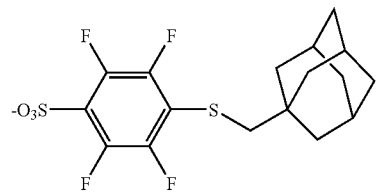
(A-155)
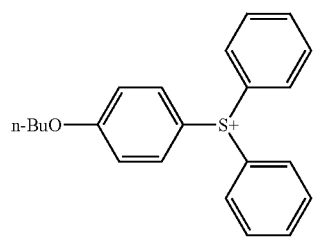
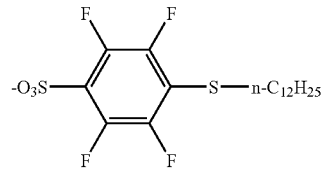
(A-157)
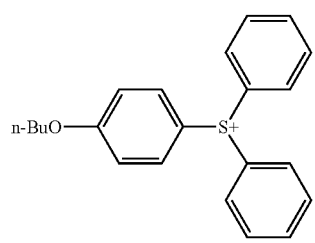
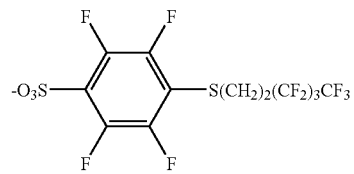
(A-159)
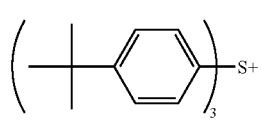
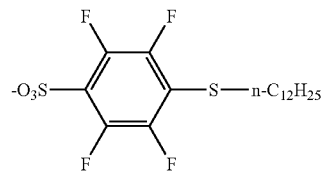
(A-154)
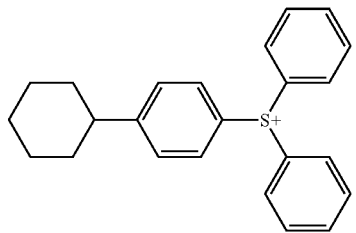
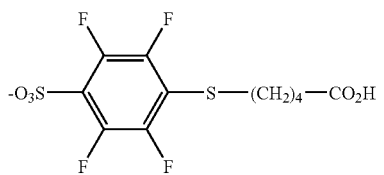
(A-156)
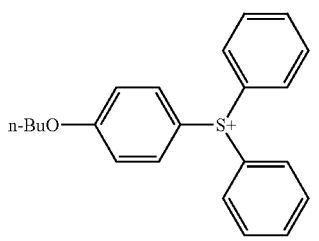
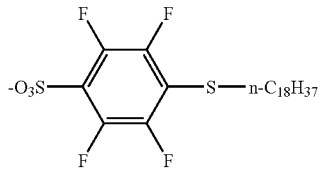
(A-158)
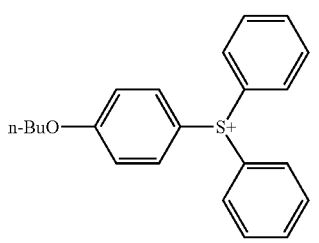
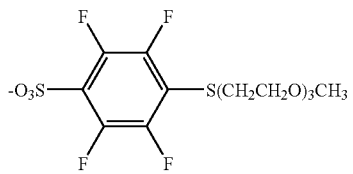
(A-160)
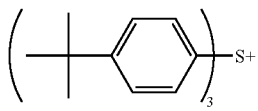
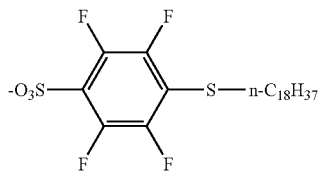

-continued
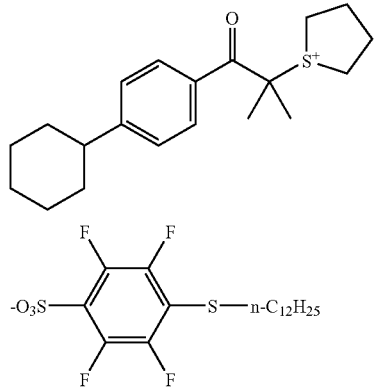
(A-161)
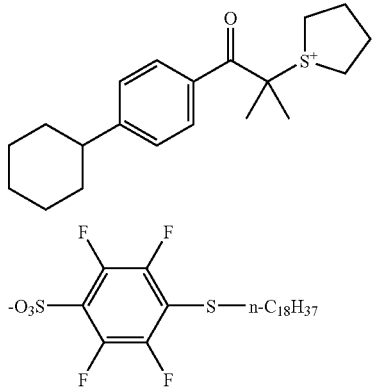
(A-162)
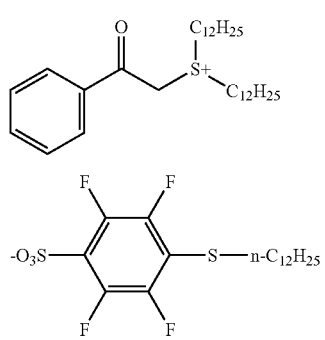
(A-163)
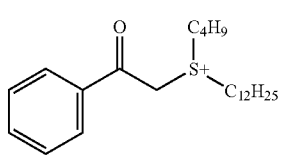
(A-164)
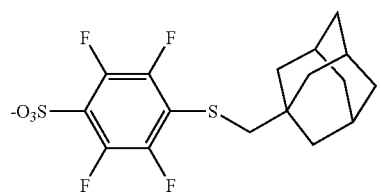
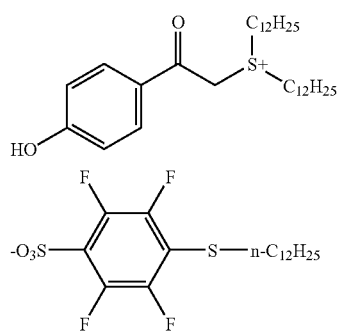
(A-165)
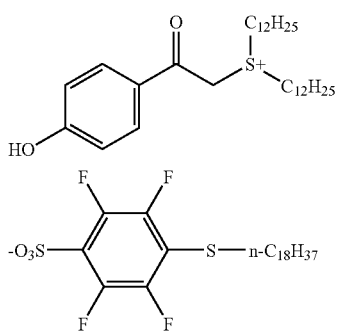
(A-166)
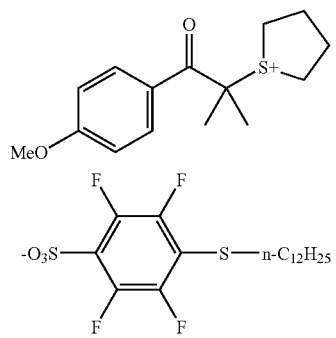
(A-167)
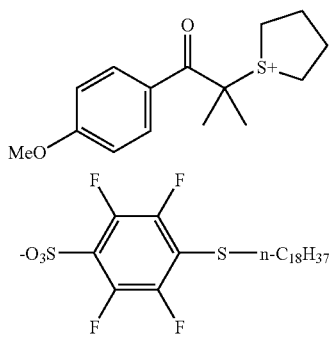
(A-168)

-continued
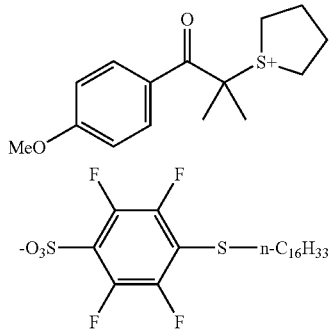
(A-169)
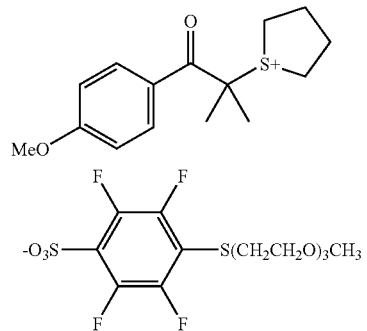
(A-170)
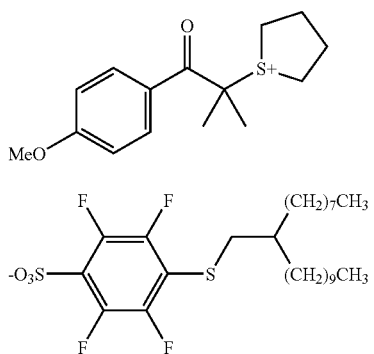
(A-171)
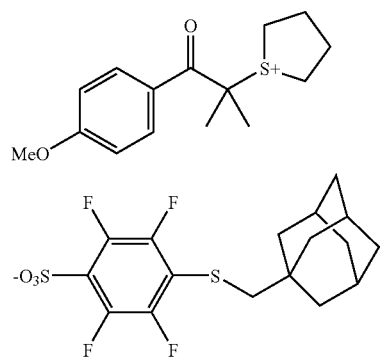
(A-172)
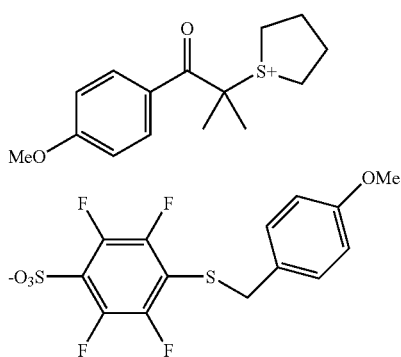
(A-173)
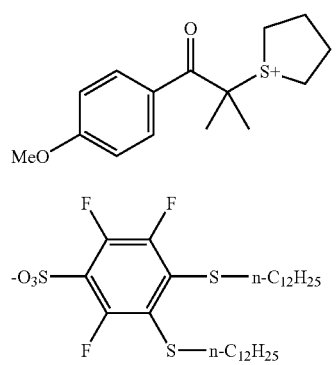
(A-174)
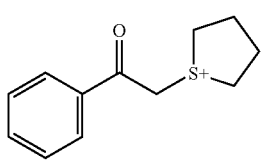
(A-175)
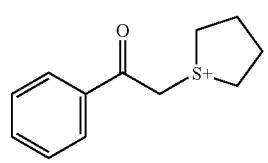
(A-176)
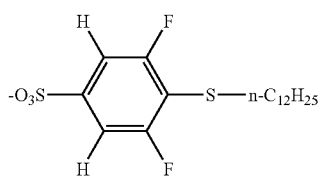
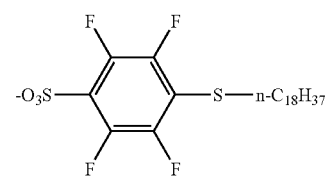

-continued
(A-177)
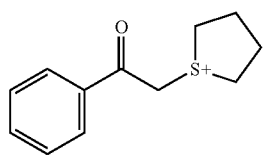
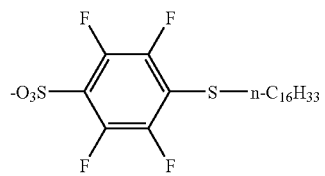
(A-178)
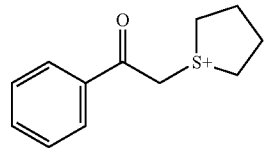
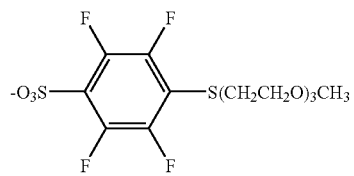
(A-179)
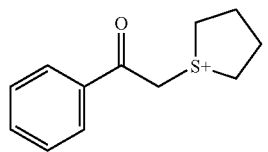
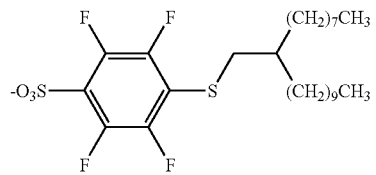
(A-180)
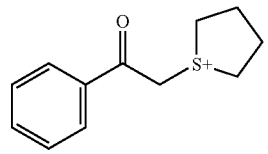
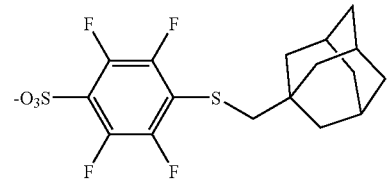
(A-181)
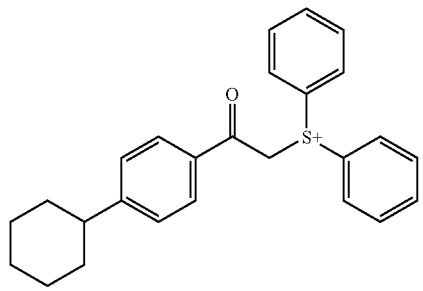
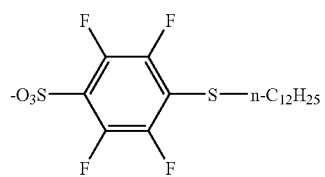
(A-182)
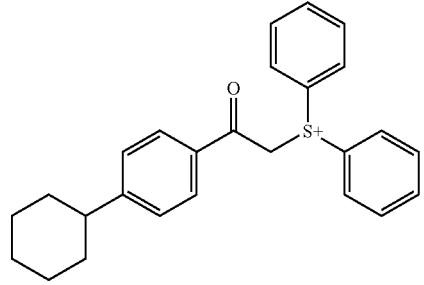
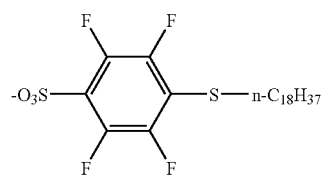

-continued
(A-183)
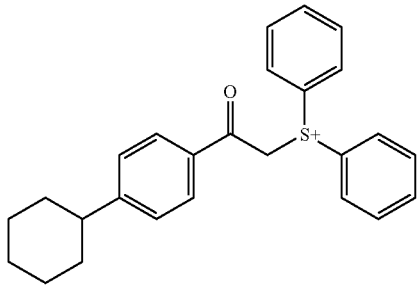
(A-184)
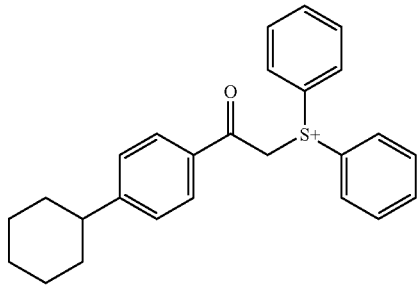
(A-185)
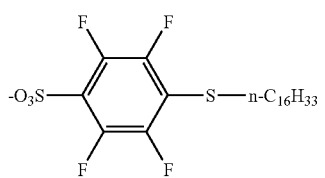
(A-186)
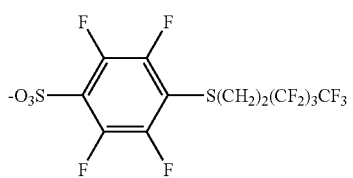
(A-187)
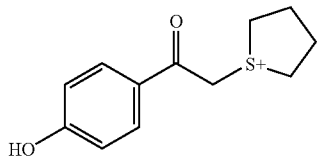
(A-188)
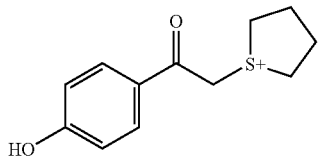
(A-189)
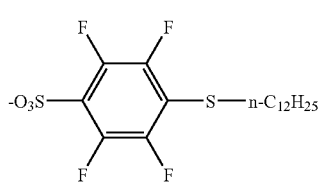
(A-190)
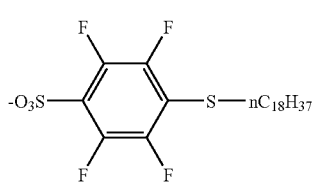
(A-191)
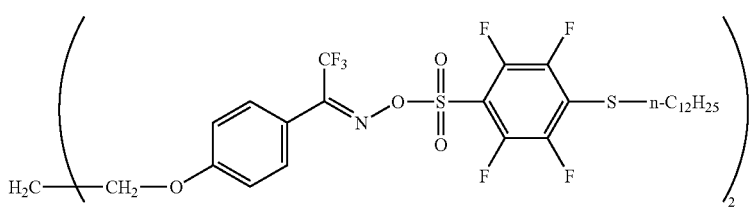

$^{19}$F-NMR (300 MHz, (CD$_3$)$_2$SO) δ:
−140.11 (m, 2F), −156.00 (m, 2F).

Synthesis Example 7

Synthesis of Compound (A-91)

A BF$_4$ salt of Compound (A-91) (1.8 g (4.41 mmol)) and 2.0 g (4.58 mmol) of 4-dodecyloxy-2,3,5,6-tetrafluoro-benzenesulfonic acid were dissolved in a mixed solvent of chloroform (100 mL), acetonitrile (100 mL) and water (100 mL) and stirred at room temperature for 2 hours. The resulting solution was concentrated and after adding chloroform (200 mL), washed three times with water (200 mL) The solvent was removed and the residue was purified by column chromatography (SiO$_2$, ethyl acetate/hexane=1/1) to obtain the objective solid (2.42 g, 60%).

$^1$H-NMR (300 MHz, CDCl$_3$) δ:

0.877 (t, 9H), 1.262 (bs, 48H), 1.431 (m, 6H), 1.773 (m, 6H), 3.521 (m, 4H), 4.210 (t, 2H), 5.430 (s, 2H), 6.833 (d, 2H), 7.774 (d, 2H), 9.483 (s, 1H).

$^{19}$F-NMR (300 MHz, CDCl$_3$) δ: −141.02 (m, 2F), −156.33 (m, 2F).

Synthesis Example 8

Synthesis of Compound (A-95)

A Br salt of Compound (A-95) (1.3 g (4.36 mmol)) and 2.0 g (4.58 mmol) of 4-dodecyloxy-2,3,5,6-tetrafluoro-benzenesulfonic acid were dissolved in a mixed solvent of acetonitrile (100 mL) and water (50 mL) and stirred at room temperature for 2 hours. The resulting solution was concentrated and after adding chloroform (200 mL), washed three times with water (200 mL). Then, the solvent was removed to obtain the objective solid (2.27 g, 82%).

$^1$H-NMR (300 MHz, (CD$_3$)$_2$SO) δ:

0.877 (t, 3H), 1.264 (bs, 16H), 1.431 (m, 2H), 1.729 (m, 2H), 2.225 (m, 4H), 3.511 (m, 4H), 4.212 (t, 2H), 5.223 (s, 2H), 6.933 (d, 2H), 7.871 (d, 2H), 10.761 (s, 1H). $^{19}$F-NMR (300 MHz, (CD$_3$)$_2$SO) δ:

−140.88 (m, 2F), −156.55 (m, 2F).

Synthesis Example 9

Synthesis of Compound (A-4)

Methylpropanyl pentafluorobenzenesulfonic acid ester (10.0 g (32.9 mmol)) and 1.12 g (3.3 mmol) of tetrabutylammonium hydrogensulfate were dissolved in 50 mL of 1,2-dichloroethane and the resulting solution was ice-cooled. Thereto, 6.65 g (32.9 mmol) of 1-dodecanethiol and subsequently 50 mL of an aqueous 1M-sodium hydroxide solution were added and stirred under ice cooling for 40 minutes. The obtained reaction solution was transferred to a separating funnel, the organic phase was washed twice with water and then dried over anhydrous magnesium sulfate, and the solvent was removed to obtain 15.6 g (32.0 mmol) of a colorless transparent oil. Thereafter, 8.0 g (16.43 mmol) of this colorless transparent oil was dissolved in 60 mL of acetonitrile and after adding 2.96 g (19.7 mmol) of sodium iodide, stirred at room temperature for 5 hours in a nitrogen atmosphere. The resulting reaction solution was ice-cooled and further stirred for 1 hour, the precipitated solid was filtered, and the filtered material was thermally recrystallized from methanol to obtain 6.7 g (14.8 mmol) of 4-dodecylsulfanyl-2,3,5,6-tetrafluorobenzenesulfonic acid as a plate-like white crystal.

$^1$H-NMR (300 MHz, CD$_3$OD) δ:

0.880 (t, 3H), 1.258 (bs, 18H), 1.412 (m, 2H), 3.090 (t, 2H).

$^{19}$F-NMR (300 MHz, CD$_3$OD) δ: −140.81 (m, 2F), −136.61 (m, 2F).

Subsequently, 5.07 g (11.2 mmol) of the white crystal obtained was dissolved in 200 mL of methanol and after adding 3.84 g (11.2 mmol) of triphenylsulfonium bromide, stirred at room temperature for 2 hours. Thereto, 300 mL of chloroform was added and the organic layer was washed several times with water. The organic layer was filtered through a 0.1-µm filter and then the solvent was removed to obtain 6.2 g (9.81 mmol) of the objective compound as a colorless transparent oil.

$^1$H-NMR (300 MHz, CDCl$_3$) δ:

0.8 (t, 3H), 1.250-1.523 (bs, 18H), 1.523 (m, 2H), 2.882 (t, 2H), 7.661-7.811 (m, 15H).

$^{19}$F-NMR (300 MHz, CDCl$_3$) δ: −135.16 (m, 2F), −138.56 (m, 2F).

Other acid generators were synthesized in the same manner.

<Synthesis of Resin (B)>

Synthesis Example 1

Synthesis of Resin (1) (Side Chain Type)

2-Ethyl-2-adamantyl methacrylate and butyrolactone methacrylate were charged at a ratio of 55/45 and dissolved in methyl ethyl ketone/tetrahydrofuran=5/5 to prepare 100 mL of a solution having a solid concentration of 20%. To this solution, 2 mol % of V-65 produced by Wako Pure Chemical Industries, Ltd. was added and the resulting solution was added dropwise to 10 mL of methyl ethyl ketone heated at 60° C., over 4 hours in a nitrogen atmosphere. After the completion of dropwise addition, the reaction solution was heated for 4 hours, 1 mol % of V-65 was again added thereto and the resulting solution was stirred for 4 hours. After the completion of reaction, the reaction solution was cooled to room temperature and crystallized in 3 L of a mixed solvent of distilled water/ISO propyl alcohol (=1/1) and Resin (1) as the precipitated white powder was recovered.

The polymer composition ratio determined from $C^{13}$NMR was 46/54. The mass average molecular weight in terms of standard polystyrene as determined by GPC was 10,700.

Resins (2) to (12) and (26) to (31) were synthesized in the same manner as in Synthesis Example 1.

Synthesis Example 2

Synthesis of Resin (13) (Main Chain Type)

Into a separable flask, tert-butyl norbornene-carboxylate, butyrolactone norbornenecarboxylate and maleic anhydride (molar ratio: 40/10/50) and also THF (reaction temperature, 60 mass %) were charged and heated at 60° C. in a nitrogen stream. When the reaction temperature was stabilized, 2 mol % of radical initiator V-601 produced by Wako Pure Chemical Industries, Ltd. was added to initiate the reaction. After heating for 12 hours, the obtained reaction mixture was 2-fold diluted with tetrahydrofuran and then charged into a mixed solution of hexane/isopropyl alcohol=1/1 to precipitate white powder. The precipitated powder was collected by filtration and dried to obtain the objective Resin (13).

The molecular weight of Resin (13) obtained was analyzed by GPC and found to be 8,300 (mass average) in terms of polystyrene. Also, by NMR spectrum, the molar ratio of tert-butyl norbornenecarboxylate/butyrolactone norbornenecarboxylate/malic anhydride repeating units in Resin (1) was confirmed to be 42/8/50.

Resins (14) to (19) were synthesized in the same manner as in Synthesis Example 2.

Synthesis Example 3

Synthesis of Resin (20) (Hybrid Type)

Norbornene, maleic anhydride, tert-butyl acrylate and 2-methylcyclohexyl-2-propyl acrylate at a molar ratio of 35/35/20/10 were charged into a reaction vessel and dissolved in tetrahydrofuran to prepare a solution having a solid content of 60%. This solution was heated at 65° C. in a nitrogen stream. When the reaction temperature was stabilized, 1 mol % of radical initiator V-601 produced by Wako Pure Chemical Industries, Ltd. was added to initiate the reaction. After heating for 8 hours, the obtained reaction mixture was 2-fold diluted with tetrahydrofuran and then charged into hexane in a volume of 5 times the reaction mixture to precipitate white powder. The precipitated powder was collected by filtration, dissolved in methyl ethyl ketone and re-precipitated in a 5-fold volume of a mixed solvent of hexane/tert-butyl methyl ether (=1/1). The white powder precipitated was collected by filtration and dried to obtain the objective Resin (20).

The molecular weight of Resin (20) obtained was analyzed by GPC and found to be 12,100 (mass average) in terms of polystyrene. Also, by NMR spectrum, the molar ratio of norbornene/maleic anhydride/tert-butyl acrylate/2-methylcyclohexyl-2-propyl acrylate in the composition of Resin (20) was found to be 32/39/19/10.

Resins (21) to (25) were synthesized in the same manner as in Synthesis Example 3.

The structure and molecular weight of each of Resins (1) to (31) are shown below.

|  | Molecular Weight |
|---|---|
| (1) | 10700 |

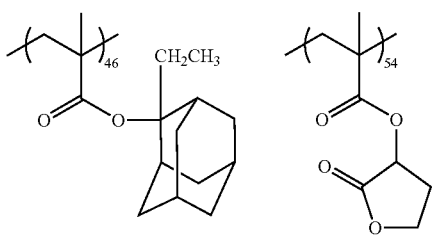

-continued
| | Molecular Weight |
|---|---|
| (2) 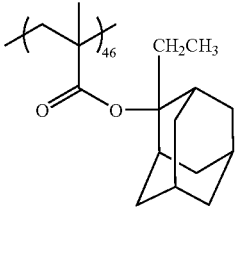 | 9400 |
| (3) 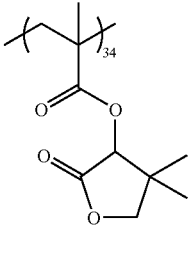 | 8300 |
| (4) 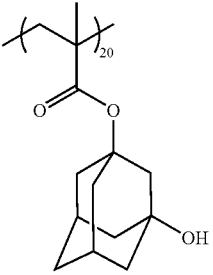 | 10300 |
| (5) 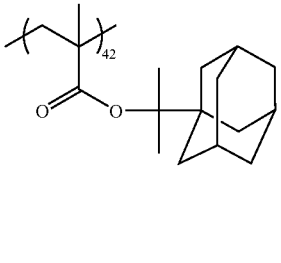 | 8900 |
| (6) 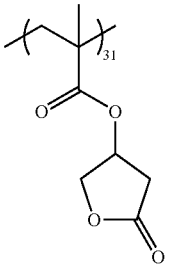 | 11300 |

|  | Molecular Weight |
|---|---|
| (7) 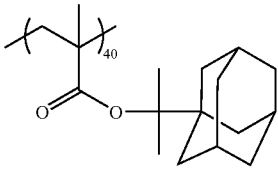 | 8900 |
| (8) 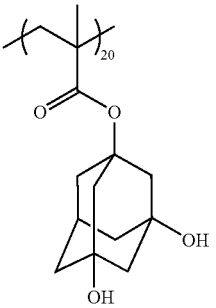 | 11700 |
| (9) 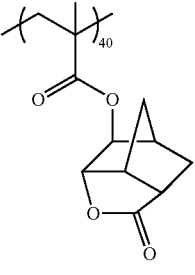 | 9800 |
| (10) 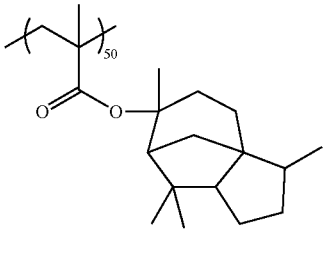 | 8700 |

| | Molecular Weight |
|---|---|
| (11) | 13400 |
| (12) | 10900 |
| (13) | 8300 |
| (14) | 8200 |
| (15) | 9600 |
| (16) | 5800 |

-continued

| | Molecular Weight |
|---|---|
| (17) | 4700 |
| (18) | 8500 |
| (19) | 8900 |
| (20) | 12100 |
| (21) | 13900 |
| (22) | 12400 |

-continued
| | Molecular Weight |
|---|---|
| (23) 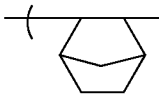 | 12700 |
| (24) 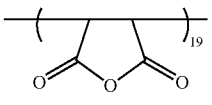 | 10800 |
| (25) 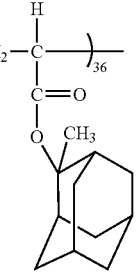 | 9300 |
| (26) 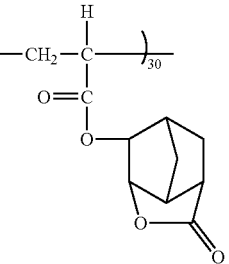 | 9300 |
| (27) 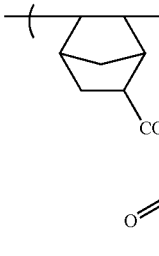 | 7600 |

-continued
| | Molecular Weight |
|---|---|
| (28) | 7300 |
| (29) | 7600 |
| (30) | 8400 |
| (31) | 6500 |
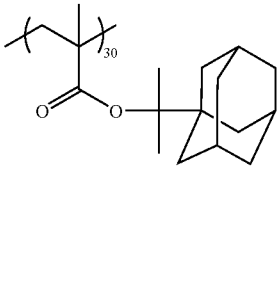

<Fluorine Group-Containing Resin>
Structures of Fluorine Group-Containing Resins (FII-1) to (FII-40) used in Examples are shown below.
Also, the weight average molecular weight and the like of each of Fluorine Group-Containing Resins (FII-1) to (FII-40) are shown in Tables 1 and 2 below.
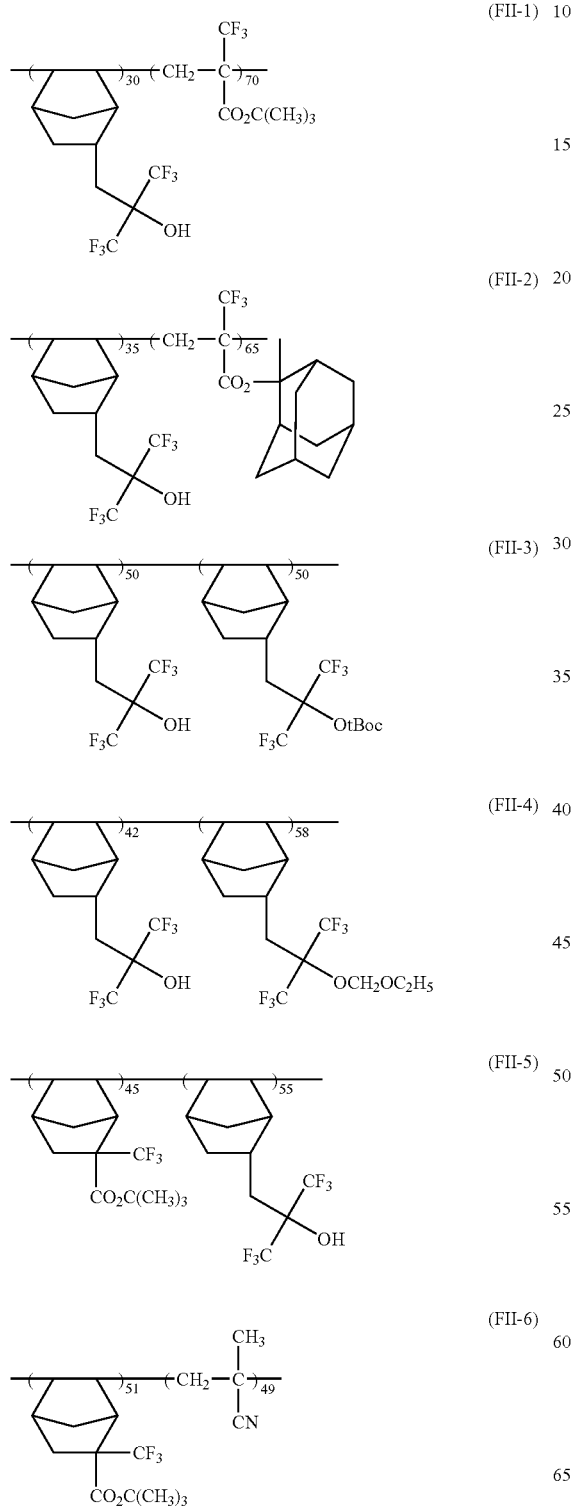
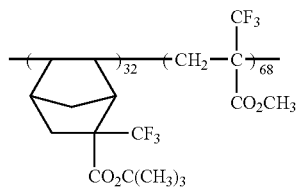
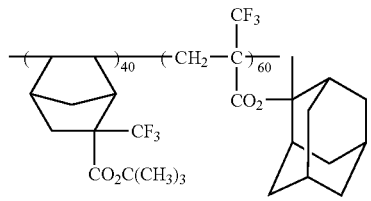
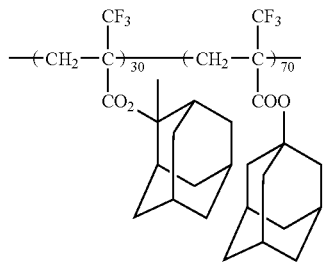
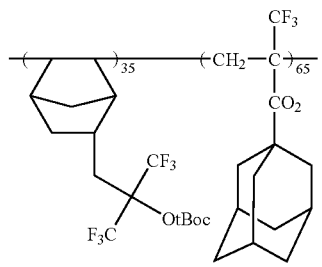
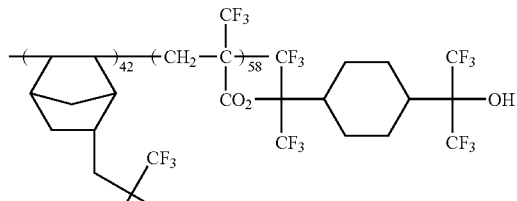
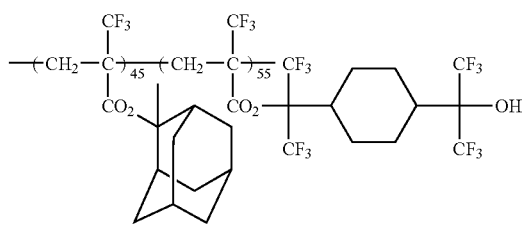

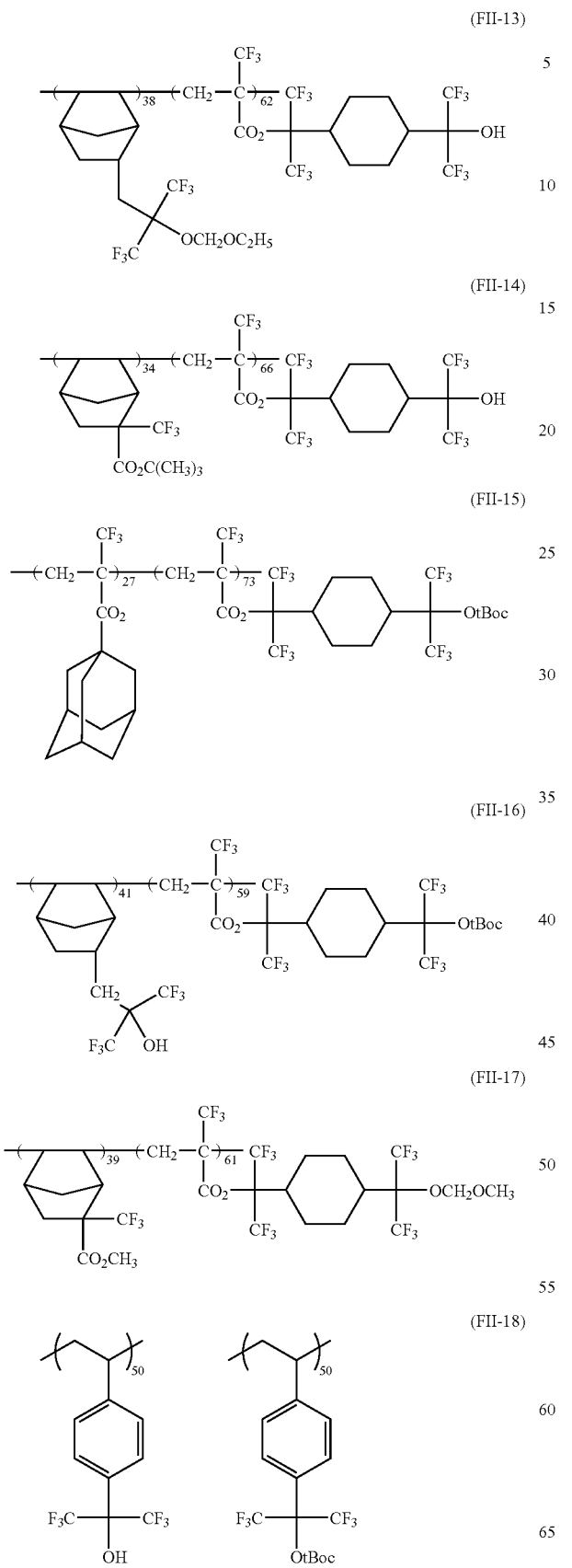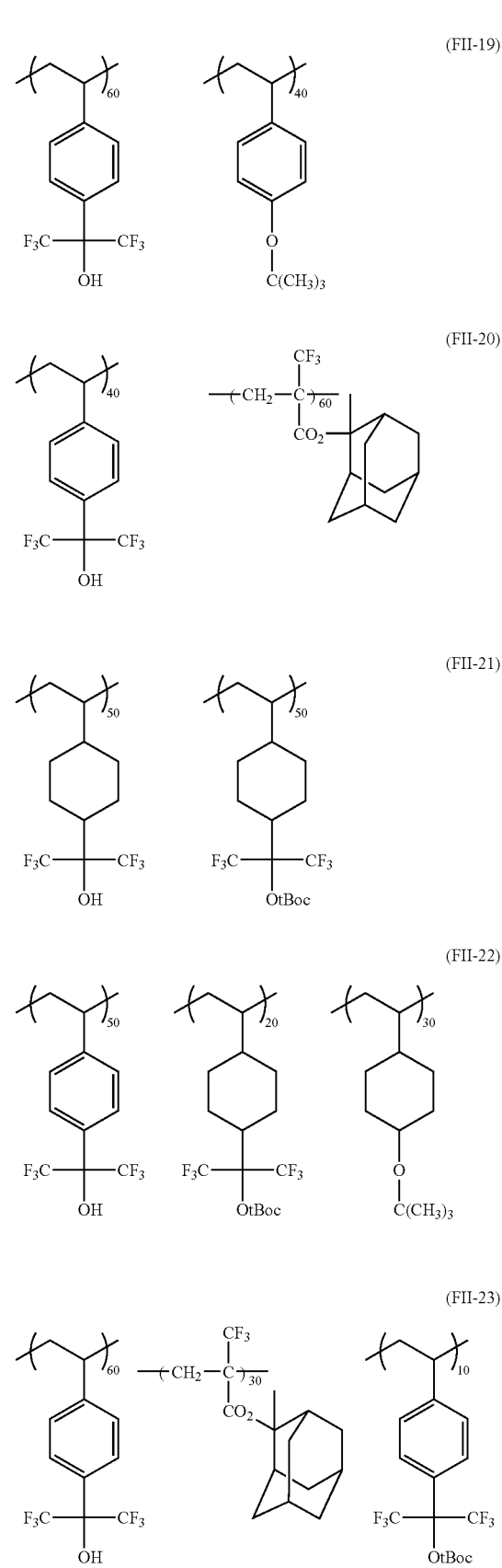

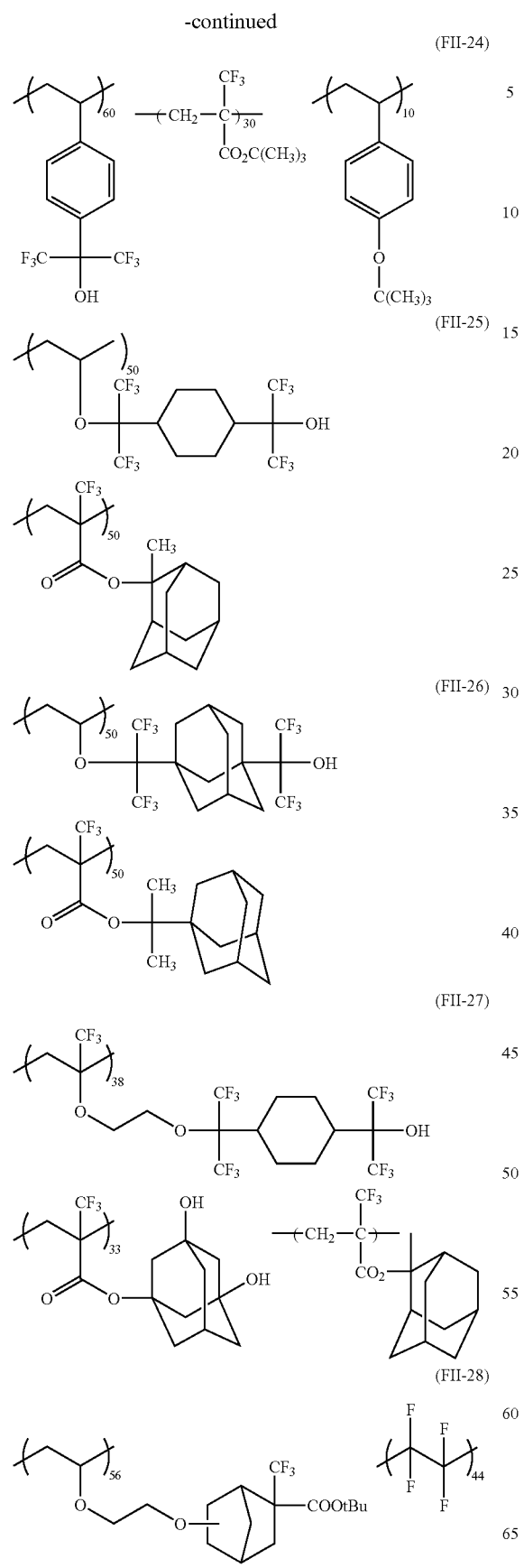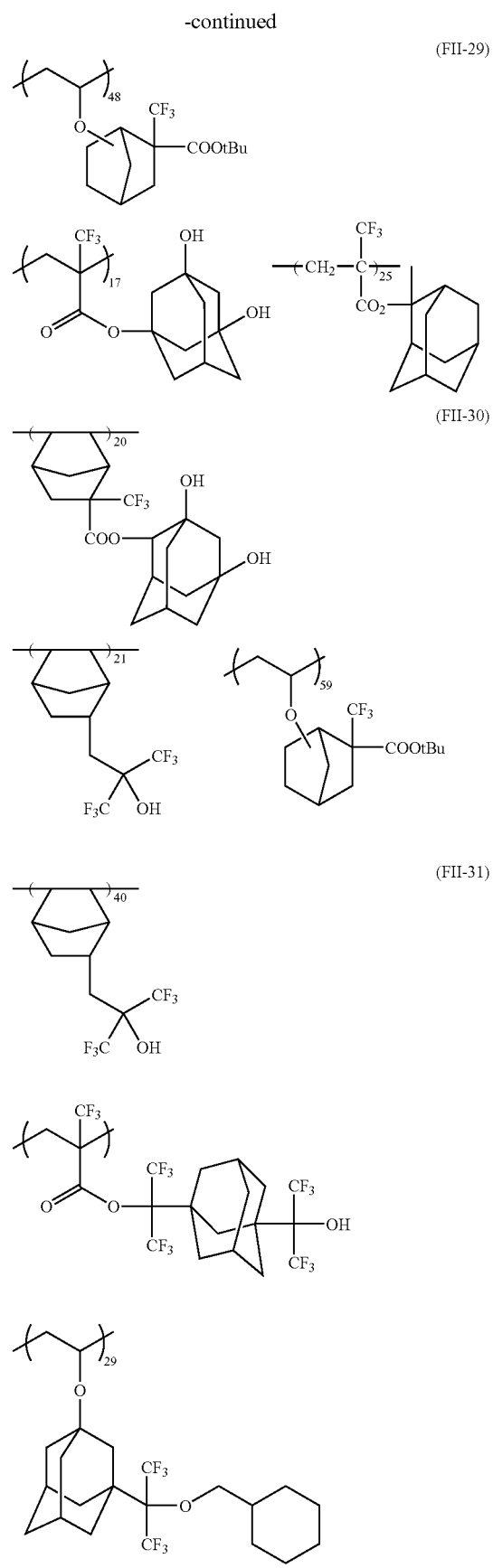

-continued
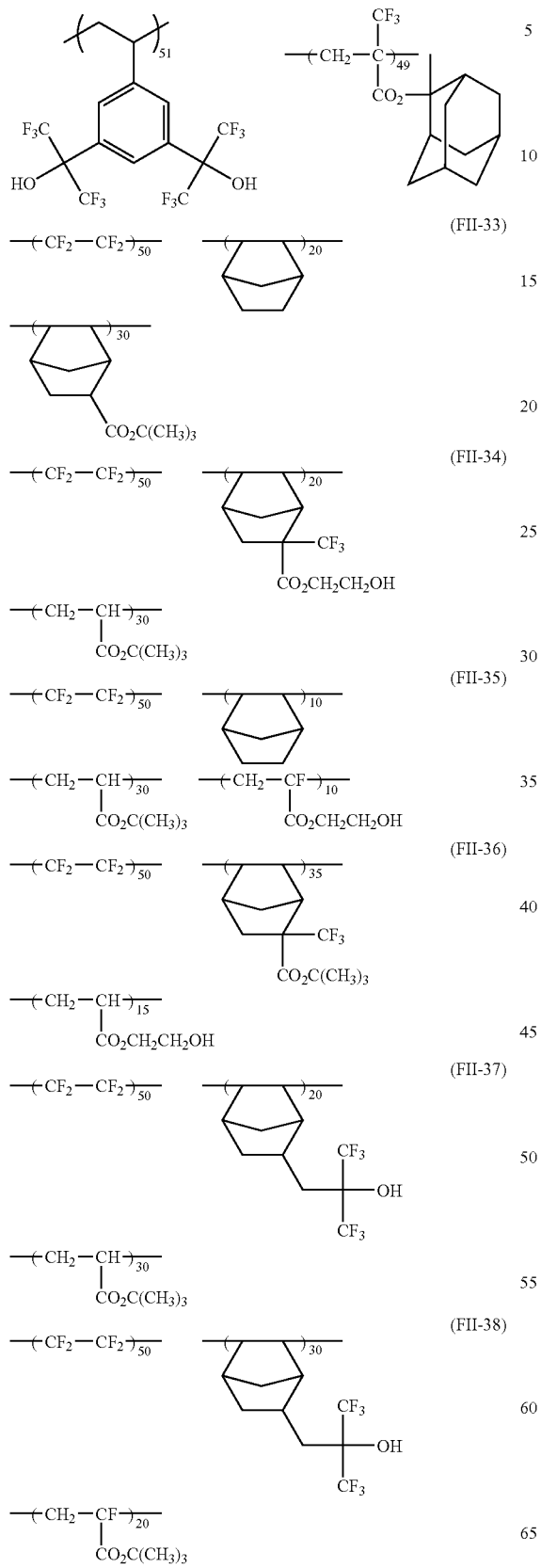
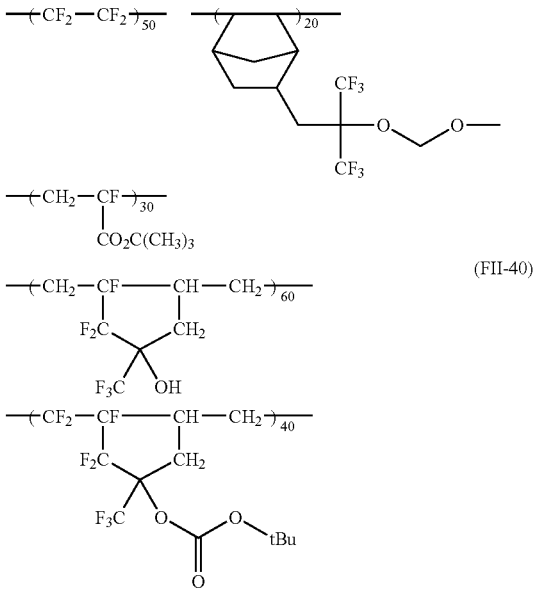
TABLE 1
| Resin | Weight Average Molecular Weight, Mw | Dispersity | Content of Oligomer Having Molecular Weight of 1,000 or Less |
|---|---|---|---|
| (FII-1) | 15200 | 1.45 | 5 |
| (FII-2) | 24000 | 1.75 | 8 |
| (FII-3) | 18200 | 1.85 | 7 |
| (FII-4) | 16500 | 1.46 | 6 |
| (FII-5) | 9500 | 1.58 | 8 |
| (FII-6) | 19500 | 2.02 | 8 |
| (FII-7) | 6500 | 1.85 | 7 |
| (FII-8) | 28400 | 1.68 | 9 |
| (FII-9) | 28600 | 1.44 | 5 |
| (FII-10) | 12800 | 1.65 | 8 |
| (FII-11) | 16800 | 1.68 | 9 |
| (FII-12) | 28400 | 1.58 | 6 |
| (FII-13) | 19800 | 1.69 | 8 |
| (FII-14) | 8700 | 1.95 | 8 |
| (FII-15) | 15200 | 1.46 | 7 |
| (FII-16) | 19500 | 1.65 | 4 |
| (FII-17) | 16900 | 1.42 | 8 |
| (FII-18) | 15900 | 1.85 | 9 |
| (FII-19) | 15000 | 1.55 | 4 |
| (FII-20) | 12500 | 1.88 | 8 |
| (FII-21) | 25000 | 1.68 | 9 |
| (FII-22) | 16000 | 1.54 | 7 |
| (FII-23) | 14600 | 1.95 | 5 |
| (FII-24) | 17500 | 1.48 | 5 |
| (FII-25) | 16500 | 1.52 | 6 |
| (FII-26) | 14600 | 1.63 | 5 |
TABLE 2
| Resin | Weight Average Molecular Weight, Mw | Dispersity |
|---|---|---|
| (FII-27) | 8300 | 1.55 |
| (FII-28) | 8300 | 1.62 |
| (FII-29) | 8000 | 1.52 |
| (FII-30) | 9200 | 1.71 |
| (FII-31) | 10200 | 1.47 |
| (FII-32) | 7900 | 1.35 |

TABLE 2-continued

| Resin | Weight Average Molecular Weight, Mw | Dispersity |
| --- | --- | --- |
| (FII-33) | 6800 | 1.60 |
| (FII-34) | 7400 | 1.59 |
| (FII-35) | 8300 | 1.70 |
| (FII-36) | 4800 | 1.55 |
| (FII-37) | 4700 | 1.51 |
| (FII-38) | 6400 | 1.69 |
| (FII-39) | 9600 | 1.70 |
| (FII-40) | 4600 | 1.68 |

Examples 1 to 58 and Comparative Examples 1 and 2

<Preparation of Resist>

The components shown in Tables 3 to 7 below were dissolved in a solvent to prepare a solution having a solid concentration of 12 mass % and this solution was filtered through a 0.1-μm polytetrafluoroethylene filter or polyethylene filter to prepare a positive resist solution. The prepared positive resist solutions were evaluated by the following methods and the results are shown in Tables 3 to 7.

Abbreviations in Tables are as follows. The resins and acid generators not shown below are already exemplified above. In each Table, when multiple resins or solvents are used, the ratio is a ratio by mass.

[Acid Generator]
TPSB: triphenylsulfonium pentafluorobenzenesulfonate
MSDBS: 4-methylphenyldiphenylsulfonium 4-(n-dodecyl)benzene-sulfonate
TPSPFBSI: triphenylsulfonium-bis(perfluorobutanesulfonyl)imide
Other acid generators are already exemplified above.

[Basic Compound]
DBN: 1,5-diazabicyclo[4.3.0]-non-5-ene
TPI: 2,4,5-triphenylimidazole
TPSA: triphenylsulfonium acetate
HEP: N-hydroxyethylpiperidine
DIA: 2,6-diisopropylaniline
DCMA: dicyclohexylmethylamine
TPA: tripentylamine
TOA: tri-n-octylamine
HAP: hydroxyantipyrine
TBAH: tetrabutylammonium hydroxide
TMEA: tris(methoxyethoxyethyl)amine
PEN: N-phenyldiethanolamine

[Surfactant]
W-1: Megafac F176 (produced by Dainippon Ink & Chemicals, Inc.) (fluorine-containing surfactant)
W-2: Megafac R08 ((produced by Dainippon Ink & Chemicals, Inc.) (fluorine/silicon-containing surfactant)
W-3: polysiloxane polymer KP-341 (produced by Shin-Etsu Chemical Co., Ltd.) (silicon-containing surfactant)
W-4: Troysol S-366 (produced by Troy Chemical)

[Solvent]
A1: propylene glycol methyl ether acetate
A2: 2-heptanone
A3: ethyl ethoxypropionate
A4: γ-butyrolactone
A5: cyclohexanone
B1: propylene glycol methyl ether
B2: ethyl lactate

[Dissolution Inhibitor]
LCB: tert-butyl lithocholate

<Evaluation of Resist>

On a silicon substrate treated with hexamethyl-disilazane, an antireflective film DUV-42 produced by Brewer Science Co., Ltd. was uniformly coated to a thickness of 600 Å, dried on a hot plate at 100° C. for 90 seconds and then dried under heating at 190° C. for 240 seconds. Thereafter, each positive resist solution was coated by a spin coater and dried at 120° C. for 90 seconds to form a resist film of 0.30 μm.

The formed resist film was exposed by an ArF excimer laser stepper (manufactured by ISI, NA=0.6) through a mask and immediately after the exposure, heated on a hot plate at 120° C. for 90 seconds. Thereafter, the resist film was developed with an aqueous 2.38 mass % tetramethylammonium hydroxide solution at 23° C. for 60 seconds, rinsed with pure water for 30 seconds and dried to obtain a line pattern.

PEB Temperature Dependency

Assuming that the exposure amount necessary for reproducing a 1/1 line-and-space pattern with a mask size of 130 nm after heating at 120° C. for 90 seconds is an optimal exposure amount, the sample was exposed with the optimal exposure amount and post-heated at two temperatures of +2° C. and −2° C. (122° C., 118° C.) with respect to the post-heating temperature. The length of each line-and-space pattern obtained was measured and the line width ($L_1$, $L_2$) was determined. The PEB temperature dependency was defined as the fluctuation in the line width per 1° C. change of the PEB temperature and calculated according to the following formula:

$$\text{PEB Temperature Dependency (nm/° C.)} = |L_1 - L_2|/4$$

A smaller value reveals smaller change in the performance against change in the temperature, and higher performance.

Pattern Profile

The profile at the optimal exposure amount was observed by a scanning microscope (SEM).

TABLE 3

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
| --- | --- | --- | --- | --- | --- | --- | --- | --- | --- |
| 1 | A-1 (0.3) | — | 1 | DIA (0.02) | W-1 | A1/B1 (60/40) | — | 3.8 | rectangular |

TABLE 3-continued

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 2 | A-12 (0.3) | z14 (0.15) | 2 | PEA (0.02) | W-4 | A1/B1 (60/40) | — | 2.3 | rectangular |
| 3 | A-1 (0.2) | Z1 (0.20) | 3 | DIA (0.02) | W-3 | A1/B1 (60/40) | — | 3.4 | rectangular |
| 4 | A-13 (0.3) | Z38 (0.20) | 4 | TMEA (0.02) | W-4 | A1/B1 (80/20) | — | 2.2 | rectangular |
| 5 | A-17 (0.3) | z52 (0.20) | 5 | DIA (0.02) | W-3 | A1/B1 (60/40) | — | 4.7 | rectangular |
| 6 | A-1 (0.2) | Z44 (0.15) | 6 | PEA (0.02) | W-1 | A1/B1 (60/40) | — | 2.5 | rectangular |
| 7 | A-3 (0.3) | Z50 (0.10) | 7 | PEA (0.02) | W-4 | A1/A5 (40/60) | — | 3.0 | rectangular |
| 8 | A-1 (0.3) | z36 (0.10) | 8 | PEA (0.02) | W-2 | A1/B1 (60/40) | LCB (2) | 3.8 | rectangular |
| 9 | A-2 (0.2) | Z52 (0.15) | 9 | DIA (0.02) | W-4 | A1/A5 (30/70) | — | 2.8 | rectangular |
| 10 | A-22 (0.3) | z1 (0.10) | 10 | DIA (0.02) | W-2 | A1/B1 (90/10) | — | 3.6 | rectangular |

TABLE 4

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 11 | A-29 (0.2) | z2 (0.20) | 11 | PEA (0.02) | W-1 | A1/A4 (95/5) | — | 4.8 | rectangular |
| 12 | A-40 (0.2) | z5 (0.20) | 12 | TPSA (0.02) | W-3 | A1/B2 (80/20) | — | 7.7 | rectangular |
| 13 | A-37 (0.2) | z44 (0.20) | 13 | TBAH (0.02) | W-1 | A1/B1 (60/40) | — | 3.6 | rectangular |
| 14 | A-44 (0.2) | z46 (0.15) | 14 | HAP (0.02) | W-4 | A1/B1 (95/5) | — | 4.0 | rectangular |
| 15 | A-49 (0.15) | Z51 (0.20) | 15 | DCMA (0.02) | W-2 | A1/B1 (60/40) | — | 4.1 | rectangular |
| 16 | A-53 (0.15) | Z25 (0.10) | 16 | TOA (0.02) | W-4 | A1/B1 (60/40) | — | 2.6 | rectangular |
| 17 | A-61 (0.10) | Z38 (0.20) | 17 | DIA (0.02) | W-3 | A1/A4 (95/5) | — | 3.7 | rectangular |
| 18 | A-63 (0.15) | Z14 (0.20) | 18 | HEP (0.02) | W-1 | A1/B2 (80/20) | — | 3.0 | rectangular |
| 19 | A-69 (0.15) | Z1 (0.20) | 19 | DIA (0.02) | W-2 | A1/B1 (60/40) | — | 4.5 | rectangular |
| 20 | A-78 (0.2) | z38 (0.15) | 20 | TPSA (0.02) | W-1 | A1/B1 (40/40) | — | 2.9 | rectangular |

TABLE 5

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 21 | A-79 (0.2) | z52 (0.1) | 21 | PEA (0.02) | W-3 | A1/B2 (80/20) | — | 3.2 | rectangular |
| 22 | A-81 (0.15) | z50 (0.2) | 22 | TPA (0.02) | W-1 | A1/B1 (60/40) | — | 2.6 | rectangular |
| 23 | A-83 (0.25) | z44 (0.1) | 23 | DIA (0.02) | W-4 | A1/A4 (95/5) | — | 3.9 | rectangular |
| 24 | A-88 (0.25) | Z54 (0.1) | 24 | TOA (0.02) | W-2 | A1/B1 (60/40) | — | 2.4 | rectangular |
| 25 | A-1 (0.1) A-91 (0.1) | Z42 (0.15) | 25 | PEA (0.02) | W-4 | A1/B2 (80/20) | — | 2.9 | rectangular |

TABLE 5-continued

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 26 | A-99 (0.2) | Z21 (0.1) | 26 | DIA (0.02) | W-1 | A1/B1 (60/40) | — | 2.6 | rectangular |
| 27 | A-107 (0.2) | Z38 (0.2) | 27 | TBAH (0.02) | W-3 | A1/B1 (60/40) | — | 3.0 | rectangular |
| 28 | A-1 (0.15) | Z14 (0.15) | 28 | DIA (0.02) | W-4 | A1/B1 (60/40) | — | 1.4 | rectangular |
| 29 | A-5 (0.15) | z53 (0.15) z14 (0.10) | 29 | PEA (0.02) | W-4 | A1/B1 (60/40) | — | 2.3 | rectangular |
| 30 | A-8 (0.1) | Z54 (0.2) | 30 | PEA (0.02) | W-4 | A1/A5 (30/70) | — | 2.8 | rectangular |
| 31 | A-10 (0.1) | z14 (0.2) | 31 | PEA (0.02) | W-4 | A1/B1 (60/40) | — | 3.0 | rectangular |

TABLE 6

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 32 | A-4 (0.3) | — | 1 | DIA (0.02) | W-1 | A1/B1 (60/40) | — | 2.1 | rectangular |
| 33 | A-4 (0.3) | z2 (0.2) | 2 | PEA (0.02) | W-1 | A1/B1 (60/40) | — | 2.1 | rectangular |
| 34 | A-4 (0.3) | z3 (0.2) | 3 | PEA (0.03) | W-1 | A1/B1 (60/40) | — | 2.3 | rectangular |
| 35 | A-4 (0.3) | z8 (0.2) | 6 | PEA (0.04) | W-1 | A1/B1 (60/40) | LCB (2) | 2.4 | rectangular |
| 36 | A-4 (0.3) | z15 (0.2) | 7 | PEA (0.05) | W-1 | A1/B1 (60/40) | — | 2.6 | rectangular |
| 37 | A-127 (0.3) | z16 (0.2) | 12 | DIA (0.02) | W-1 | A1/B1 (60/40) | — | 2.8 | rectangular |
| 38 | A-127 (0.3) | z22 (0.2) | 13 | TMEA (0.02) | W-1 | A1/B1 (60/40) | — | 3.0 | rectangular |
| 39 | A-129 (0.3) | z30 (0.2) | 23 | DIA (0.02) | W-1 | A1/B1 (60/40) | — | 3.0 | rectangular |
| 40 | A-129 (0.3) | z34 (0.2) | 28 | PEA (0.02) | W-1 | A1/B1 (60/40) | — | 3.1 | rectangular |
| 41 | A-131 (0.3) | z36 (0.2) | 29 | PEA (0.02) | W-1 | A1/A5 (60/40) | — | 3.2 | rectangular |
| 42 | A-131 (0.3) | z38 (0.2) | 30 | PEA (0.02) | W-1 | A1/B1 (60/40) | — | 3.2 | rectangular |
| 43 | A-136 (0.3) | z40 (0.2) | 31 | DIA (0.02) | W-1 | A1/A5 (60/40) | — | 3.3 | rectangular |
| 44 | A-137 (0.3) | z51 (0.2) | 1 | DIA (0.02) | W-1 | A1/B1 (60/40) | — | 3.4 | rectangular |
| 45 | A-140 (0.3) | z52 (0.2) | 2 | PEA (0.02) | W-1 | A1/A4 (60/40) | — | 3.6 | rectangular |
| 46 | A-140 (0.3) | z38 (0.2) | 3 | TPSA (0.02) | W-1 | A1/B1 (60/40) | — | 3.7 | rectangular |

TABLE 7

| Example | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 47 | A-141 (0.3) | z38 (0.2) | 6 | TBAH (0.02) | W-1 | A1/B1 (60/40) | — | 3.8 | rectangular |
| 48 | A-143 (0.3) | z38 (0.2) | 7 | HAP (0.02) | W-1 | A1/B1 (60/40) | — | 3.8 | rectangular |

TABLE 7-continued

| | Acid Generator (g) | Acid Generator Used in Combination (g) | Resin (10 g) | Basic Compound (g) | Surfactant (0.03 g) | Solvent (mass ratio) | Component (C) (g) | PEB Temperature Dependency (nm/° C.) | Pattern Profile |
|---|---|---|---|---|---|---|---|---|---|
| 49 | A-144 (0.3) | z38 (0.2) | 12 | DCMA (0.02) | W-1 | A1/B1 (60/40) | — | 3.9 | rectangular |
| 50 | A-149 (0.3) | z2 (0.2) | 13 | TOA (0.02) | W-1 | A1/B1 (60/40) | — | 3.9 | rectangular |
| 51 | A-155 (0.3) | z2 (0.2) | 23 | DIA (0.02) | W-1 | A1/A4 (60/40) | — | 4.0 | rectangular |
| 52 | A-159 (0.3) | z2 (0.2) | 28 | HEP (0.02) | W-1 | A1/B2 (60/40) | — | 4.0 | rectangular |
| 53 | A-161 (0.3) | z2 (0.2) | 29 | DIA (0.02) | W-1 | A1/B1 (60/40) | — | 4.2 | rectangular |
| 54 | A-163 (0.3) | z2 (0.2) | 30 | TPSA (0.02) | W-1 | A1/B1 (60/40) | — | 4.2 | rectangular |
| 55 | A-167 (0.3) | z2 (0.2) | 31 | PEA (0.02) | W-1 | A1/B2 (60/40) | — | 4.8 | rectangular |
| 56 | A-175 (0.3) | z2 (0.2) | 27 | TPA (0.02) | W-1 | A1/B1 (60/40) | — | 4.8 | rectangular |
| 57 | A-188 (0.3) | z2 (0.2) | 26 | DIA (0.02) | W-1 | A1/A4 (60/40) | — | 4.8 | rectangular |
| 58 | A-187 (0.3) | z2 (0.2) | 4 | TPA (0.02) | W-1 | A1/B2 (60/40) | — | 5.2 | rectangular |
| Comp. Example | | | | | | | | | |
| 1 | TPSB (0.3) | — | 1 | DIA (0.02) | W-1 | A1/B1 (60/40) | — | 10.3 | slightly tapered |
| 2 | MSDBS (0.3) | — | 1 | DIA (0.02) | W-1 | A1/B1 (60/40) | — | image was not formed | image was not formed |

As apparent from the results in Tables 3 to 7, the photosensitive composition of the present invention exhibits small PEB temperature dependency at the ArF exposure and gives an excellent pattern profile.

Examples 59 to 71 and Comparative Examples 3 to 7

(1) Formation of Lower Resist Layer

FHi-028DD Resist (resist for i-line, produced by Fujifilm Olin Co., Ltd.) was coated on a 6-inch silicon wafer by using a spin coater Mark 8 manufactured by Tokyo Electron Ltd. and then baked at 90° C. for 90 seconds to obtain a uniform film having a thickness of 0.55 μm.

This film was further heated at 200° C. for 3 minutes to form a lower resist layer having a thickness of 0.40 μm.

(2) Formation of Upper Resist Layer

The components shown in Tables 8 and 9 below were dissolved in a solvent to prepare a solution having a solid concentration of 11 mass % and this solution was microfiltered through a membrane filter having a pore size of 0.1 μm to prepare an upper resist composition.

The prepared upper resist composition was coated on the lower resist layer in the same manner and heated at 130° C. for 90 seconds to form an upper resist layer having a thickness of 0.20 μm.

Resins (SI-1) to (SI-5) in Tables 8 and 9 are shown below.

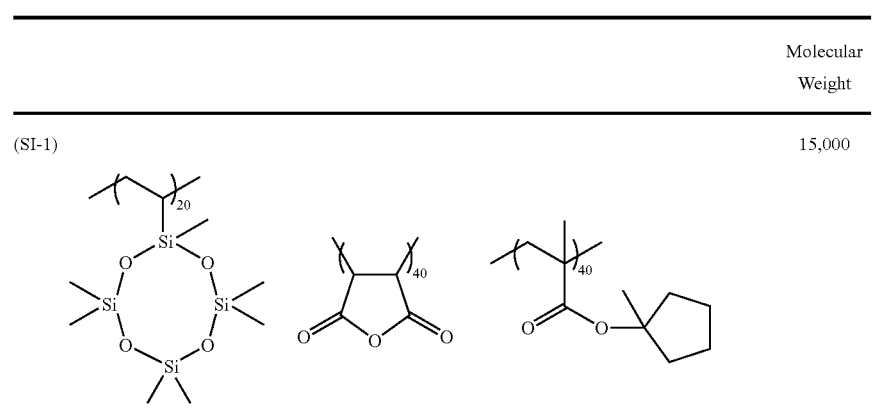

Molecular Weight (SI-1)   15,000

-continued

| | Molecular Weight |
|---|---|
| (SI-2) | 14,500 |

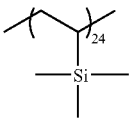

(SI-3) 9,600

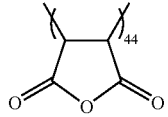

(SI-4) 8900

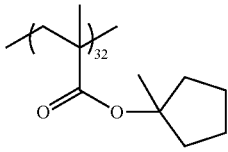

(SI-5) 10800

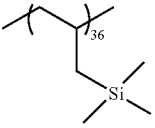

(3) Evaluation of Resist

The wafer obtained above was exposed by an ArF excimer stepper 9300 (manufactured by ISI) having mounted thereon a resolution mask, while changing the exposure amount.

Subsequently, the wafer was heated at 120° C. for 90 seconds, developed with a tetrahydroammonium hydroxide developer (2.38 mass %) for 60 seconds, rinsed with distilled water and dried to obtain an upper layer pattern.

The PEB temperature dependency and pattern profile were evaluated in the same manner as in Examples 1 to 58. The results are shown in Tables 8 and 9.

TABLE 8

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 59 | A-12 (0.3) | z14 (0.15) | SI-1 | DIA (0.02) | W-1 | A1/B1 (60/40) | 4.7 | rectangular |
| 60 | A-49 (0.15) | z50 (0.2) | SI-2 | PEA (0.02) | W-4 | A1/B1 (60/40) | 4.9 | rectangular |
| 61 | A-1 (0.15) | Z14 (0.15) | SI-3 | DIA (0.02) | W-3 | A1/B1 (60/40) | 3.3 | rectangular |
| 62 | A-2 (0.2) | Z52 (0.15) | SI-4 | TMEA (0.02) | W-4 | A1/B1 (80/20) | 4.2 | rectangular |
| 63 | A-10 (0.1) | z14 (0.2) | SI-5 | DIA (0.02) | W-3 | A1/B1 (60/40) | 3.9 | rectangular |

TABLE 9

| | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| Example | | | | | | | | |
| 64 | A-4 (0.3) | z2 (0.15) | SI-1 | PEA (0.02) | W-1 | A1/B1 (60/40) | 3.2 | rectangular |
| 65 | A-127 (0.3) | z2 (0.15) | SI-2 | PEA (0.02) | W-1 | A1/B1 (60/40) | 3.0 | rectangular |
| 66 | A-131 (0.2) | z2 (0.2) | SI-3 | DIA (0.02) | W-1 | A1/B1 (60/40) | 2.8 | rectangular |
| 67 | A-137 (0.3) | z2 (0.2) | SI-4 | TMEA (0.02) | W-4 | A1/B1 (80/20) | 3.9 | rectangular |
| 68 | A-143 (0.3) | z36 (0.2) | SI-5 | DIA (0.02) | W-3 | A1/B1 (60/40) | 3.9 | rectangular |
| 69 | A-149 (0.2) | Z38 (0.15) | SI-4 | PEA (0.02) | W-4 | A1/B1 (60/40) | 2.1 | rectangular |
| 70 | A-163 (0.3) | z38 (0.1) | SI-5 | DIA (0.02) | W-4 | A1/A5 (40/60) | 2.5 | rectangular |
| 71 | A-167 (0.25) | z38 (0.1) | SI-1 | TMEA (0.02) | W-4 | A1/A4 (95/5) | 2.2 | rectangular |
| Comp. Example | | | | | | | | |
| 3 | TPSB (0.3) | z14 (0.15) | SI-1 | DIA (0.02) | W-1 | A1/B1 (60/40) | 10.3 | slightl tapered |
| 4 | MSDBS (0.3) | z14 (0.15) | SI-1 | DIA (0.02) | W-1 | A1/B1 (60/40) | image was not formed | image was not formed |
| 5 | TPSB (0.3) | — | SI-1 | DIA (0.02) | W-1 | A1/B1 (60/40) | 7.8 | slightly tapered |
| 6 | MSDBS (0.3) | — | SI-1 | DIA (0.02) | W-1 | A1/B1 (60/40) | image was not formed | image was not formed |
| 7 | TPSPFBSI (0.3) | — | SI-1 | DIA (0.03) | W-1 | A1/B2 (60/40) | 6.5 | tapered |

As apparent from the results in Tables 8 and 9, the photosensitive composition of the present invention exhibits small PEB dependency even when used as a two-layer resist, and gives an excellent pattern profile.

Examples 72 to 105 and Comparative Examples 8 to 12

<Preparation of Resist>

The components shown in Tables 10 to 12 below were dissolved in a solvent to prepare a solution having a solid concentration of 5 mass % and the resulting solution was filtered through a 0.1-μm polyethylene filter to prepare a resist solution.

On a silicon wafer treated with hexamethyldisilazane, each resist solution was coated by a spin coater and dried under heating on a vacuum contact-type hot plate at 120° C. for 90 seconds to obtain a resist film having a thickness of 0.1 μm.

The obtained resist film was pattern-exposed by using an $F_2$ excimer laser stepper (157 nm) and immediately after the exposure, heated on a hot plate at 120° C. for 90 seconds. Thereafter, the resist film was developed with an aqueous 2.38 mass % tetramethylammonium hydroxide solution for 60 seconds and rinsed with pure water to obtain a sample wafer. These wafers were evaluated on the PEB temperature dependency and pattern profile.

PEB Temperature Dependency

Assuming that the exposure amount necessary for reproducing a 1/1 line-and-space pattern with a mask size of 80 nm after heating at 120° C. for 90 seconds is an optimal exposure amount, the sample was exposed with the optimal exposure amount and post-heated at two temperatures of +2° C. and −2° C. (122° C., 118° C.) with respect to the post-heating temperature. The length of each line-and-space pattern obtained was measured and the line width ($L_1$, $L_2$) was determined. The PEB temperature dependency was defined as the fluctuation in the line width per 1° C. change of the PEB temperature and calculated according to the following formula:

PEB Temperature Dependency (nm/° C.)=$|L_1-L_2|/4$

A smaller value reveals smaller change in the performance against change in the temperature, and higher performance.

Pattern Profile

The profile at the optimal exposure amount was observed by a scanning microscope (SEM).

The results are shown in Tables 10 to 12.

TABLE 10

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 72 | A-1 (0.3) | — | FII-1 | DIA (0.02) | W-1 | A1/B1 (60/40) | 4.5 | rectangular |
| 73 | A-12 (0.3) | Z14 (0.15) | FII-2 | PEA (0.02) | W-4 | A1/B1 (60/40) | 5.2 | rectangular |
| 74 | A-1 (0.2) | Z1 (0.20) | FII-3 | DIA (0.02) | W-3 | A1/B1 (60/40) | 5.5 | rectangular |
| 75 | A-13 (0.3) | Z38 (0.20) | FII-4 | TMEA (0.02) | W-4 | A1/B1 (80/20) | 4.7 | rectangular |
| 76 | A-17 (0.3) | Z52 (0.20) | FII-5 | DIA (0.02) | W-3 | A1/B1 (60/40) | 5.7 | rectangular |
| 77 | A-1 (0.2) | Z44 (0.15) | FII-6 | PEA (0.02) | W-1 | A1/B1 (60/40) | 6.5 | rectangular |
| 78 | A-3 (0.3) | Z50 (0.10) | FII-7 | PEA (0.02) | W-4 | A1/A5 (40/60) | 3.9 | rectangular |
| 79 | A-1 (0.3) | Z36 (0.10) | FII-8 | PEA (0.02) | W-2 | A1/B1 (60/40) | 5.8 | rectangular |
| 80 | A-2 (0.2) | Z52 (0.15) | FII-9 | DIA (0.02) | W-4 | A1/A5 (30/70) | 5.7 | rectangular |
| 81 | A-22 (0.3) | Z1 (0.10) | FII-10 | DIA (0.02) | W-2 | A1/B1 (90/10) | 3.6 | rectangular |
| 82 | A-29 (0.2) | Z2 (0.20) | FII-11 | PEA (0.02) | W-1 | A1/A4 (95/5) | 4.4 | rectangular |
| 83 | A-40 (0.2) | Z5 (0.20) | FII-12 | TPSA (0.02) | W-3 | A1/B2 (80/20) | 7.4 | rectangular |
| 84 | A-37 (0.2) | Z44 (0.20) | FII-13 | TBAH (0.02) | W-1 | A1/B1 (60/40) | 5.6 | rectangular |

TABLE 11

| Example | Acid Generator (g) | Acid Generator Used in Combination (g) | Resin (10 g.) | Basic Compound (g) | Surfactant (0.03 g) | Solvent (mass ratio) | PEB Temperature Dependency (nm/° C.) | Pattern Profile |
|---|---|---|---|---|---|---|---|---|
| 85 | A-44 (0.2) | Z46 (0.15) | FII-14 | HAP (0.02) | W-4 | A1/B1 (95/5) | 4.5 | rectangular |
| 86 | A-49 (0.15) | Z51 (0.20) | FII-15 | DCMA (0.02) | W-2 | A1/B1 (60/40) | 7.1 | rectangular |
| 87 | A-53 (0.15) | Z25 (0.10) | FII-16 | TOA (0.02) | W-4 | A1/B1 (60/40) | 6.6 | rectangular |
| 88 | A-2 (0.2) | Z52 (0.15) | FII-17 | DIA (0.02) | W-3 | A1/A4 (95/5) | 6.7 | rectangular |
| 89 | A-63 (0.15) | Z14 (0.20) | FII-18 | HEP (0.02) | W-1 | A1/B2 (80/20) | 5.9 | rectangular |
| 90 | A-69 (0.15) | Z1 (0.20) | FII-19 | DIA (0.02) | W-2 | A1/B1 (60/40) | 7.5 | rectangular |
| 91 | A-78 (0.2) | Z38 (0.15) | FII-20 | TPSA (0.02) | W-1 | A1/B1 (60/40) | 6.9 | rectangular |
| 92 | A-1 (0.15) | Z14 (0.15) | FII-28 | DIA (0.02) | W-4 | A1/B1 (60/40) | 5.4 | rectangular |
| 93 | A-5 (0.15) | z53 (0.15) z14 (0.10) | FII-29 | PEA (0.02) | W-4 | A1/B1 (60/40) | 3.3 | rectangular |

TABLE 11-continued

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 94 | A-8 (0.1) | Z54 (0.2) | FII-30 | PEA (0.02) | W-4 | A1/A5 (30/70) | 4.8 | rectangular |
| 95 | A-10 (0.1) | z14 (0.2) | FII-31 | PEA (0.02) | W-4 | A1/B1 (70/30) | 6.0 | rectangular |
| 96 | A-1 (0.1) A-91 (0.1) | Z42 (0.15) | FII-25 FII-1 | PEA (0.02) | W-4 | A1/B2 (80/20) | 4.9 | rectangular |
| 97 | A-99 (0.2) | Z21 (0.1) | FII-26 | DIA (0.02) | W-1 | A1/B1 (60/40) | 2.6 | rectangular |

TABLE 12

| | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| Example | | | | | | | | |
| 98 | A-4 (0.3) | z2 (0.2) | FII-1 | PEA (0.02) | W-1 | A1/B1 (60/40) | 3.3 | rectangular |
| 99 | A-127 (0.3) | z2 (0.15) | FII-2 | THEA (0.02) | W-1 | A1/B1 (95/5) | 3.6 | rectangular |
| 100 | A-131 (0.2) | z2 (0.2) | FII-4 | DIA (0.02) | W-4 | A1/B1 (60/40) | 3.0 | rectangular |
| 101 | A-137 (0.3) | z2 (0.2) | FII-5 | DIA (0.02) | W-4 | A1/B1 (60/40) | 2.0 | rectangular |
| 102 | A-143 (0.3) | z36 (0.2) | FII-20 | DIA (0.02) | W-3 | A1/B1 (60/40) | 3.5 | rectangular |
| 103 | A-149 (0.2) | z38 (0.15) | FII-1 | DIA (0.02) | W-1 | A1/B1 (60/40) | 4.0 | rectangular |
| 104 | A-163 (0.3) | z38 (0.1) | FII-8 | DIA (0.02) | W-1 | A1/A5 (40/60) | 2.2 | rectangular |
| 105 | A-167 (0.25) | z38 (0.1) | FII-2 | PEA (0.02) | W-4 | A1/A4 (60/40) | 3.9 | rectangular |
| Comp. Example | | | | | | | | |
| 8 | TPSB (0.3) | z14 (0.15) | FII-1 | DIA (0.02) | W-4 | A1/B1 (60/40) | 11.1 | slightly tapered |
| 9 | MSDBS (0.3) | z14 (0.15) | FII-1 | DIA (0.02) | W-4 | A1/B1 (60/40) | image was not formed | image was not formed |
| 10 | TPSB (0.3) | — | FII-1 | DIA (0.02) | W-1 | A1/B1 (60/40) | 6.2 | tapered |
| 11 | MSDBS (0.3) | — | FII-1 | DIA (0.02) | W-1 | A1/B1 (60/40) | image was not formed | image was not formed |
| 12 | TPSPFBSI (0.3) | — | FII-1 | DIA (0.03) | W-1 | A1/B2 (60/40) | 5.5 | slightly tapered |

As apparent from the results in Tables 10 to 12, the photosensitive composition of the present invention exhibits small PEB temperature dependency even at $F_2$ excimer laser exposure and gives an excellent pattern profile.

Examples 106 to 123 and Comparative Examples 13 to 17

<Preparation of Resist>

The components shown in Tables 14 and 15 below were dissolved in a solvent and the resulting solution was filtered through a 0.1-μm polytetrafluoroethylene filter to prepare a positive resist solution having a solid concentration of 14 mass %.

The prepared positive resist solutions were evaluated by the following methods and the results are shown in Tables 14 and 15.

The molar ratio and weight average molecular weight of each of Resins (R-2) to (R-27) in Tables 14 and 15 are shown in Table 13 below.

TABLE 13

| Resin | Molar Ratio of Repeating Units (in the order from left) | Weight Average Molecular Weight |
|---|---|---|
| R-2 | 60/40 | 12000 |
| R-7 | 60/30/10 | 18000 |
| R-8 | 60/20/20 | 12000 |
| R-9 | 10/50/40 | 13000 |

TABLE 13-continued

| Resin | Molar Ratio of Repeating Units (in the order from left) | Weight Average Molecular Weight |
|---|---|---|
| R-14 | 75/25 | 12000 |
| R-17 | 10/70/20 | 15000 |
| R-19 | 10/70/20 | 11000 |
| R-22 | 70/30 | 12000 |
| R-23 | 10/60/30 | 8000 |
| R-24 | 50/20/30 | 16000 |
| R-25 | 10/70/20 | 13000 |
| R-27 | 70/10/20 | 12000 |

<Evaluation of Resist>

On a silicon substrate treated with hexamethyl-disilazane, the prepared positive resist solution was uniformly coated by a spin coater and dried under heating on a hot plate at 120° C. for 90 seconds to form a resist film having a thickness of 0.6 μm.

The obtained resist film was exposed through a mask for a line-and-space pattern by using a KrF excimer laser stepper (NA=0.63) and immediately after the exposure, heated on a hot plate at 110° C. for 90 seconds. Thereafter, the resist film was developed with an aqueous 2.38 mass % tetramethylammonium hydroxide solution at 23° C. for 60 seconds, rinsed with pure water for 30 seconds and then dried to form a line pattern. These samples were evaluated on the PEB temperature dependency and pattern profile.

PEB Temperature Dependency

Assuming that the exposure amount necessary for reproducing a 1/1 line-and-space pattern with a mask size of 130 nm after heating at 110° C. for 90 seconds is an optimal exposure amount, the sample was exposed with the optimal exposure amount and post-heated at two temperatures of +2° C. and −2° C. (112° C., 108° C.) with respect to the post-heating temperature. The length of each line-and-space pattern obtained was measured and the line width ($L_1$, $L_2$) was determined. The PEB temperature dependency was defined as the fluctuation in the line width per 1° C. change of the PEB temperature and calculated according to the following formula:

$$\text{PEB Temperature Dependency (nm/° C.)} = |L_1 - L_2|/4$$

A smaller value reveals smaller change in the performance against change in the temperature, and higher performance.

Pattern Profile

The profile at the optimal exposure amount was observed by a scanning microscope (SEM).

TABLE 14

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 106 | A-1 (0.3) | — | R-2 | DIA (0.02) | W-1 | A1/B1 (60/40) | 1.5 | rectangular |
| 107 | A-12 (0.3) | z38 (0.15) | R-9 | PEA (0.02) | W-4 | A1/B1 (60/40) | 2.2 | rectangular |
| 108 | A-1 (0.2) | z31 (0.2) | R-14 | DIA (0.02) | W-3 | A1/B1 (60/40) | 1.5 | rectangular |
| 109 | A-13 (0.3) | z34 (0.2) | R-23 | TMEA (0.02) | W-4 | A1/B1 (80/20) | 3.7 | rectangular |
| 110 | A-17 (0.3) | z44 (0.2) | R-25 | DIA (0.02) | W-3 | A1/B1 (60/40) | 1.7 | rectangular |
| 111 | A-1 (0.2) | — | R-24 | PEA (0.02) | W-1 | A1/B1 (60/40) | 2.5 | rectangular |
| 112 | A-3 (0.3) | z30 (0.4) | R-8 | PEA (0.02) | W-4 | A1/A5 (40/60) | 3.9 | rectangular |
| 113 | A-1 (0.3) | z6 (0.1) | R-24 | PEA (0.02) | W-2 | A1/B1 (60/40) | 1.0 | rectangular |
| 114 | A-2 (0.2) | z14 (0.2) | R-19 | DIA (0.02) | W-4 | A1/A5 (30/70) | 1.6 | rectangular |
| 115 | A-22 (0.3) | z40 (0.3) | R-27 | DIA (0.02) | W-2 | A1/B1 (90/10) | 2.7 | rectangular |

TABLE 15

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 116 | A-4 (0.2) | z2 (0.18) | R-2 | DIA (0.02) | W-1 | A1/B1 (60/40) | 3.0 | rectangular |
| 117 | A-127 (0.2) | z2 (0.15) | R-2 | DIA (0.02) | W-3 | A1/B1 (60/40) | 2.0 | rectangular |
| 118 | A-131 (0.25) | z2 (0.2) | R-2 | TMEA (0.02) | W-4 | A1/B1 (60/40) | 2.8 | rectangular |
| 119 | A-137 (0.3) | z2 (0.2) | R-2 | TMEA (0.02) | W-4 | A1/B1 (60/40) | 1.9 | rectangular |

TABLE 15-continued

| | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 120 | A-143 (0.3) | z36 (0.2) | R-24 | DIA (0.02) | W-4 | A1/B1 (60/40) | 3.2 | rectangular |
| 121 | A-149 (0.3) | z38 (0.15) | R-2 | DIA (0.02) | W-1 | A1/B1 (60/40) | 1.7 | rectangular |
| 122 | A-163 (0.3) | z38 (0.1) | R-2 | PEA (0.02) | W-1 | A1/A5 (40/60) | 2.0 | rectangular |
| 123 | A-167 (0.3) | z38 (0.1) | R-2 | PEA (0.02) | W-1 | A1/A4 (60/40) | 1.8 | rectangular |
| Comp. Example | | | | | | | | |
| 13 | TPSB (0.3) | — | R-2 | DIA (0.02) | W-1 | A1/B1 (60/40) | 5.4 | slightly tapered |
| 14 | MSDBS (0.3) | — | R-2 | DIA (0.02) | W-1 | A1/B1 (60/40) | 10.7 | rectangular |
| 15 | TPSB (0.3) | — | R-24 | DIA (0.02) | W-1 | A1/B1 (60/40) | 3.3 | inversely tapered |
| 16 | MSDBS (0.3) | — | R-24 | DIA (0.02) | W-1 | A1/B1 (60/40) | image was not formed | image was not formed |
| 17 | TPSPFBSI (0.3) | — | R-24 | DIA (0.03) | W-1 | A1/B2 (60/40) | 2.9 | slightly tapered |

As apparent from the results in Tables 14 and 15, the photosensitive composition of the present invention exhibits small PEB temperature dependency even when used as a positive resist composition for KrF excimer laser exposure, and gives an excellent pattern profile.

Examples 124 to 142 and Comparative Examples 18 to 22

<Preparation of Resist>

The components shown in Tables 16 and 17 below were dissolved in a solvent and the resulting solution was filtered through a 0.1-μm polytetrafluoroethylene filter to prepare a negative resist solution having a solid concentration of 14 mass %.

The prepared negative resist solutions were evaluated by the same methods as in Examples 106 to 123 and the results are shown in Tables 16 and 17.

The structure, molecular weight and molecular-weight distribution of each alkali-soluble resin in Tables 16 and 17 are shown below.

| | Mw | Mw/Mn |
|---|---|---|
| P-1 | 17000 | 2.15 |

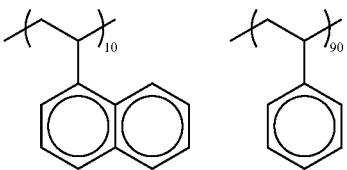

| | Mw | Mw/Mn |
|---|---|---|
| P-2 | 16000 | 2.30 |

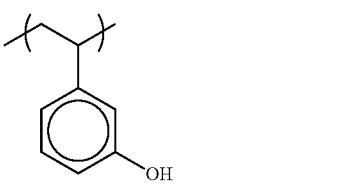

| P-3 | 19000 | 2.2 |

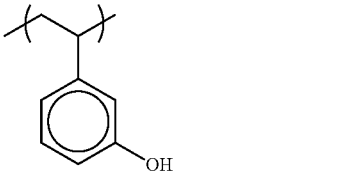

| P-4 | 12000 | 1.2 |

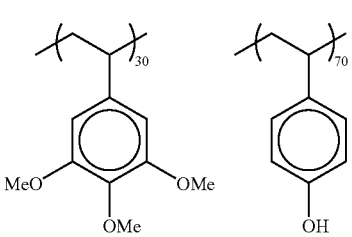

| P-5 | 21000 | 2.1 |

-continued
| | | Mw | Mw/Mn |
|---|---|---|---|
| P-6 | 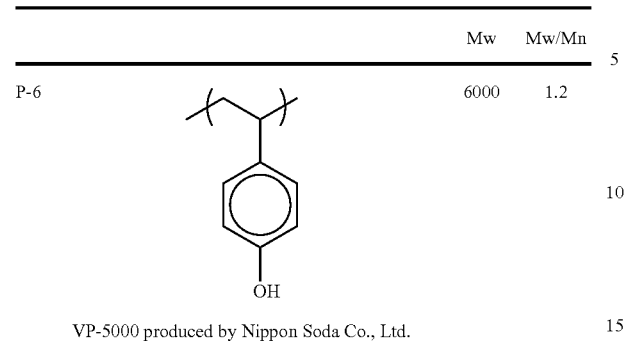 | 6000 | 1.2 |
VP-5000 produced by Nippon Soda Co., Ltd.
The structures of the crosslinking agents in Tables 16 and 17 is shown below.
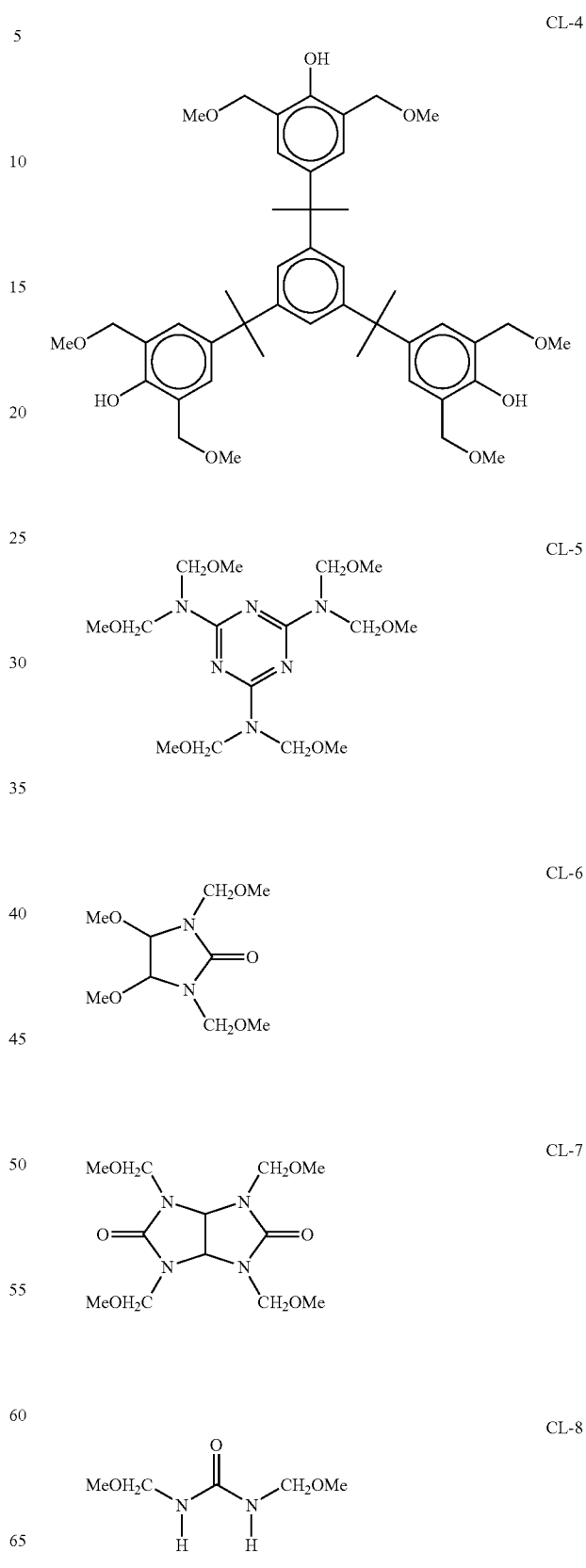

TABLE 16

| Example | Acid Generator (g) | Acid Generator Used in Combination (g) | Resin (10 g) | Basic Compound (g) | Surfactant (0.03 g) | Solvent (mass ratio) | Cross-linking Agent (g) | PEB Temperature Dependency (nm/° C.) | Pattern Profile |
|---|---|---|---|---|---|---|---|---|---|
| 124 | A-1 (0.3) |  | P-1 | DIA (0.05) | W-1 | A1/B1 (60/40) | CL-1 (2) | 2.5 | rectangular |
| 125 | A-12 (0.3) | z38 (0.15) | P-2 | TPI (0.03) | W-1 | A1/B1 (60/40) | CL-2 (3) | 2.6 | rectangular |
| 126 | A-1 (0.2) | z31 (0.2) | P-3 | TOA (0.005) | W-2 | A1/B1 (60/40) | CL-3 (2.5) | 3.5 | rectangular |
| 127 | A-13 (0.3) | z34 (0.2) | P-4 | HEP (0.02) | W-2 | A1/B1 (80/20) | CL-4 (3) | 3.1 | rectangular |
| 128 | A-17 (0.3) | z44 (0.2) | P-5 | DBN (0.02) | W-3 | A1/B1 (60/40) | CL-5 (1.5) | 3.7 | rectangular |
| 129 | A-1 (0.2) |  | P-6 | DCMA (0.03) | W-4 | A1/B1 (60/40) | CL-6 (3) | 4.5 | rectangular |
| 130 | A-3 (0.3) | z30 (0.4) | P-1 | TPA (0.01) | W-4 | A1/A5 (40/60) | CL-7 (2.5) | 4.9 | rectangular |
| 131 | A-1 (0.3) | z6 (0.1) | P-2/P-6 (80/20) | TPSA (0.1) | W-4 | A1/B1 (60/40) | CL-8 (2.5) | 2.0 | rectangular |
| 132 | A-2 (0.2) | z14 (0.2) | P-3 | TBAH (0.015) | W-4 | A1/A5 (30/70) | CL-1 (2) CL-5 (2) | 3.6 | rectangular |
| 133 | A-22 (0.3) | z40 (0.3) | P-4 | TMEA (0.02) | W-4 | A1/B1 (90/10) | CL-2 (1) CL-7 (2) | 2.9 | rectangular |
| 134 | A-1 (0.15) | Z14 (0.15) | P-5 | HAP (0.01) | W-1 | A1/B1 (80/20) | CL-1 (2.5) | 3.6 | rectangular |

TABLE 17

| Example | Acid Generator (g) | Acid Generator Used in Combination (g) | Resin (10 g) | Basic Compound (g) | Surfactant (0.03 g) | Solvent (mass ratio) | Cross-linking Agent (g) | PEB Temperature Dependency (nm/° C.) | Pattern Profile |
|---|---|---|---|---|---|---|---|---|---|
| Example |  |  |  |  |  |  |  |  |  |
| 135 | A-4 (0.2) | z2 (0.14) | P-1 | TPI (0.02) | W-1 | A1/B1 (60/40) | CL-1 | 3.2 | rectangular |
| 136 | A-127 (0.2) | z2 (0.15) | P-5 | TOA (0.02) | W-2 | A1/B1 (60/40) | CL-2 (3) | 2.5 | rectangular |
| 137 | A-131 (0.25) | z2 (0.2) | P-4 | HEP (0.02) | W-3 | A1/B1 (60/40) | CL-3 (2.5) | 3.0 | rectangular |
| 138 | A-137 (0.3) | z2 (0.2) | P-2 | DBN (0.02) | W-1 | A1/B1 (60/40) | CL-4 (3) | 2.5 | rectangular |
| 139 | A-143 (0.3) | z36 (0.2) | P-6 | DCMA (0.02) | W-4 | A1/B1 (60/40) | CL-5 (1.5) | 3.3 | rectangular |
| 140 | A-149 (0.3) | z38 (0.15) | P-4 | TPA (0.02) | W-3 | A1/B1 (60/40) | CL-6 (3) | 2.4 | rectangular |
| 141 | A-163 (0.3) | z38 (0.1) | P-6 | TPSA (0.02) | W-4 | A1/A5 (60/40) | CL-7 (2.5) | 2.6 | rectangular |
| 142 | A-167 (0.3) | z38 (0.1) | P-3 | TBAH (0.02) | W-1 | A1/A4 (80/20) | CL-8 (2.5) | 2.4 | rectangular |
| Comp. Example |  |  |  |  |  |  |  |  |  |
| 18 | TPSB (0.3) | — | P-1 | DIA (0.05) | W-1 | A1/B1 (60/40) | CL-1 (2) | 9.4 | inversely tapered |
| 19 | MSDBS (0.3) | — | P-1 | DIA (0.05) | W-1 | A1/B1 (60/40) | CL-1 (2) | 11.2 | rectangular |
| 20 | TPSB (0.3) | — | P-2 | HAP (0.02) | W-1 | A1/B1 (60/40) | CL-1 (2) | 5.0 | tapered |
| 21 | MSDBS (0.3) | — | P-2 | DIA (0.02) | W-1 | A1/B1 (60/40) | CL-1 (2) | image was not formed | image was not formed |
| 22 | TPSPFBSI (0.3) | — | P-2 | DIA (0.03) | W-1 | A1/B2 (60/40) | CL-1 (2) | 4.1 | slightly tapered |

As apparent from the results in Tables 16 and 17, the photosensitive composition of the present invention exhibits small PEB temperature dependency even when used as a negative resist composition for KrF excimer laser exposure, and gives an excellent pattern profile.

Examples 143 to 156 and Comparative Examples 23 to 27

<Preparation of Resist>

The components shown in Tables 18 and 19 below were dissolved in a solvent and the resulting solution was filtered through a 0.1-μm polytetrafluoroethylene filter to prepare a positive resist solution having a solid concentration of 12 mass %.

The positive resist solutions prepared were evaluated by the following methods and the results are shown in Tables 18 and 19.

<Evaluation of Resist>

On a silicon substrate treated with hexamethyl-disilazane, the prepared positive resist solution was uniformly coated by a spin coater and dried under heating on a hot plate at 120° C. for 60 seconds to form a resist film having a thickness of 0.3 μm.

The obtained resist film was irradiated by an electron beam projection lithography apparatus manufactured by Nikon Corp. (accelerating voltage: 100 KeV) and immediately after the irradiation, heated on a hot plate at 110° C. for 90 seconds. Thereafter, the resist film was developed with an aqueous tetramethylammonium hydroxide solution having a concentration of 2.38 mass % at 23° C. for 60 seconds, rinsed with pure water for 30 seconds and then dried to form a contact hole pattern.

PEB Temperature Dependency

Assuming that the irradiation dosage necessary for reproducing a 110-nm dense line-and-space pattern (pitch: 200 nm) after heating at 110° C. for 90 seconds is an optimal irradiation dosage, the sample was exposed with the optimal irradiation dosage and post-heated at two temperatures of +2° C. and −2° C. (112° C., 108° C.) with respect to the post-heating temperature. The length of each line-and-space pattern obtained was measured and the line width ($L_1$, $L_2$) was determined. The PEB temperature dependency was defined as the fluctuation in the line width per 1° C. change of the PEB temperature and calculated according to the following formula:

PEB Temperature Dependency (nm/° C.)=$|L_1-L_2|/4$

A smaller value reveals smaller change in the performance against change in the temperature, and higher performance.

Pattern Profile

The profile at the optimal exposure amount was observed by a scanning microscope (SEM).

TABLE 18

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 143 | A-1 (0.3) |  | R-2 | DIA (0.02) | W-1 | A1/B1 (60/40) | 2.5 | rectangular |
| 144 | A-12 (0.3) | z38 (0.15) | R-9 | PEA (0.02) | W-4 | A1/B1 (60/40) | 2.9 | rectangular |
| 145 | A-1 (0.2) | z31 (0.2) | R-14 | DIA (0.02) | W-3 | A1/B1 (60/40) | 3.5 | rectangular |
| 146 | A-13 (0.3) | z34 (0.2) | R-23 | TMEA (0.02) | W-4 | A1/B1 (80/20) | 3.9 | rectangular |
| 147 | A-17 (0.3) | z44 (0.2) | R-25 | DIA (0.02) | W-3 | A1/B1 (60/40) | 3.7 | rectangular |
| 148 | A-1 (0.2) |  | R-24 | PEA (0.02) | W-1 | A1/B1 (60/40) | 2.6 | rectangular |
| 149 | A-3 (0.3) | z30 (0.4) | R-8 | PEA (0.02) | W-4 | A1/A5 (40/60) | 4.9 | rectangular |
| 150 | A-1 (0.3) | z6 (0.1) | R-24 | PEA (0.02) | W-2 | A1/B1 (60/40) | 4.0 | rectangular |
| 151 | A-2 (0.2) | z14 (0.2) | R-19 | DIA (0.02) | W-4 | A1/A5 (30/70) | 3.6 | rectangular |
| 152 | A-22 (0.3) | z40 (0.3) | R-27 | DIA (0.02) | W-2 | A1/B1 (90/10) | 3.7 | rectangular |

TABLE 19

| Example | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 153 | A-4 (0.2) | z2 (0.2) | R-2 | DIA (0.02) | W-1 | A1/B1 (60/40) | 4.1 | rectangular |

TABLE 19-continued

| | Acid Generator (g) | Acid Generator Used in Combination (g) | Resin (10 g) | Basic Compound (g) | Surfactant (0.03 g) | Solvent (mass ratio) | PEB Temperature Dependency (nm/° C.) | Pattern Profile |
|---|---|---|---|---|---|---|---|---|
| 154 | A-4 (0.2) | z2 (0.15) | R-2 | DIA (0.02) | W-2 | A1/B1 (60/40) | 3.6 | rectangular |
| 155 | A-149 (0.3) | z38 (0.2) | R-2 | PEA (0.02) | W-2 | A1/B1 (60/40) | 3.8 | rectangular |
| 156 | A-175 (0.4) | z38 (0.2) | R-2 | PEA (0.02) | W-1 | A1/B1 (60/40) | 4.0 | rectangular |
| Comp. Example | | | | | | | | |
| 23 | TPSB (0.3) | — | R-2 | DIA (0.02) | W-1 | A1/B1 (60/40) | 9.4 | tapered |
| 24 | MSDBS (0.3) | — | R-2 | DIA (0.02) | W-1 | A1/B1 (60/40) | 8.7 | tapered |
| 25 | TPSB (0.3) | — | R-24 | DIA (0.02) | W-1 | A1/B1 (60/40) | 7.9 | tapered |
| 26 | MSDBS (0.3) | — | R-24 | DIA (0.02) | W-1 | A1/B1 (60/40) | image was not formed | image was not formed |
| 27 | TPSPFBSI (0.3) | — | R-24 | DIA (0.03) | W-1 | A1/B2 (60/40) | 8.0 | slightly tapered |

As apparent from the results in Tables 18 and 19, the photosensitive composition of the present invention exhibits small PEB temperature dependency even when used as a positive resist composition for electron beam irradiation, and gives an excellent pattern profile.

Examples 157 to 170 and Comparative Examples 28 to 32

<Preparation of Resist>

The components shown in Tables 20 and 21 below were dissolved in a solvent and the resulting solution was filtered through a 0.1-μm polytetrafluoroethylene filter to prepare a negative resist solution having a solid concentration of 12 mass %.

The negative resist solutions prepared were evaluated by the following methods and the results are shown in Tables 20 and 21.

<Evaluation of Resist>

On a silicon substrate treated with hexamethyl-disilazane, the prepared negative resist solution was uniformly coated by a spin coater and dried under heating on a hot plate at 120° C. for 60 seconds to form a resist film having a thickness of 0.3 μm.

The obtained resist film was irradiated by an electron beam projection lithography apparatus manufactured by Nikon Corp. (accelerating voltage: 100 KeV) and immediately after the irradiation, heated on a hot plate at 110° C. for 90 seconds. Thereafter, the resist film was developed with an aqueous tetramethylammonium hydroxide solution having a concentration of 2.38 mass % at 23° C. for 60 seconds, rinsed with pure water for 30 seconds and then dried to form a line-and-space pattern.

PEB Temperature Dependency

Assuming that the irradiation dosage necessary for reproducing a 110-nm dense line-and-space pattern (pitch: 200 nm) after heating at 110° C. for 90 seconds is an optimal irradiation dosage, the sample was exposed with the optimal irradiation dosage and post-heated at two temperatures of +2° C. and −2° C. (112° C., 108° C.) with respect to the post-heating temperature. The length of each line-and-space pattern obtained was measured and the line width ($L_1$, $L_2$) was determined. The PEB temperature dependency was defined as the fluctuation in the line width per 1° C. change of the PEB temperature and calculated according to the following formula:

PEB Temperature Dependency (nm/° C.)=$|L_1-L_2|$/4

A smaller value reveals smaller change in the performance against change in the temperature, and higher performance.

Pattern Profile

The profile at the optimal exposure amount was observed by a scanning microscope (SEM).

TABLE 20

| Example | Acid Generator (g) | Acid Generator Used in Combination (g) | Resin (10 g) | Basic Compound (g) | Surfactant (0.03 g) | Solvent (mass ratio) | Cross-linking Agent (g) | PEB Temperature Dependency (nm/° C.) | Pattern Profile |
|---|---|---|---|---|---|---|---|---|---|
| 157 | A-1 (0.3) | | P-1 | DIA (0.05) | W-1 | A1/B1 (60/40) | CL-1 (2) | 3.5 | rectangular |
| 158 | A-12 (0.3) | z38 (0.15) | P-2 | TPI (0.03) | W-1 | A1/B1 (60/40) | CL-2 (3) | 2.1 | rectangular |

TABLE 20-continued

| Example | Acid Generator (g) | Acid Generator Used in Combination (g) | Resin (10 g) | Basic Compound (g) | Surfactant (0.03 g) | Solvent (mass ratio) | Cross-linking Agent (g) | PEB Temperature Dependency (nm/° C.) | Pattern Profile |
|---|---|---|---|---|---|---|---|---|---|
| 159 | A-1 (0.2) | z31 (0.2) | P-3 | TOA (0.005) | W-2 | A1/B1 (60/40) | CL-3 (2.5) | 2.5 | rectangular |
| 160 | A-13 (0.3) | z34 (0.2) | P-4 | HEP (0.02) | W-2 | A1/B1 (80/20) | CL-4 (3) | 4.9 | rectangular |
| 161 | A-17 (0.3) | z44 (0.2) | P-5 | DBN (0.02) | W-3 | A1/B1 (60/40) | CL-5 (1.5) | 3.9 | rectangular |
| 162 | A-1 (0.2) | | P-6 | DCMA (0.03) | W-4 | A1/B1 (60/40) | CL-6 (3) | 4.6 | rectangular |
| 163 | A-3 (0.3) | z30 (0.4) | P-1 | TPA (0.01) | W-4 | A1/A5 (40/60) | CL-7 (2.5) | 4.1 | rectangular |
| 164 | A-1 (0.3) | z6 (0.1) | P-2/P-6 80/20) | TPSA (0.1) | W-4 | A1/B1 (60/40) | CL-8 (2.5) | 3.0 | rectangular |
| 165 | A-2 (0.2) | z14 (0.2) | P-3 | TBAH (0.015) | W-4 | A1/A5 (30/70) | CL-1 (2) CL-5 (2) | 3.9 | rectangular |
| 166 | A-22 (0.3) | z40 (0.3) | P-4 | TMEA (0.02) | W-4 | A1/B1 (90/10) | CL-2 (1) CL-7 (2) | 2.7 | rectangular |

TABLE 21

| | Acid Generator (g) | Acid Generator Used in Combination (g) | Resin (10 g) | Basic Compound (g) | Surfactant (0.03 g) | Solvent (mass ratio) | Cross-linking Agent (g) | PEB Temperature Dependency (nm/° C.) | Pattern Profile |
|---|---|---|---|---|---|---|---|---|---|
| Example | | | | | | | | | |
| 167 | A-4 (0.2) | z2 (0.2) | P-1 | DIA (0.02) | W-1 | A1/B1 (60/40) | CL-1 (2) | 3.3 | rectangular |
| 168 | A-4 (0.2) | z2 (0.15) | P-2 | PEA (0.02) | W-1 | A1/B1 (60/40) | CL-2 (2) | 4.1 | rectangular |
| 169 | A-149 (0.3) | z38 (0.2) | P-1 | PEA (0.02) | W-1 | A1/B1 (60/40) | CL-3 (2) | 2.1 | rectangular |
| 170 | A-175 (0.4) | z38 (0.2) | P-2 | PEA (0.02) | W-1 | A1/B1 (60/40) | CL-4 (2) | 4.1 | rectangular |
| Comp. Example | | | | | | | | | |
| 28 | TPSB (0.3) | — | P-1 | DIA (0.05) | W-1 | A1/B1 (60/40) | CL-1 (2) | 10.3 | inversely tapered |
| 29 | MSDBS (0.3) | — | P-1 | DIA (0.05) | W-1 | A1/B1 (60/40) | CL-1 (2) | 11.3 | rectangular |
| 30 | TPSB (0.3) | — | P-2 | DIA (0.02) | W-1 | A1/B1 (60/40) | CL-2 (2) | 8.5 | tapered |
| 31 | MSDBS (0.3) | — | P-2 | DIA (0.02) | W-1 | A1/B1 (60/40) | CL-2 (2) | image was not formed | image was not formed |
| 32 | TPSPFBSI (0.3) | — | P-2 | DIA (0.03) | W-1 | A1/B2 (60/40) | CL-1 (1) | 7.1 | slightly tapered |

As apparent from the results in Tables 20 and 21, the photosensitive composition of the present invention exhibits small PEB temperature dependency even when used as a negative resist composition for electron beam irradiation, and gives an excellent pattern profile.

(Immersion Exposure)

<Preparation of Resist>

The components in each of Examples 1 to 14 were dissolved in a solvent to prepare a solution having a solid concentration of 7 mass % and this solution was filtered through a 0.1-μm polyethylene filter to prepare a positive resist solution. The prepared positive resist solutions were evaluated by the following methods.

<Evaluation of Resolution>

An organic antireflection film ARC29A (produced by Nissan Chemical Industries, Ltd.) was coated on a silicon wafer and baked at 205° C. for 60 seconds to form a 78-nm antireflection film. On this film, the positive resist solution prepared was coated and baked at 115° C. for 60 seconds to form a 150-nm resist film. The thus-obtained wafer was subjected to two-beam interference exposure (wet exposure) by using pure water as the immersion solution. In the two-beam interference exposure (wet exposure), the wafer was exposed through a prism and an immersion solution (pure water) by using a laser, a diaphragm, a shutter, three reflecting mirrors and a condenser lens. The wavelength of the laser used was 193 nm and a prism of forming a 65-nm line-and-space pattern was used. Immediately after the exposure, the resist film was heated at 115° C. for 90 seconds, then developed with an aqueous tetramethylammonium hydroxide solution (2.38%) for 60 seconds and after rinsing with pure water, spin-dried. The obtained resist pattern was observed by a scanning electron microscope (S-9260, manufactured by Hitachi Ltd.), as a result, a 65-nm line-and-space pattern was resolved.

The positive resist composition of the present invention exhibits good image-forming capability even in the exposure method through an immersion solution.

According to the present invention, a photosensitive composition exhibiting small PEB temperature dependency and giving a good profile, a pattern forming method using the photosensitive composition, and a compound useful for the photosensitive composition can be provided.

The entire disclosure of each and every foreign patent application from which the benefit of foreign priority has been claimed in the present application is incorporated herein by reference, as if fully set forth.

What is claimed is:

1. A photosensitive composition comprising (A) a compound capable of generating a sulfonic acid, the sulfonic acid being represented by formula (I) upon irradiation with one of an actinic ray and a radiation:

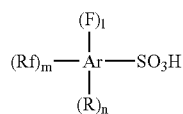

wherein

Rf represents an organic group having a fluorine atom,

R represents a hydroxyl group or an organic group,

Ar represents an aromatic group, l represents an integer of 2 to 5, m represents an integer of 0 to 4, and n represents an integer of 0 to 4, provided that m+n represents an integer of 1 or more.

2. The photosensitive composition according to claim 1, wherein the compound (A) comprises at least one of: a sulfonium salt compound of the sulfonic acid represented by formula (I); an iodonium salt compound of the sulfonic acid represented by formula (I); and an ester compound of the sulfonic acid represented by formula (I).

3. The photosensitive composition according to claim 1, wherein the compound (A) is represented by any one of formulae (A1) to (A5):

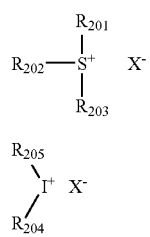

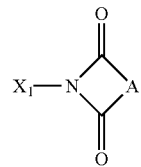

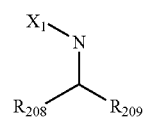

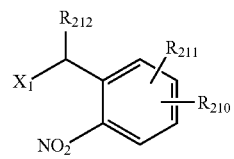

wherein in formula (A1),

R$_{201}$, R$_{202}$ and R$_{203}$ each independently represents an organic group, and X$^-$ represents a sulfonate anion resulting from removal of the hydrogen atom from the sulfonic acid (—SO$_3$H) of formula (I);

in formula (A2),

R$_{204}$ and R$_{205}$ each independently represents an aryl group, an alkyl group or a cycloalkyl group, and X$^-$ represents a sulfonate anion resulting from removal of the hydrogen atom from the sulfonic acid (—SO$_3$H) of formula (I);

in formula (A3),

A represents an alkylene group, an alkenylene group or an arylene group, and

X$_1$ represents a monovalent group resulting from removal of the hydrogen atom from the sulfonic acid (—SO$_3$H) of formula (I);

in formula (A4),

R$_{208}$ represents an alkyl group or an aryl group,

R$_{209}$ represents an alkyl group, a cyano group or an alkoxycarbonyl group, and X$_1$ represents a monovalent group resulting from removal of the hydrogen atom from the sulfonic acid (—SO$_3$H) of formula (I); and in formula (A5), R$_{210}$ and R$_{211}$ each independently represents a hydrogen atom, an alkyl group, a cyano group, a nitro group or an alkoxycarbonyl group, R$_{212}$ represents a hydrogen atom, an alkyl group, a cyano group or an alkoxycarbonyl group, and X$_1$ represents a monovalent group resulting from removal of the hydrogen atom from the sulfonic acid (—SO$_3$H) of formula (I).

4. A compound (A) capable of generating a sulfonic acid, the sulfonic acid being represented by formula (I) upon irradiation with one of an actinic ray and a radiation:

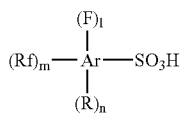

wherein
Rf represents an organic group having a fluorine atom,
R represents a hydroxyl group or an organic group,
Ar represents an aromatic group,
l represents an integer of 2 to 5,
m represents an integer of 0 to 4, and
n represents an integer of 0 to 4,
provided that m+n represents an integer of 1 or more.

5. The compound according to claim 4, wherein the compound (A) comprises at least one of: a sulfonium salt compound of the sulfonic acid represented by formula (I); an iodonium salt compound of the sulfonic acid represented by formula (I); and an ester compound of the sulfonic acid represented by formula (I).

6. A compound represented by formula (I) or a salt thereof:

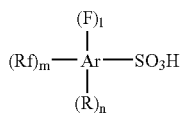

wherein
Rf represents an organic group having a fluorine atom,
R represents a hydroxyl group or an organic group,
Ar represents an aromatic group,
l represents an integer of 2 to 5,
m represents an integer of 0 to 4, and
n represents an integer of 0 to 4,
provided that m+n represents an integer of 1 or more.

7. A compound represented by any one of formulae (A1) to (A5):

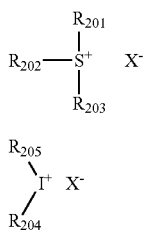

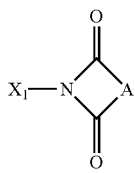

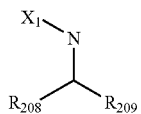

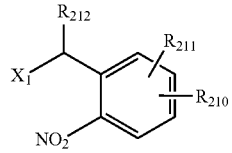

wherein
in formula (A1),
$R_{201}$, $R_{202}$ and $R_{203}$ each independently represents an organic group, and
$X^-$ represents a sulfonate anion resulting from removal of the hydrogen atom from a sulfonic acid (—$SO_3H$) of formula (I);
in formula (A2),
$R_{204}$ and $R_{205}$ each independently represents an aryl group, an alkyl group or a cycloalkyl group, and
$X^-$ represents a sulfonate anion resulting from removal of the hydrogen atom from a sulfonic acid (—$SO_3H$) of formula (I);
in formula (A3),
A represents an alkylene group, an alkenylene group or an arylene group, and
$X_1$ represents a monovalent group resulting from removal of the hydrogen atom from a sulfonic acid (—$SO_3H$) of formula (I);
in formula (A4),
$R_{208}$ represents an alkyl group or an aryl group,
$R_{209}$ represents an alkyl group, a cyano group or an alkoxycarbonyl group, and
$X_1$ represents a monovalent group resulting from removal of the hydrogen atom from a sulfonic acid (—$SO_3H$) of the following formula (I); and
in formula (A5),
$R_{210}$ and $R_{211}$ each independently represents a hydrogen atom, an alkyl group, a cyano group, a nitro group or an alkoxycarbonyl group,
$R_{212}$ represents a hydrogen atom, an alkyl group, a cyano group or an alkoxycarbonyl group, and
$X_1$ represents a monovalent group resulting from removal of the hydrogen atom from a sulfonic acid (—$SO_3H$) of formula (I):

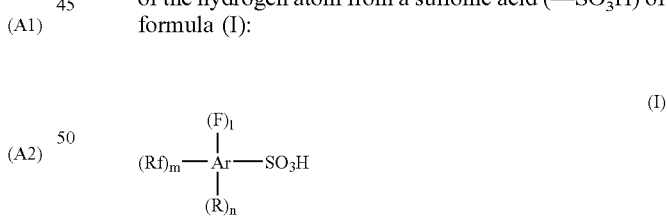

wherein
Rf represents an organic group having a fluorine atom,
R represents a hydroxyl group or an organic group,
Ar represents an aromatic group,
l represents an integer of 2 to 5,
m represents an integer of 0 to 4, and
n represents an integer of 0 to 4,
provided that m+n represents an integer of 1 or more.

8. A pattern forming method comprising:
forming a resist film from the photosensitive composition according to claim 1; and
exposing and developing the resist film.

9. The photosensitive composition according to claim 1, which further comprises (A') a compound capable of generating a sulfonic acid except for formula (I) upon irradiation with one of an actinic ray and a radiation.

10. The photosensitive composition according to claim 9, wherein the component (A') is a sulfonium salt of a fluorine-substituted alkanesulfonic acid.

11. A positive photosensitive composition comprising:
(A) a compound capable of generating a sulfonic acid, the sulfonic acid represented by formula (I) upon irradiation with one of an actinic ray and a radiation:

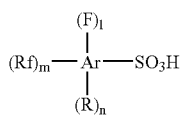

wherein
Rf represents an organic group having a fluorine atom,
R represents a hydroxyl group or an organic group,
Ar represents an aromatic group,
l represents an integer of 2 to 5,
m represents an integer of 0 to 4, and
n represents an integer of 0 to 4,
provided that m+n represents an integer of 1 or more; and
(B) a resin capable of decomposing under the action of an acid to increase a solubility of the resin in an alkali developer.

12. The positive photosensitive composition according to claim 11, wherein the resin (B) has a fluorine atom.

13. The positive photosensitive composition according to claim 12, wherein the resin (B) has a hexafluoroisopropanol structure.

14. The positive photosensitive composition according to claim 11, wherein the resin (B) has a hydroxystyrene structural unit.

15. The positive photosensitive composition according to claim 14, wherein the resin (B) further has at least one repeating unit selected from 2-alkyl-2-adamantyl (meth)acrylate and dialkyl(1-adamantyl)methyl (meth)acrylate.

16. The positive photosensitive composition according to claim 11, wherein the resin (B) has a monocyclic or polycyclic alicyclic hydrocarbon structure.

17. The positive photosensitive composition according to claim 16, wherein the resin (B) has: at least one repeating unit selected from 2-alkyl-2-adamantyl (meth)acrylate and dialkyl(1-adamantyl)methyl (meth)acrylate; at least one repeating unit having a lactone structure; and at least one repeating unit having a hydroxyl group.

18. The positive photosensitive composition according to claim 16, wherein the resin (B) further has a repeating unit having a carboxyl group.

19. The positive photosensitive composition according to claim 11, wherein the resin (B) has a silicon atom.

20. The positive photosensitive composition according to claim 11, wherein the resin (B) further has a repeating unit having a lactone structure.

21. The positive photosensitive composition according to claim 11, which further comprises (C) a dissolution inhibiting compound capable of decomposing under the action of an acid to increase a solubility of the dissolution inhibiting compound in an alkali developer, the dissolution inhibiting compound having a molecular weight of 3,000 or less.

22. A positive photosensitive composition comprising:
(A) a compound capable of generating a sulfonic acid, the sulfonic acid represented by formula (I) upon irradiation with one of an actinic ray and a radiation:

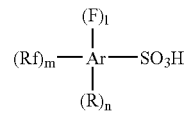

wherein
Rf represents an organic group having a fluorine atom,
R represents a hydroxyl group or an organic group,
Ar represents an aromatic group,
l represents an integer of 2 to 5,
m represents an integer of 0 to 4, and
n represents an integer of 0 to 4,
provided that m+n represents an integer of 1 or more;
(D) a resin soluble in an alkali developer; and
(C) a dissolution inhibiting compound capable of decomposing under the action of an acid to increase a solubility of the dissolution inhibiting compound in an alkali developer, the dissolution inhibiting compound having a molecular weight of 3,000 or less.

23. A negative photosensitive composition comprising:
(A) a compound capable of generating a sulfonic acid, the sulfonic acid represented by formula (I) upon irradiation with one of an actinic ray and a radiation:

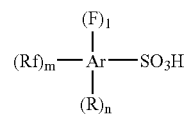

wherein
Rf represents an organic group having a fluorine atom,
R represents a hydroxyl group or an organic group,
Ar represents an aromatic group,
l represents an integer of 2 to 5,
m represents an integer of 0 to 4, and
n represents an integer of 0 to 4,
provided that m+n represents an integer of 1 or more;
(D) a resin soluble in an alkali developer; and
(E) an acid crosslinking agent capable of crosslinking with the alkali developer-soluble resin under the action of an acid.

24. The photosensitive composition according to claim 1, which further comprises at least one of:
(F) a basic compound; and
(G) a surfactant containing at least one of a fluorine atom and a silicon atom.

25. The photosensitive composition according to claim 11, which further comprises at least one of:
(F) a basic compound; and
(G) a surfactant containing at least one of a fluorine atom and a silicon atom.

26. The photosensitive composition according to claim 22, which further comprises at least one of:
(F) a basic compound; and
(G) a surfactant containing at least one of a fluorine atom and a silicon atom.

27. The photosensitive composition according to claim 23, which further comprises at least one of:
(F) a basic compound; and
(G) a surfactant containing at least one of a fluorine atom and a silicon atom.

28. The photosensitive composition according to claim 24, wherein the basic compound (F) is at least one of (a) a compound having a structure selected from an imidazole structure, a diazabicyclo structure, an onium hydroxide structure, an onium carboxylate structure, a trialkylamine structure, an aniline structure and a pyridine structure, (b) an alkylamine derivative having at least one of a hydroxyl group and an ether bond, and (c) an aniline derivative having at least one of a hydroxyl group and an ether bond.

29. The photosensitive composition according to claim 25, wherein the basic compound (F) is at least one of (a) a compound having a structure selected from an imidazole structure, a diazabicyclo structure, an onium hydroxide structure, an onium carboxylate structure, a trialkylamine structure, an aniline structure and a pyridine structure, (b) an alkylamine derivative having at least one of a hydroxyl group and an ether bond, and (c) an aniline derivative having at least one of a hydroxyl group and an ether bond.

30. The photosensitive composition according to claim 26, wherein the basic compound (F) is at least one of (a) a compound having a structure selected from an imidazole structure, a diazabicyclo structure, an onium hydroxide structure, an onium carboxylate structure, a trialkylamine structure, an aniline structure and a pyridine structure, (b) an alkylamine derivative having at least one of a hydroxyl group and an ether bond, and (c) an aniline derivative having at least one of a hydroxyl group and an ether bond.

31. The photosensitive composition according to claim 27, wherein the basic compound (F) is at least one of (a) a compound having a structure selected from an imidazole structure, a diazabicyclo structure, an onium hydroxide structure, an onium carboxylate structure, a trialkylamine structure, an aniline structure and a pyridine structure, (b) an alkylamine derivative having at least one of a hydroxyl group and an ether bond, and (c) an aniline derivative having at least one of a hydroxyl group and an ether bond.

* * * * *